(12) United States Patent
Bhalay et al.

(10) Patent No.: US 8,039,472 B2
(45) Date of Patent: Oct. 18, 2011

(54) PYRAZINE-2-CARBOXAMIDE DERIVATIVES TO TREAT DISEASES MEDIATED BY BLOCKADE OF THE EPITHELIAL SODIUM CHANNEL

(75) Inventors: Gurdip Bhalay, Horsham (GB); Emma Budd, Horsham (GB); Graham Charles Bloomfield, Horsham (GB); Stephen Paul Collingwood, Horsham (GB); Andrew Dunstan, Horsham (GB); Lee Edwards, Horsham (GB); Peter Gedeck, Basel (CH); Catherine Howsham, Horsham (GB); Peter Hunt, Horsham (GB); Thomas Anthony Hunt, Horsham (GB); Paul Oakley, Horsham (GB); Nichola Smith, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/332,086

(22) Filed: Dec. 10, 2008

(65) Prior Publication Data
US 2010/0130506 A1 May 27, 2010

(30) Foreign Application Priority Data

Dec. 10, 2007 (EP) .................................. 07122739

(51) Int. Cl.
*A61K 31/497* (2006.01)
*A61K 31/50* (2006.01)
*C07D 237/00* (2006.01)
(52) U.S. Cl. ............... 514/252.15; 514/255.05; 514/230
(58) Field of Classification Search .................. None
See application file for complete search history.

(56) References Cited

U.S. PATENT DOCUMENTS

| 3,573,306 A | 3/1971 | Shepard et al. |
| 3,577,418 A | 5/1971 | Cragoe, Jr. et al. |
| 4,085,211 A | 4/1978 | Cragoe, Jr. et al. |
| 4,272,537 A | 6/1981 | Woltersdorf, Jr. et al. |

FOREIGN PATENT DOCUMENTS
GB        1158399        7/1969

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Andrew Hirsh, "Altering Airway Surface Liquid Volume: Inhalation Therapy with Amiloride and Hyperosmotic Agents" Advanced Drug Delivery Reviews 54:1445-1462, 2000.

* cited by examiner

*Primary Examiner* — Brandon Fetterolf
*Assistant Examiner* — Anna Pagonakis
(74) *Attorney, Agent, or Firm* — Mark Milstead; Michael G. Smith

(57) ABSTRACT

A compound of Formula I

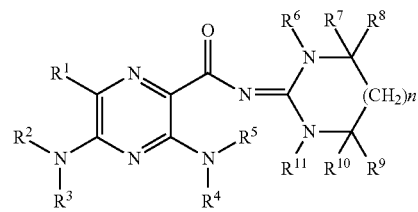

in free or salt or solvate form, where $R^1$, $R^2$, $R^3$, $R^4$, $R^5$, $R^6$, $R^7$, $R^8$, $R^9$, $R^{10}$ and $R^{11}$ have the meanings as indicated in the specification, is useful for treating diseases which respond to the blockade of the epithelial sodium channel. Pharmaceutical compositions that contain the compounds and processes for preparing the compounds are also described.

19 Claims, No Drawings

PYRAZINE-2-CARBOXAMIDE DERIVATIVES TO TREAT DISEASES MEDIATED BY BLOCKADE OF THE EPITHELIAL SODIUM CHANNEL

This application claims priority to E.P. Application Serial No. 07122739.1 filed 10 Dec. 2007, the contents of which are incorporated herein by reference in their entirety.

This invention relates to organic compounds, their preparation and use as pharmaceuticals.

In one aspect, the invention provides compounds according to Formula I:

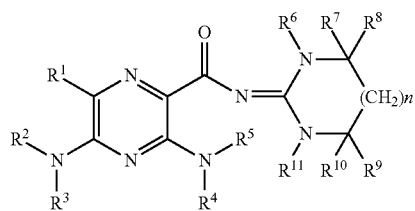

or solvates, hydrates or pharmaceutically acceptable salts thereof, wherein
$R^1$ is H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, or a $C_1$-$C_8$-alkyl substituted by a $C_6$-$C_{15}$-membered aromatic carbocyclic group;
$R^2$, $R^3$, $R^4$ and $R^5$ are each independently selected from H and $C_1$-$C_6$ alkyl;
$R^6$, $R^7$, $R^8$, $R^9$, $R^{10}$ and $R^{11}$ are each independently selected from H; $SO_2R^{16}$; aryl optionally substituted by one or more Z groups; a $C_3$-$C_{10}$ carbocyclic group optionally substituted by one or more Z groups; $C_3$-$C_{14}$ heterocyclic group optionally substituted by one or more Z groups; $C_1$-$C_8$ alkyl optionally substituted by an aryl group which is optionally substituted by one or more Z groups, a $C_3$-$C_{10}$ carbocyclic group optionally substituted by one or more Z groups or a $C_3$-$C_{14}$ heterocyclic group optionally substituted by one or more Z groups; or is represented by the formula 2:

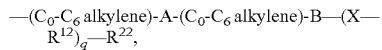

wherein the alkylene groups are optionally substituted by one or more Z groups;
or $R^6$ and $R^7$ together with the atoms to which they are attached form a 3- to 10-membered heterocyclic group, the heterocyclic group including one or more further heteroatoms selected from N, O and S, and the heterocyclic group being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2;
or $R^7$ and $R^8$ together with the carbon atom to which they are attached form a 3- to 10-membered carbocyclic or a 3- to 10-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2; or $R^9$ and $R^{10}$ together with the carbon atom to which they are attached form a 3- to 10-membered carbocyclic or a 3- to 10-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2; or $R^8$ and $R^9$ together with the carbon atoms to which they are attached form a 3- to 10-membered cycloalkyl or a 3- to 10-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2; or $R^{10}$ and $R^{11}$ together with the atoms to which they are attached form a 3- to 10-membered heterocyclic group, the heterocyclic group including one or more further heteroatoms selected from N, O and S, and the heterocyclic group being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2;

A is selected from a bond, $-NR^{13}(SO_2)-$, $-(SO_2)NR^{13}-$, $-(SO_2)-$, $-NR^{13}C(O)-$, $-C(O)NR^{13}-$, $-NR^{13}C(O)NR^{14}-$, $-NR^{13}C(O)O-$, $-NR^{13}-$, C(O)O, OC(O), C(O), O and S;

B is selected from a bond, $-(C_2$-$C_4$ alkenyl group)-, $-(C_2$-$C_4$ alkynyl group)-, $-NH-$, aryl, O-aryl, NH-aryl, a $C_3$-$C_{14}$ carbocyclic group and a 3- to 14-membered heterocyclic group, the heterocyclic group including one or more heteroatoms selected from N, O and S, wherein the aryl, carbocyclic and heterocyclic groups are each optionally substituted by one or more Z groups;

X is selected from a bond, $-NR^{15}(SO_2)-$, $-(SO_2)NR^{15}-$, $-(SO_2)-$, $-NR^{15}C(O)-$, $-C(O)NR^{15}-$, $-NR^{15}C(O)NR^{17}-$, $-NR^{15}C(O)O-$, $-NR^{15}-$, C(O)O, OC(O), C(O), O and S;

$R^{12}$ is selected from $C_1$-$C_8$ alkylene, $C_1$-$C_8$ alkenylene, $-C_3$-$C_8$ cycloalkyl-, $-C_1$-$C_8$ alkylene-$C_3$-$C_8$ cycloalkyl-, and -aryl-, wherein the alkylene, cycloalkyl and aryl groups are optionally substituted by one or more Z groups;

$R^{13}$, $R^{14}$, $R^{15}$ and $R^{17}$ are each independently selected from H and $C_1$-$C_6$ alkyl;

$R^{16}$ is selected from $C_1$-$C_8$ alkyl, aryl and a 3- to 14-membered heterocyclic group, the heterocyclic group including one or more heteroatoms selected from N, O and S;

Z is independently selected from OH, aryl, O-aryl, $C_7$-$C_{14}$ aralkyl, O—$C_7$-$C_{14}$ aralkyl, $C_1$-$C_6$ alkyl, $C_1$-$C_6$ alkoxy, $NR^{19}(SO_2)R^{21}$, $(SO_2)NR^{19}R^{21}$, $(SO_2)R^{20}$, $NR^{19}C(O)R^{20}$, $C(O)NR^{19}R^{20}$, $NR^{19}C(O)NR^{20}R^{18}$, $NR^{19}C(O)OR^{20}$, $NR^{19}R^{21}$, $C(O)OR^{19}$, $C(O)R^{19}$, $SR^{19}$, $OR^{19}$, oxo, CN, $NO_2$, and halogen, wherein the alkyl, alkoxy, aralkyl and aryl groups are each optionally substituted by one or more substituents selected from OH, halogen, $C_1$-$C_4$ haloalkyl and $C_1$-$C_4$ alkoxy;

$R^{18}$ and $R^{20}$ are each independently selected from H and $C_1$-$C_6$ alkyl;

$R^{19}$ and $R^{21}$ are each independently selected from H; $C_1$-$C_8$ alkyl; $C_3$-$C_8$ cycloalkyl;

$C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl and $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{20}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy;

$R^{22}$ is selected from H, halogen, $C_1$-$C_8$ alkyl, $C_1$-$C_8$ alkoxy, aryl, O-aryl, $S(O)_2$-aryl, $S(O)_2$—$C_1$-$C_6$ alkyl, $S(O)_2$ $NR^{23}R^{24}$, $NHS(O)_2NR^{23}R^{24}$, a $C_3$-$C_{14}$ carbocyclic group, a 3- to 14-membered heterocyclic group, the heterocyclic group including one or more heteroatoms selected from N, O and S, and O-(3- to 14-membered heterocyclic group, the heterocyclic group including one or more heteroatoms selected from N, O and S), wherein the alkyl, aryl, carbocyclic and heterocyclic groups are each optionally substituted by one or more Z groups;

$R^{23}$ and $R^{24}$ are each independently selected from H, $C_1$-$C_8$ alkyl and $C_3$-$C_8$ cycloalkyl; or $R^{23}$ and $R^{24}$ together with the nitrogen atom to which they are attached form a 5- to 10-membered heterocyclic group, optionally including one or more further heteroatoms selected from N, O and S, wherein the heterocyclic group is optionally substituted by one or more Z groups;

n is 0, 1 or 2;

o and p are each independently an integer from 0 to 6; and q is 0, 1, 2 or 3;

with the proviso that when n is 0, at least one of $R^6$, $R^7$, $R^8$, $R^9$, $R^{10}$ and $R^{11}$ is other than H.

In an embodiment of the invention, there is provided a compound according to the Formula Ia:

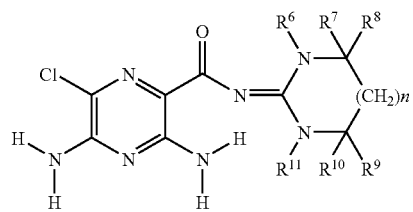

Ia wherein
$R^6$, $R^7$, $R^8$, $R^9$, $R^{10}$ and $R^{11}$ are each independently selected from H; $SO_2R^{16}$; aryl optionally substituted by one or more Z groups; a $C_3$-$C_{10}$ carbocyclic group optionally substituted by one or more Z groups; $C_3$-$C_{14}$ heterocyclic group optionally substituted by one or more Z groups; $C_1$-$C_8$ alkyl optionally substituted by an aryl group, a $C_3$-$C_{10}$ carbocyclic group optionally substituted by one or more Z groups or a $C_3$-$C_{14}$ heterocyclic group optionally substituted by one or more Z groups; or is represented by the formula 2a:

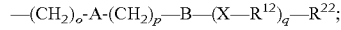

or $R^7$ and $R^8$ together with the carbon atom to which they are attached form a 3- to 7-membered carbocyclic or a 3- to 7-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2a; or $R^9$ and $R^{10}$ together with the carbon atom to which they are attached form a 3- to 7-membered carbocyclic or a 3- to 7-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2a;

or $R^8$ and $R^9$ together with the carbon atoms to which they are attached form a 3- to 7-membered cycloalkyl or a 3- to 7-membered heterocyclic group, the heterocyclic group including one or more heteroatoms selected from N, O and S, and the carbocyclic and heterocyclic groups being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2a;

A is selected from a bond, —$NR^{13}(SO_2)$—, —$(SO_2)NR^{13}$—, —$(SO_2)$—, —$NR^{13}C(O)$—, —$C(O)NR^{13}$—, —$NR^{13}C(O)NR^{14}$—, —$NR^{13}C(O)O$—, —$NR^{13}$—, C(O)O, OC(O), C(O), O and S;

B is selected from a bond, aryl, a $C_3$-$C_{14}$ carbocyclic group and a $C_3$-$C_{14}$ heterocyclic group, wherein the ring systems are optionally substituted by one or more Z groups;

X is selected from a bond, —$NR^{15}(SO_2)$—, —$(SO_2)NR^{15}$—, —$(SO_2)$—, —$NR^{15}C(O)$—, —$C(O)NR^{15}$—, —$NR^{15}C(O)NR^{17}$—, —$NR^{15}C(O)O$—, —$NR^{15}$—, C(O)O, OC(O), C(O), O and S;

$R^{12}$ is selected from H, $C_1$-$C_8$ alkyl, $C_3$-$C_8$ cycloalkyl, $C_1$-$C_8$ alkyl-$C_3$-$C_8$ cycloalkyl, $C_1$-$C_8$ alkyl-aryl and aryl, wherein the alkyl, cycloalkyl and aryl groups are optionally substituted by one or more Z groups;

$R^{13}$, $R^{14}$, $R^{15}$ and $R^{17}$ are each independently selected from H and $C_1$-$C_6$ alkyl;

$R^{16}$ is selected from $C_1$-$C_8$ alkyl, aryl and a 3- to 14-membered heterocyclic group;

Z is independently selected from OH, aryl, O-aryl, $C_7$-$C_{14}$ aralkyl, O—$C_7$-$C_{14}$ aralkyl, $C_1$-$C_6$ alkyl, $C_1$-$C_6$ alkoxy, $NR^{19}(SO_2)R^{21}$, $(SO_2)NR^{19}R^{21}$, $(SO_2)R^{20}$, $NR^{19}C(O)R^{20}$, $C(O)NR^{19}R^{20}$, $NR^{19}C(O)NR^{20}R^{18}$, $NR^{19}C(O)OR^{20}$, $NR^{19}R^{21}$, $C(O)OR^{19}$, $C(O)R^{19}$, $SR^{19}$, $OR^{19}$, oxo, CN, $NO_2$, and halogen, wherein the alkyl, alkoxy, aralkyl and aryl groups are each optionally substituted by one or more substituents selected from OH, halogen, $C_1$-$C_4$ haloalkyl and $C_1$-$C_4$ alkoxy;

$R^{18}$, $R^{19}$ and $R^{20}$ are each independently selected from H and $C_1$-$C_6$ alkyl;

$R^{21}$ is selected from $C_1$-$C_8$ alkyl, aryl and a 3- to 14-membered heterocyclic group;
$R^{22}$ is selected from H and $C_1$-$C_8$ alkyl;
n is 0, 1 or 2;
o and p are each independently an integer from 0 to 6; and
q is 0, 1, 2 or 3;
with the proviso that when n is 0, at least one of $R^6$, $R^7$, $R^8$, $R^9$, $R^{10}$ and $R^{11}$ is other than H.

In a further embodiment of the invention as defined anywhere above, $R^6$ is selected from H, $C_1$-$C_3$ alkyl and $(CH_2)_d$-phenyl, where the phenyl group is optionally substituted by $OR^{23}$;
$R^{23}$ is H or $C_1$-$C_6$ alkyl; and
d is an integer from 1 to 5 (optionally 2 to 4).

In a still further embodiment of the invention as defined anywhere above, $R^7$ is H or $C_1$-$C_6$; and
$R^8$ is selected from H, $C_1$-$C_6$ alkyl; $(CH_2)_e$phenyl, where the phenyl group is optionally substituted by one or more groups selected from halo and $OR^{24}$; $(CH_2)_fCOOR^{25}$; $(CH_2)_gOC_1$-$C_6$ alkyl, where the alkyl group is optionally substituted by 1 to 3 groups selected from OH, $C_1$-$C_3$ alkyl and phenyl; and $(CH_2)_hNHCO_2(CH_2)_i$phenyl;
$R^{24}$ is H or $C_1$-$C_6$ alkyl, where the alkyl group is optionally substituted by 1 to 3 groups selected from OH and $OC_1$-$C_3$ alkyl;
$R^{25}$ is H or $C_1$-$C_3$ alkyl;
e is 0, 1, 2, 3, 4 or 5 (optionally 0, 1, 2, 3 or 4);
f, g and h are each independently an integer from 1 to 4; and
i is 1 or 2;
or $R^7$ and $R^8$ together with the carbon atom to which they attached form a 5- or 6-membered non-aromatic carbocyclic ring system or a 5- or 6-membered non-aromatic heterocyclic ring system containing one or more heteroatoms selected from N, O and S, the ring systems being optionally substituted by one or more Z groups; $SO_2R^{16}$; $C_6$-$C_{15}$-aromatic carbocyclic group optionally substituted by one or more Z groups; a $C_3$-$C_{10}$ carbocyclic group; a $C_3$-$C_{14}$ heterocyclic group optionally substituted by one or more Z groups; or a group represented by the formula 2 or 2a. Suitably, the ring system defined by $R^7$, $R^8$ and the carbon to which they are attached is optionally substituted by $C_1$-$C_3$ alkyl, halo or benzyl.

Optionally, f is 2 or 3. Additionally or alternatively, g may be 2 or 3. Additionally or alternatively, h may be 2, 3 or 4. Additionally or alternatively, i may be 1. In the immediately preceding sub-definitions of f, g, h and i, each sub-definition may be combined with more other sub-definitions or they may be combined with the definitions for the relevant variables given above.

In a yet further embodiment of the invention as defined anywhere above, $R^9$ is H, $C_1$-$C_6$ alkyl or phenyl;
or $R^8$ and $R^9$ together with the carbon atoms to which they attached form a 5-, 6- or 7-membered non-aromatic carbocyclic ring system or a 5-, 6- or 7-membered non-aromatic heterocyclic ring system containing one or more heteroatoms selected from N, O and S, the ring systems being optionally substituted by $C_1$-$C_3$ alkyl, halo or benzyl.

In a further embodiment of the invention as defined anywhere above, $R^{11}$ is H, $SO_2C_1$-$C_6$ alkyl or $SO_2$phenyl.

In a further embodiment of the invention as defined anywhere above, $R^6$ and $R^{11}$ are both H.

A further embodiment of the invention provides a compound according to the formula 1b

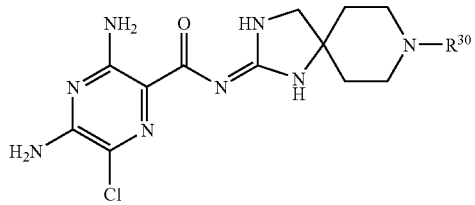

or the formula 1c

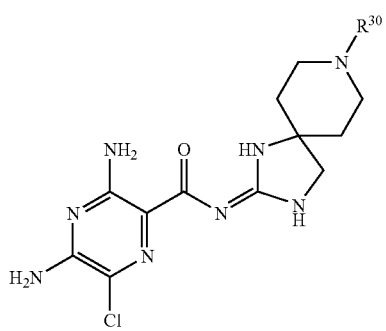

wherein $R^{30}$ is -A-($C_0$-$C_6$ alkylene)-B—$(X—R^{12})_q$—$R^{22}$ and A, B, X, $R^{12}$, q and $R^{22}$ are as defined anywhere herein.

A further aspect of the invention provides a compound of Formula 2

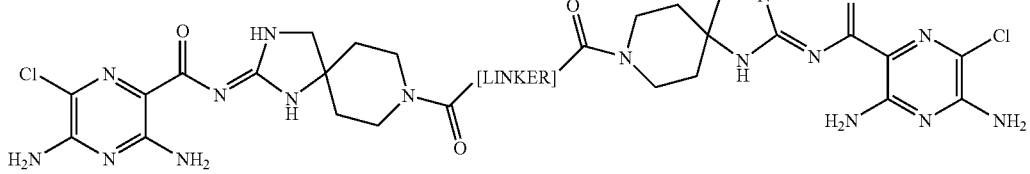

wherein [LINKER] is selected from $C_1$-$C_6$ alkylene, $C_2$-$C_6$ alkenylene, $C_2$-$C_6$ alkynylene, a 5- to 10-membered carbocyclic group, aryl, and a 5- to 10-membered heterocyclic group containing one or more heteroatoms selected from N, O and S, the ring systems being optionally substituted by one or more $Z^1$ groups; and
$Z^1$ is independently selected from OH, aryl, O-aryl, benzyl, O-benzyl, $C_1$-$C_6$ alkyl optionally substituted by one or more OH groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{19}(SO_2)R^{21}$, $(SO_2)NR^{19}R^{20}$, $(SO_2)R^{20}$, $NR^{19}C(O)R^{20}$, $C(O)NR^{19}R^{20}$, $NR^{19}C(O)NR^{20}R^{18}$, $NR^{19}C(O)OR^{20}$, $NR^{19}R^{21}$, $C(O)OR^{19}$, $C(O)R^{19}$, $SR^{19}$, $OR^{19}$, oxo, CN, $NO_2$, and halogen, wherein $R^{18}$, $R^{19}$, $R^{20}$ and $R^{21}$ are all as defined anywhere herein.

The skilled person will appreciate that the compounds of Formula 2 are dimeric forms of the compounds of formula 1b or 1c.

In a yet further embodiment of the invention as defined anywhere above, there is provided a compound according to Formula I selected from:

1

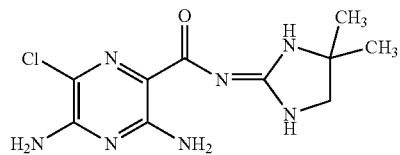

2

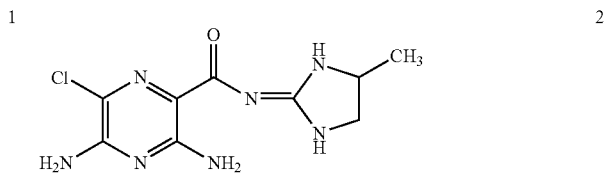

3

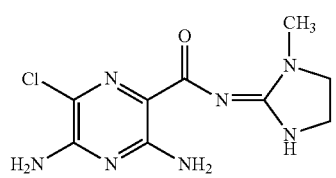

4

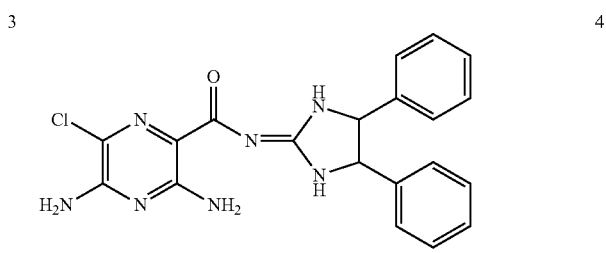

5

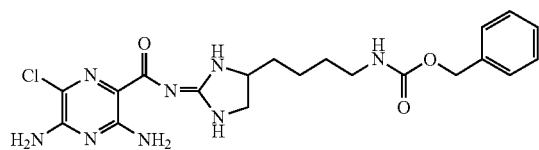

6

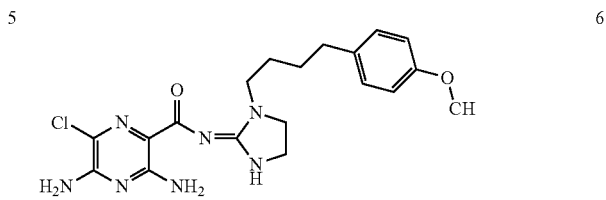

7

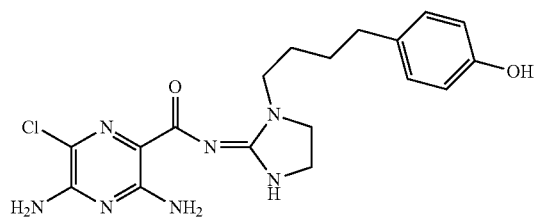

8

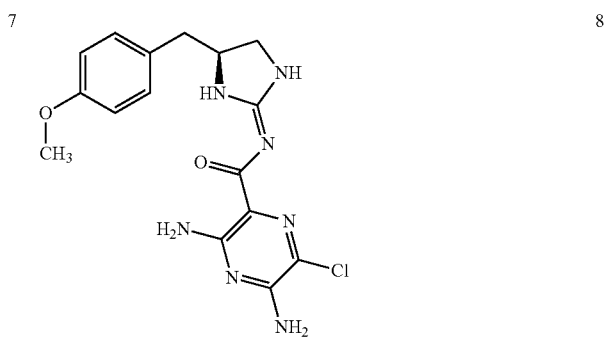

9

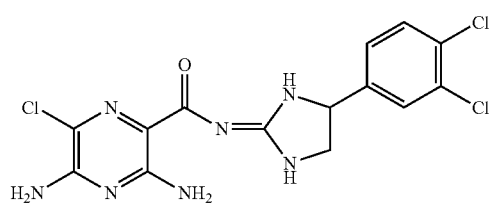

10

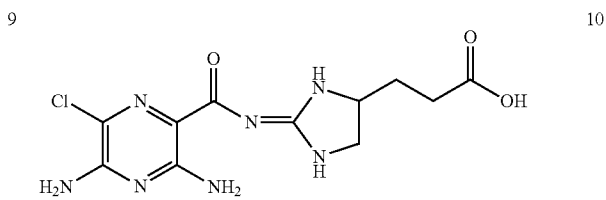

11

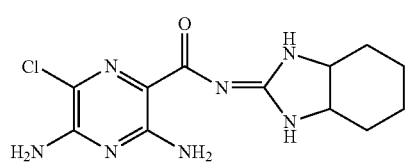

12

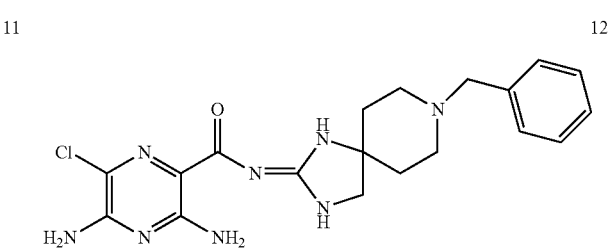

-continued
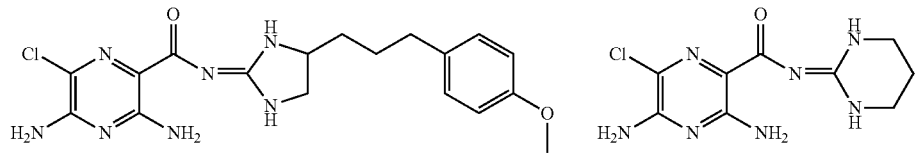
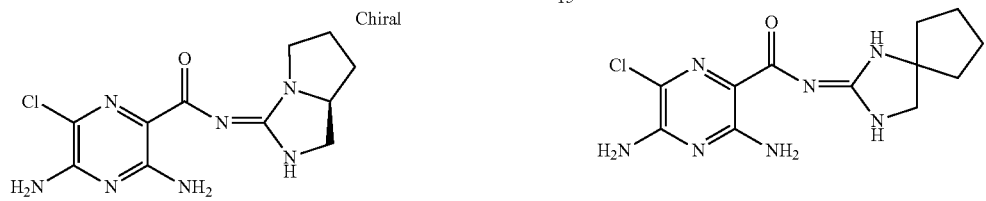
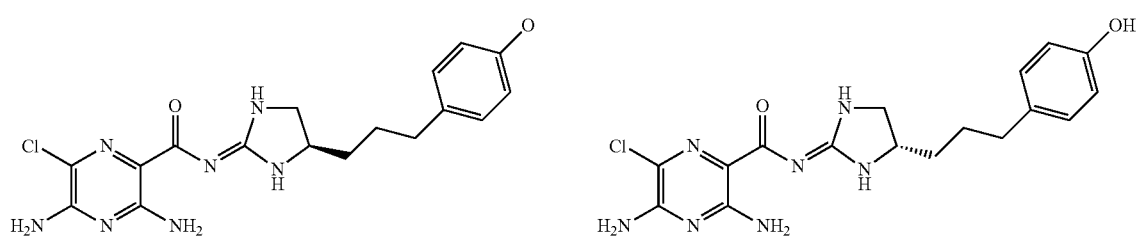
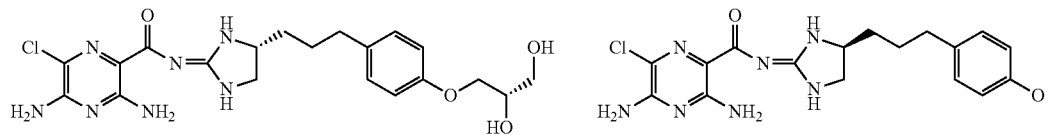
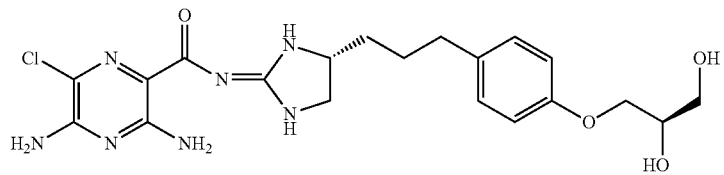
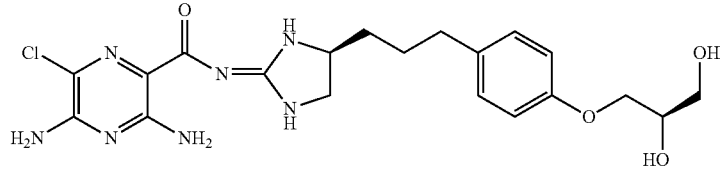
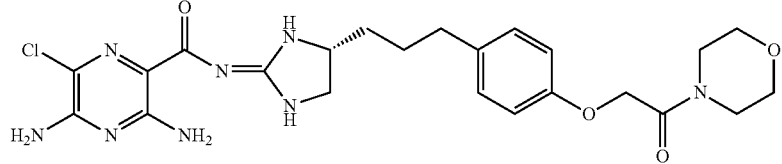
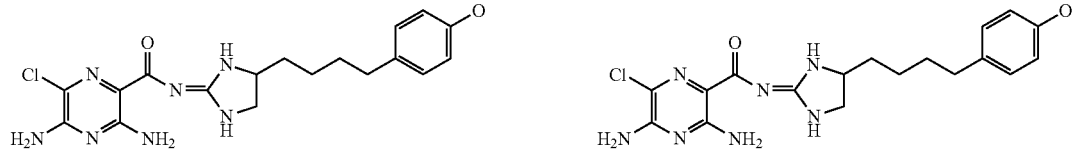

26
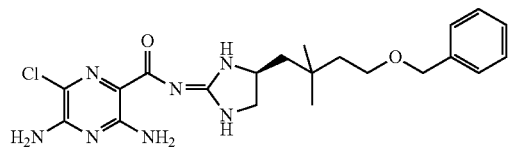
27
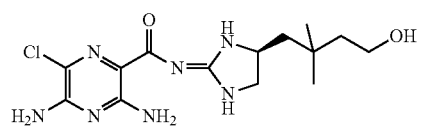
28
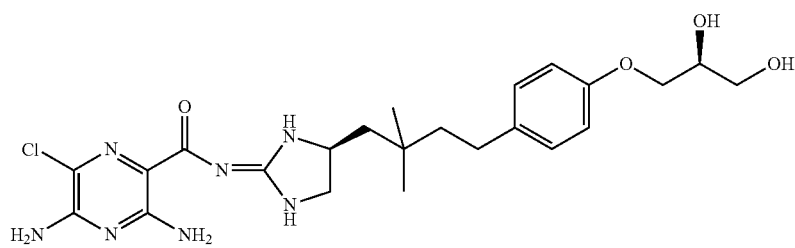
29
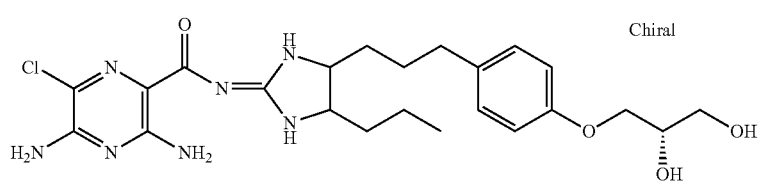
30
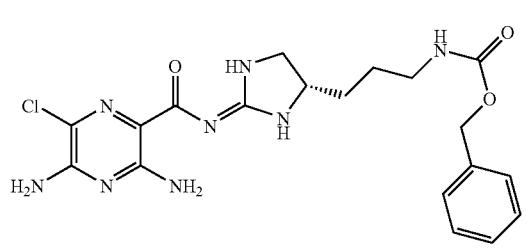
31
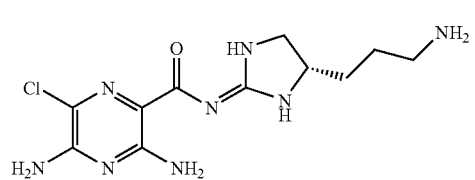
32
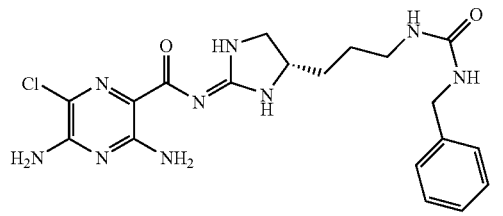
33
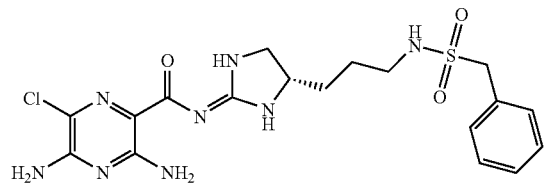
34
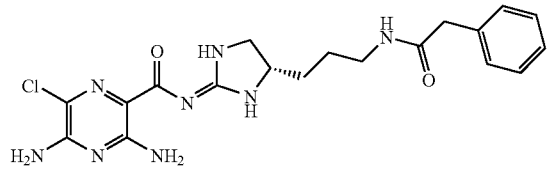
35
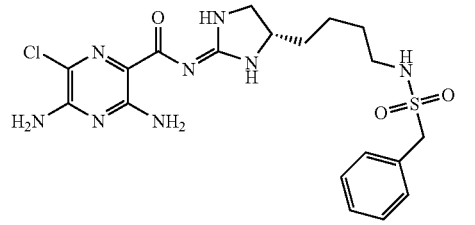
36
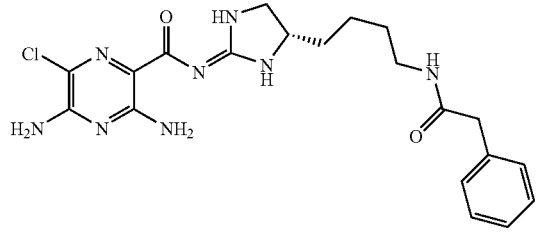
37
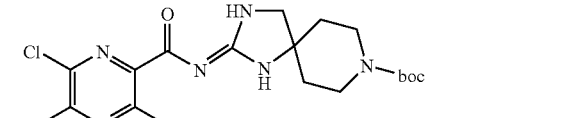

38
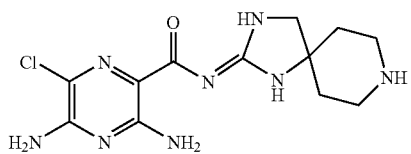
39
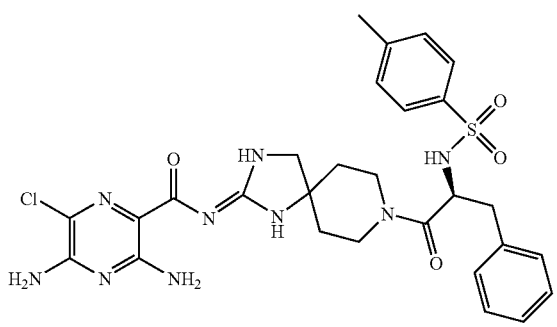
40
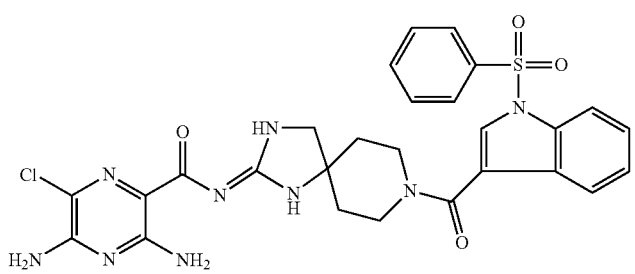
41
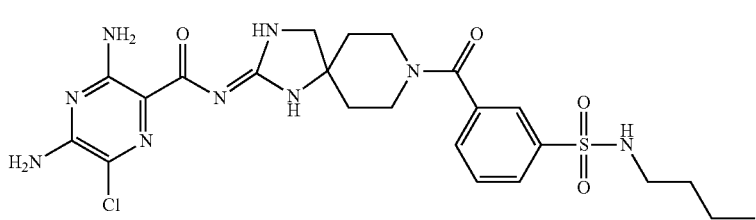
42
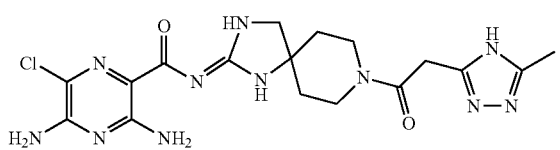
43
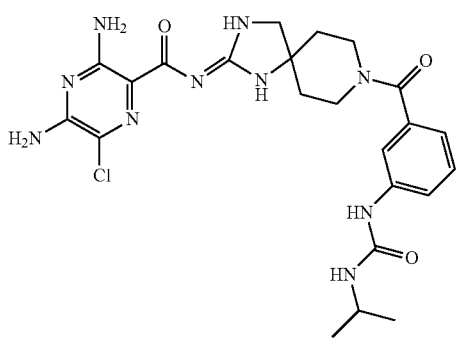
44
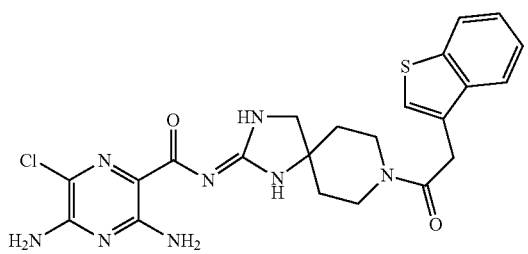
45
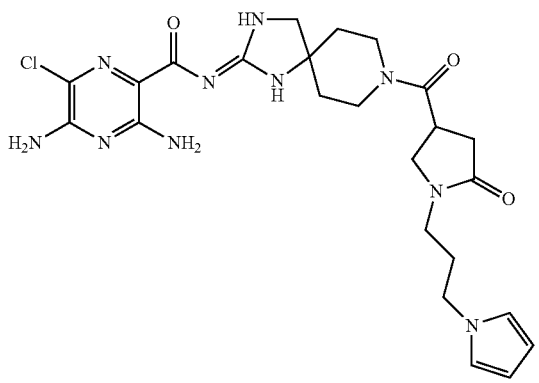

46
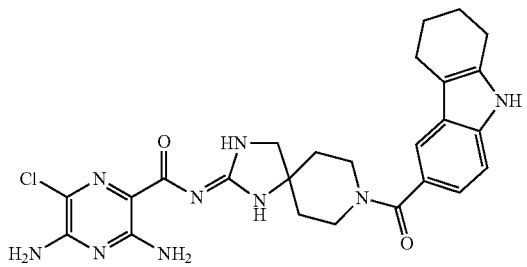
47
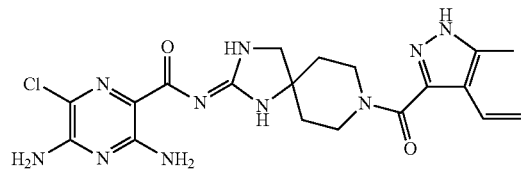
48
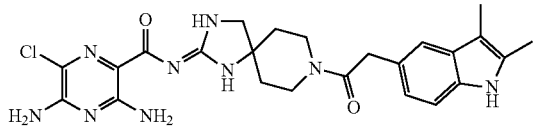
49
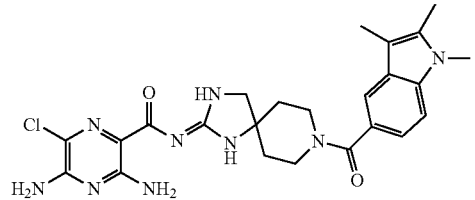
50
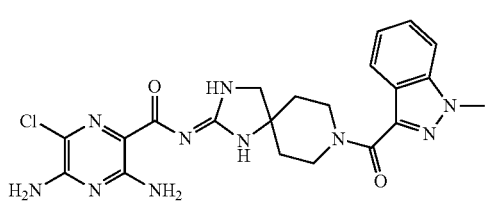
51
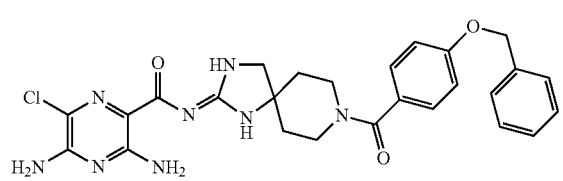
52
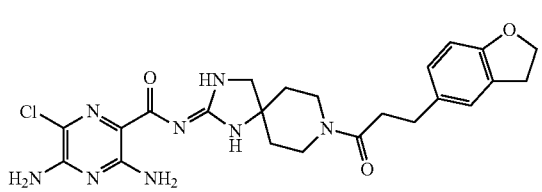
53
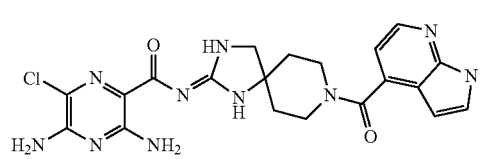
54
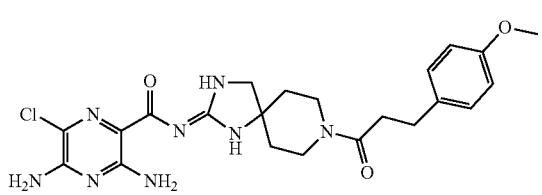
55
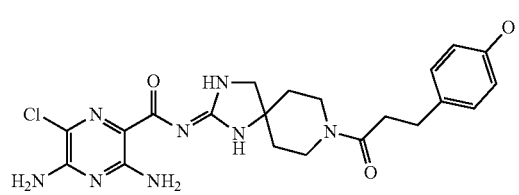
56
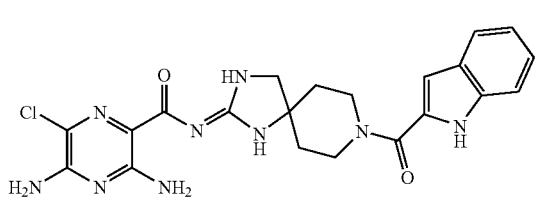
57
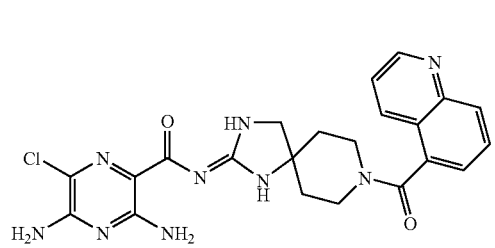
58
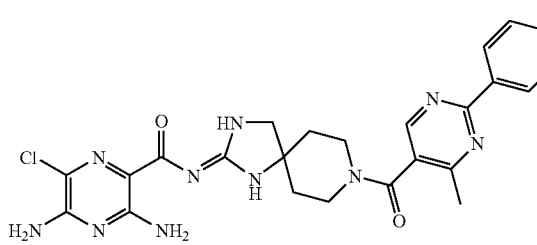
59
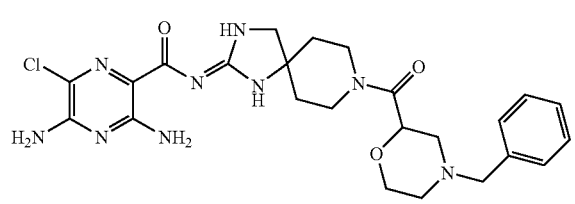

-continued
60
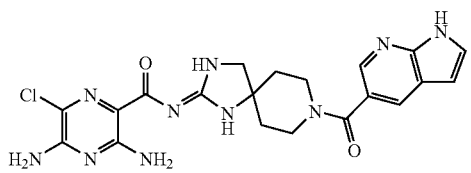
61
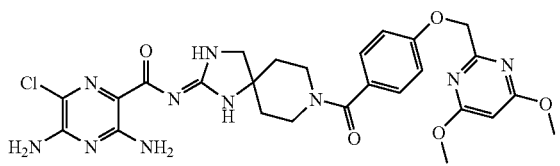
62
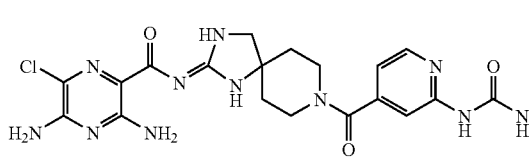
63
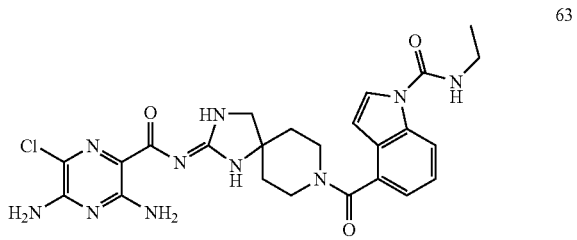
64
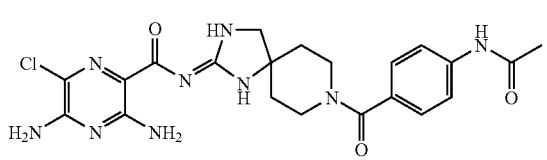
65
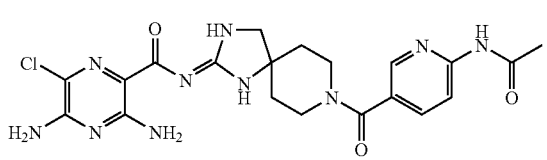
66
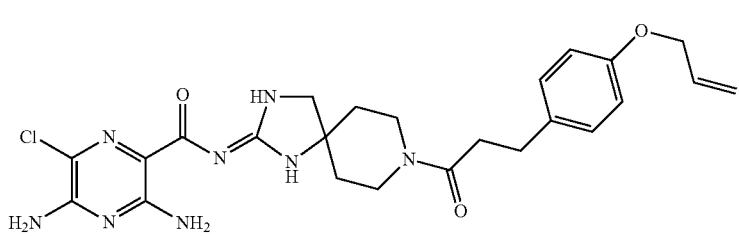
67
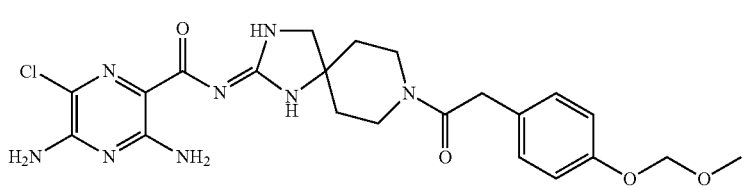
68
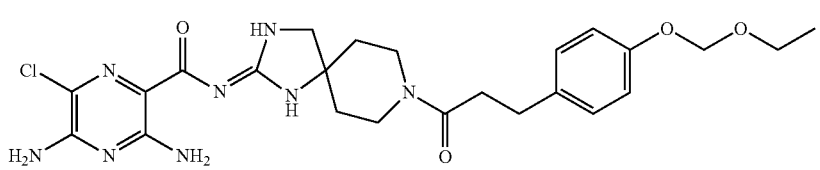
69
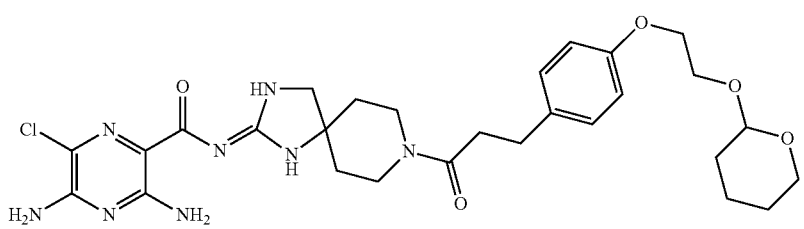

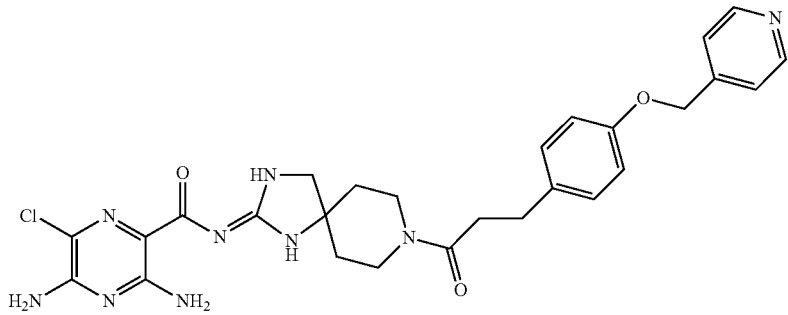
70
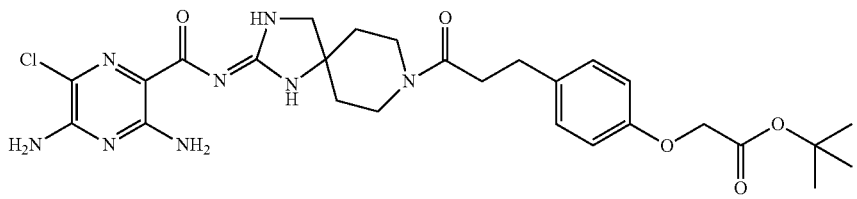
71
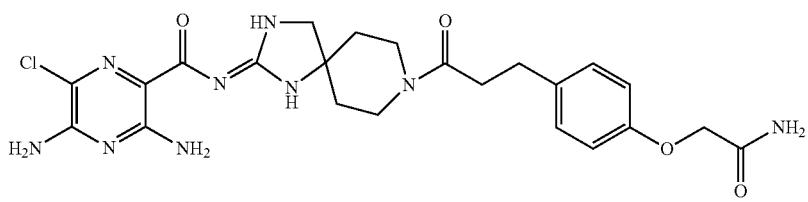
72
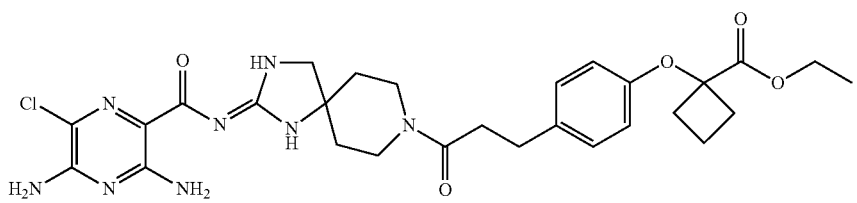
73
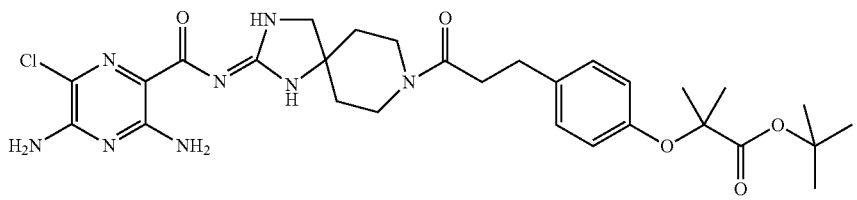
74
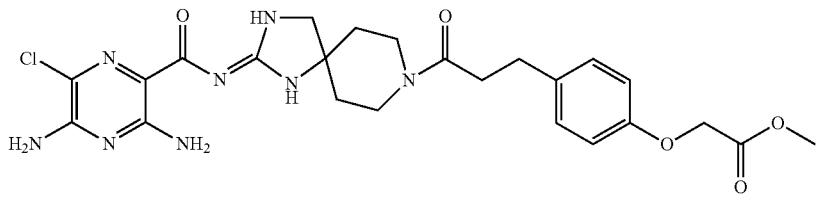
75
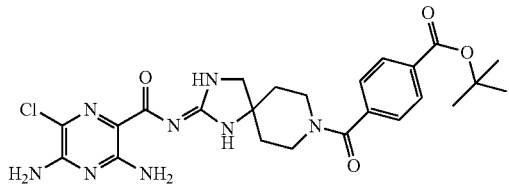
76
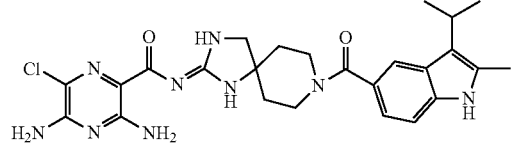
77

-continued
78
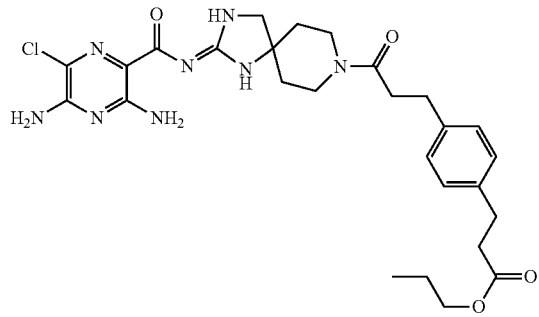
79
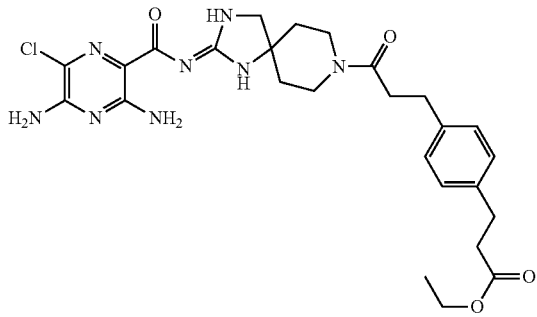
80
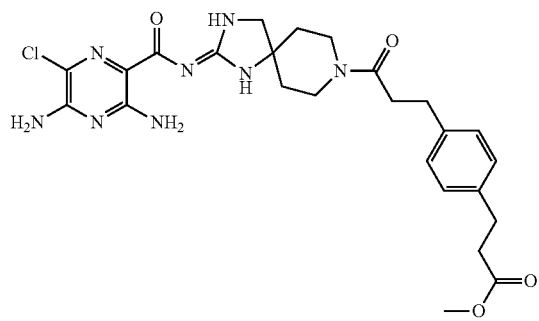
81
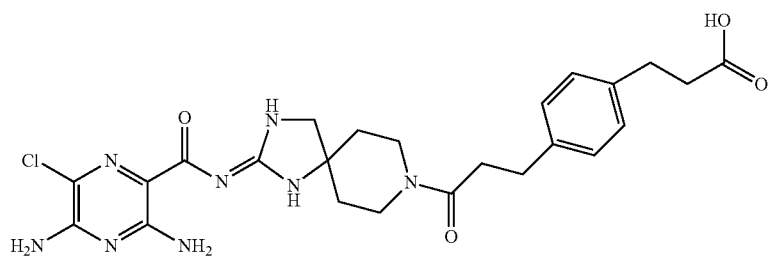
82
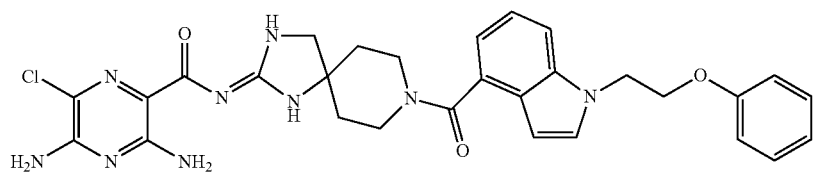
83
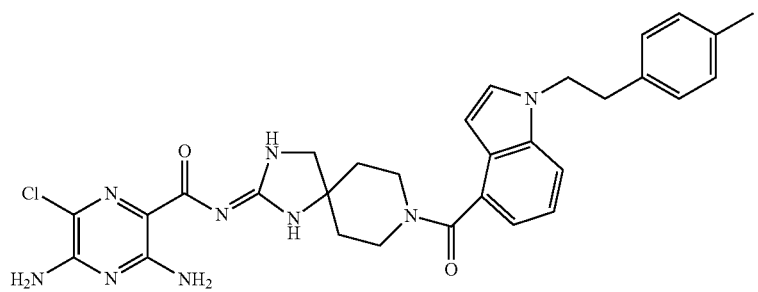
84
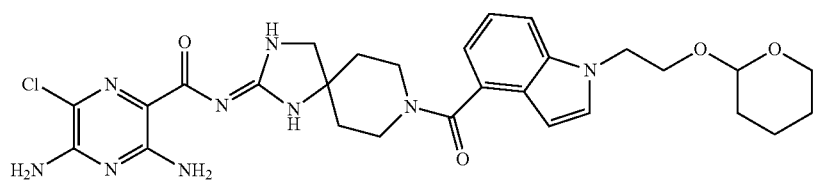

85
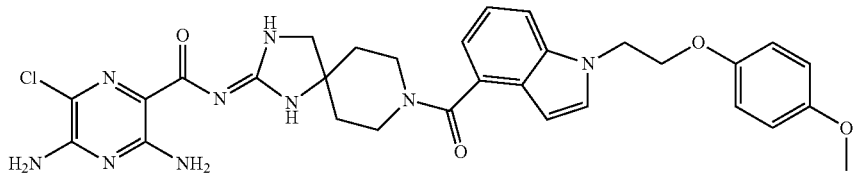
86
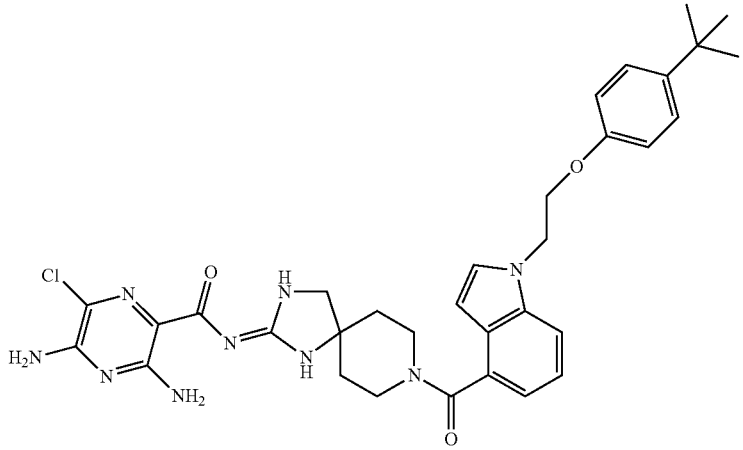
87
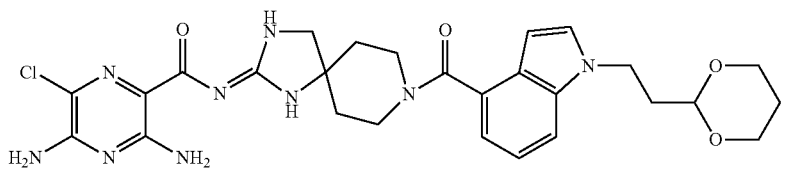
88
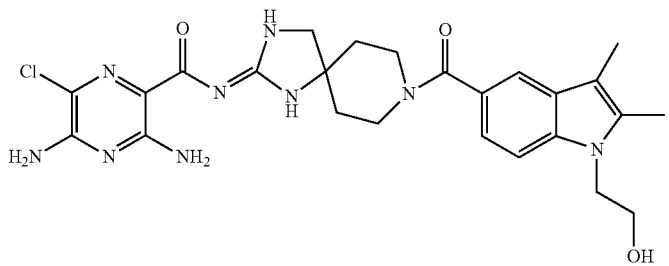
89
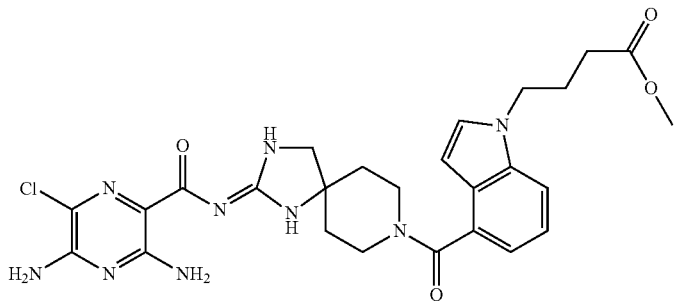
90
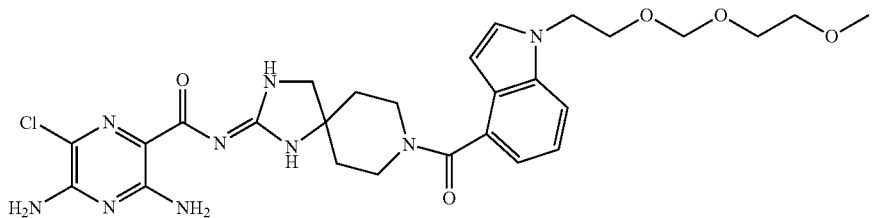

-continued
91
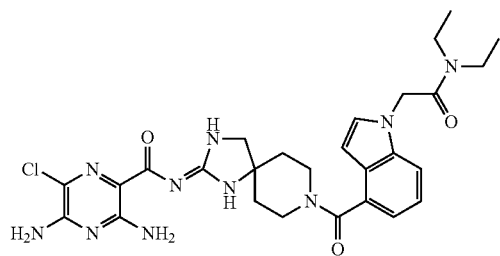
92
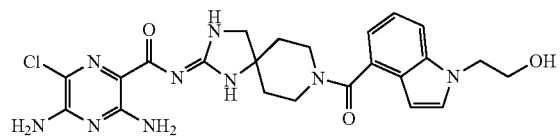
93
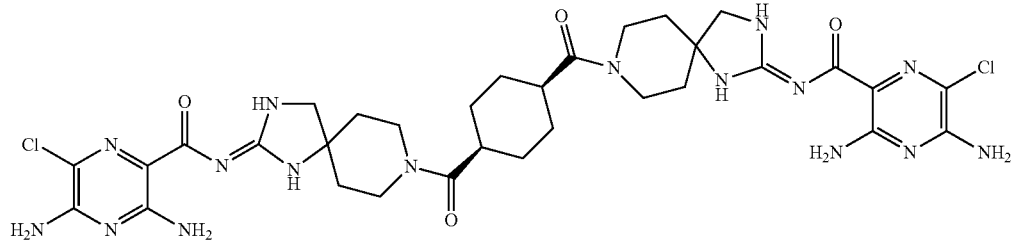
94
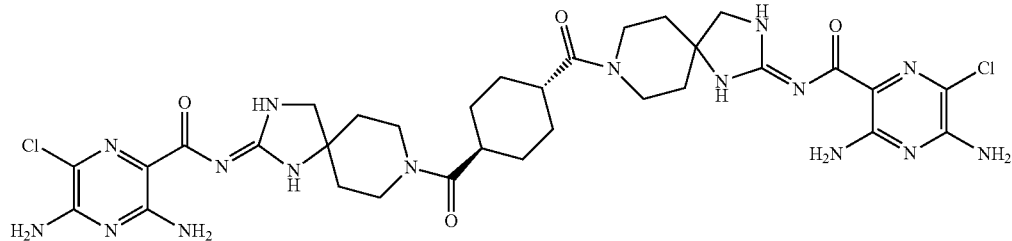
95
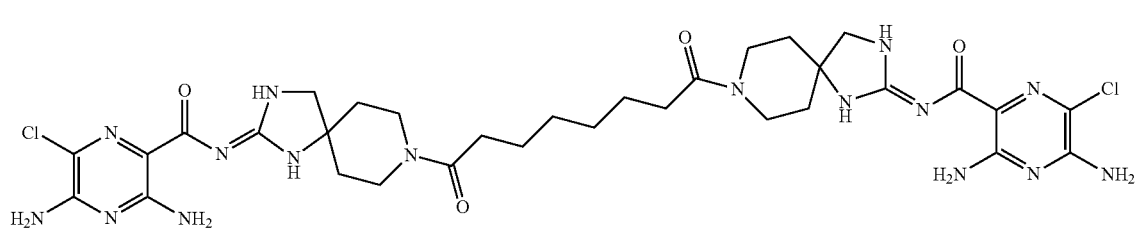
96
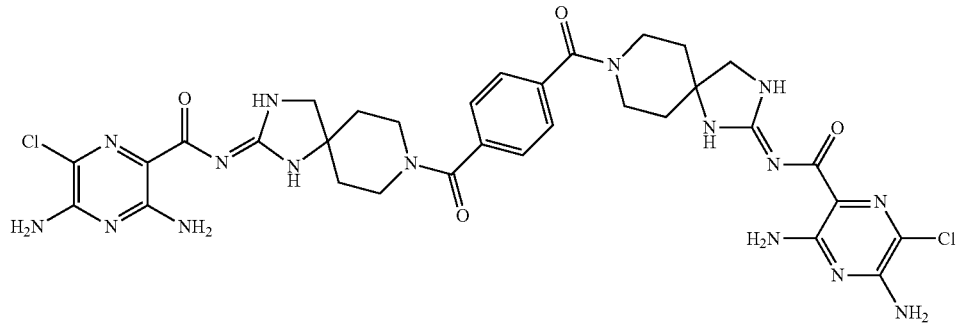
97
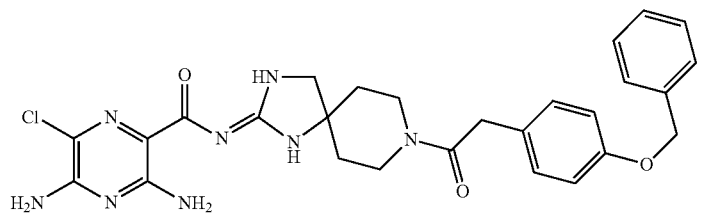

98
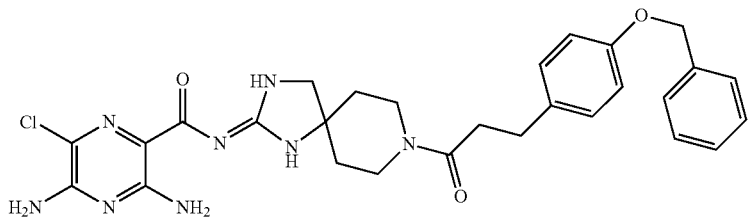
99
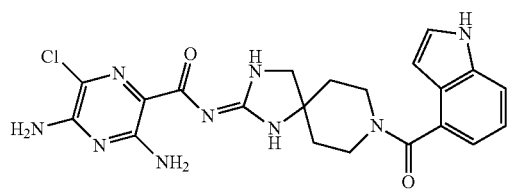
100
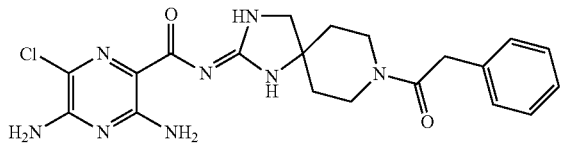
101
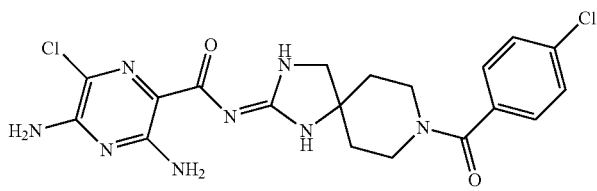
102
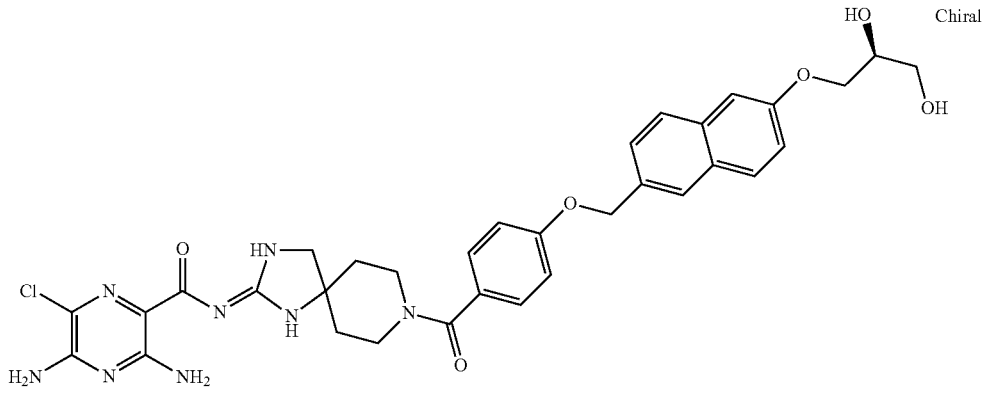
103
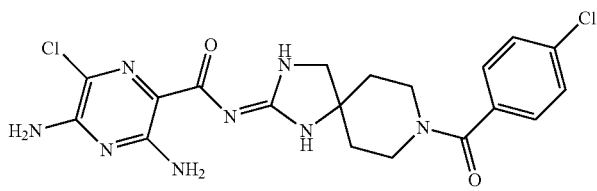
104
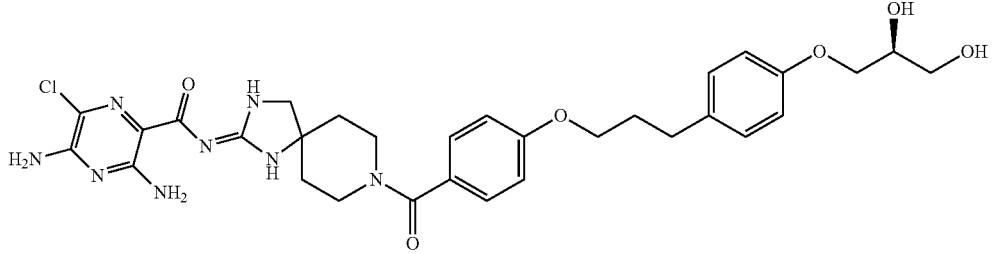
105
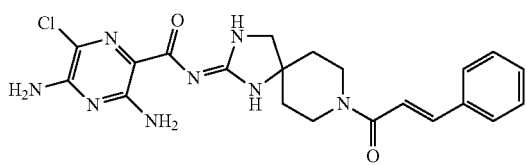
106
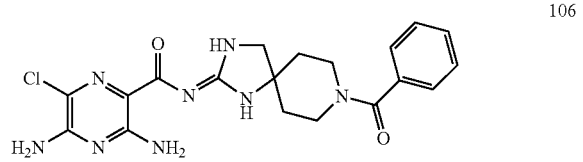

-continued
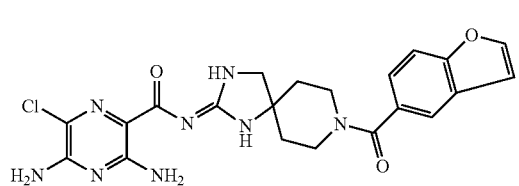
107
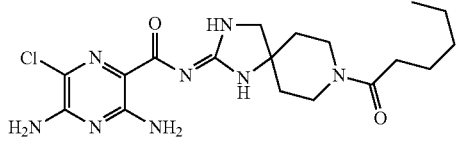
108
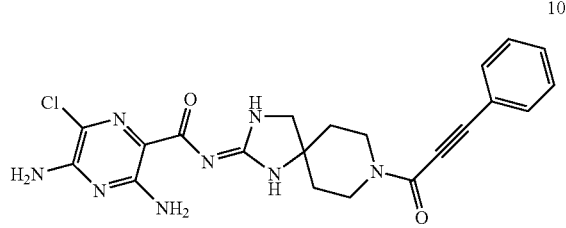
109
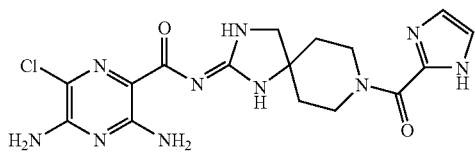
110
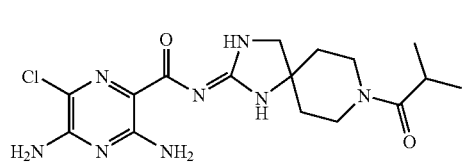
111
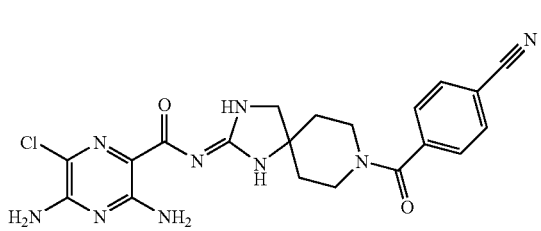
112
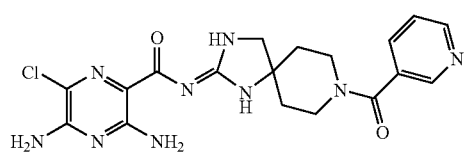
113
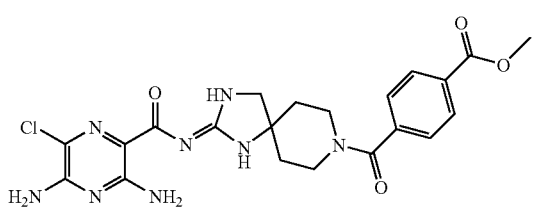
114
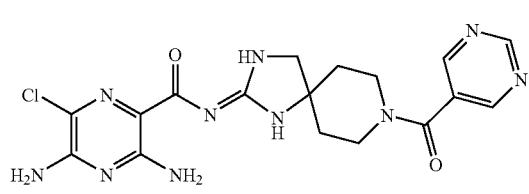
115
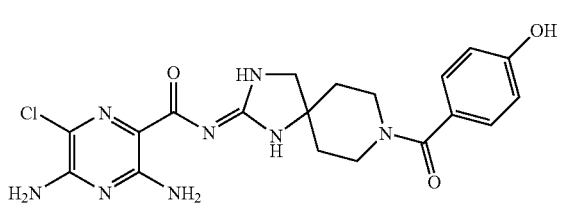
116
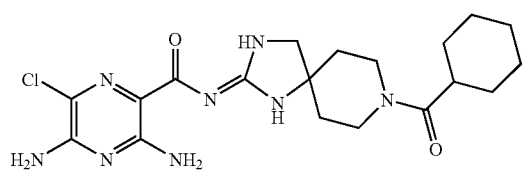
117
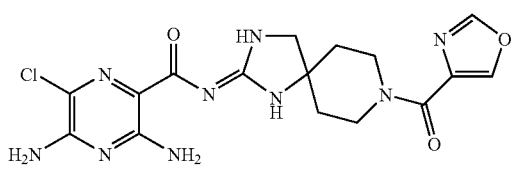
118
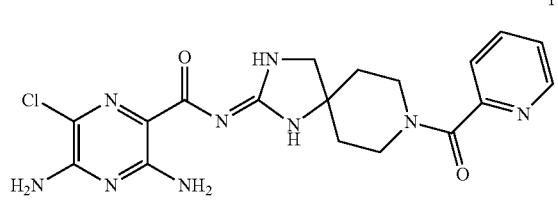
119
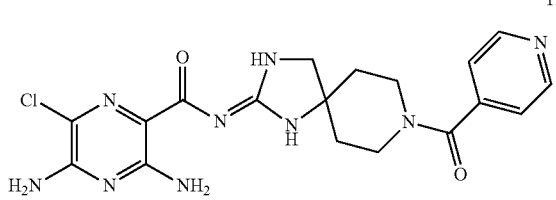
120

-continued
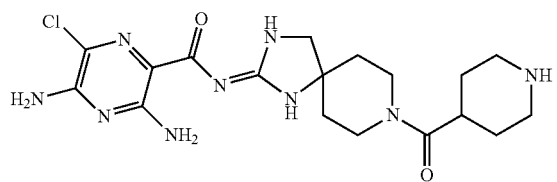
121
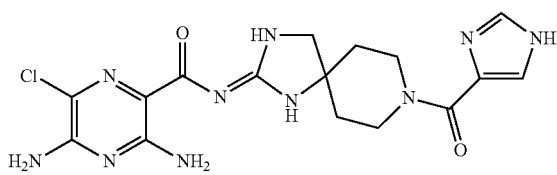
122
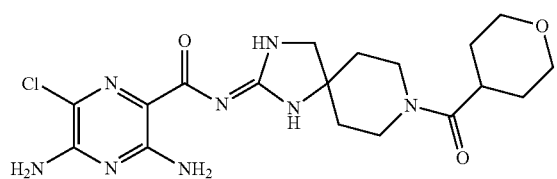
123
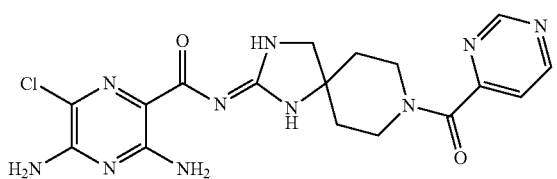
124
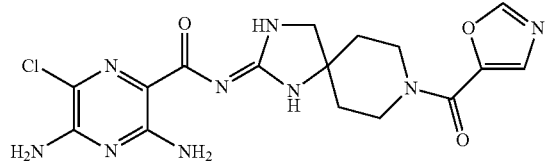
125
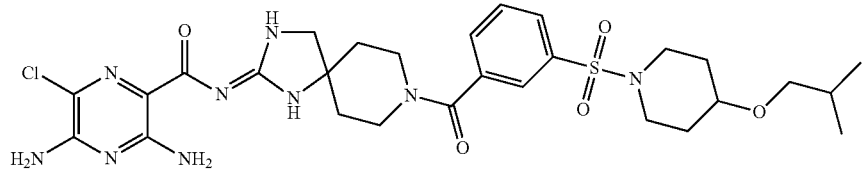
126
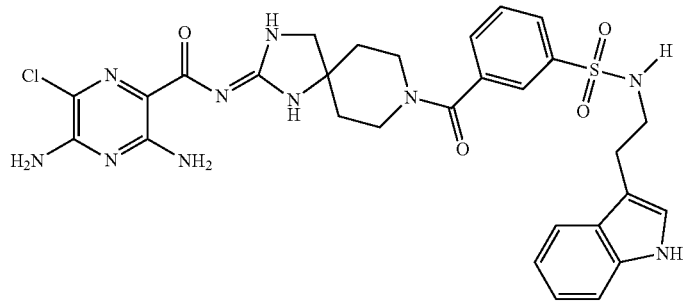
127
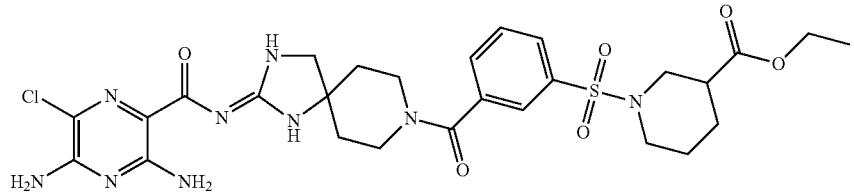
128
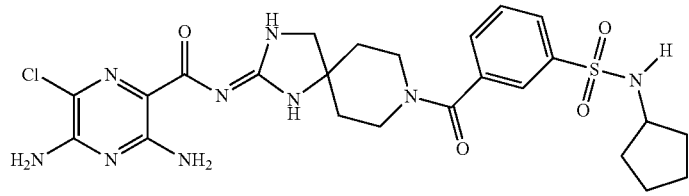
129

130
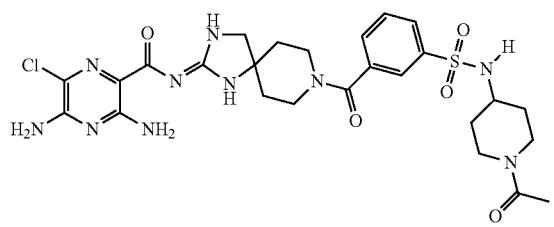
131
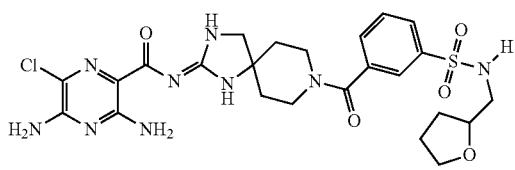
132
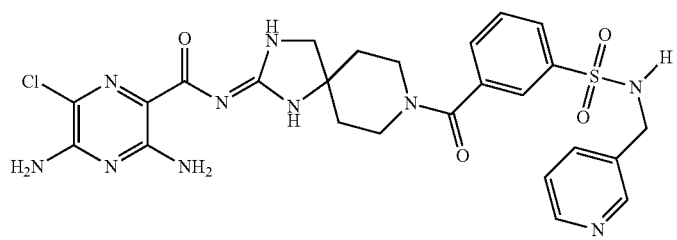
133
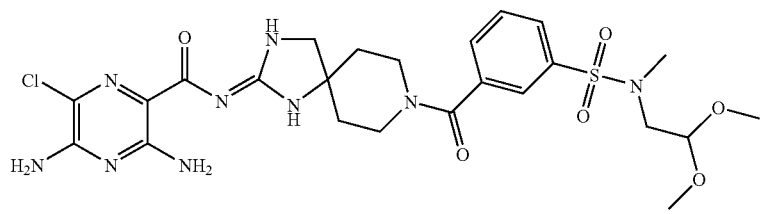
134
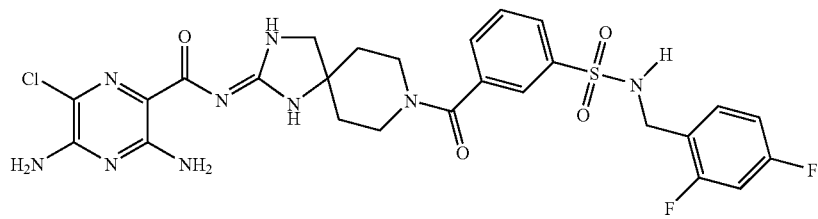
135
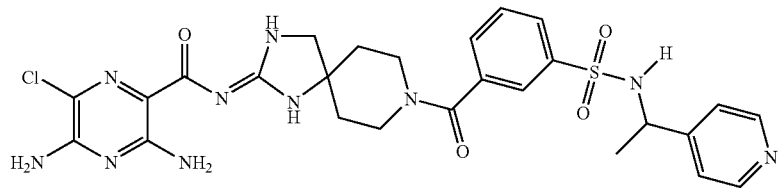
136
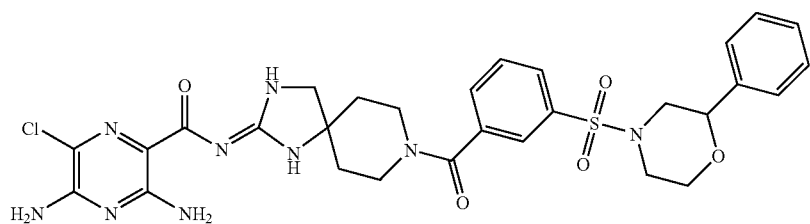

-continued
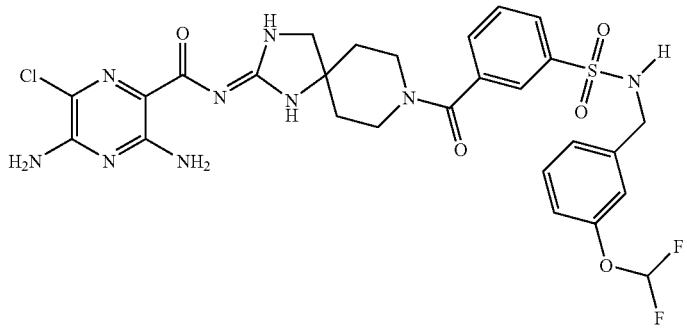
137
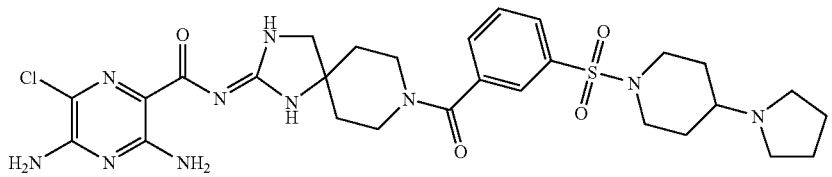
138
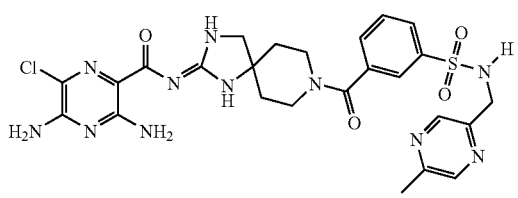
139
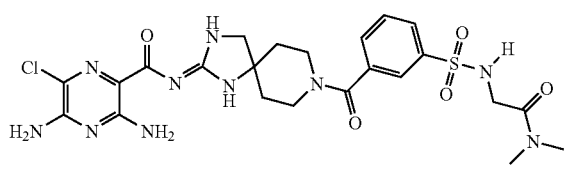
140
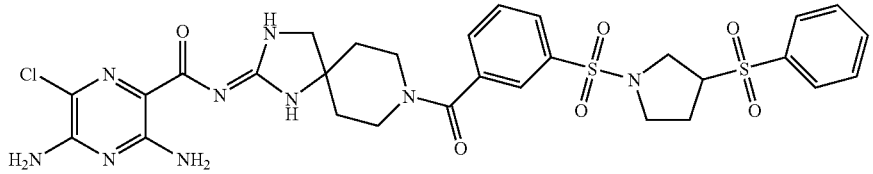
141
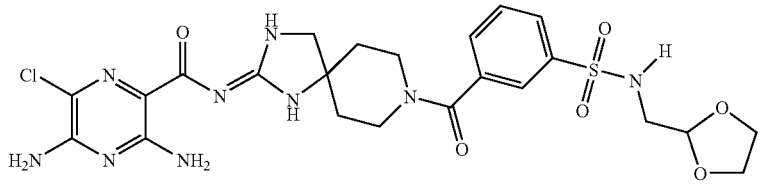
142
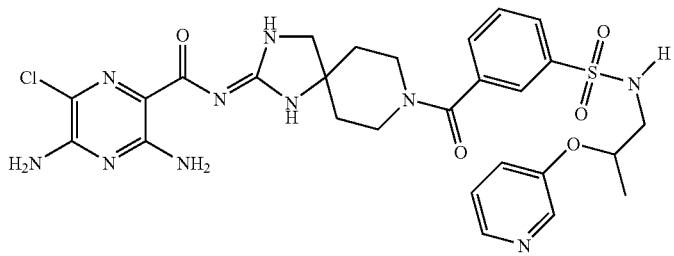
143

144
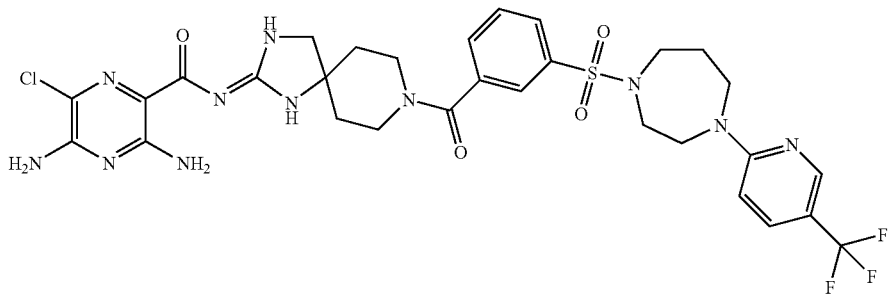
145
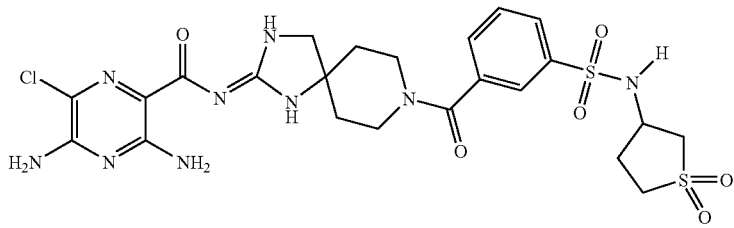
146
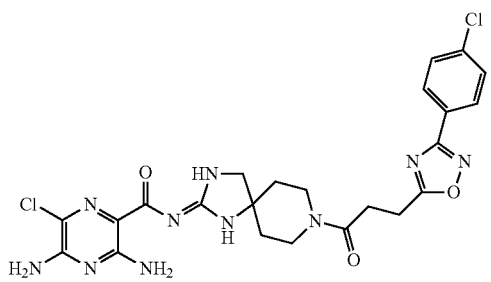
147
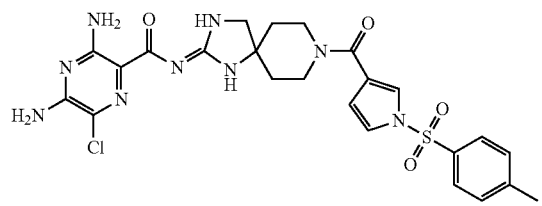
148
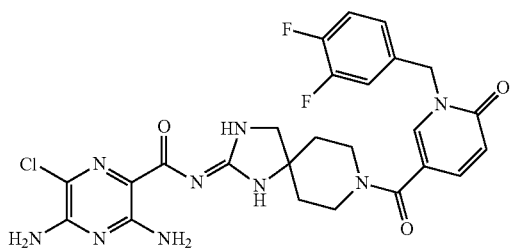
149
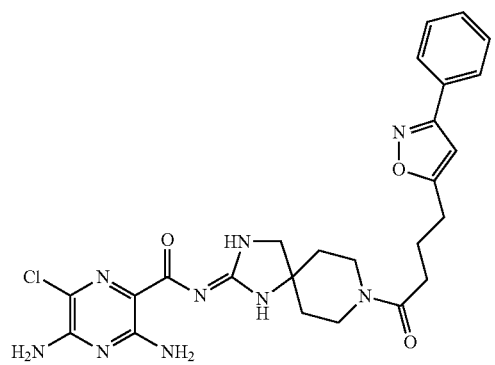
150
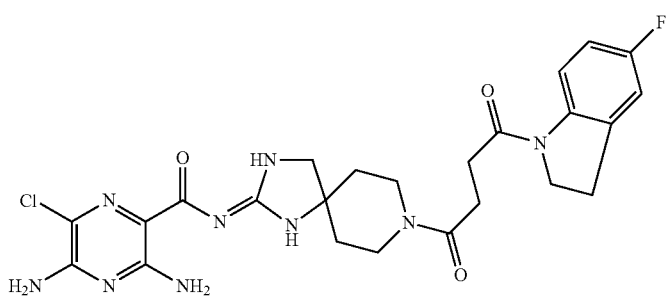

151
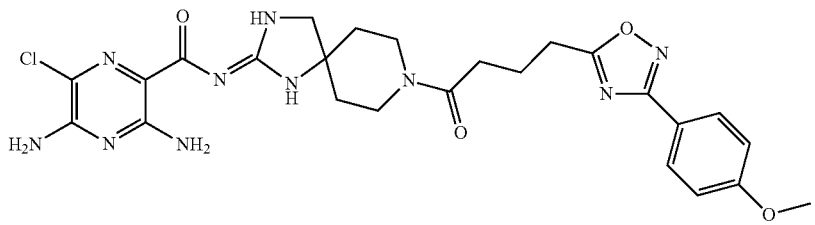
152
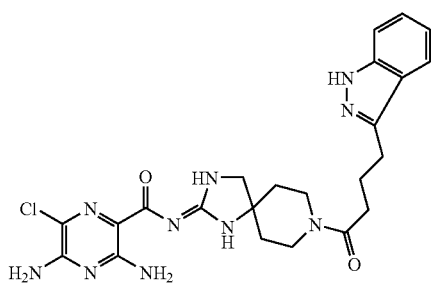
153
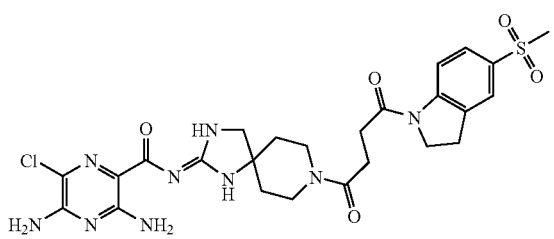
154
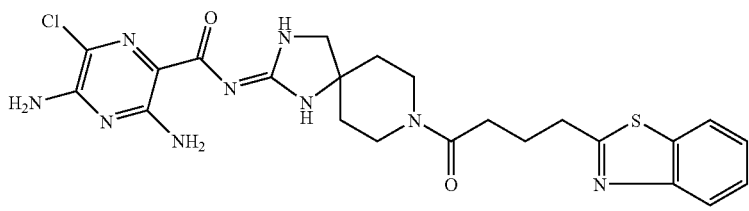
155
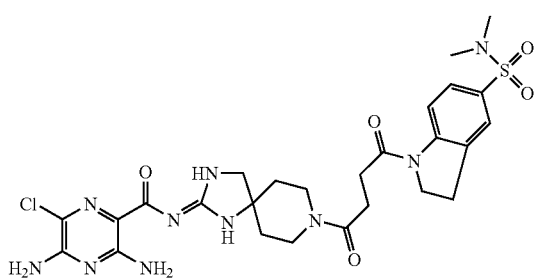
156
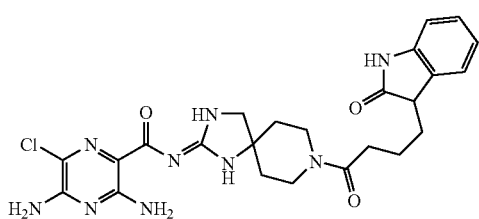
157
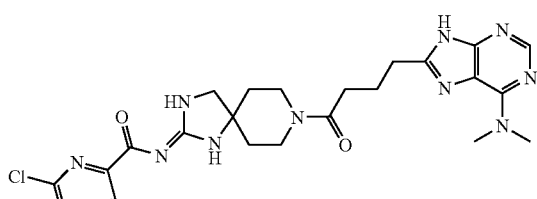
158
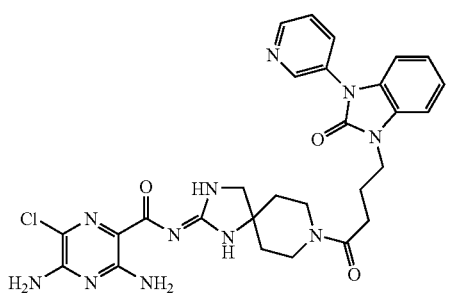

159
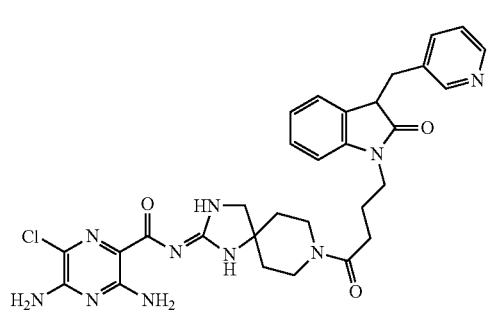
160
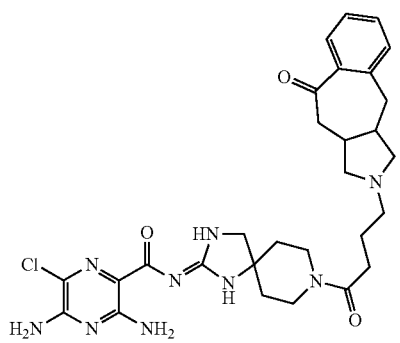
161
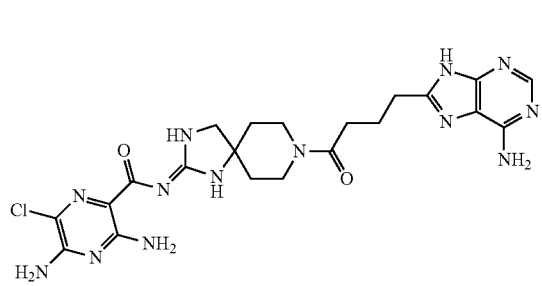
162
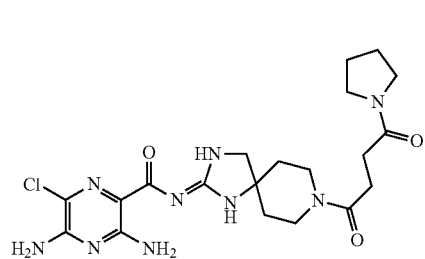
163
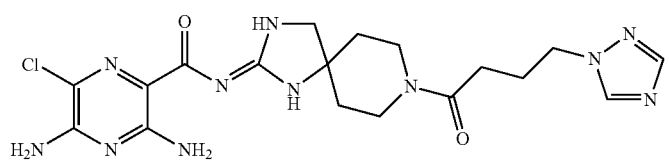
164
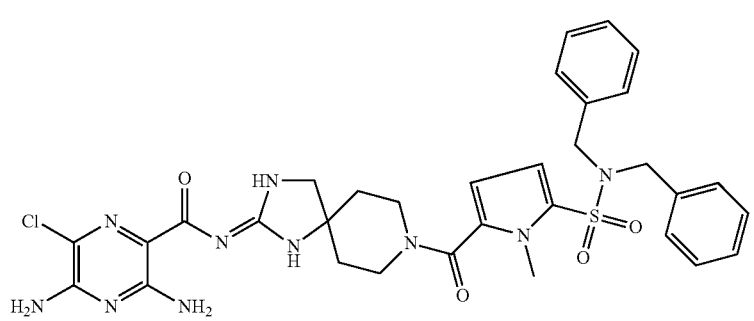

-continued
165
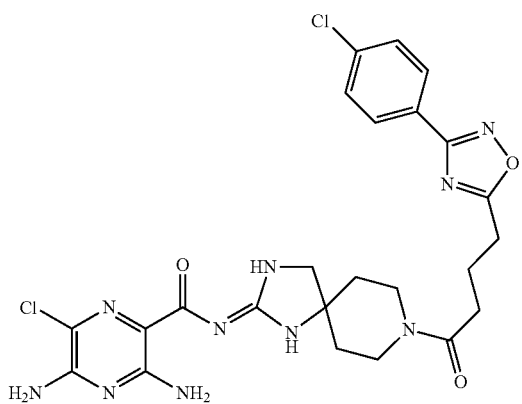
166
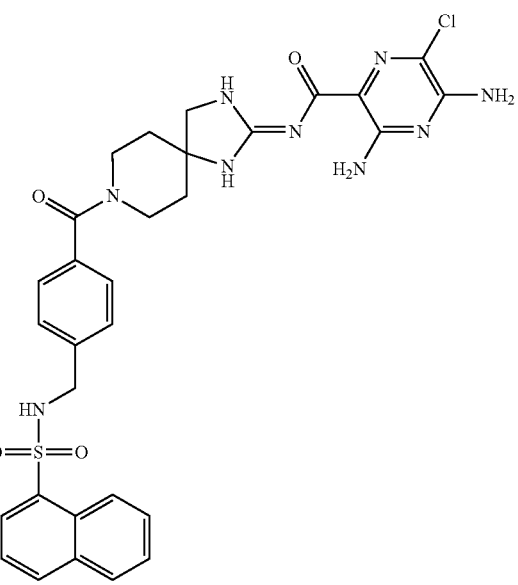
167
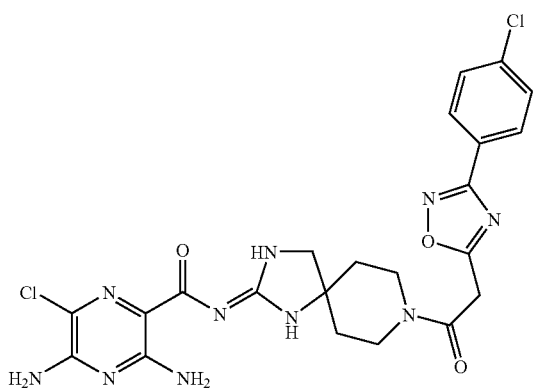
168
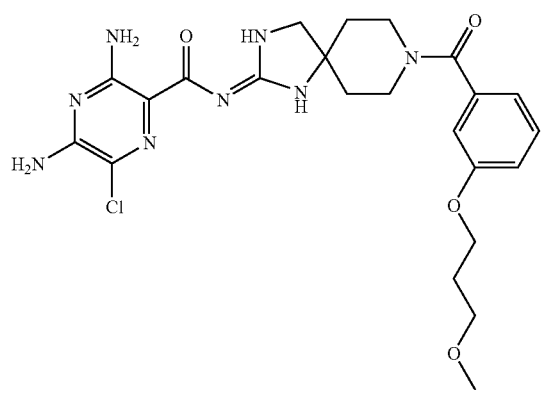
169
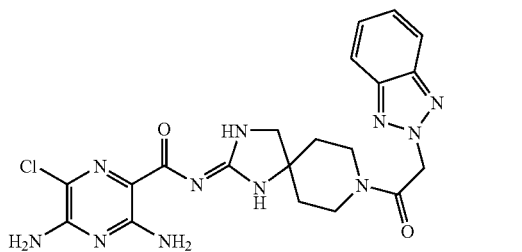
170
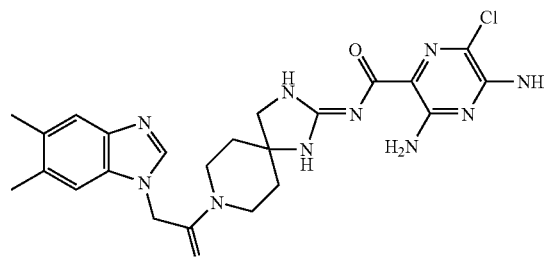
171
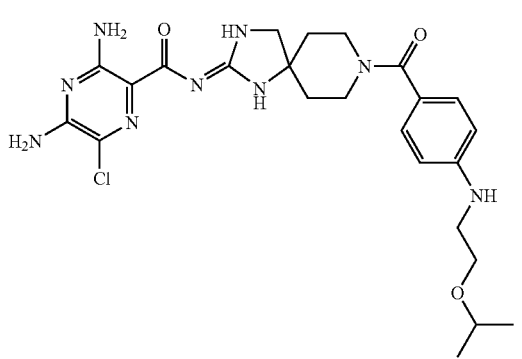
172
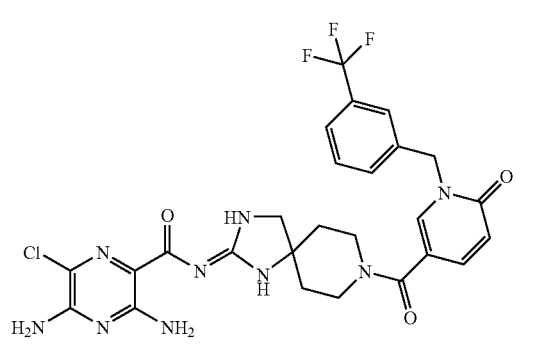

173 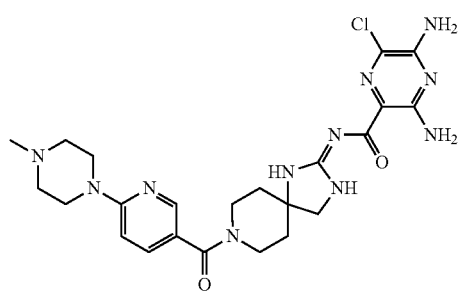
174 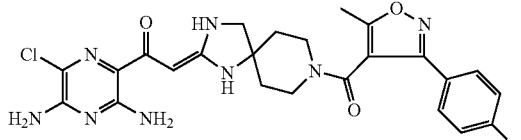
175 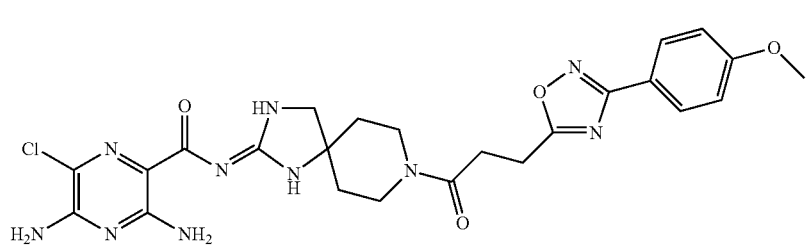
176 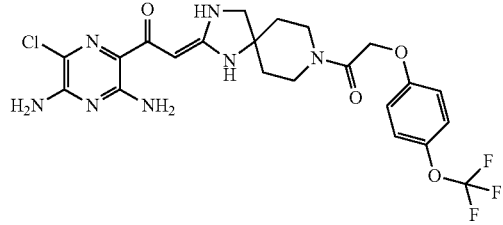
177 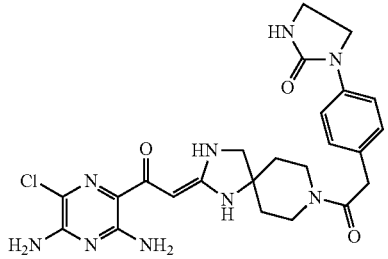
178 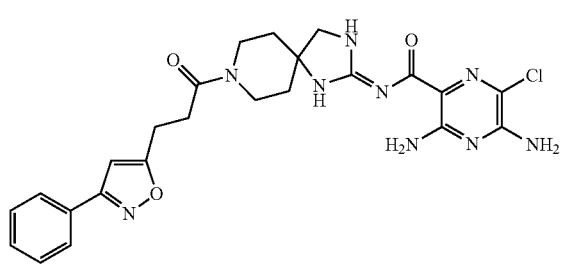
179 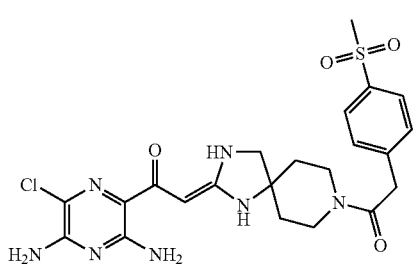
180 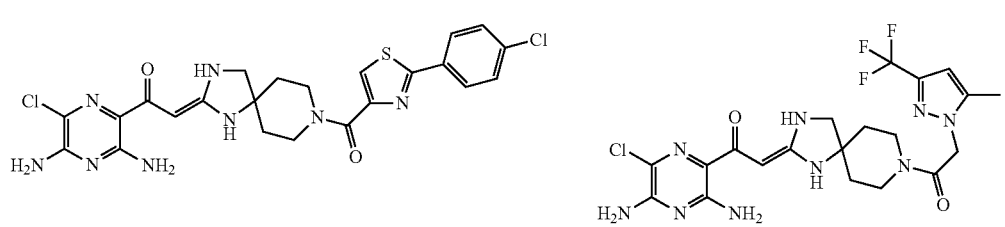
181 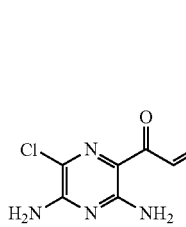
182 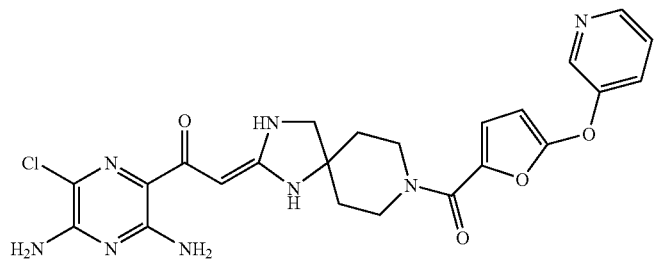

183
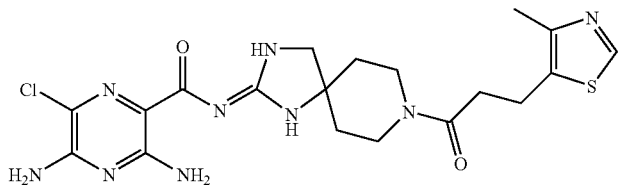
184
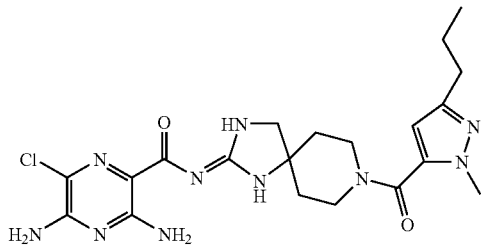
185
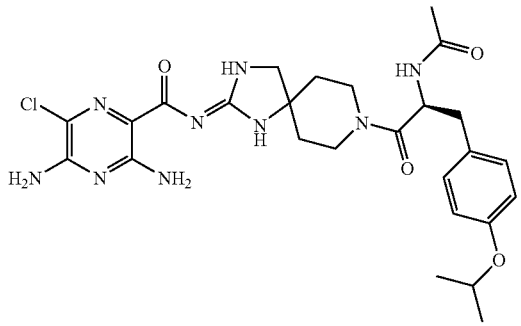
186
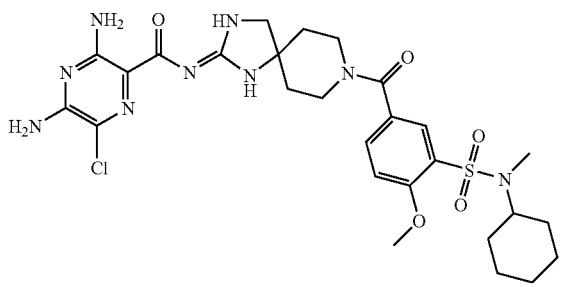
187
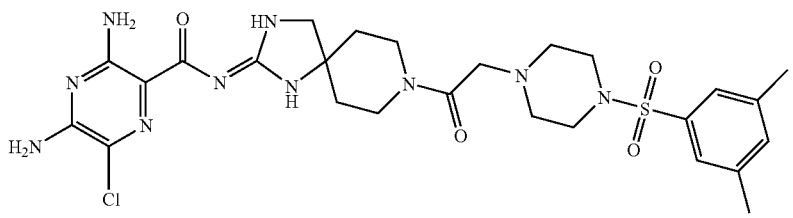
188
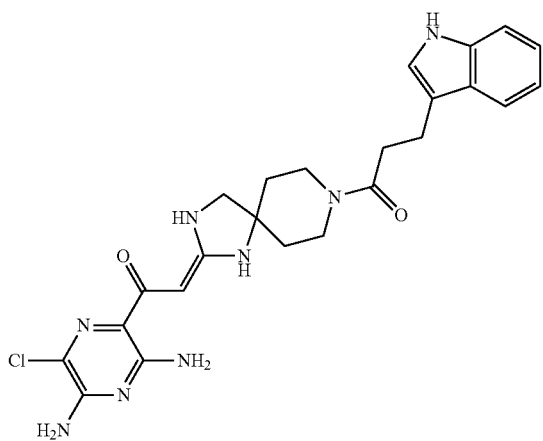

-continued
189
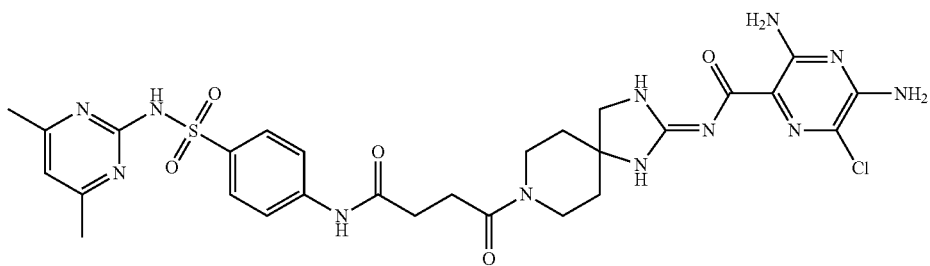
190
Chiral
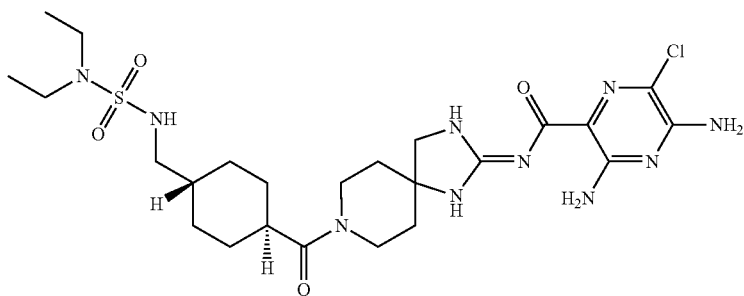
191
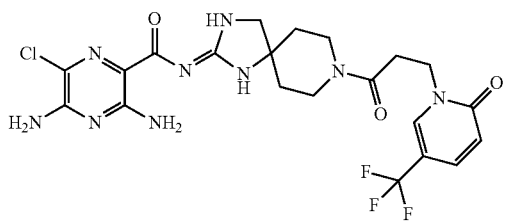
192
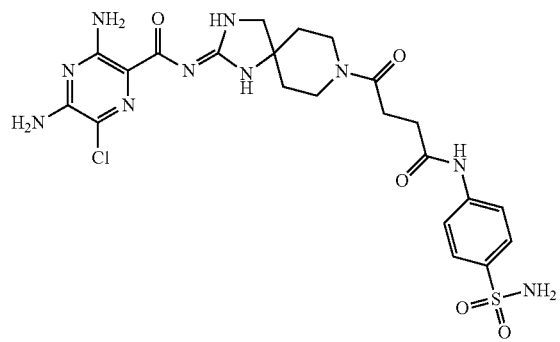
193
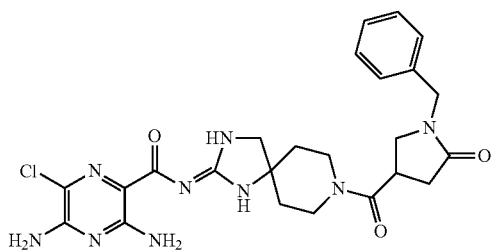
194
Chiral
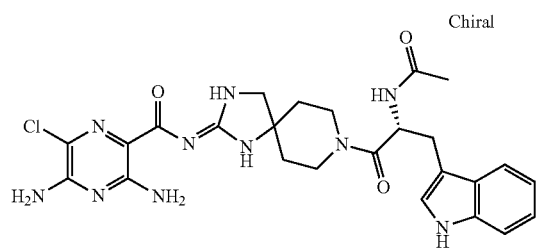
195
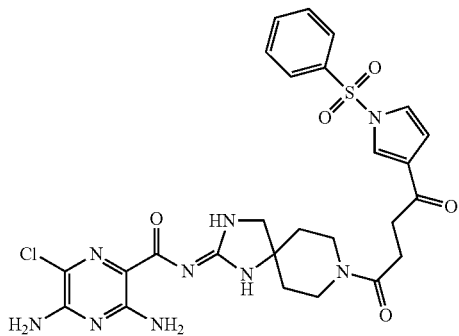
196
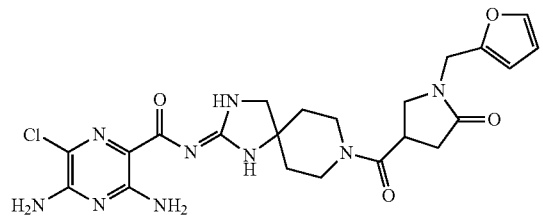

197
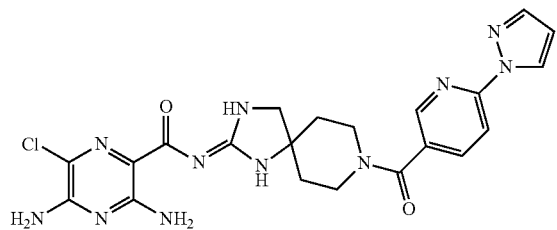
198
Chiral
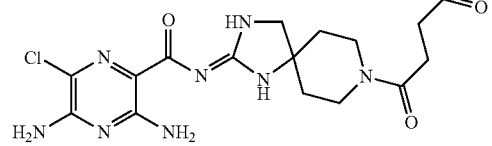
199
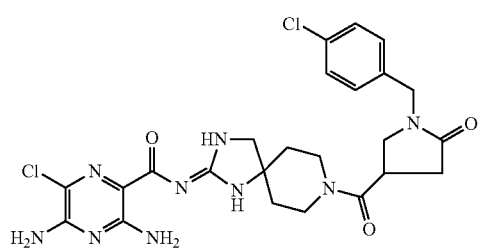
200
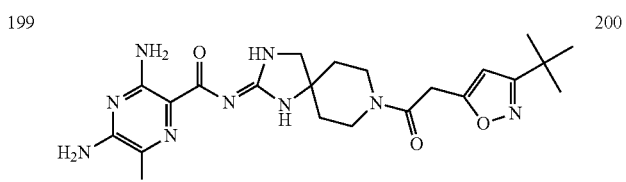
201
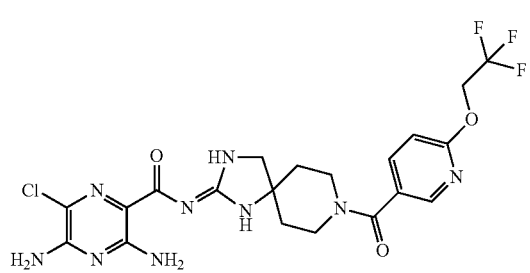
202
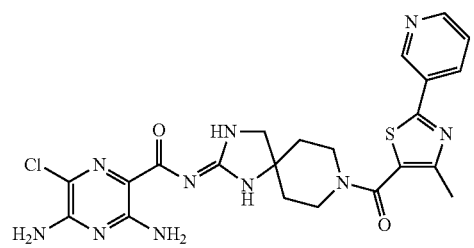
203
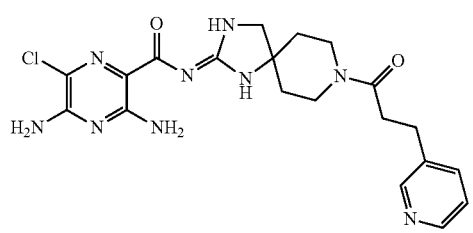
204
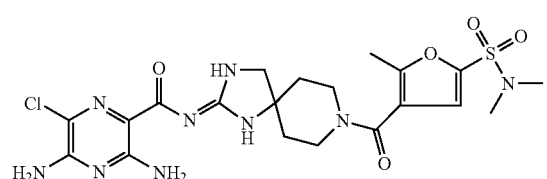
205
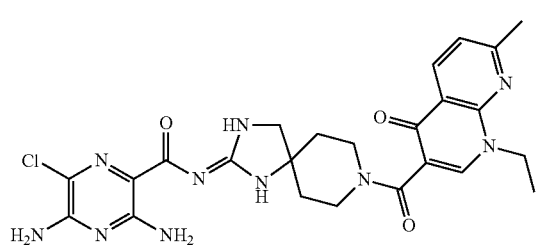
206
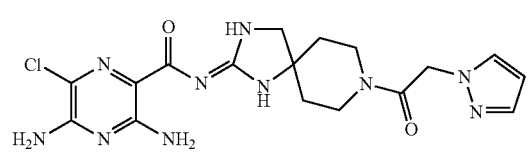

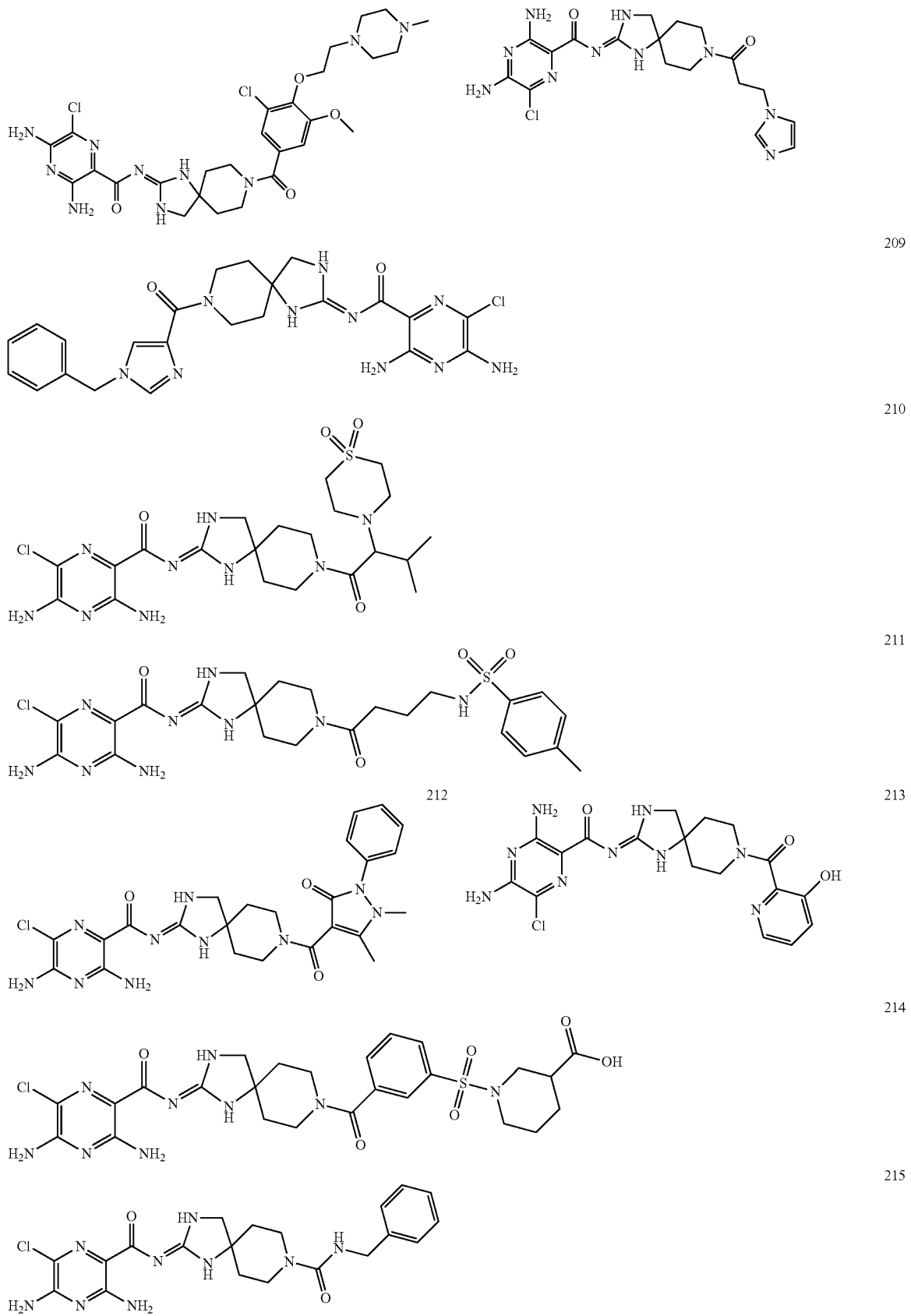

216
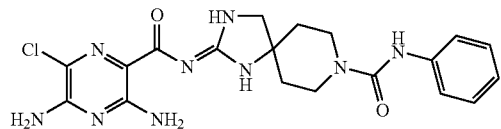
217
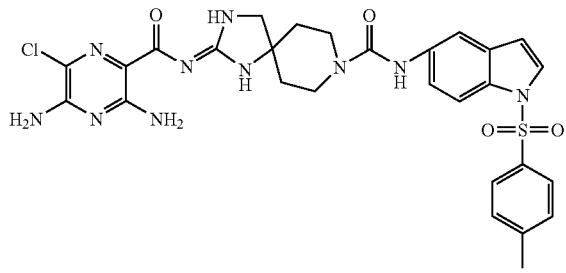
218
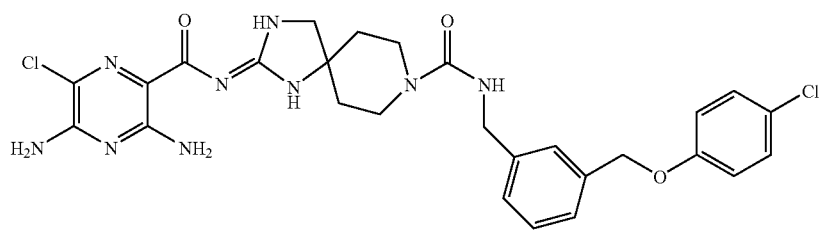
219
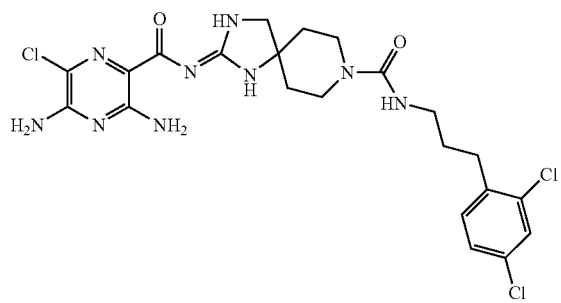
220
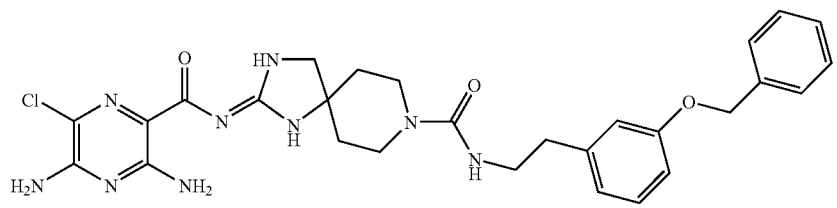
221
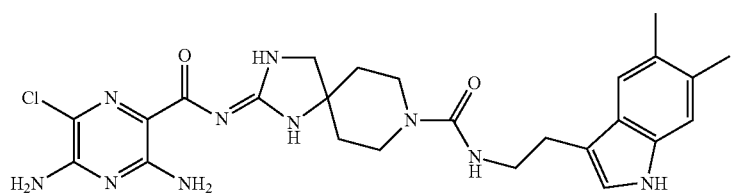
222
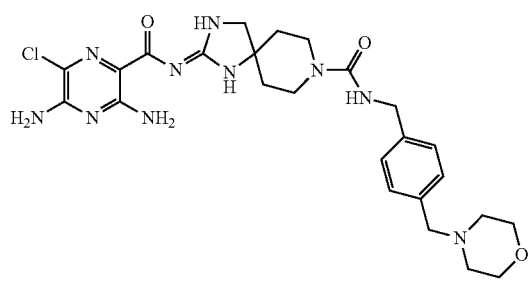
223
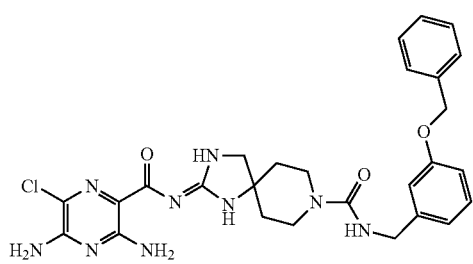

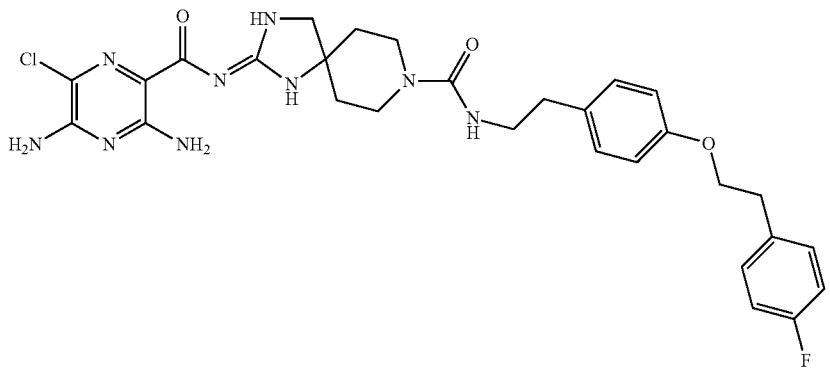
224
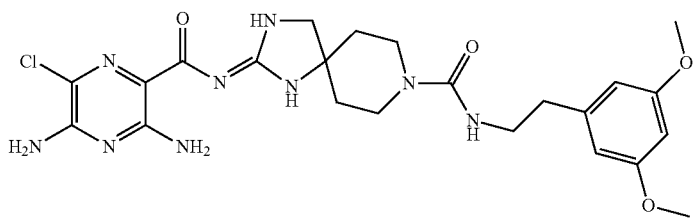
225
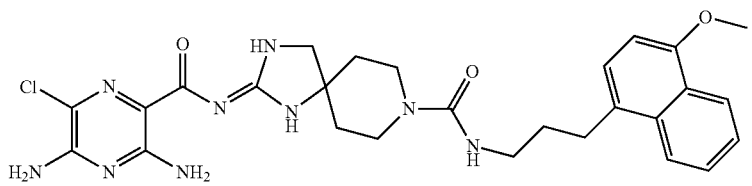
226
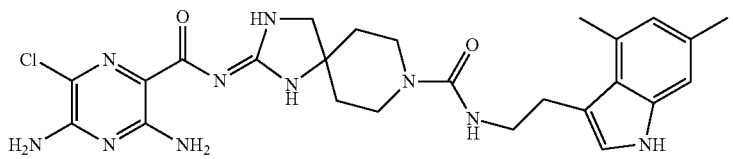
227
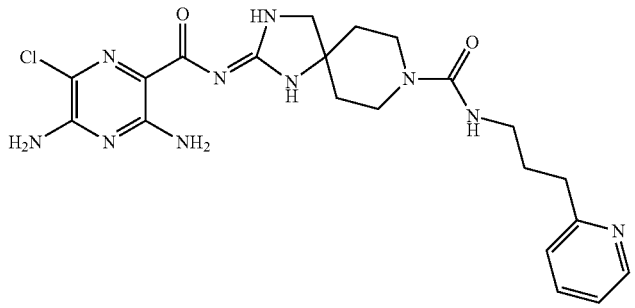
228
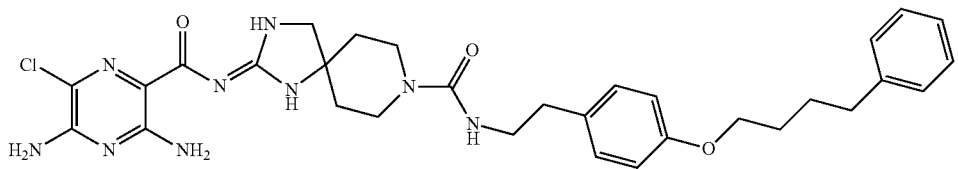
229

-continued
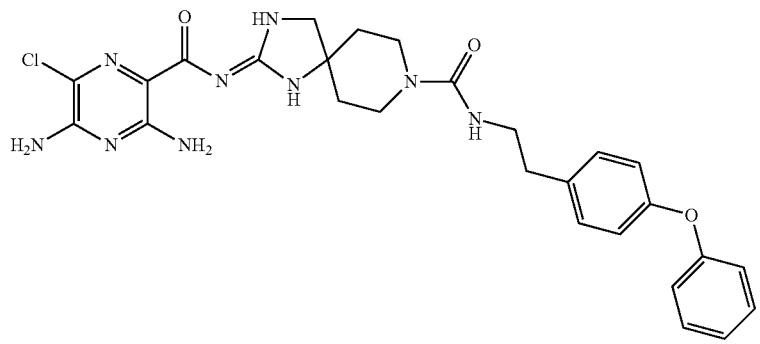
230
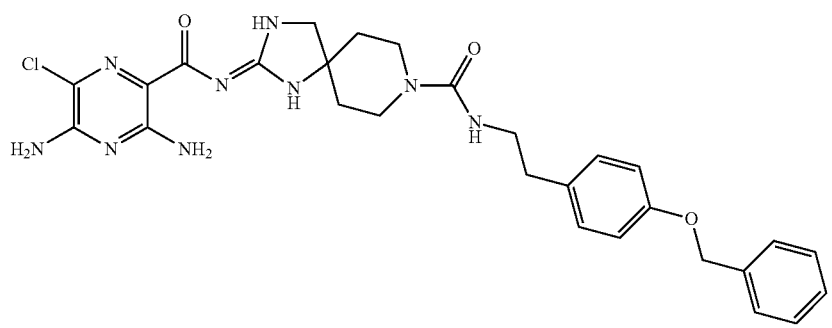
231
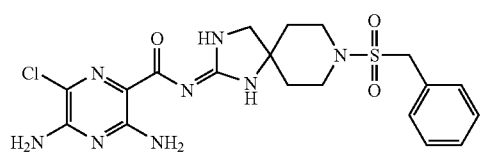
232
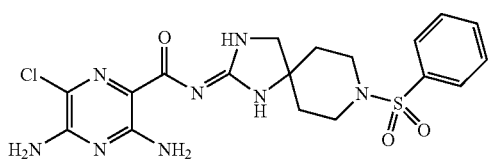
233
234
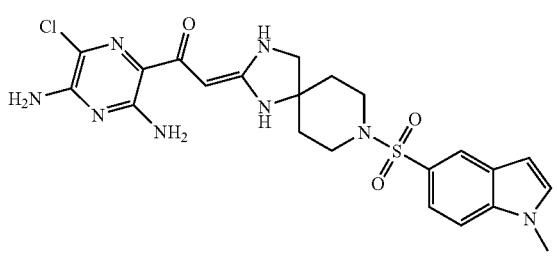
235
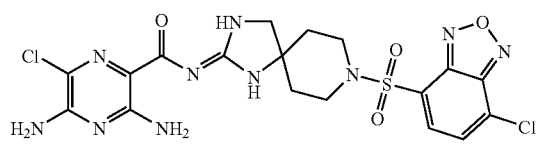
236
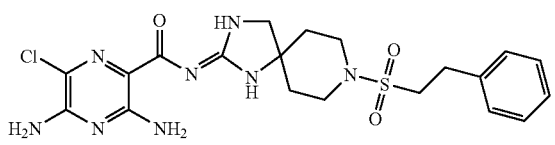
237
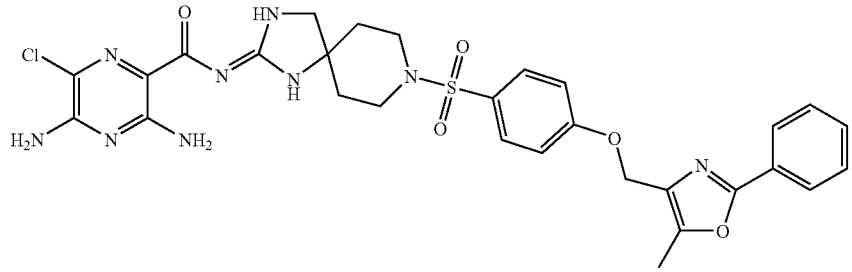
238

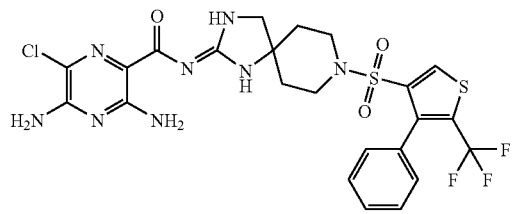
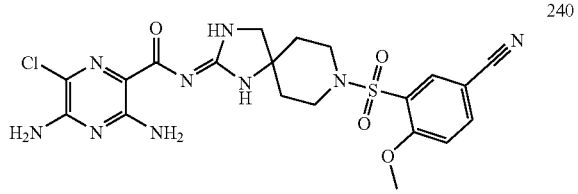
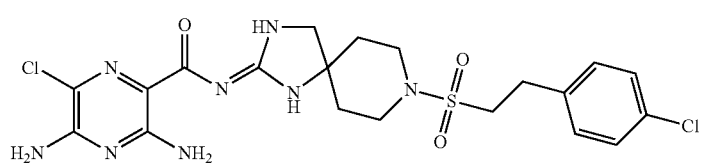
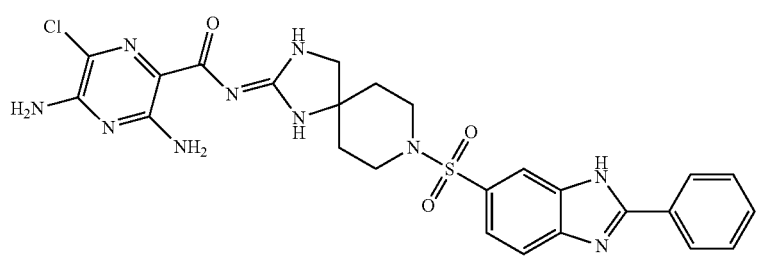
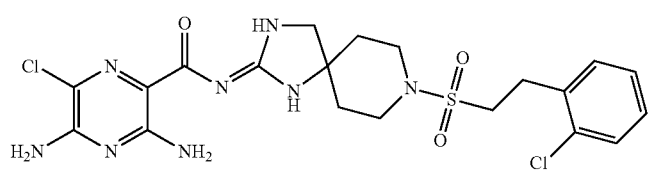
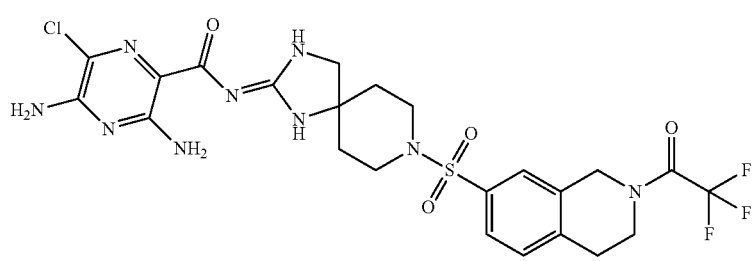
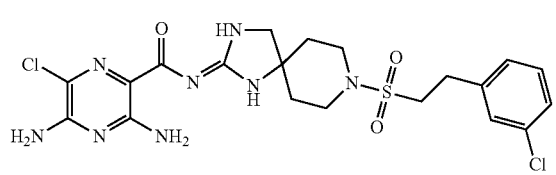
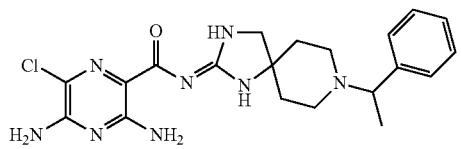
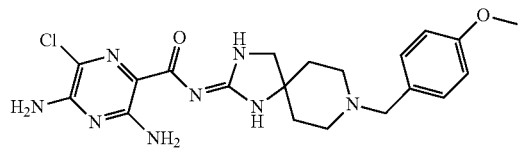
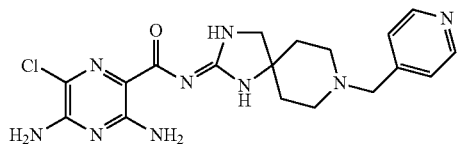
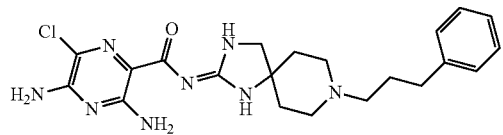
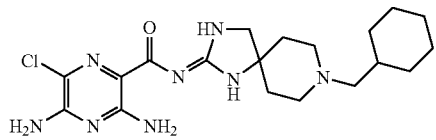

251

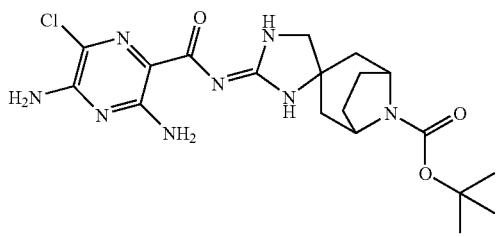

252

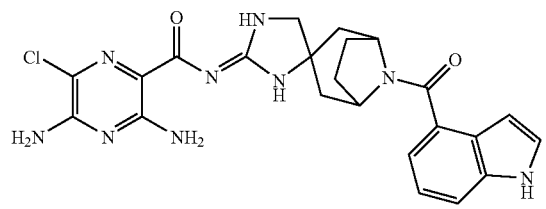

253

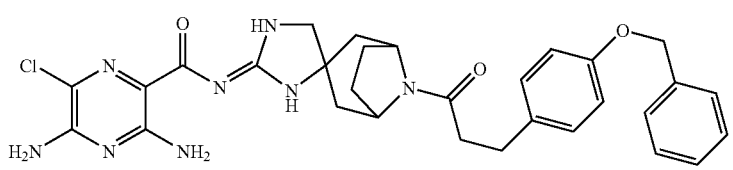

DEFINITIONS

Terms used in the specification have the following meanings:

"Optionally substituted" means the group referred to can be substituted at one or more positions by any one or any combination of the radicals listed thereafter.

"optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly.

The term "alkylene" denotes a straight chain or branched saturated hydrocarbon chain containing between 1 and 8 carbon atoms. If a different number of carbon atoms is specified, such as $C_6$ or $C_3$, then the definition is to be amended accordingly.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—. If a different number of carbon atoms is specified, such as $C_6$ or $C_3$, then the definition is to be amended accordingly.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different. If a different number of carbon atoms is specified, such as $C_6$ or $C_3$, then the definition is to be amended accordingly.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. If a different number of carbon atoms is specified, such as $C_6$ or $C_3$, then the definition is to be amended accordingly.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined, attached by a carbon atom to a carbonyl group. If a different number of carbon atoms is specified, such as $C_6$ or $C_3$, then the definition is to be amended accordingly.

"$C_3$-$C_8$-Cycloalkylcarbonyl", as used herein, denotes $C_3$-$C_8$-cycloalkyl, as hereinbefore defined, attached by a carbon atom to a carbonyl group. If a different number of carbon atoms is specified, such as $C_6$ or $C_3$, then the definition is to be amended accordingly.

"$C_7$-$C_{14}$-Aralkyl", as used herein, denotes alkyl, e.g., $C_1$-$C_4$-alkyl, as hereinbefore defined, substituted by a $C_6$-$C_{10}$-aromatic carbocyclic group, as herein defined. If a different number of carbon atoms is specified, such as $C_6$ or $C_3$, then the definition is to be amended accordingly.

"$C_3$-$C_{15}$-Carbocyclic group", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.

"4- to 8-Membered heterocyclic group", "5- to 6-membered heterocyclic group", "3- to 10-membered heterocyclic group", "3- to 14-membered heterocyclic group", "4- to 14-membered heterocyclic group" and "5- to 14-membered heterocyclic group", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclic group includes single ring groups, fused ring groups and bridged groups. Examples of such heterocyclic groups include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane or thiazole.

A second aspect of the present invention provides for the use of a compound of formula (I) in any of the aforementioned embodiments, in free or pharmaceutically acceptable salt form, for the manufacture of a medicament for the treatment of an inflammatory or allergic condition, particularly an inflammatory or obstructive airways disease or mucosal hydration.

An embodiment of the present invention provides for the use of a compound of formula (I) in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Especially preferred specific compounds of formula (I) are those described hereinafter in the Examples.

The compounds represented by formula (I) may be capable of forming acid addition salts, particularly pharmaceutically acceptable acid addition salts. Pharmaceutically acceptable acid addition salts of the compound of formula (I) include those of inorganic acids, e.g., hydrohalic acids, such as hydrofluoric acid, hydrochloric acid, hydrobromic acid or hydroiodic acid, nitric acid, sulfuric acid, phosphoric acid; and organic acids, e.g., aliphatic monocarboxylic acids, such as formic acid, acetic acid, trifluoroacetic acid, propionic acid and butyric acid; aliphatic hydroxy acids, such as lactic acid, citric acid, tartaric acid or malic acid; dicarboxylic acids, such as maleic acid or succinic acid; aromatic carboxylic acids, such as benzoic acid, p-chlorobenzoic acid, diphenylacetic acid, para-biphenyl benzoic acid or triphenylacetic acid; aromatic hydroxy acids, such as o-hydroxybenzoic acid, p-hydroxybenzoic acid, 1-hydroxynaphthalene-2-carboxylic acid or 3-hydroxynaphthalene-2-carboxylic acid; cinnamic acids, such as 3-(2-naphthalenyl)propenoic acid, para-methoxy cinnamic acid or para-methyl cinnamic acid; and sulfonic acids, such as methanesulfonic acid or benzenesulfonic acid. These salts may be prepared from compounds of formula (I) by known salt-forming procedures.

Compounds of formula (I) which may contain acidic, e.g., carboxyl, groups, are also capable of forming salts with bases, in particular, pharmaceutically acceptable bases, such as those well-known in the art; suitable such salts include metal salts, particularly alkali metal or alkaline earth metal salts, such as sodium, potassium, magnesium or calcium salts; or salts with ammonia or pharmaceutically acceptable organic amines or heterocyclic bases, such as ethanolamines, benzylamines or pyridine. These salts may be prepared from compounds of formula (I) by known salt-forming procedures.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well-known to those skilled in the art, e.g., chiral high performance liquid chromatography (HPLC).

Tautomers are one of two or more structural isomers that exist in equilibrium and are readily converted from one isomeric form to another.

More specifically, for example, compounds of Formula Ia where $R^6$ and/or $R^{11}$ are hydrogen may exist in one or both of the following tautomeric forms:

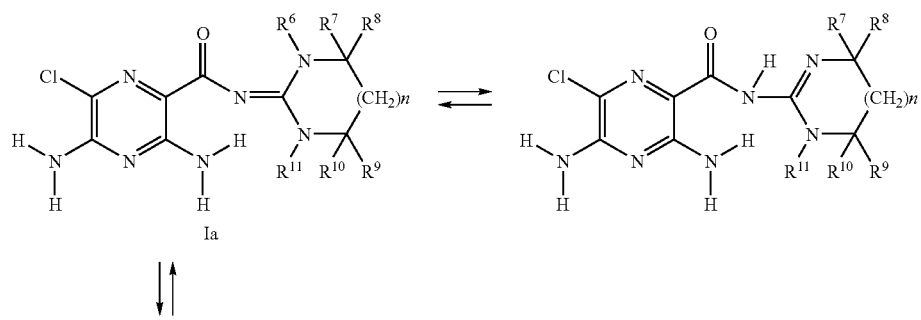

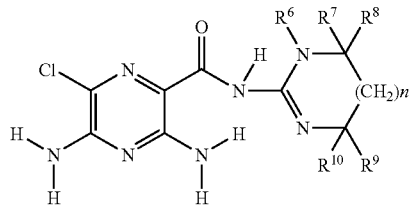

Compounds according to Formula I may exist in corresponding tautomeric forms.

Examples of tautomers include but are not limited to those compounds defined in the claims.

The compounds of the invention may exist in both unsolvated and solvated forms. The term "solvate" is used herein to describe a molecular complex comprising the compound of the invention and one or more pharmaceutically acceptable solvent molecules, e.g., ethanol. The term "hydrate" is employed when said solvent is water.

Synthesis

Generally, compounds according to Formula I can be synthesized by the routes described in Scheme 1 and the Examples.

For instance, intermediate 1 can be reacted with intermediate 2 in an organic solvent to provide compound 3 which can be isolated as the free base. The free base can then be converted to a salt form by treatment with an appropriate acid.

Intermediates can be prepared from methods known by those skilled in the art or are commercially available.

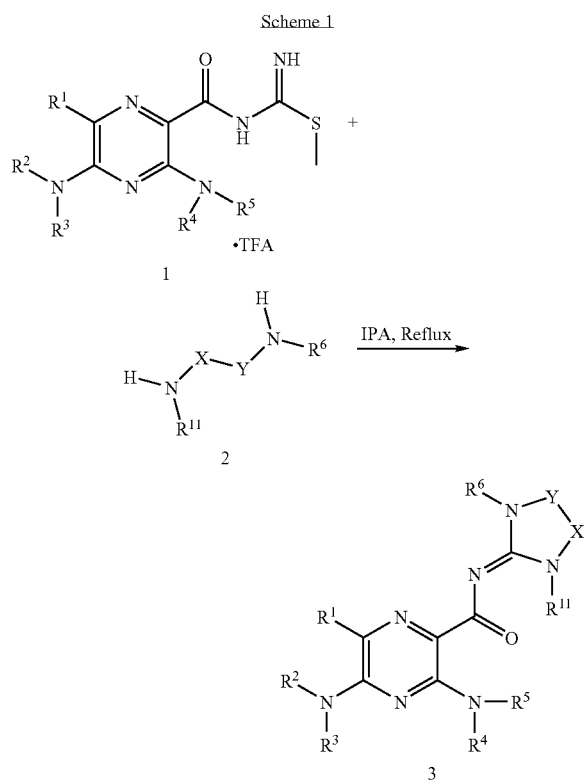

In Scheme 1, $R^1$, $R^2$, $R^3$, $R^4$, $R^5$, $R^6$ and $R^{11}$ are as defined above; Y is $CR^7R^8$; X is $CR^9R^{10}$; n is 0; and $R^7$, $R^8$, $R^9$ and $R^{10}$ are also as defined above. For compounds where n is 1 or 2, then the appropriate methylene or ethylene linking groups are inserted between X and Y in the diamine reactant 2.

The compounds of Formula 1 and Formula 2 above can be prepared according to conventional routes described in the literature.

Compounds of formula (I), in free form, may be converted into salt form, and vice versa, in a conventional manners understood by those skilled in the art. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995);

and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Pharmacological Activity

Having regard to their blockade of the epithelial sodium channel (ENaC), compounds of formula (I), in free or pharmaceutically acceptable salt form, hereinafter alternately referred to as "agents of the invention", are useful in the treatment of conditions which respond to the blockade of the epithelial sodium channel, particularly conditions benefiting from mucosal hydration.

Diseases mediated by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

The agents of the invention may also be useful as acid-sensing ion channel (ASIC) blockers. Thus they may be useful in the treatment of conditions which respond to the blockade of the acid-sensing ion channel.

The suitability of epithelial sodium channel blocker as a treatment of a disease benefiting from mucosal hydration, may be tested by determining the inhibitory effect of the channel blocker on ENaC in a suitable cell-based assay. For example single cells or confluent epithelia, endogenously expressing or engineered to overexpress ENaC can be used to assess channel function using electrophysiological techniques or ion flux studies. See methods described in: Hirsh et al., *J Pharm Exp Ther* (2004); Moody et al., *Am J Physiol Cell Physiol* (2005).

Epithelial sodium channel blockers, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The epithelial sodium channel blocker may be mixed with the other drug substance in a fixed pharmaceutical composition or it may be administered separately, before, simultaneously with or after the other drug substance.

Accordingly, the invention includes as a further aspect a combination of epithelial sodium channel blocker with osmotic agents (hypertonic saline, dextran, mannitol, Xylitol)+modifiers of CFTR function, both wild-type and mutant (correctors+potentiators), e.g., those described in WO 2007/021982, WO 2006/099256, WO 2006/127588, WO 2004/080972, WO 2005/026137, WO 2005/035514, WO 2005/075435, WO 2004/111014, WO 2006/101740, WO 2004/110352, WO 2005/120497 and US 2005/0176761, an anti-inflammatory, bronchodilatory, antihistamine, anti-tussive, antibiotic or DNase drug substance, said epithelial sodium channel blocker and said drug substance being in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H- benzo-cyclohepten-8-yl]carbonyl]amino]phenyl]-methyl]tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

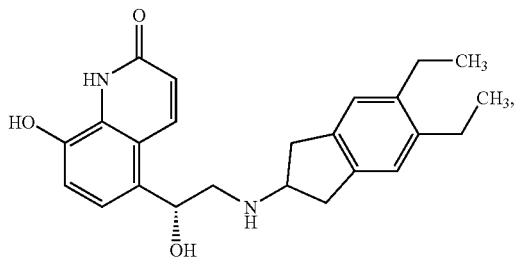

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

In accordance with the foregoing, the invention also provides as a further aspect a method for the treatment of a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I), in free form or in the form of a pharmaceutically acceptable salt.

In another aspect the invention provides a compound of formula (I), in free form or in the form of a pharmaceutically acceptable salt, for use in the manufacture of a medicament for the treatment of a condition responsive to blockade of the epithelial sodium channel, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

Further aspects of the invention include:
(a) a compound of formula (I) in inhalable form, e.g., in an aerosol or other atomisable composition or in inhalable particulate, e.g., micronised form;
(b) an inhalable medicament comprising a compound of formula (I) in inhalable form;
(c) a pharmaceutical product comprising a compound of formula (I) in inhalable form in association with an inhalation device; and
(d) an inhalation device containing a compound of formula I in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I) and their pharmaceutically acceptable salts, hereinafter referred to alternatively as "agents of the invention", are useful as pharmaceuticals. In particular, the compounds have good ENaC blocker activity and may be tested in the following assays.

Cell Culture

Human Bronchial Epithelial cells (HBECs) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 μg/mL), hydrocortisone (0.5 μg/mL), human recombinant epidermal growth factor (0.5 ng/mL), epinephrine (0.5 μg/mL), transferrin (10 μg/mL), insulin (5 μg/mL), retinoic acid (0.1 μg/mL), triiodothyronine (6.5 μg/mL), gentamycin (50 μg/mL) and amphotericin B (50 ng/mL). Medium was changed every 48 hours until cells were 90% confluent. Cells were then passaged and seeded ($8.25 \times 10^5$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 μL, resulting in a final 1× concentration the 5 mL volume of the Ussing chamber. Subsequent additions of compound were added in a 3.3 μL volume of the 1000× serially diluted stock solution. At the completion of the concentration-response experiment, amiloride (10 μM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02. Cell inserts were typically run in duplicate and the $IC_{50}$ calculated on the mean % inhibition data.

Compounds of the Examples, herein below, generally have $IC_{50}$ values in the data measurements described above below 10 μM. For example, the compounds of the Examples shown below have the indicated $IC_{50}$ values.

| Ex | $IC_{50}$ (μM) |
| --- | --- |
| 5 | 0.065 |
| 11 | 1.686 |
| 19 | 0.018 |
| 23 | 0.0335 |
| 25 | 0.270 |
| 26 | 0.011 |
| 29 | 0.005 |
| 32 | 0.018 |
| 34 | 0.095 |
| 35 | 0.031 |
| 39 | 0.0055 |
| 40 | 0.0055 |
| 41 | 0.0095 |
| 42 | 0.011 |
| 43 | 0.013 |
| 44 | 0.0295 |
| 45 | 0.0426 |
| 48 | 0.0165 |
| 58 | 0.143 |
| 61 | 0.3465 |
| 62 | 0.013 |
| 64 | 0.0255 |
| 65 | 0.0395 |
| 70 | 0.074 |
| 71 | 0.042 |
| 76 | 0.012 |
| 86 | 0.008 |
| 91 | 0.0885 |
| 94 | 0.009 |
| 96 | 0.037 |
| 99 | 0.019 |
| 118 | 0.175 |
| 126 | 0.025 |
| 128 | 0.0115 |

-continued
| Ex | IC$_{50}$ (μM) |
|---|---|
| 141 | 0.002 |
| 146 | 0.006 |
| 147 | 0.016 |
| 185 | 0.062 |
| 215 | 0.036 |
| 220 | 0.0085 |
| 228 | 0.0935 |
| 232 | 0.054 |
| 235 | 0.364 |
| 238 | 0.119 |
| 246 | 0.025 |
| 252 | 0.028 |
The invention is illustrated by the following Examples.
EXAMPLES
Compounds of Formula Ib
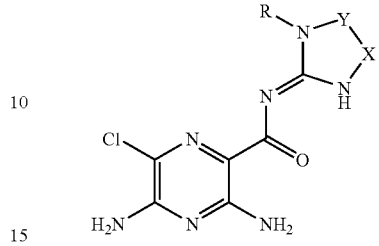
are shown in Table 1. Methods for preparing such compounds are described hereinafter. The table also shows mass spectrometry [M+H]$^+$ data.
TABLE 1
| Ex. | Structure | M/s [M + H]$^+$ |
|---|---|---|
| 1 | 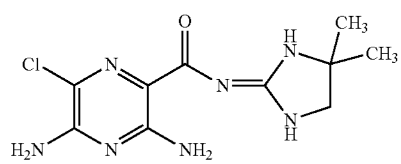 | 284 |
| 2 | 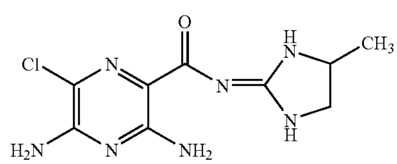 | 270 |
| 3 | 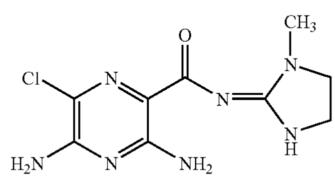 | 270 |
| 4 | 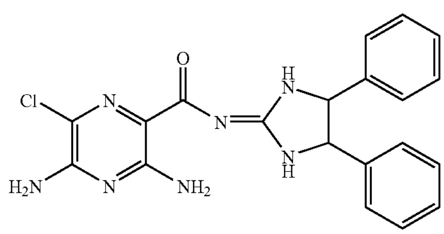 | 408 |
| 5 | 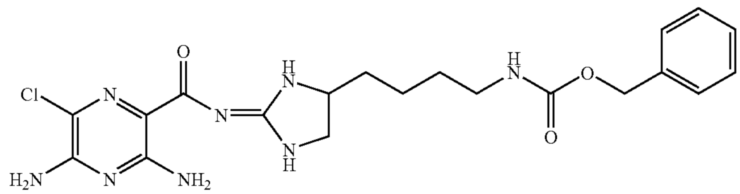 | 461 |

TABLE 1-continued

| Ex. | Structure | M/s [M + H]⁺ |
|---|---|---|
| 6 | 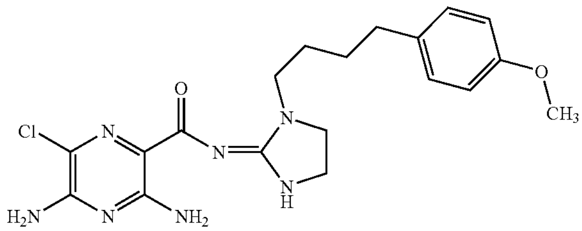 | 418 |
| 7 | 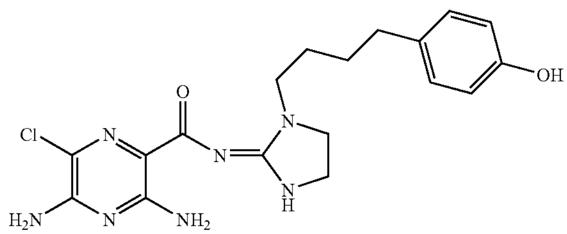 | 404 |
| 8 | 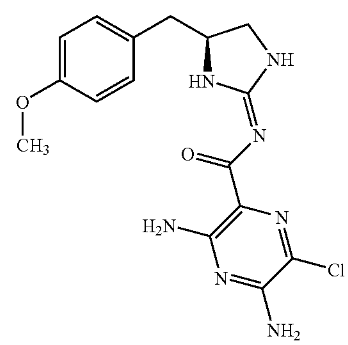 | 376/378 |
| 9 | 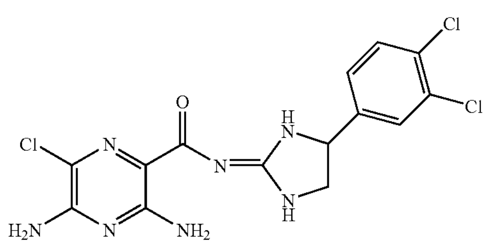 | 400 |
| 10 | 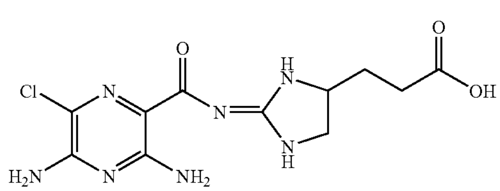 | 328 |
| 11 | 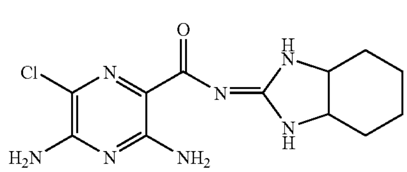 | 310 |

TABLE 1-continued

| Ex. | Structure | M/s [M + H]+ |
|---|---|---|
| 12 | 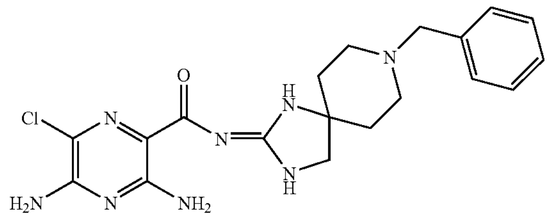 | 415 |
| 13 | 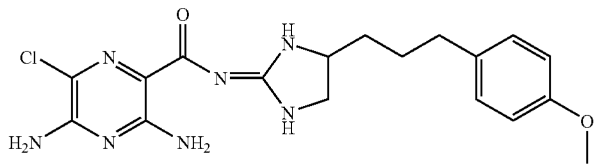 | 404 |
| 14 | 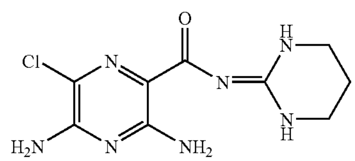 | 270 |
| 15 | (Chiral) | 296 |
| 16 | 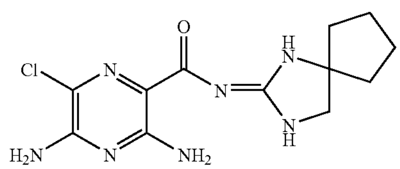 | 310 |
| 17 | 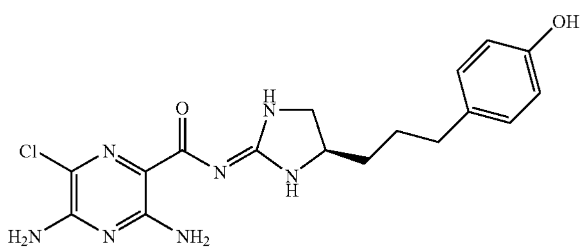 | 390 |
| 18 | 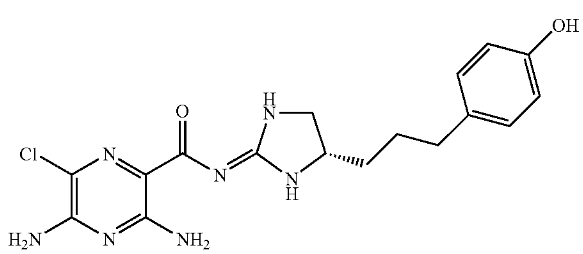 | 390 |

TABLE 1-continued

| Ex. | Structure | M/s [M + H]+ |
|---|---|---|
| 19 | 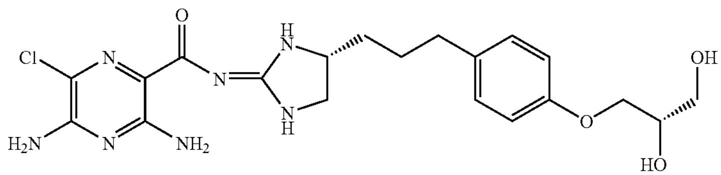 | 464 |
| 20 | 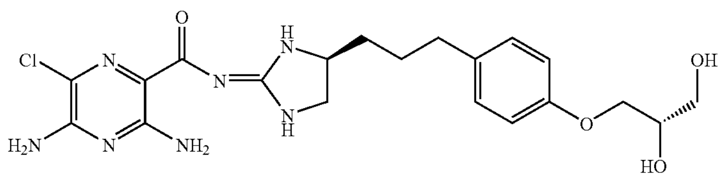 | 464 |
| 21 | 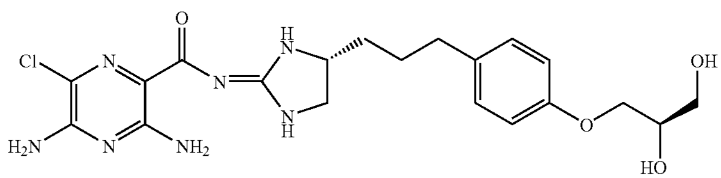 | 464 |
| 22 | 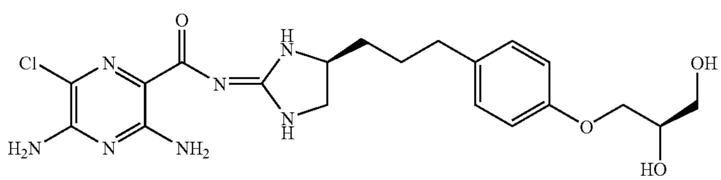 | 464 |
| 23 | 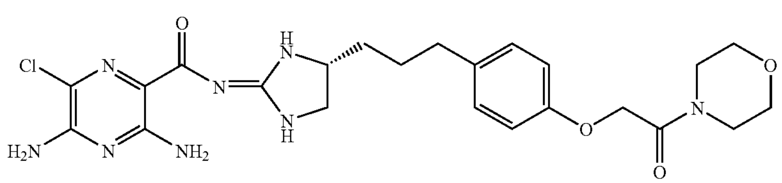 | 517 |
| 24 | 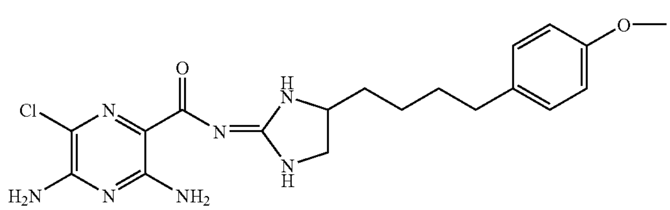 | 418.2 |
| 25 | 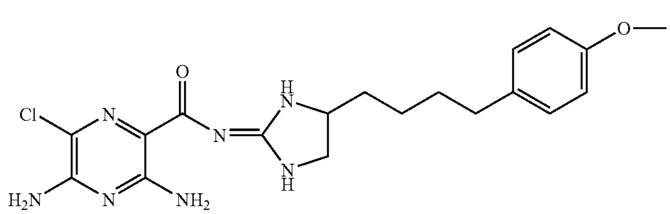 | 418.2 |

TABLE 1-continued

| Ex. | Structure | M/s [M + H]+ |
|---|---|---|
| 26 | Chiral | 446 |
| 27 | Chiral | 356 |
| 28 | Chiral | 506 |
| 29 | Chiral | 506.37 |
| 30 | 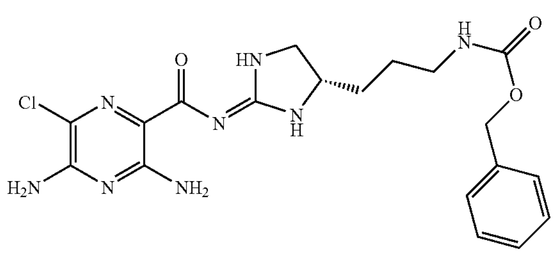 | 447.1 |
| 31 | 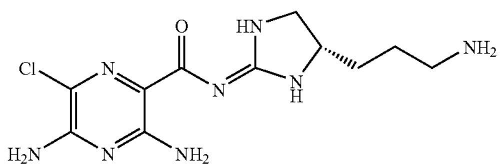 | 313.1 |

TABLE 1-continued

| Ex. | Structure | M/s [M + H]+ |
|---|---|---|
| 32 | 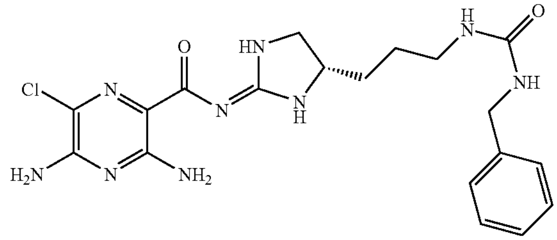 | 446.1 |
| 33 | 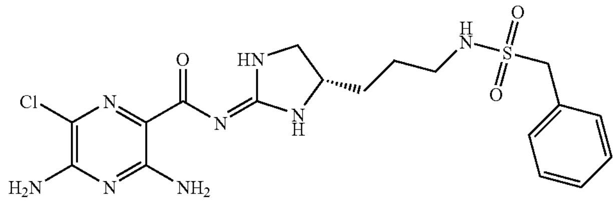 | 467.0 |
| 34 | 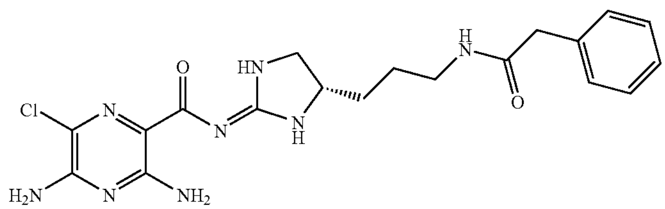 | 430.98 |
| 35 | 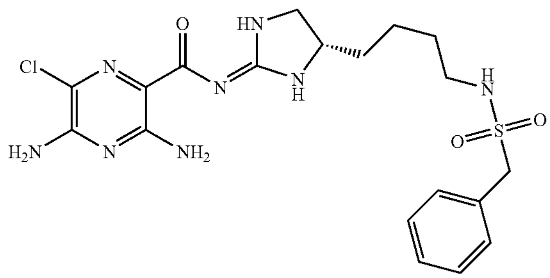 | 481.0 |
| 36 | 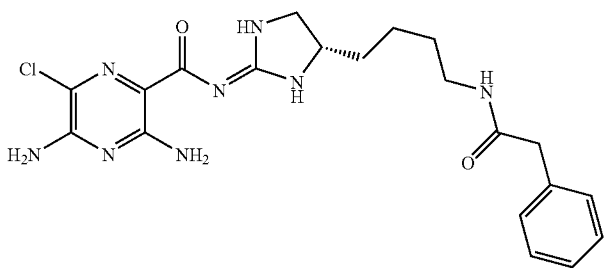 | 445.1 |
| 37 | 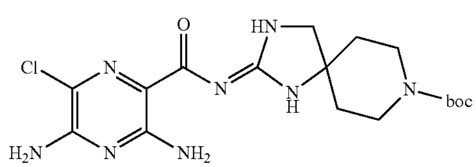 | 425 |
| 38 | 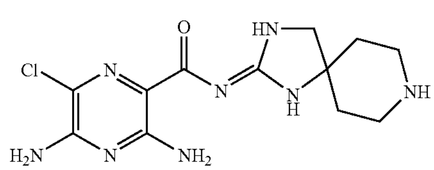 | 325 |

US 8,039,472 B2
87                                                                            88
TABLE 1-continued
| Ex. | Structure | M/s [M + H]+ |
|---|---|---|
| 39 | 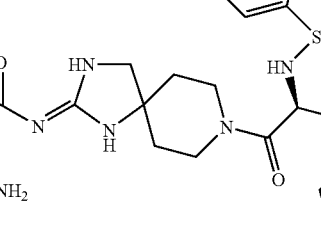 | 626.4 |
| 40 | 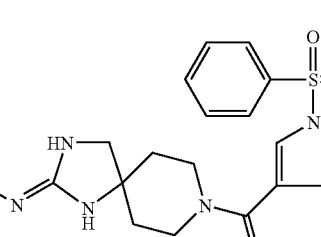 | 607.42 |
| 41 | 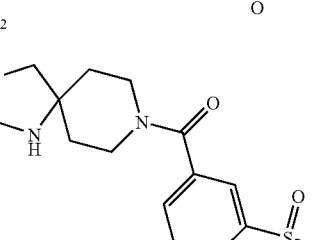 | 607.98 |
| 42 | 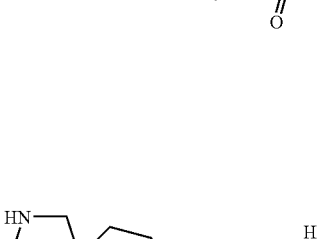 | 510.4 |
| 43 | 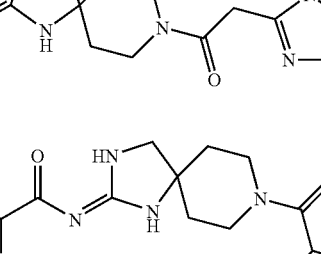 | 529.05 |

TABLE 1-continued

| Ex. | Structure | M/s [M + H]⁺ |
|---|---|---|
| 44 | 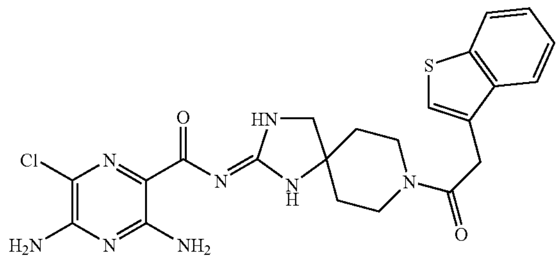 | 499.0 |
| 45 | 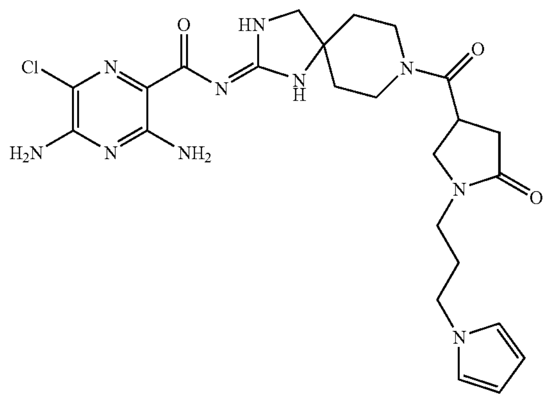 | 542.91 |
| 46 | 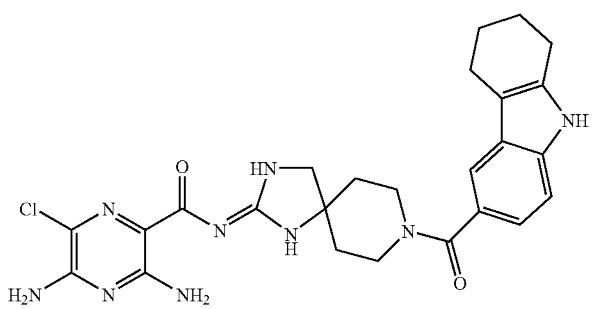 | 552.1 |
| 47 | 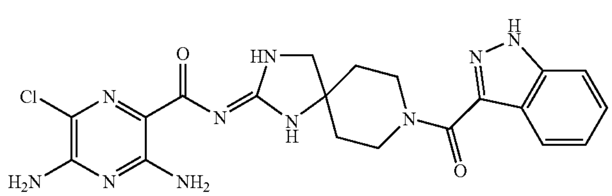 | 469.17 |
| 48 | 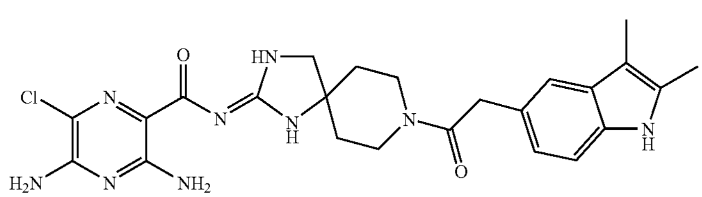 | 510.23 |

TABLE 1-continued

| Ex. | Structure | M/s [M + H]+ |
|---|---|---|
| 49 | 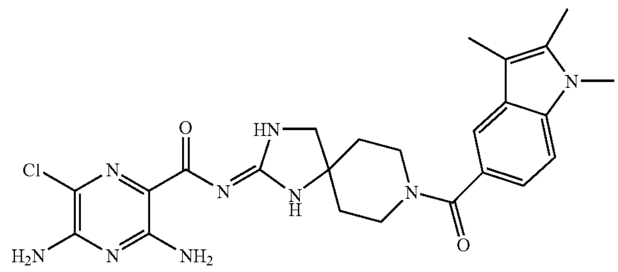 | 510.1 |
| 50 | 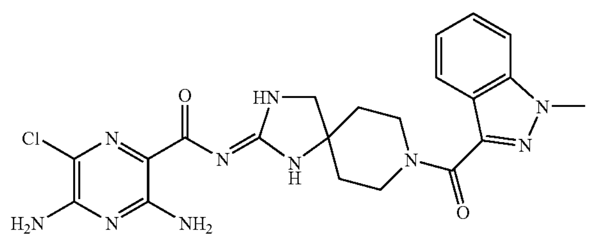 | 483.1 |
| 51 | 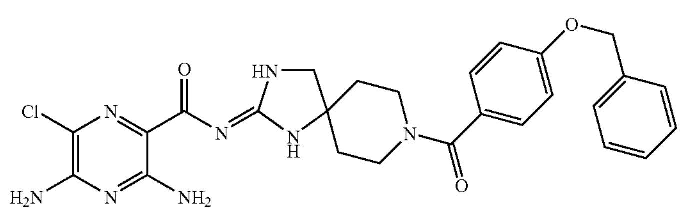 | 535.1 |
| 52 | 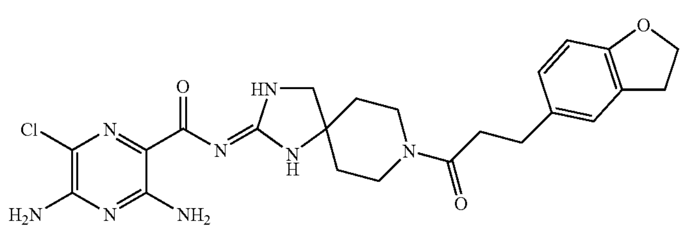 | 499.1 |
| 53 | 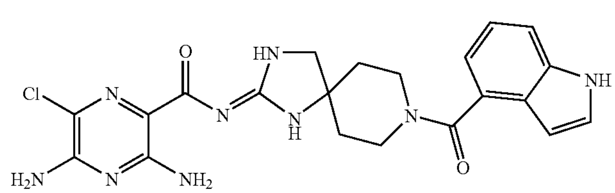 | 469.14 |
| 54 | 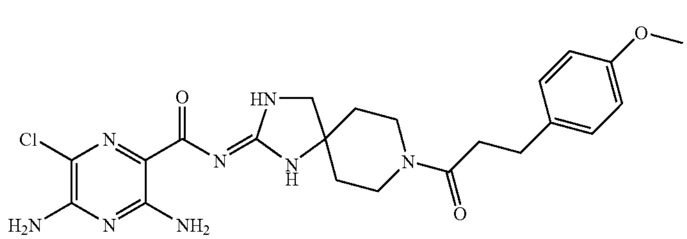 | 487.0 |

TABLE 1-continued

| Ex. | Structure | M/s [M + H]+ |
|---|---|---|
| 55 | 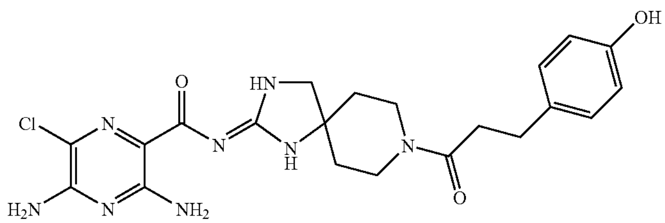 | 472.98 |
| 56 | 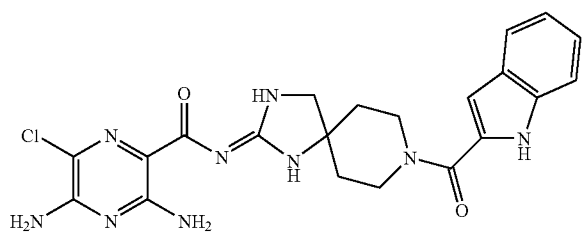 | 468.1 |
| 57 | 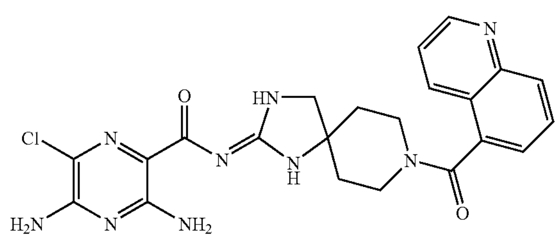 | 480.1 |
| 58 | 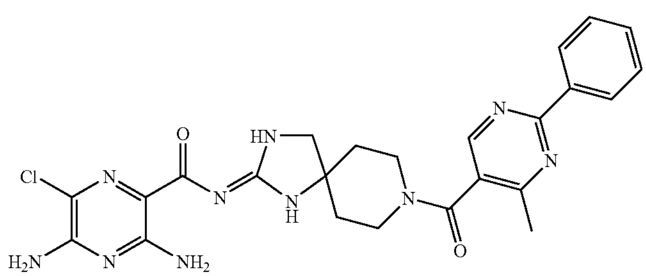 | 521.1 |
| 59 | 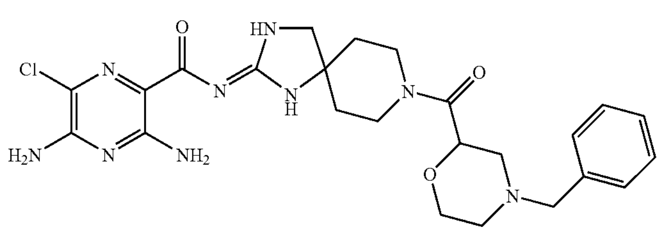 | 528.2 |
| 60 | 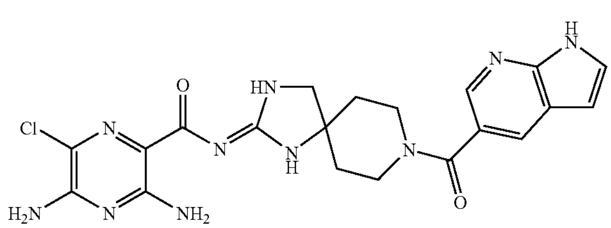 | 469.08 |

TABLE 1-continued

| Ex. | Structure | M/s [M + H]+ |
|---|---|---|
| 61 | 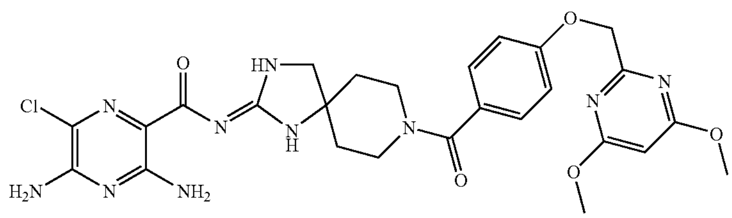 | 597.07 |
| 62 | 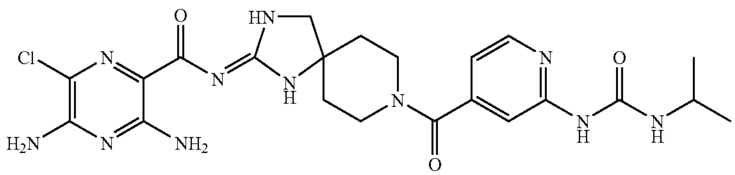 | 530.21 |
| 63 | 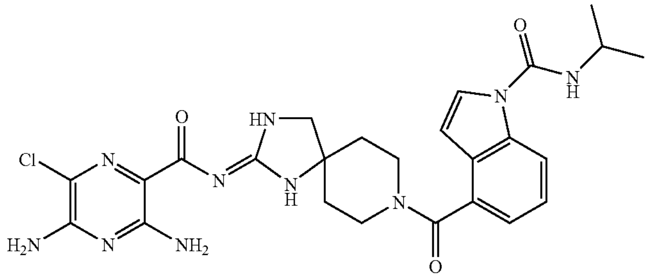 | 553.54 |
| 64 | 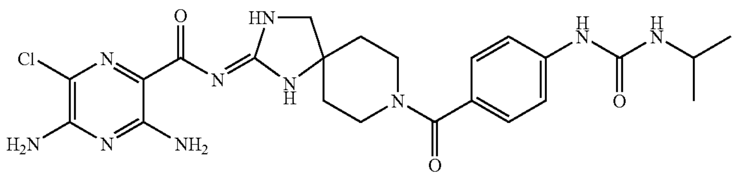 | 529.54 |
| 65 | 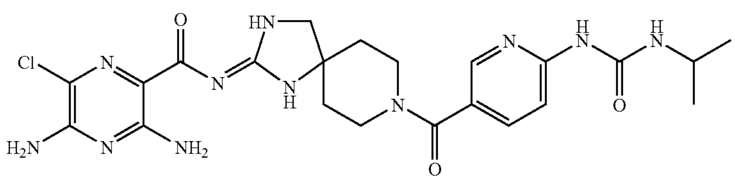 | 530.46 |
| 66 | 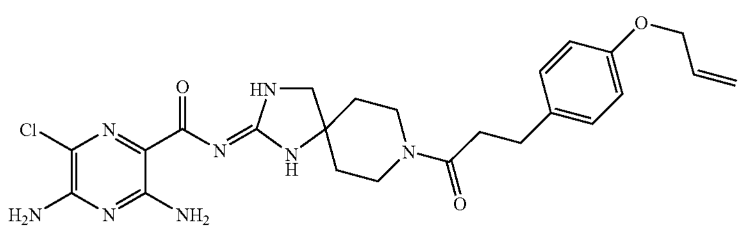 | 513.40 |
| 67 | 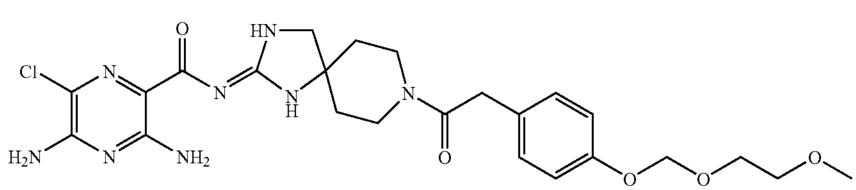 | 547.42 |

TABLE 1-continued
| Ex. | Structure | M/s [M + H]+ |
|---|---|---|
| 68 | 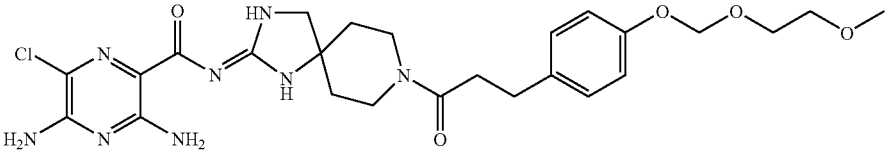 | 561.04 |
| 69 | 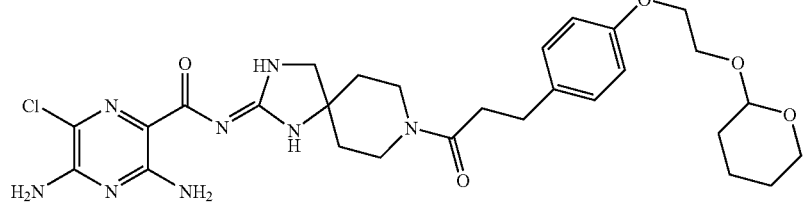 | 601.10 |
| 70 | 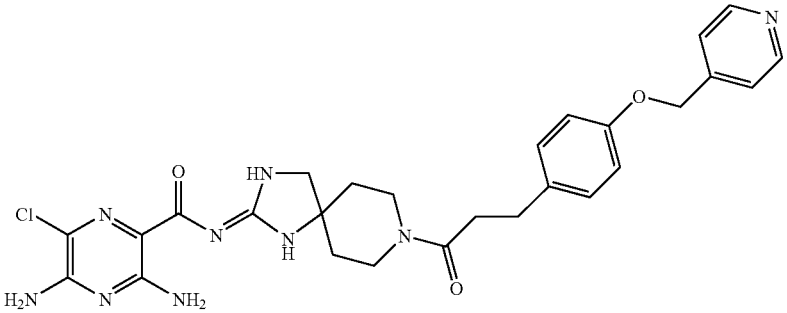 | 564.10 |
| 71 | 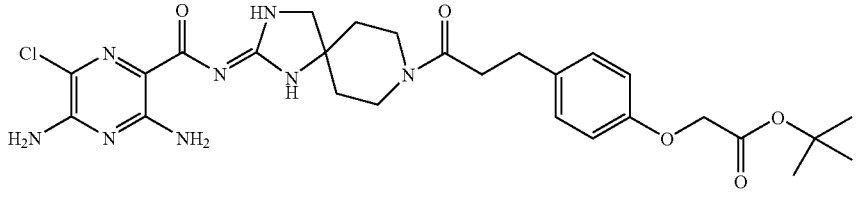 | 587.50 |
| 72 | 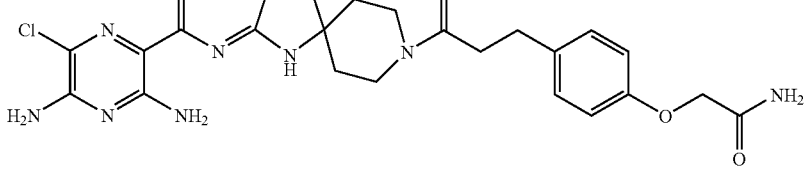 | 530.10 |
| 73 | 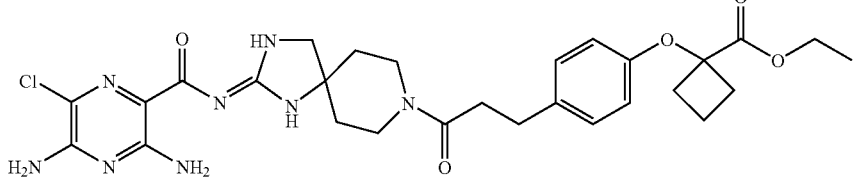 | 599.10 |
| 74 | 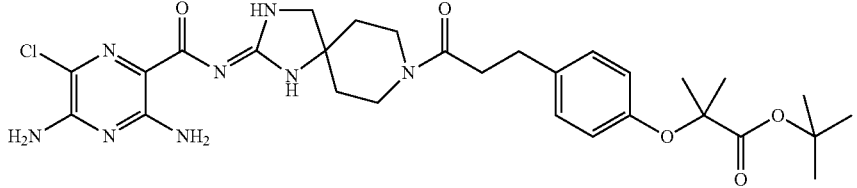 | 615.20 |

TABLE 1-continued

| Ex. | Structure | M/s [M + H]+ |
|---|---|---|
| 75 | 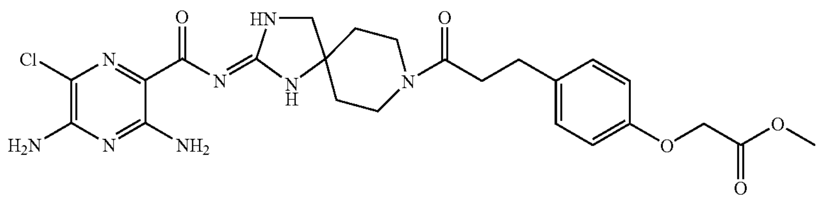 | 545.10 |
| 76 | 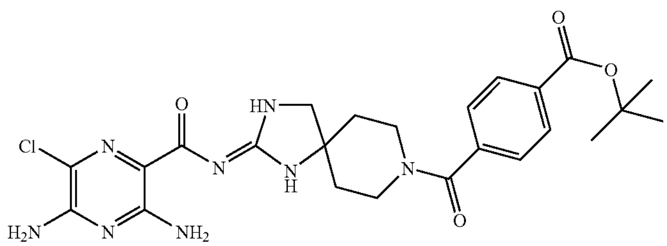 | 529.41 |
| 77 | 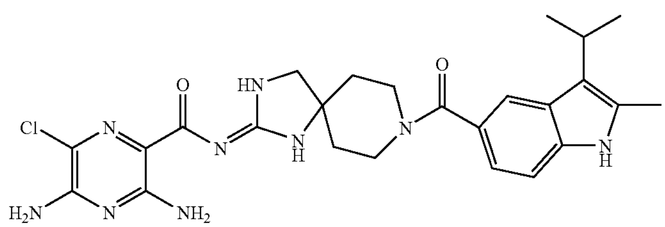 | 524 |
| 78 | 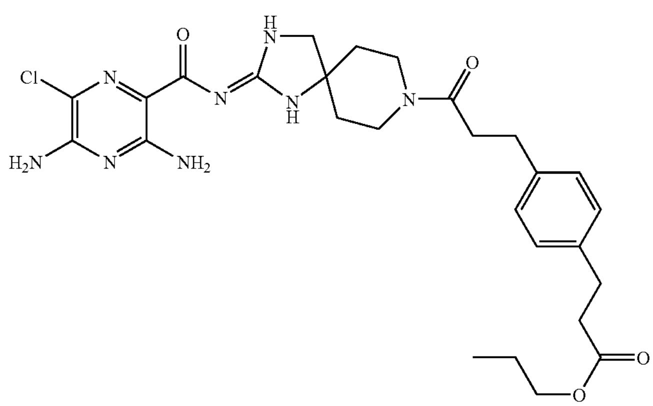 | 571 |
| 79 | 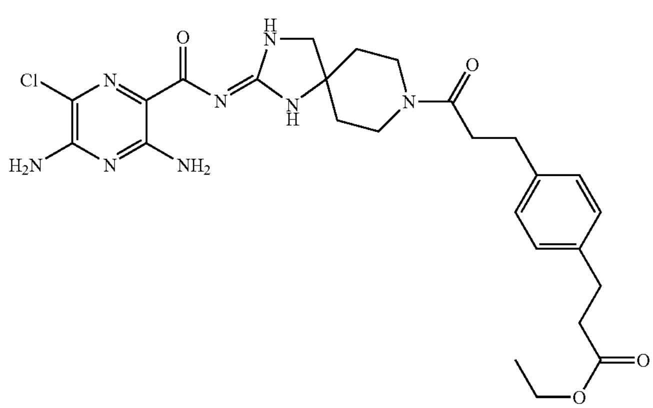 | 557 |

TABLE 1-continued

| Ex. | Structure | M/s [M + H]+ |
|---|---|---|
| 80 | 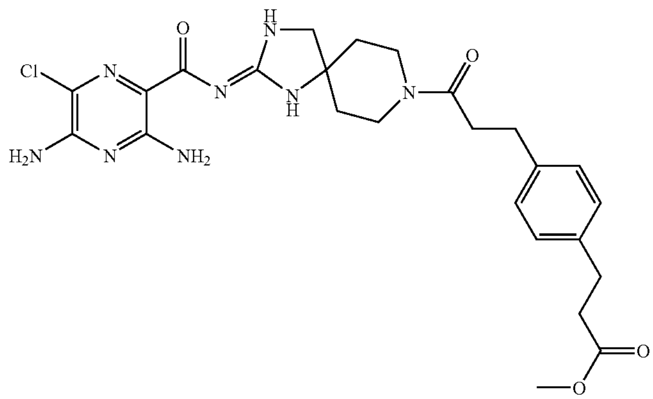 | 543 |
| 81 | 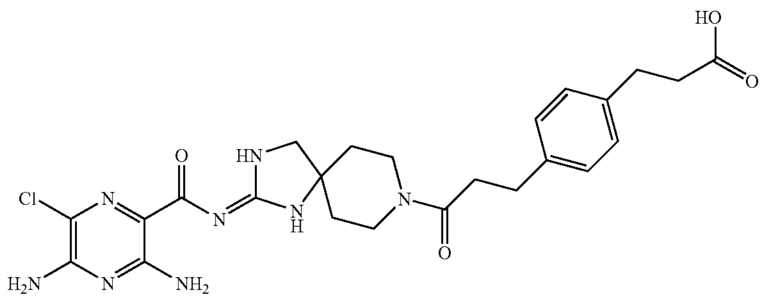 | 529 |
| 82 | 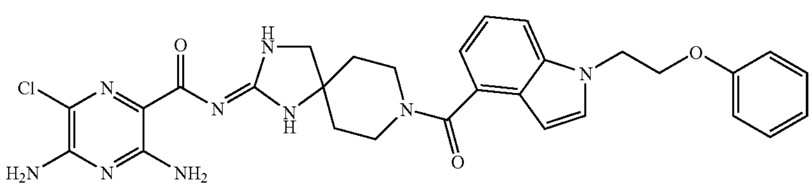 | 588 |
| 83 | 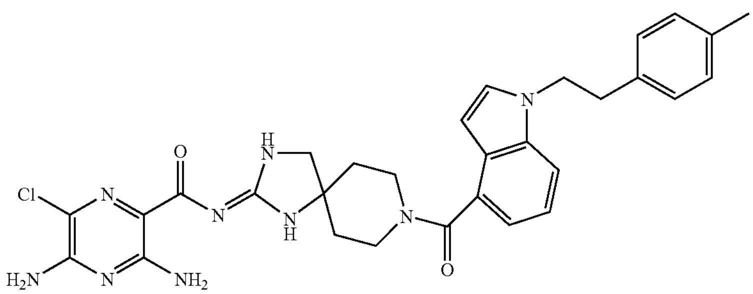 | 586/588 |
| 84 | 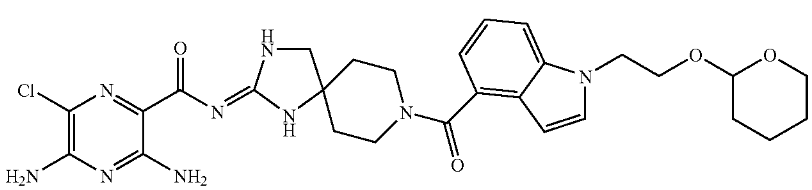 | 597 |
| 85 | 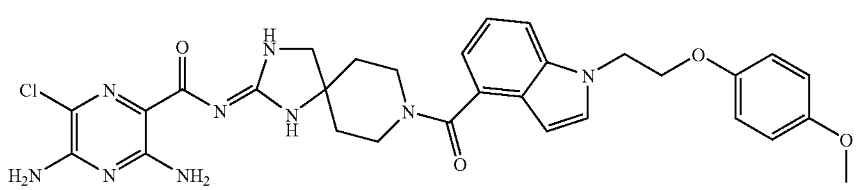 | 618 |

TABLE 1-continued

| Ex. | Structure | M/s [M + H]+ |
|---|---|---|
| 86 | 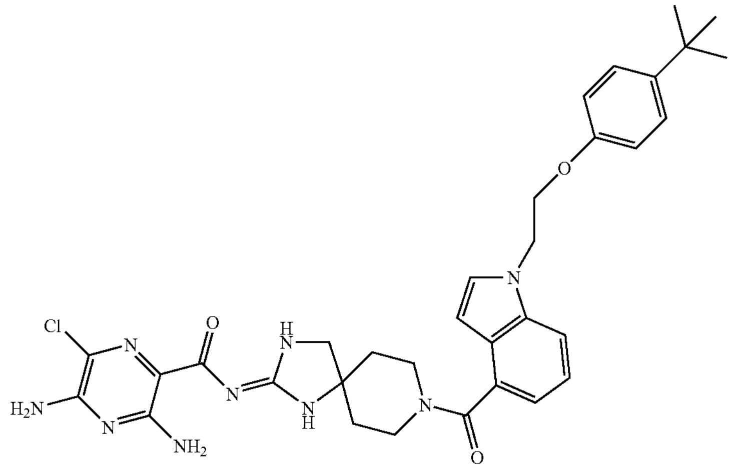 | 644/646 |
| 87 | 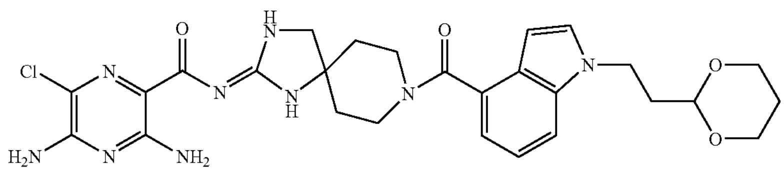 | 582/584 |
| 88 | 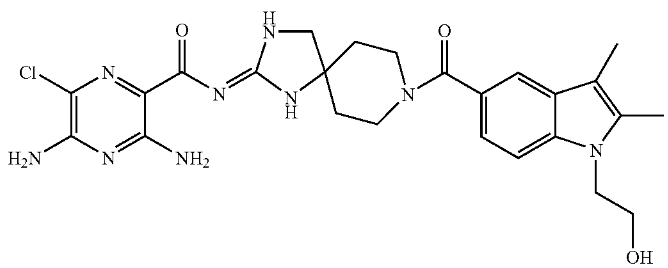 | 540 |
| 89 | 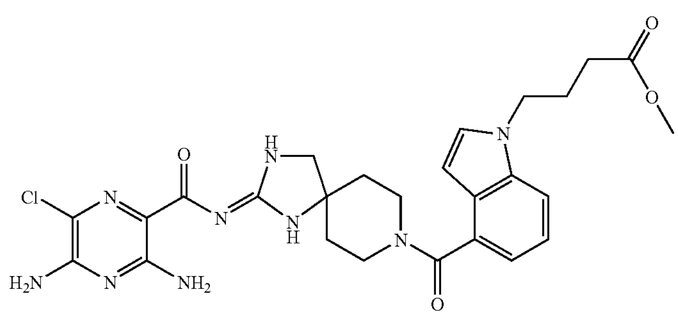 | 568/570 |
| 90 | 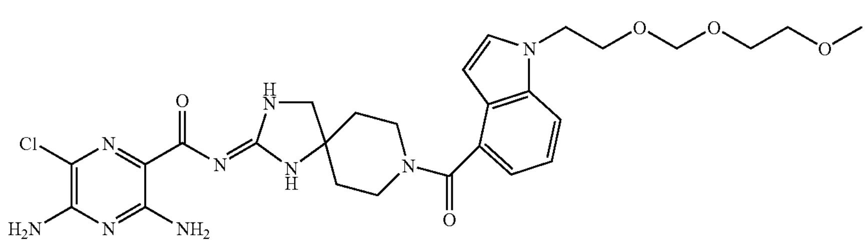 | 600/602 |

TABLE 1-continued

| Ex. | Structure | M/s [M + H]+ |
|---|---|---|
| 91 | 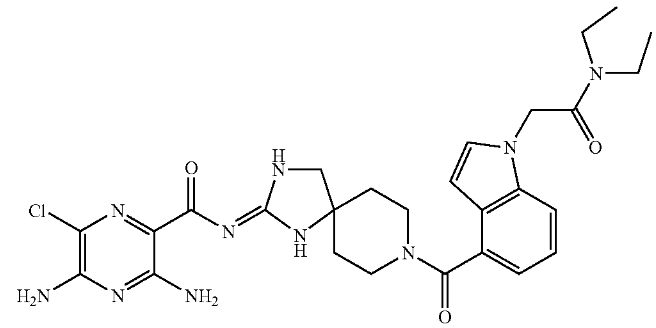 | 581/583 |
| 92 | 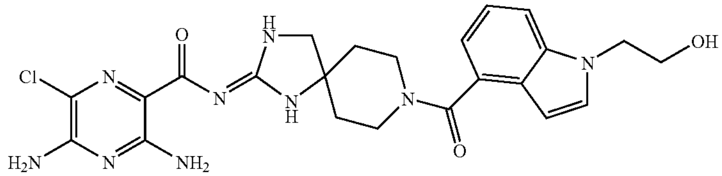 | 512/514 |
| 93 | 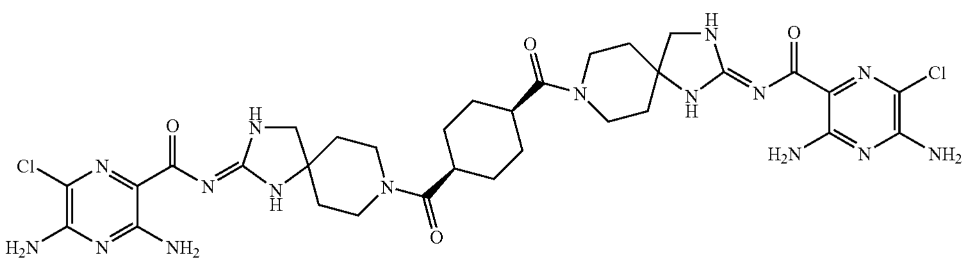 | 785 |
| 94 | 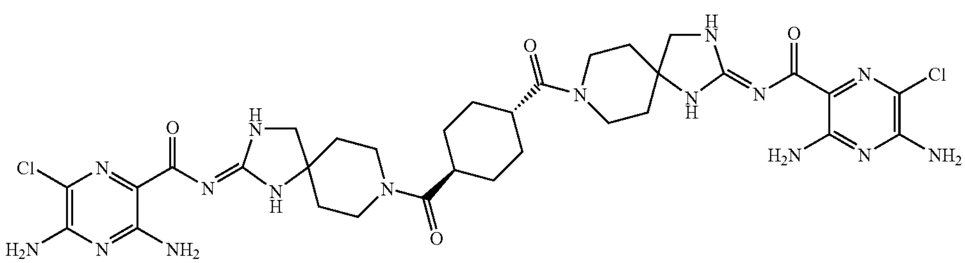 | [M + 2H]²⁺ = 393 |
| 95 | 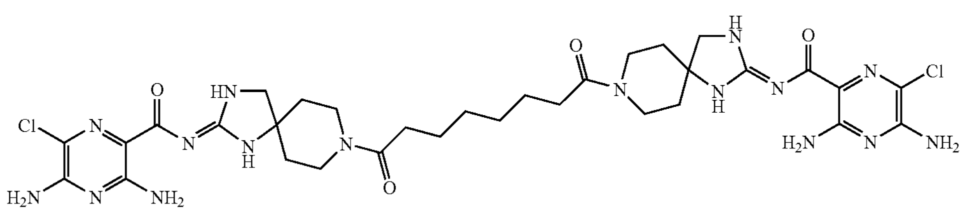 | 787 |
| 96 | 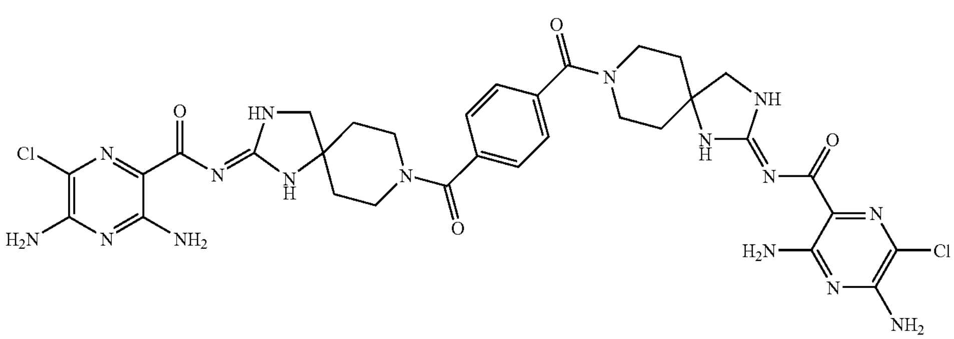 | 779 |

TABLE 1-continued

| Ex. | Structure | M/s [M + H]+ |
|---|---|---|
| 97 | 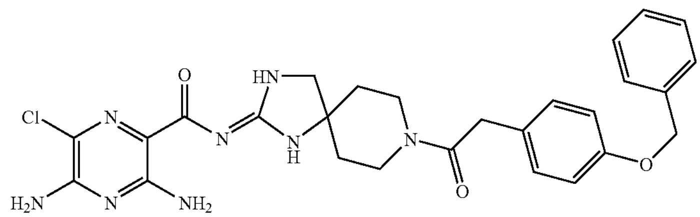 | 549 |
| 98 | 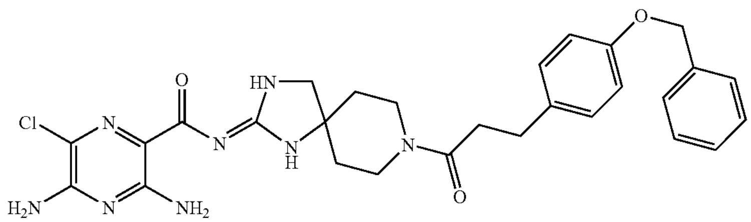 | 563 |
| 99 | 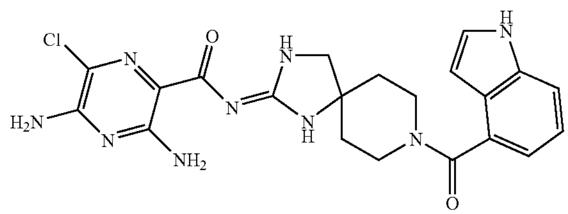 | 468 |
| 100 | 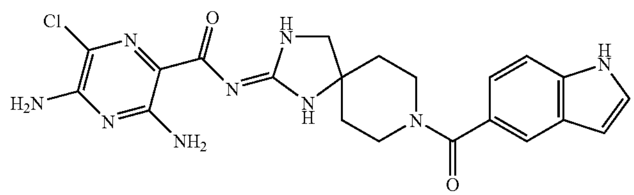 | 468 |
| 101 | 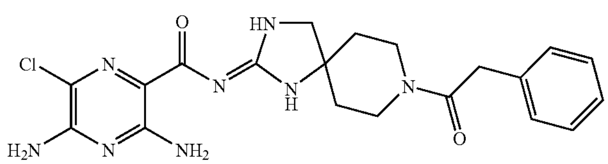 | 443 |
| 102 | Chiral | 675 |

TABLE 1-continued

| Ex. | Structure | M/s [M + H]+ |
|---|---|---|
| 103 | 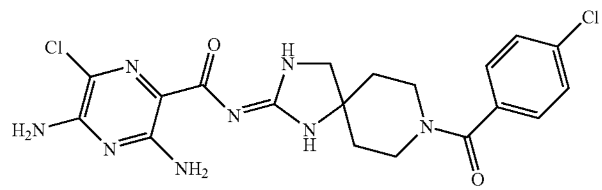 | 463 |
| 104 | 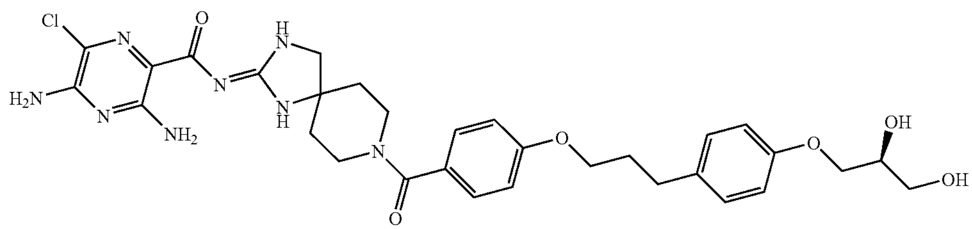 | 653 |
| 105 | 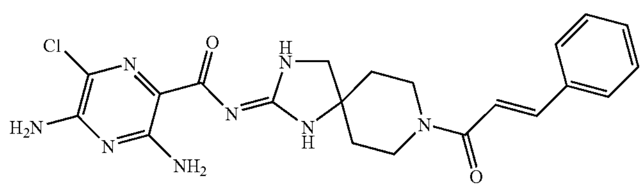 | 455 |
| 106 | 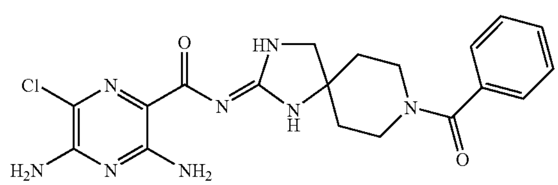 | 429 |
| 107 | 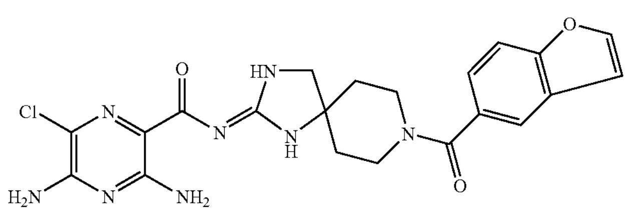 | 469 |
| 108 | 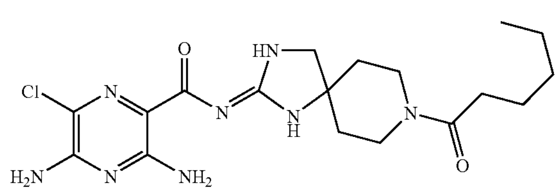 | 423 |
| 109 | 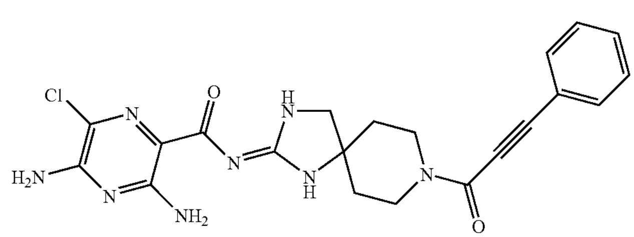 | 453 |

TABLE 1-continued

| Ex. | Structure | M/s [M + H]+ |
|---|---|---|
| 110 | 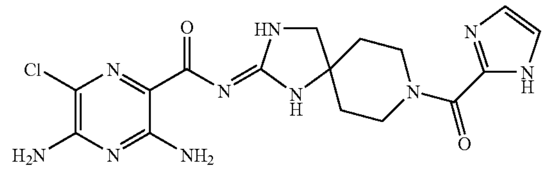 | 419 |
| 111 | 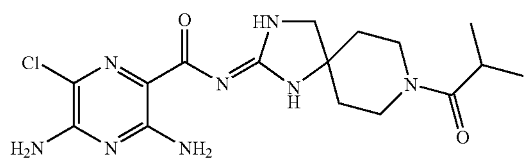 | 395 |
| 112 | 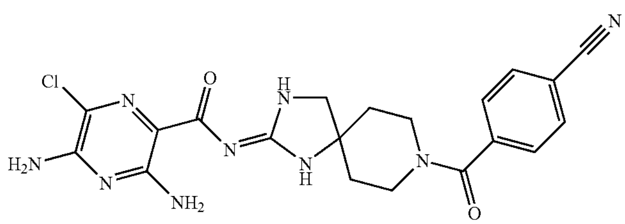 | 454 |
| 113 | 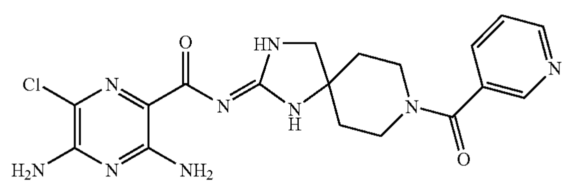 | 430 |
| 114 | 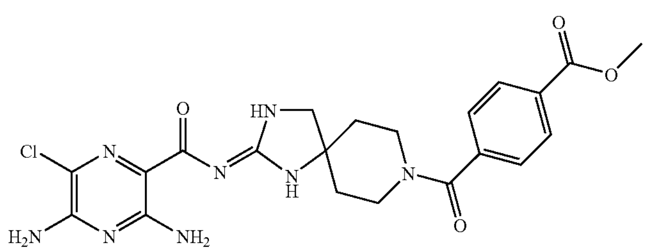 | 487 |
| 115 | 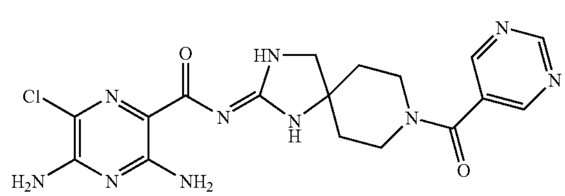 | 431 |
| 116 | 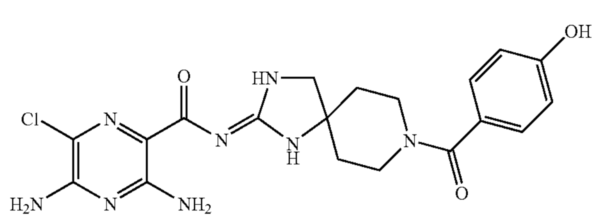 | 445 |

TABLE 1-continued

| Ex. | Structure | M/s [M + H]+ |
|---|---|---|
| 117 | 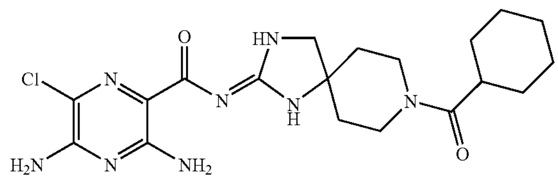 | 435 |
| 118 | 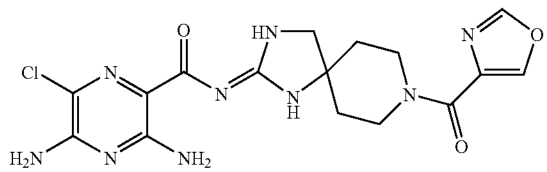 | 420 |
| 119 | 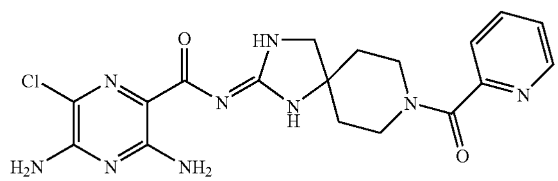 | 430 |
| 120 | 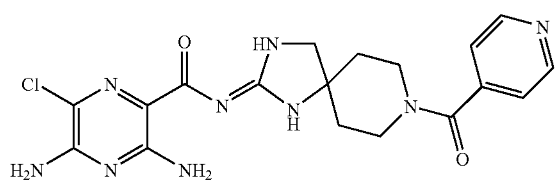 | 430 |
| 121 | 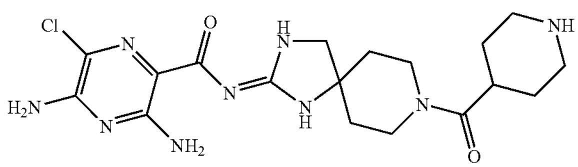 | 436 |
| 122 | 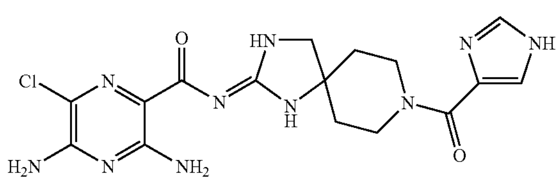 | 419 |
| 123 | 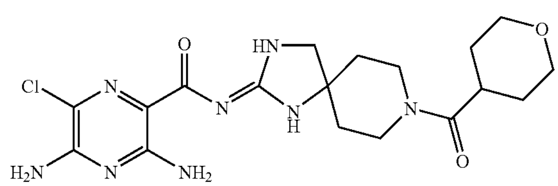 | 437 |
| 124 | 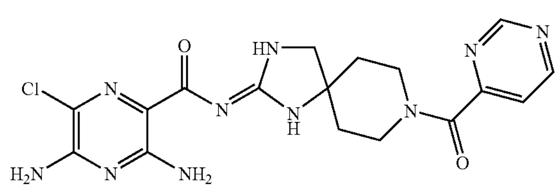 | 431 |

TABLE 1-continued

| Ex. | Structure | M/s [M + H]+ |
|---|---|---|
| 125 | 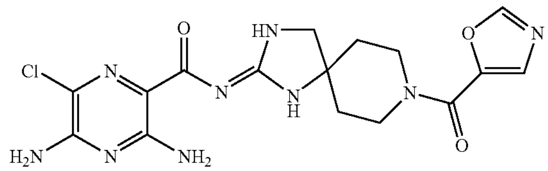 | 420 |
| 126 | 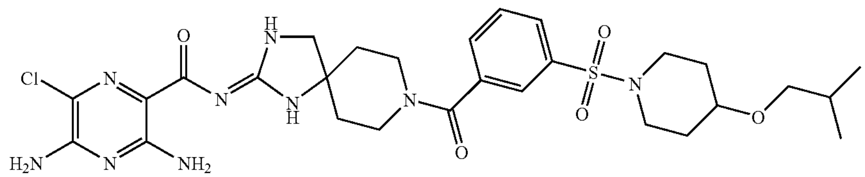 | 648.4 |
| 127 | 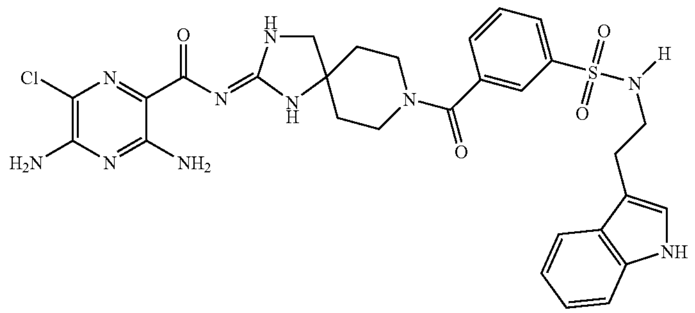 | 651.3 |
| 128 | 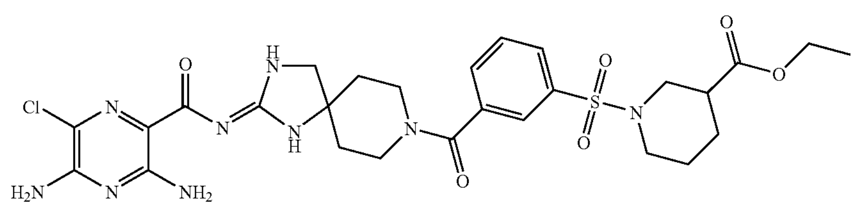 | 648.3 |
| 129 | 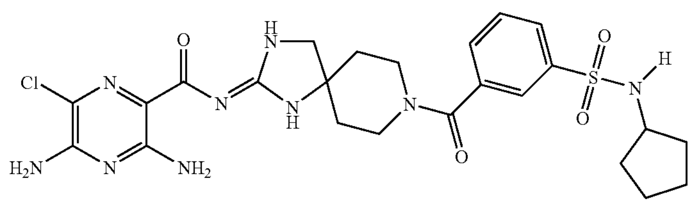 | 576.3 |
| 130 | 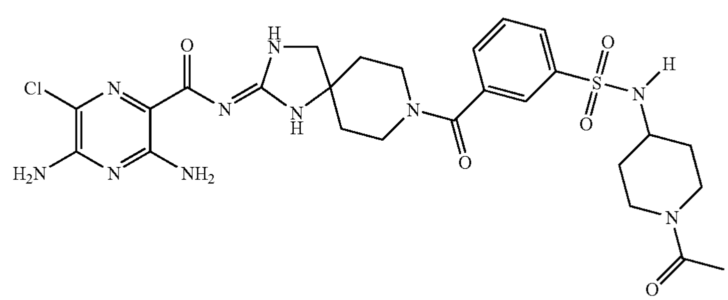 | 633.3 |

TABLE 1-continued

| Ex. | Structure | M/s [M + H]+ |
|---|---|---|
| 131 | 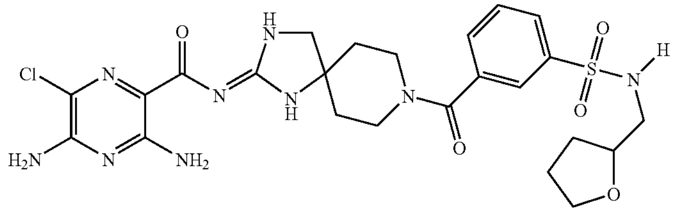 | 592.3 |
| 132 | 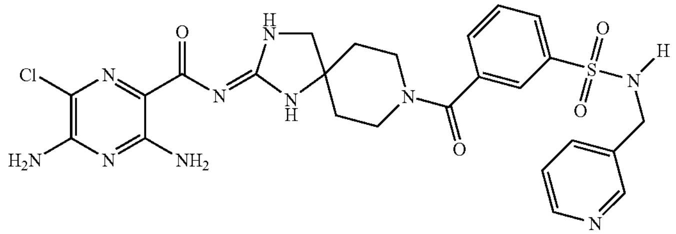 | 599.3 |
| 133 | 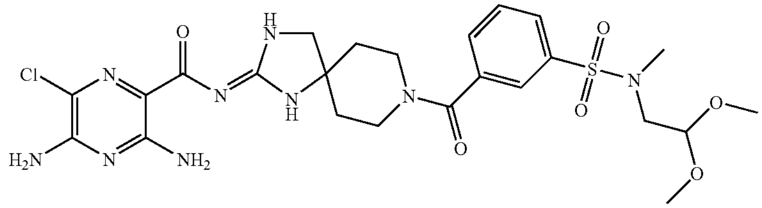 | 610.3 |
| 134 | 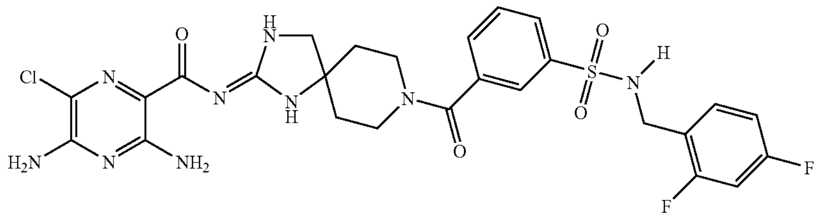 | 634.3 |
| 135 | 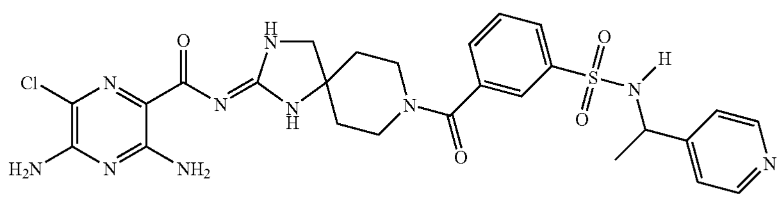 | 613.3 |
| 136 | 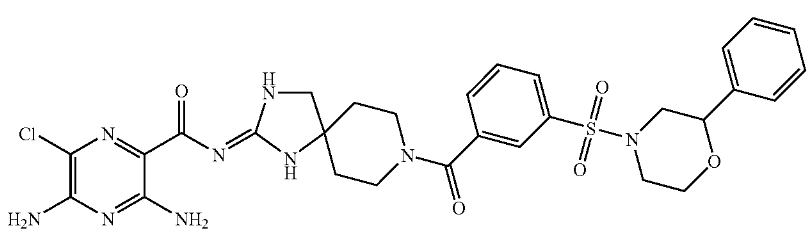 | 654.3 |

TABLE 1-continued

| Ex. | Structure | M/s [M + H]+ |
|---|---|---|
| 137 | 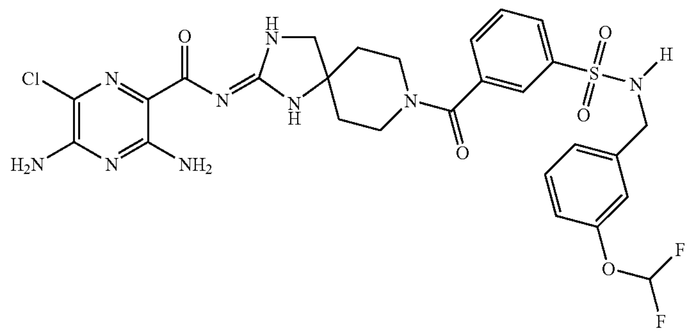 | 664.3 |
| 138 | 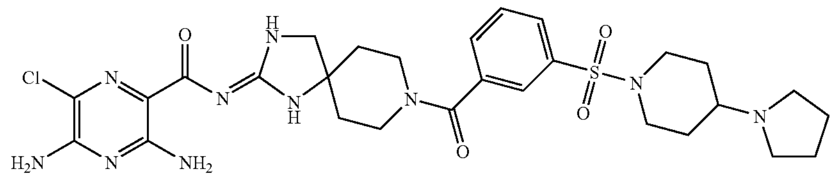 | 645.4 |
| 139 | 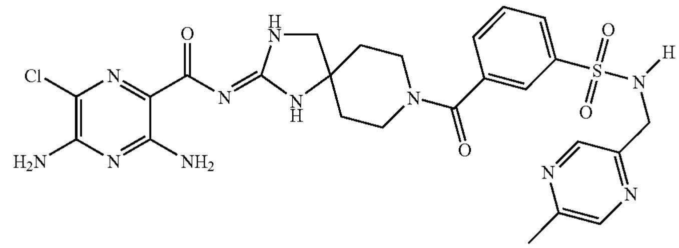 | 614.3 |
| 140 | 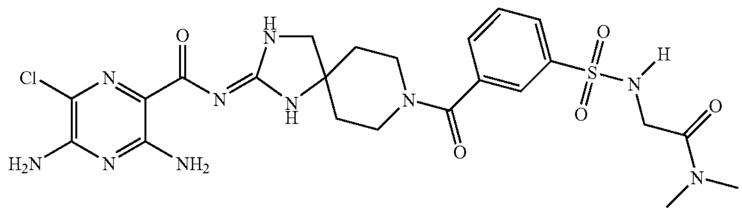 | 593.4 |
| 141 | 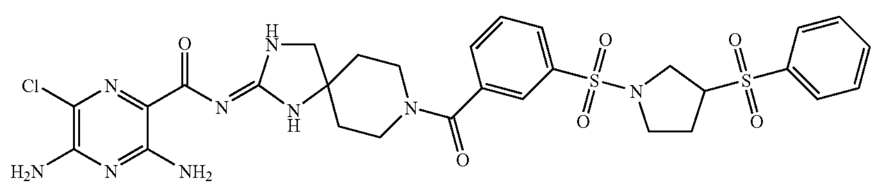 | 702.3 |
| 142 | 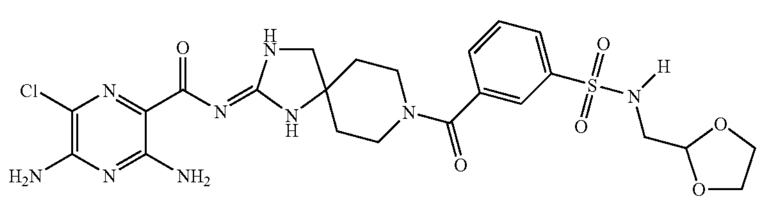 | 594.3 |

TABLE 1-continued

| Ex. | Structure | M/s [M + H]+ |
|---|---|---|
| 143 | 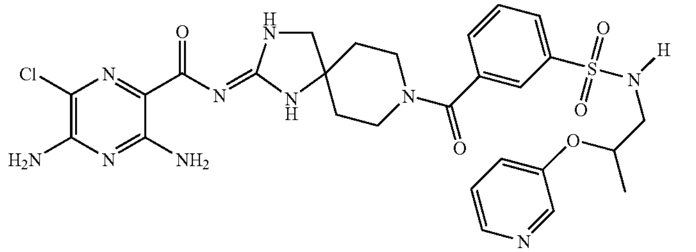 | 643.3 |
| 144 | 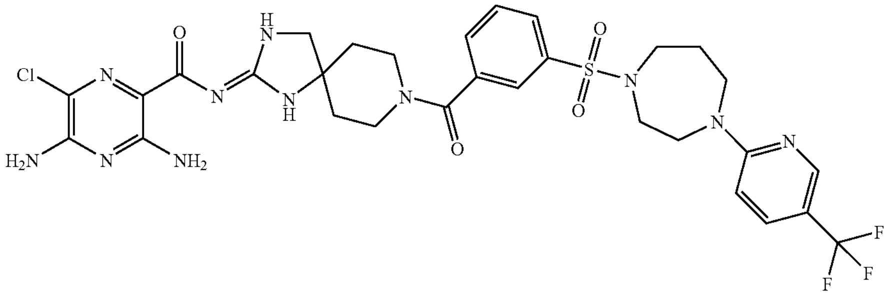 | 736.4 |
| 145 | 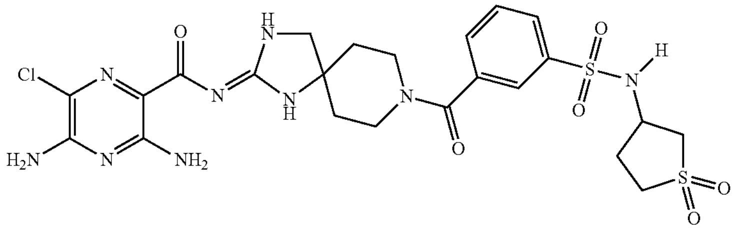 | 626.3 |
| 146 | 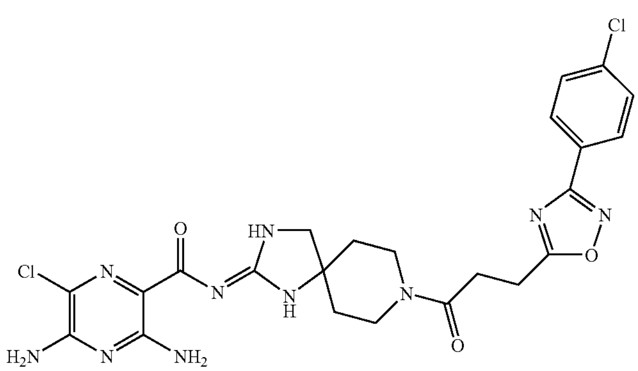 | 559.3 |
| 147 | 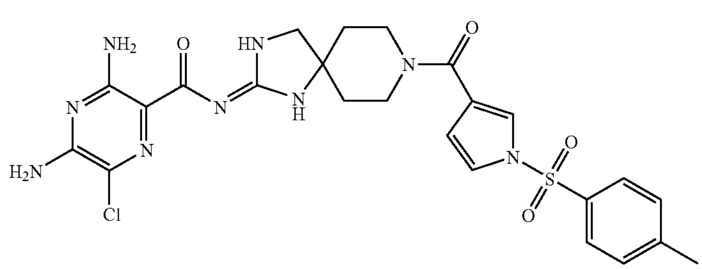 | 572.08 |

TABLE 1-continued

| Ex. | Structure | M/s [M + H]+ |
|---|---|---|
| 148 | 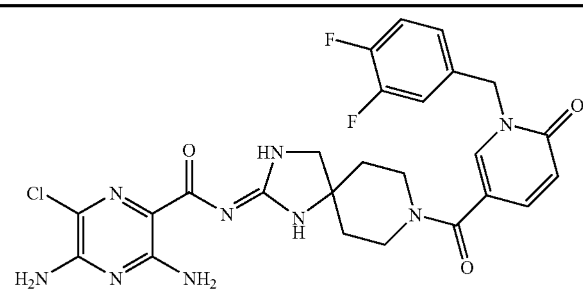 | 572.0 |
| 149 | 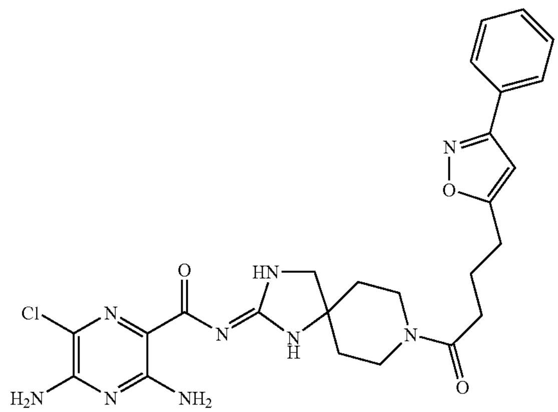 | 538.4 |
| 150 | 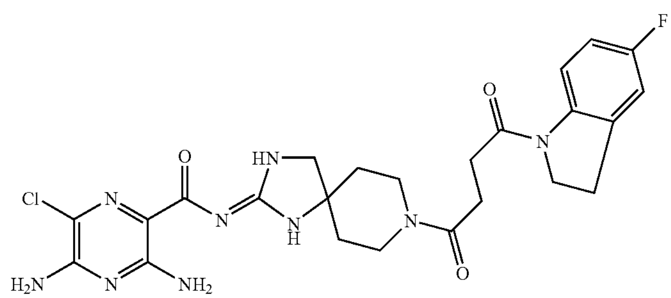 | 544.4 |
| 151 | 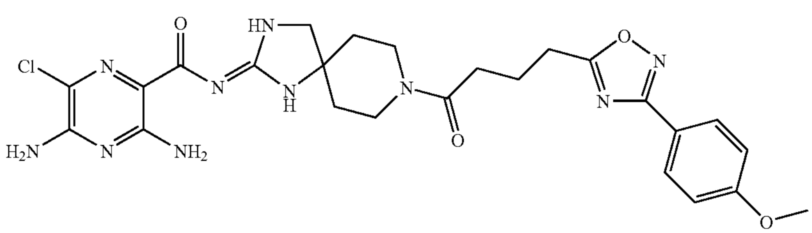 | 569.4 |
| 152 | 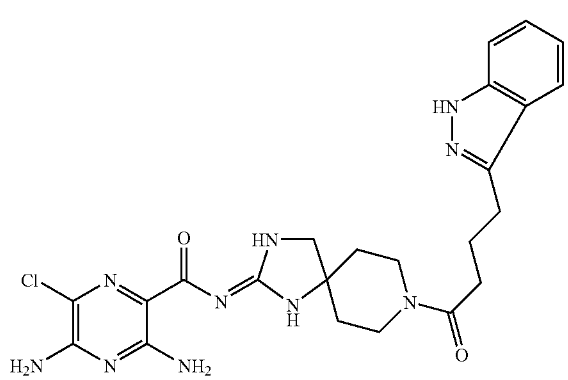 | 511.4 |

TABLE 1-continued
| Ex. | Structure | M/s [M + H]+ |
|---|---|---|
| 153 | 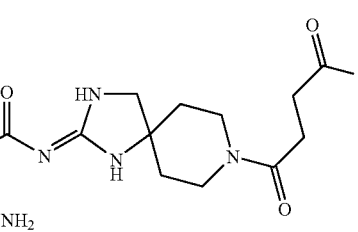 | 604.3 |
| 154 | 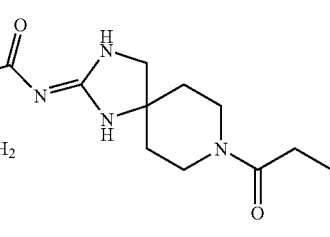 | 528.3 |
| 155 | 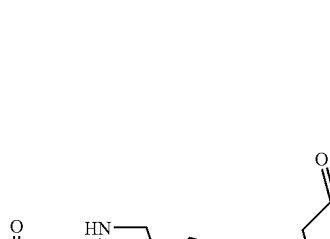 | 633.4 |
| 156 | 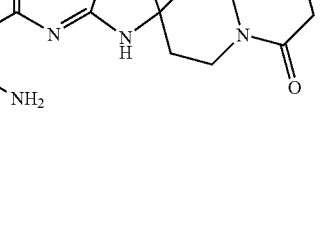 | 526.3 |
| 157 | 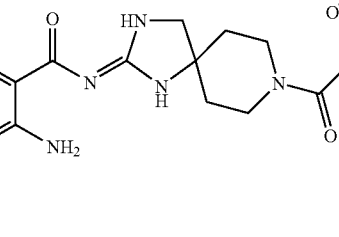 | 556.4 |

TABLE 1-continued

| Ex. | Structure | M/s [M + H]+ |
|---|---|---|
| 158 | 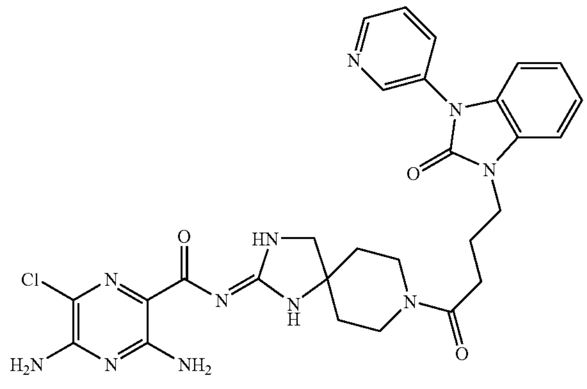 | 604.4 |
| 159 | 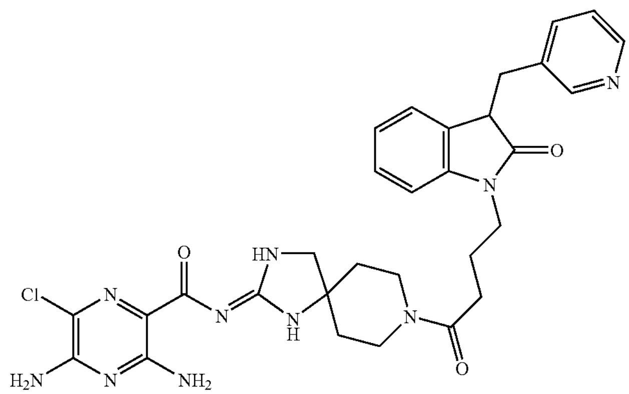 | 617.4 |
| 160 | 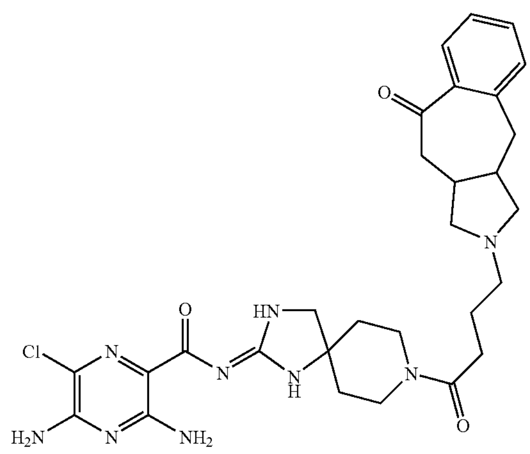 | 594.4 |
| 161 | 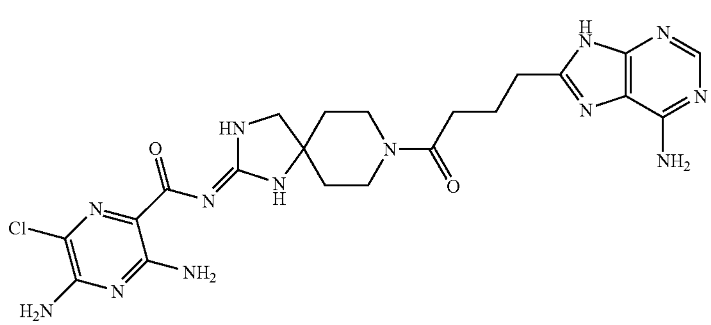 | 528.4 |

TABLE 1-continued

| Ex. | Structure | M/s [M + H]+ |
|---|---|---|
| 162 | 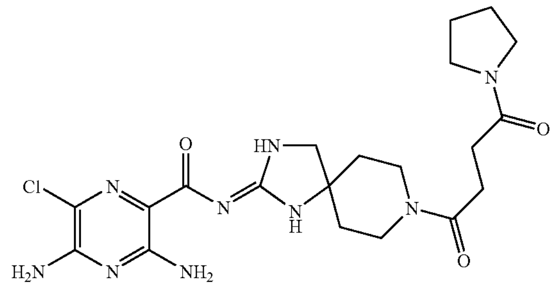 | 478.3 |
| 163 | 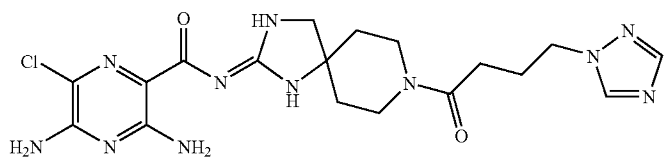 | 462.3 |
| 164 | 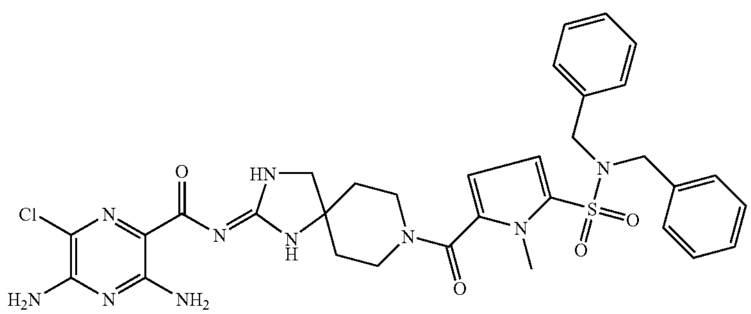 | 691.04 |
| 165 | 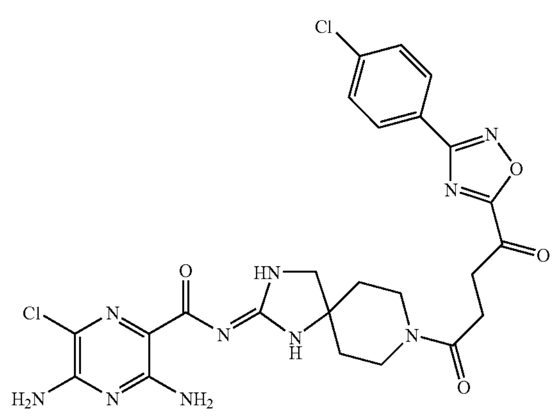 | 573.05 |

TABLE 1-continued
| Ex. | Structure | M/s [M + H]+ |
|---|---|---|
| 166 | 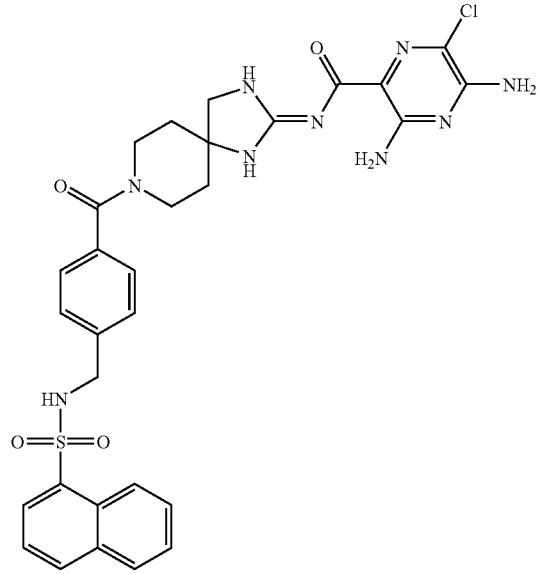 | 648.06 |
| 167 | 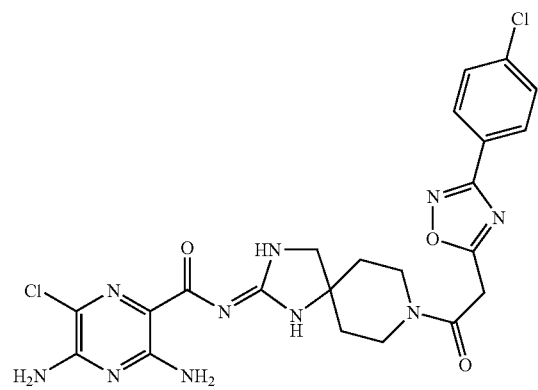 | 545.3 |
| 168 | 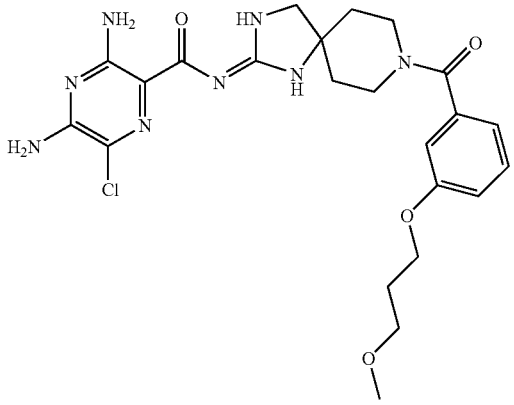 | 517.07 |

TABLE 1-continued

| Ex. | Structure | M/s [M + H]+ |
|---|---|---|
| 169 | 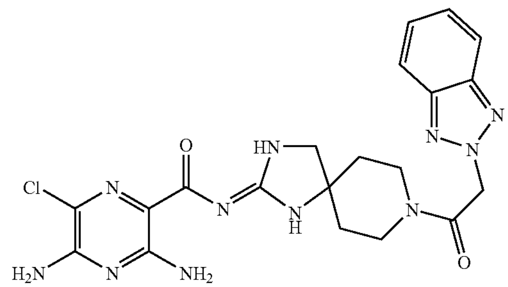 | 484.04 |
| 170 | 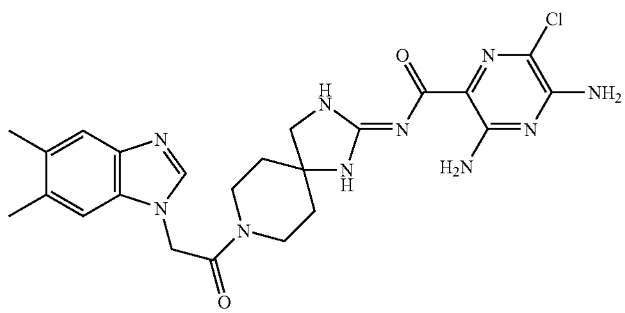 | 511.04 |
| 171 | 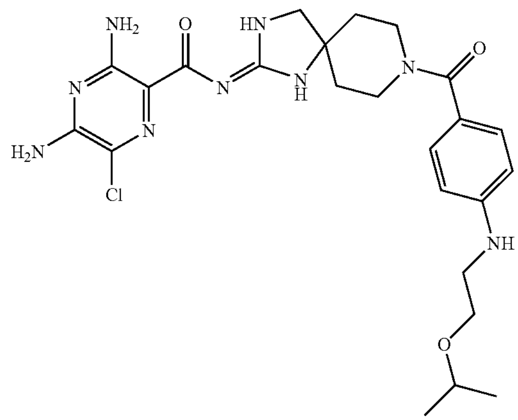 | 530.08 |
| 172 | 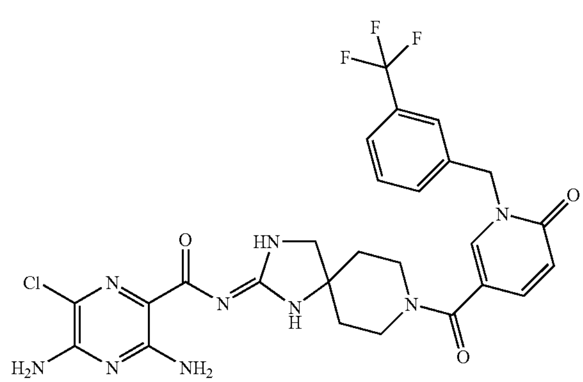 | 603.99 |

TABLE 1-continued

| Ex. | Structure | M/s [M + H]+ |
|---|---|---|
| 173 | 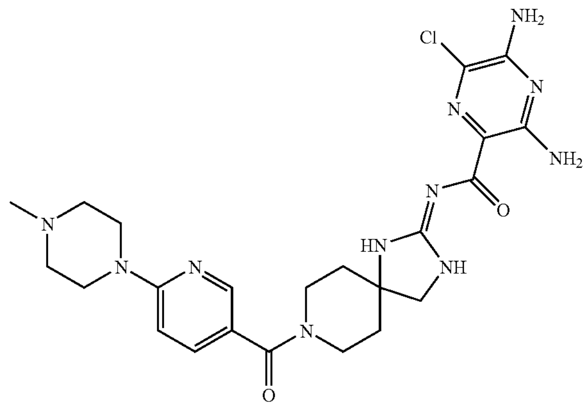 | 530.19 |
| 174 | 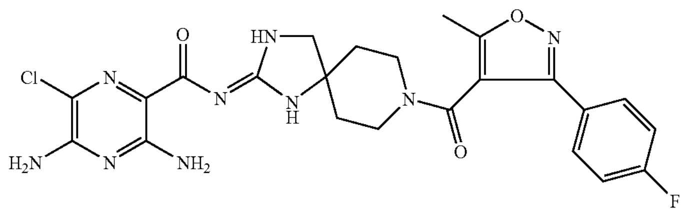 | 527.99 |
| 175 | 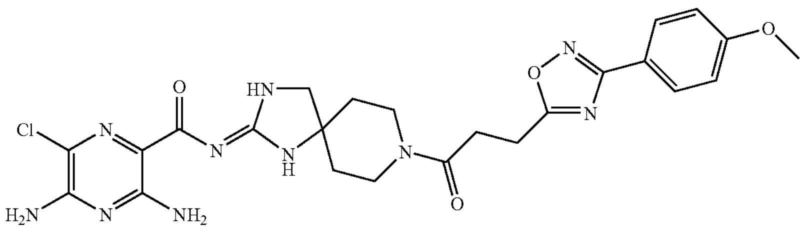 | 555.07 |
| 176 | 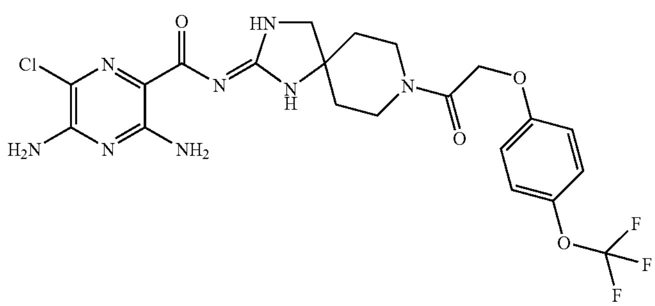 | 608.05 |
| 177 | 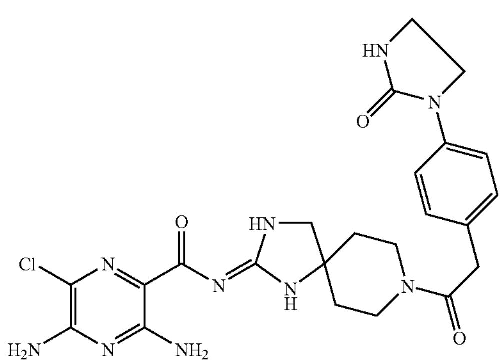 | 527.07 |

TABLE 1-continued

| Ex. | Structure | M/s [M + H]+ |
|---|---|---|
| 178 | 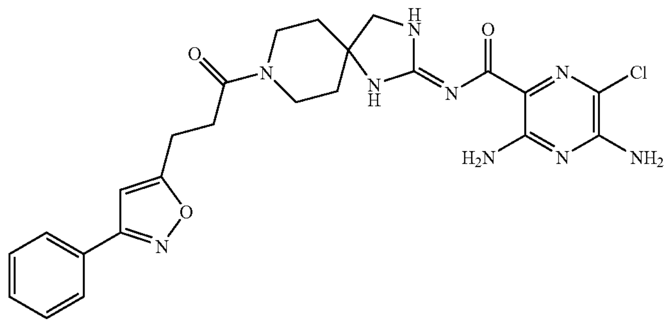 | 524.1 |
| 179 | 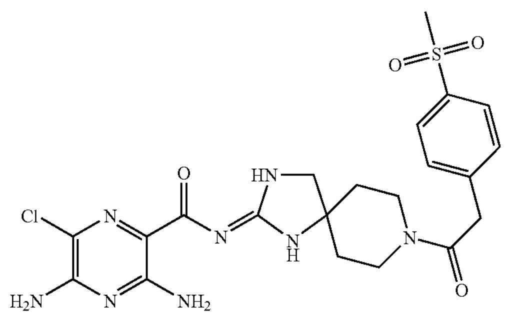 | 520.99 |
| 180 | 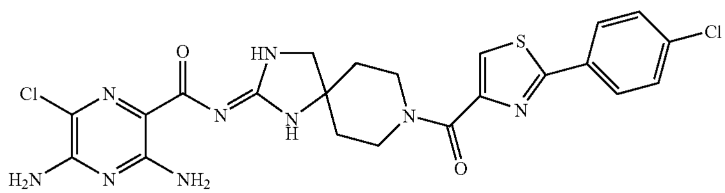 | 545.95 |
| 181 | 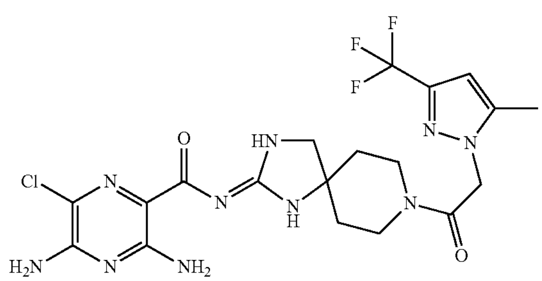 | 514.98 |
| 182 | 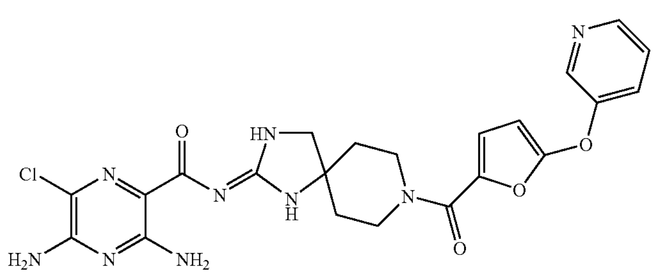 | 512.01 |
| 183 | 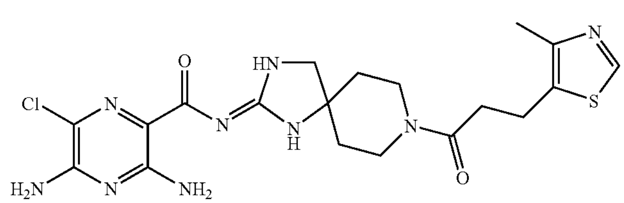 | 478.01 |

TABLE 1-continued

| Ex. | Structure | M/s [M + H]+ |
|---|---|---|
| 184 | 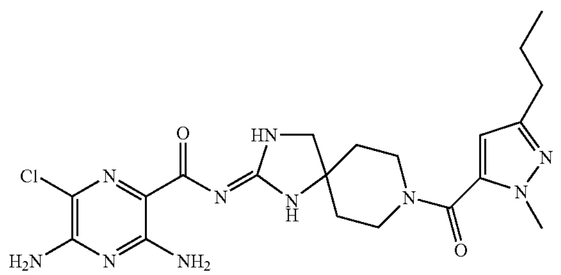 | 475.08 |
| 185 | 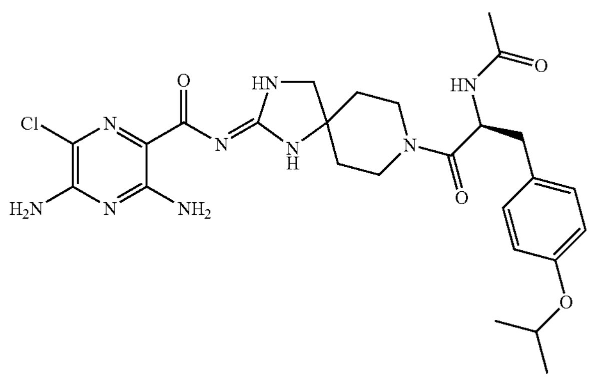 | 572.09 |
| 186 | 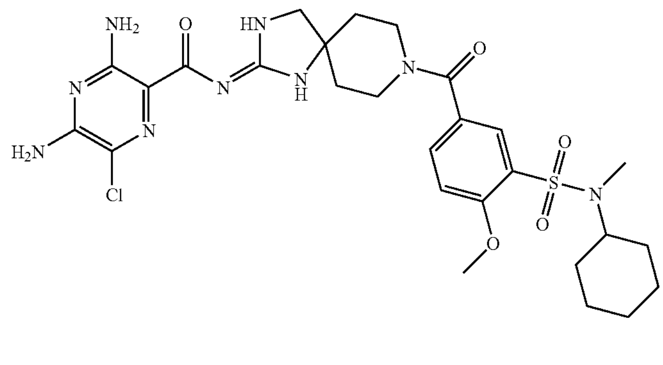 | 634.09 |
| 187 | 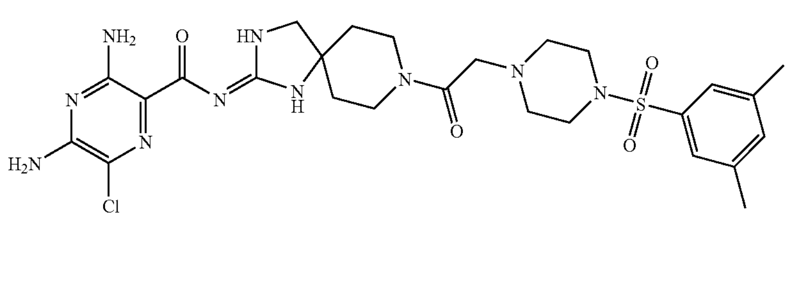 | 619.12 |

| Ex. | Structure | M/s [M + H]+ |
|---|---|---|
| 188 | 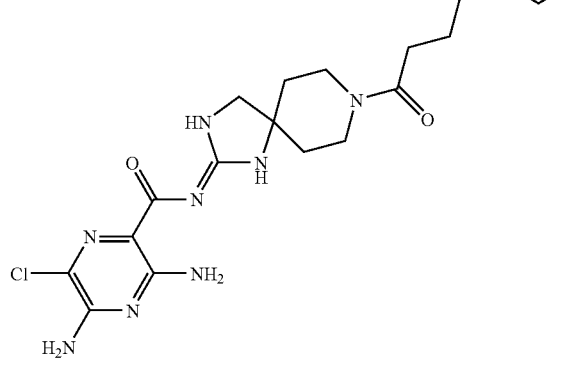 | 496.02 |
| 189 | 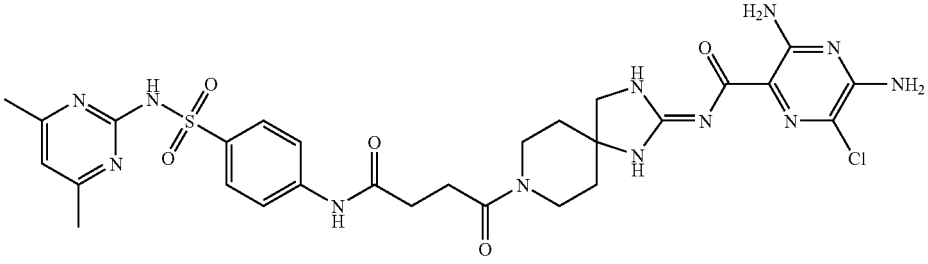 | 685.08 |
| 190 | 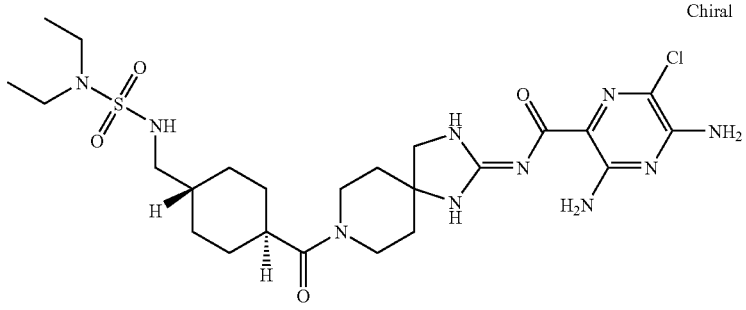  Chiral | 599.2 |
| 191 | 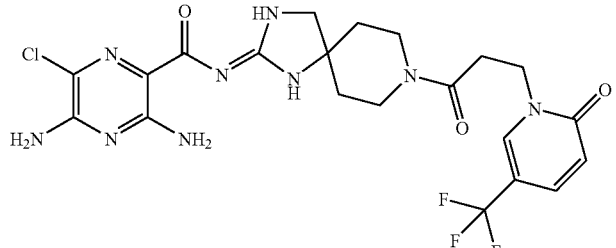 | 542.01 |

TABLE 1-continued

| Ex. | Structure | M/s [M + H]+ |
|---|---|---|
| 192 | 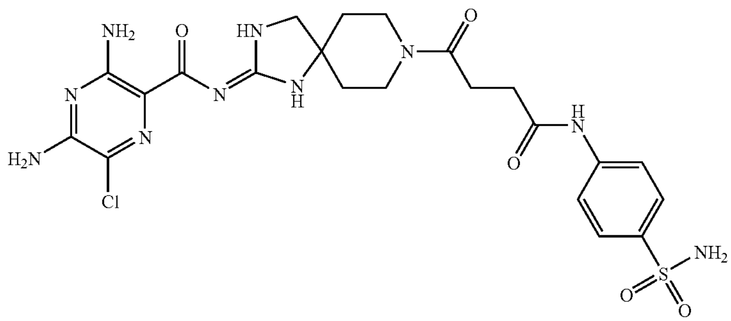 | 579.03 |
| 193 | 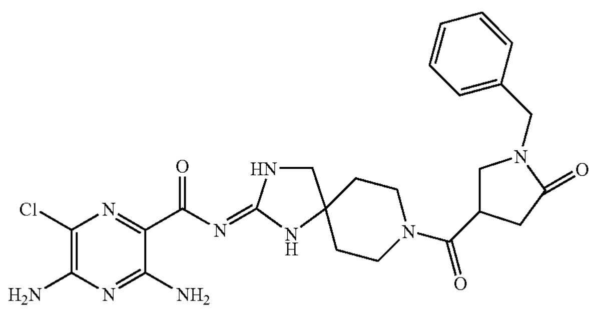 | 526.05 |
| 194 | Chiral | 553.09 |
| 195 | 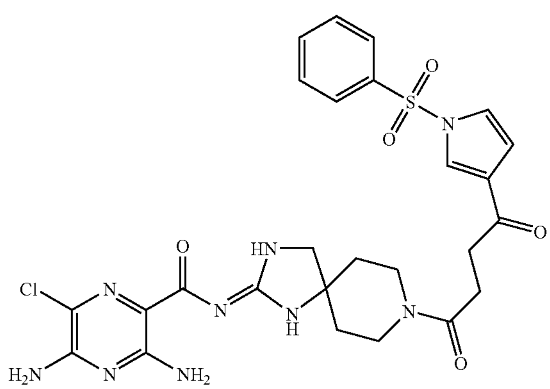 | 614.3 |
| 196 | 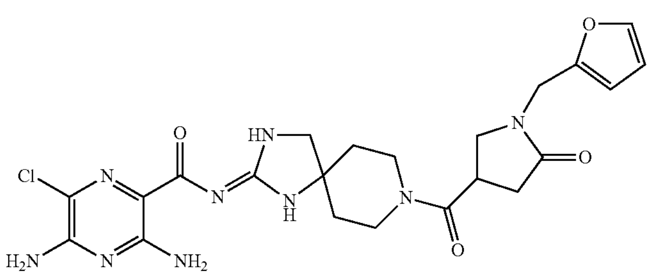 | 516.06 |

TABLE 1-continued

| Ex. | Structure | M/s [M + H]+ |
|---|---|---|
| 197 | 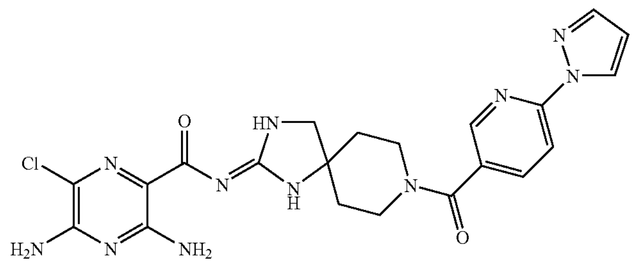 | 496.01 |
| 198 | Chiral | 528.04 |
| 199 | 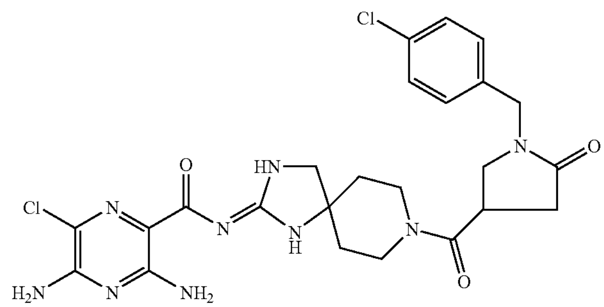 | 560.14 |
| 200 | 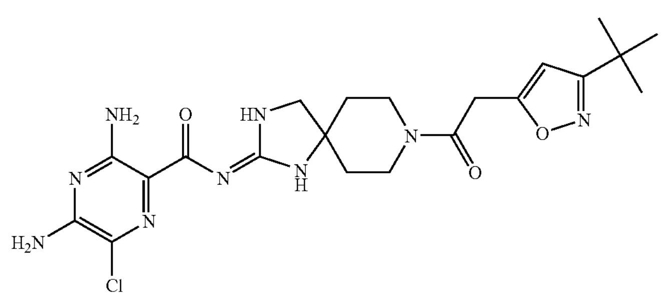 | 490.05 |

TABLE 1-continued

| Ex. | Structure | M/s [M + H]+ |
|---|---|---|
| 201 | 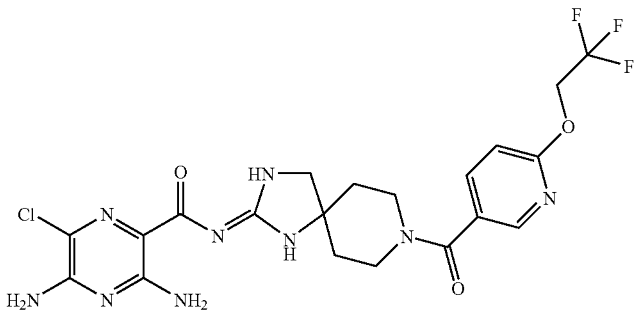 | 528.06 |
| 202 | 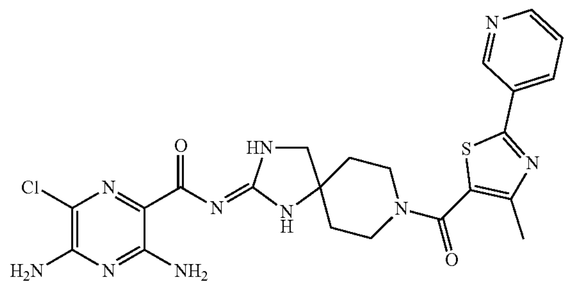 | 527.02 |
| 203 | 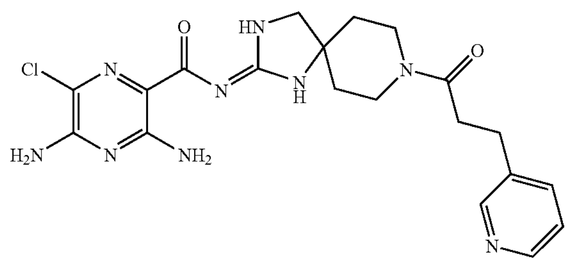 | 458.1 |
| 204 | 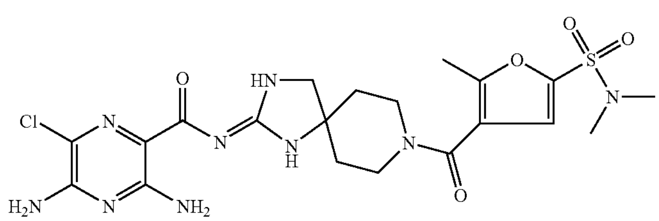 | 540.02 |
| 205 | 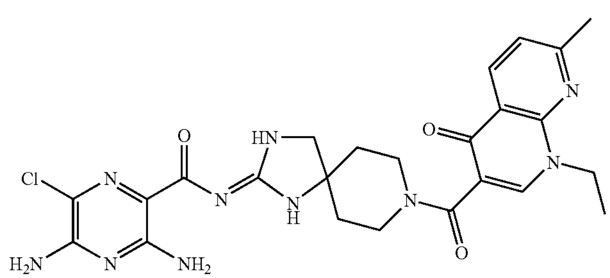 | 539.11 |
| 206 | 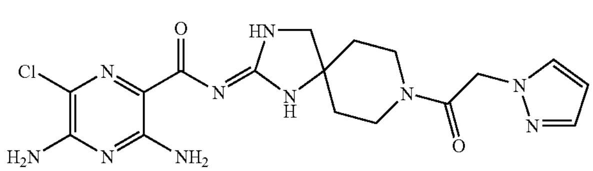 | 433.05 |

TABLE 1-continued

| Ex. | Structure | M/s [M + H]+ |
|---|---|---|
| 207 | 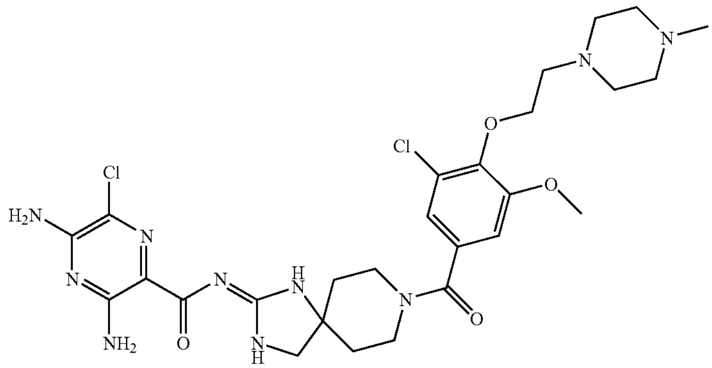 | 635.19 |
| 208 | 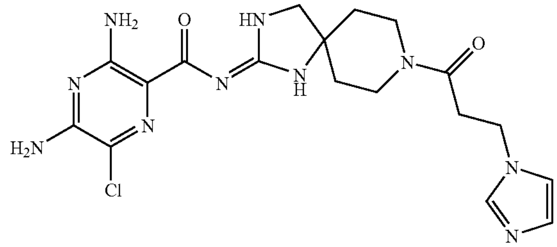 | 447.09 |
| 209 | 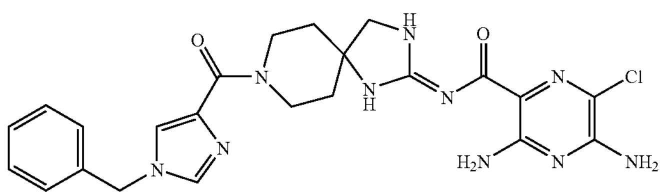 | 509.09 |
| 210 | 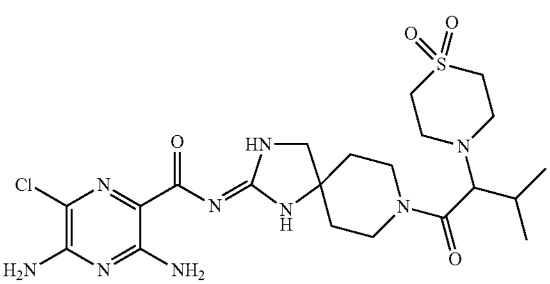 | 542.00 |
| 211 | 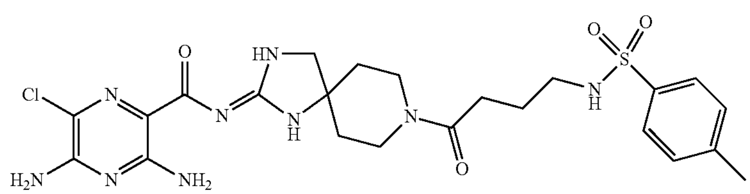 | 564.06 |
| 212 | 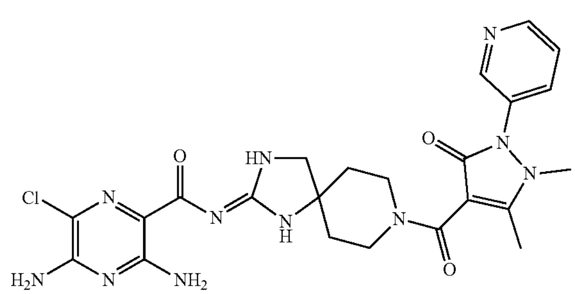 | 539.11 |

TABLE 1-continued

| Ex. | Structure | M/s [M + H]⁺ |
|---|---|---|
| 213 | 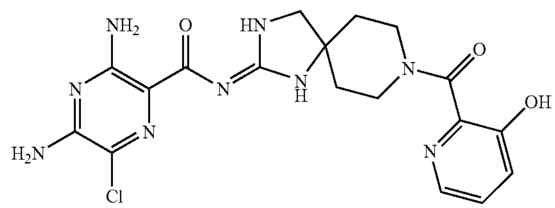 | 445.96 |
| 214 | 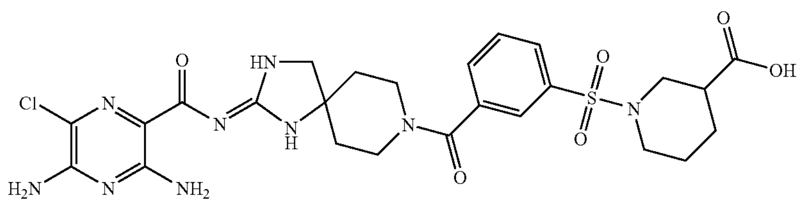 | 620.1 |
| 215 | 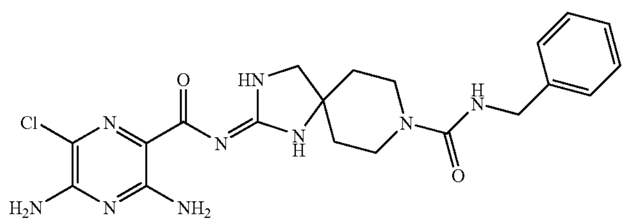 | 458.1 |
| 216 | 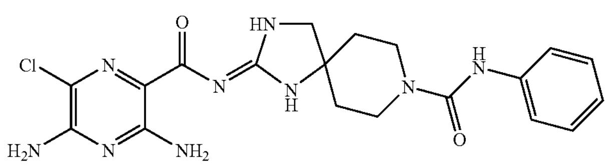 | |
| 217 | 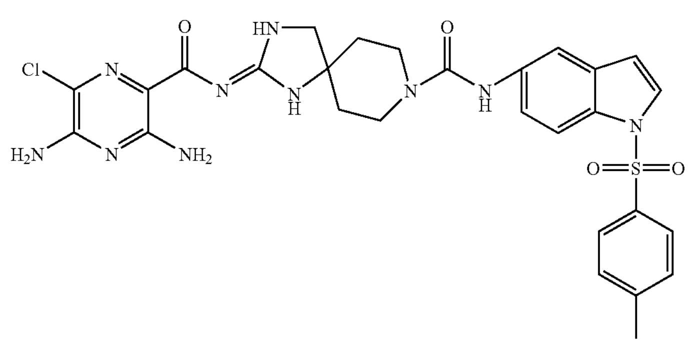 | 637.1 |
| 218 | 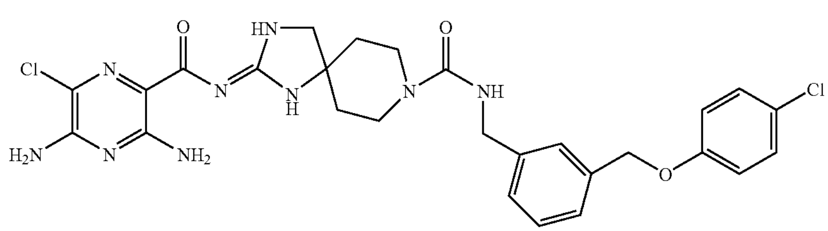 | 598.05 |

TABLE 1-continued

| Ex. | Structure | M/s [M + H]+ |
|---|---|---|
| 219 | 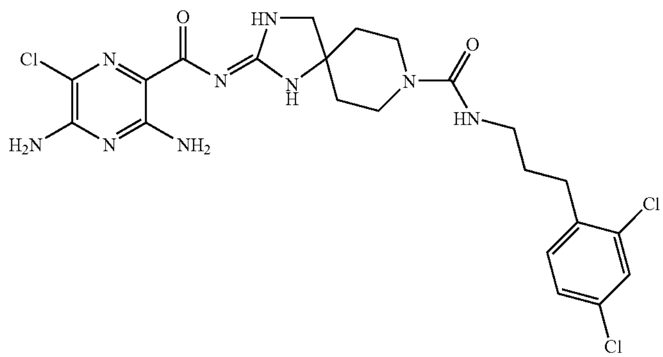 | 554.0 |
| 220 | 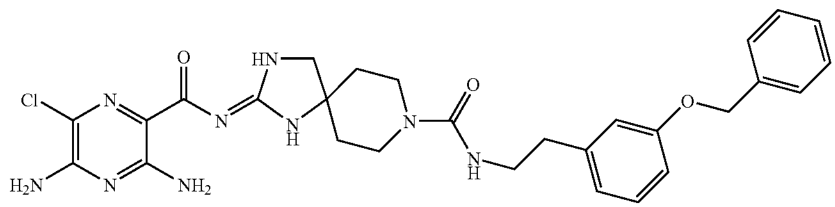 | 578.2 |
| 221 | 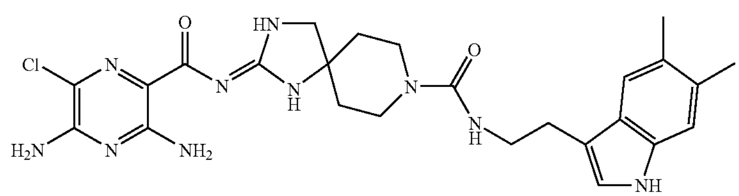 | 539.2 |
| 222 | 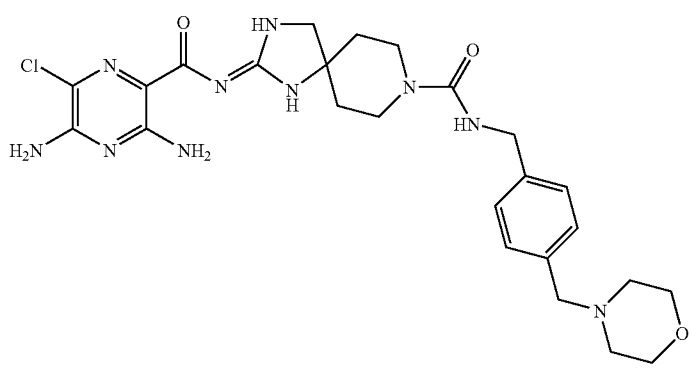 | 557.2 |
| 223 | 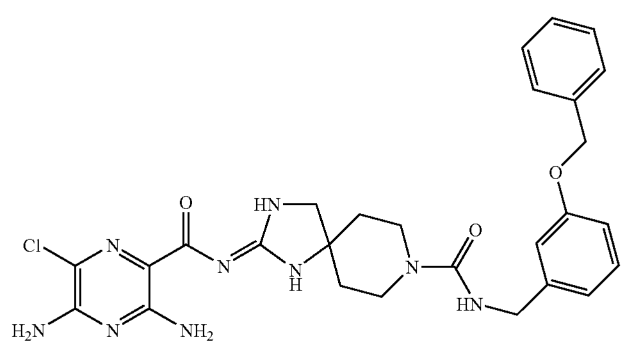 | 564.1 |

TABLE 1-continued

| Ex. | Structure | M/s [M + H]+ |
|---|---|---|
| 224 | 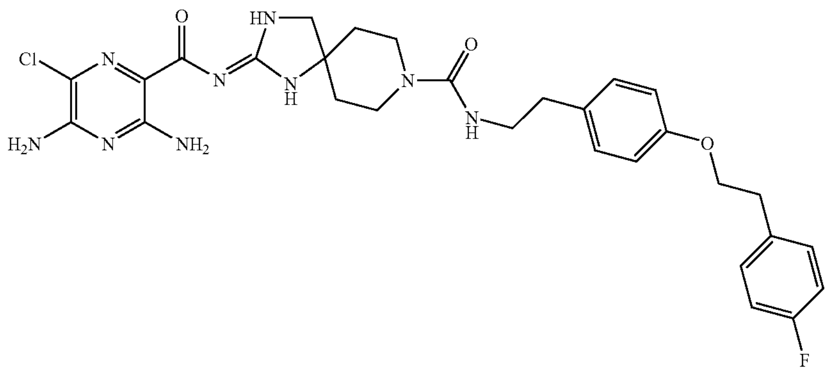 | 610.2 |
| 225 | 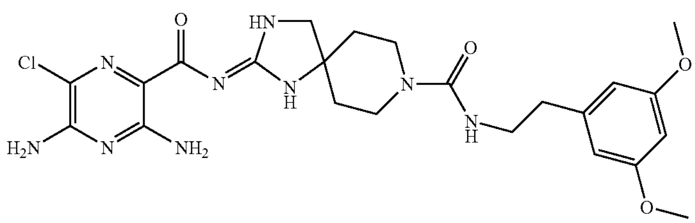 | 532.1 |
| 226 | 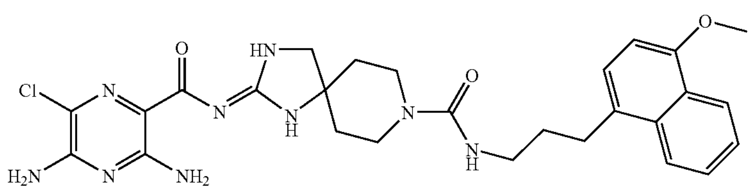 | 566.1 |
| 227 | 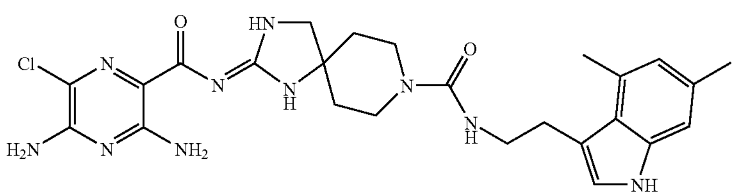 | 539.2 |
| 228 | 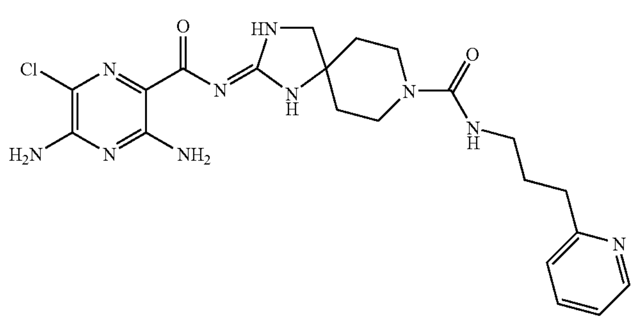 | 487.1 |
| 229 | 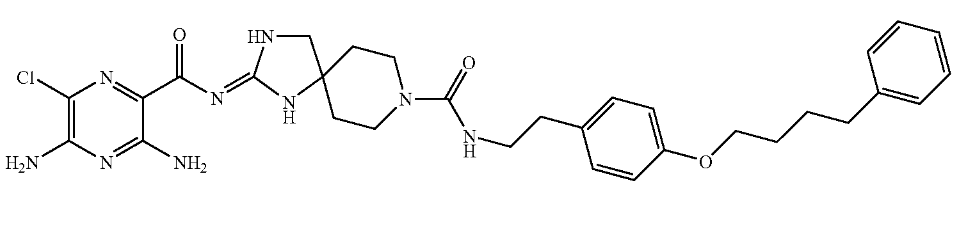 | 620.2 |

TABLE 1-continued

| Ex. | Structure | M/s [M + H]+ |
|---|---|---|
| 230 | 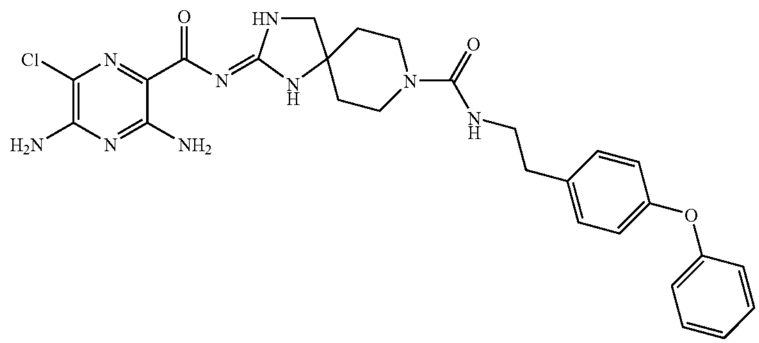 | 564.2 |
| 231 | 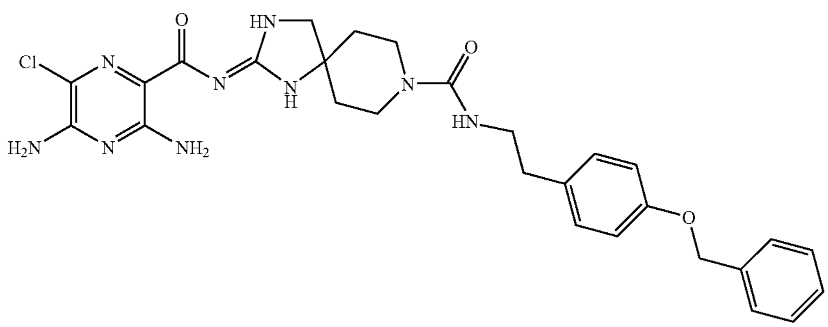 | 578.2 |
| 232 | 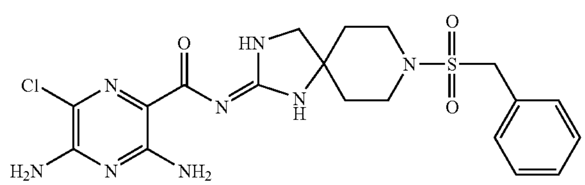 | 478.98 |
| 233 | 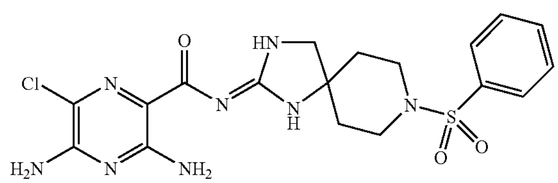 | 517.9 |
| 234 | 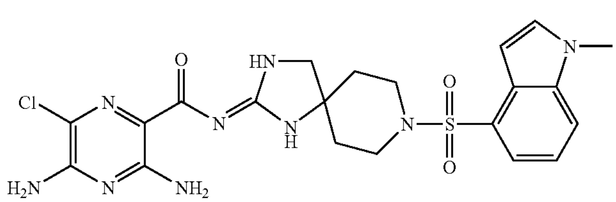 | 517.9 |
| 235 | 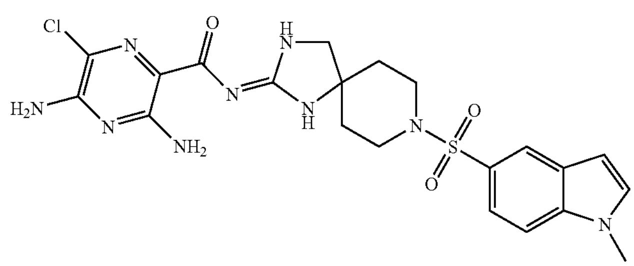 | 518.1 |

TABLE 1-continued

| Ex. | Structure | M/s [M + H]+ |
|---|---|---|
| 236 | 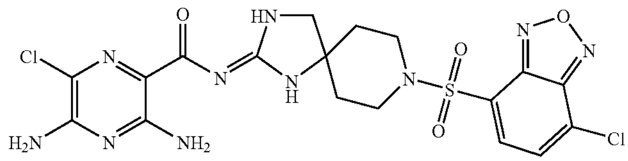 | 540.9 |
| 237 | 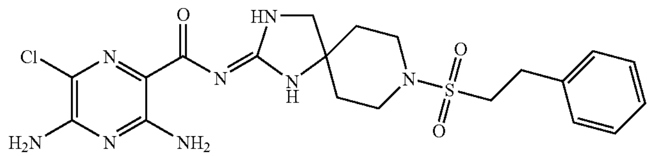 | 493.1 |
| 238 | 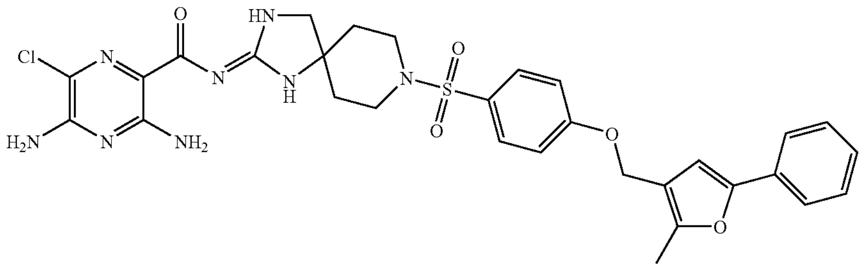 | 652.2 |
| 239 | 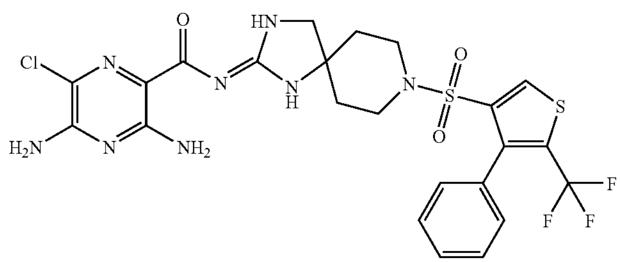 | 615.1 |
| 240 | 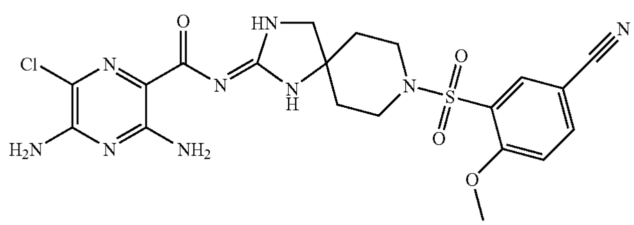 | 520.1 |
| 241 | 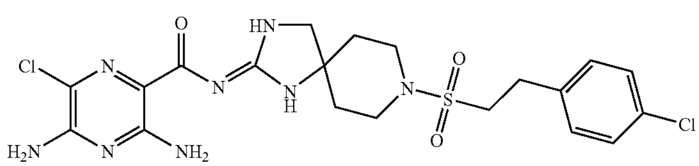 | 527.0 |
| 242 | 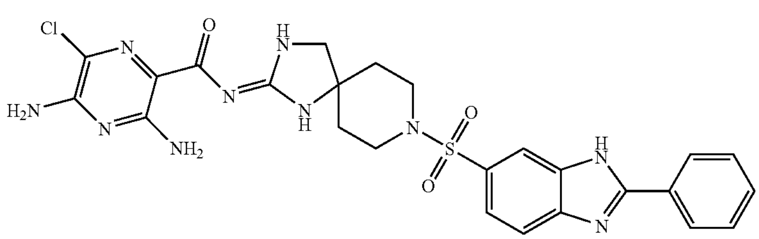 | 581.1 |

TABLE 1-continued

| Ex. | Structure | M/s [M + H]+ |
|---|---|---|
| 243 | 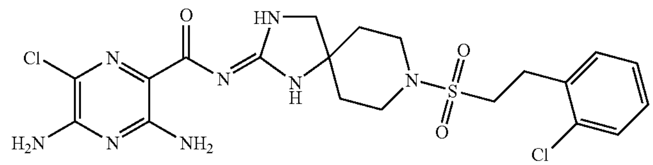 | 527.1 |
| 244 | 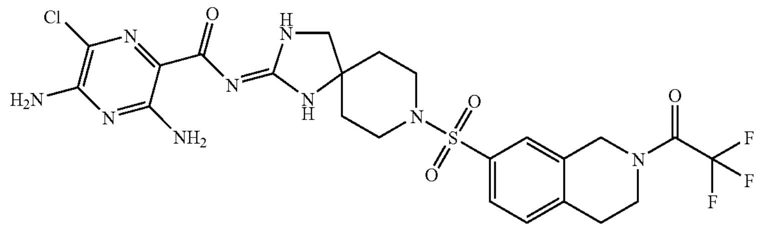 | 616.1 |
| 245 | 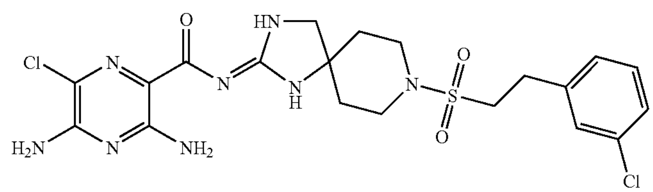 | 527.0 |
| 246 | 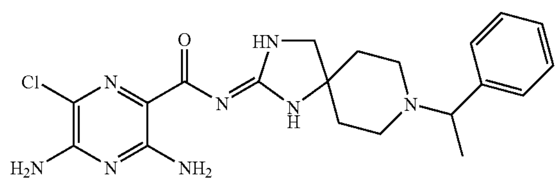 | 429 |
| 247 | 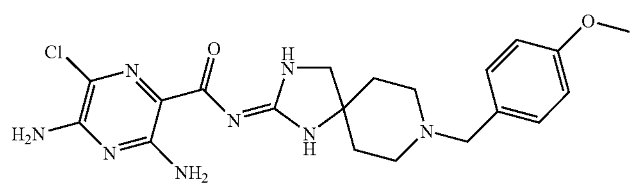 | 445 |
| 248 | 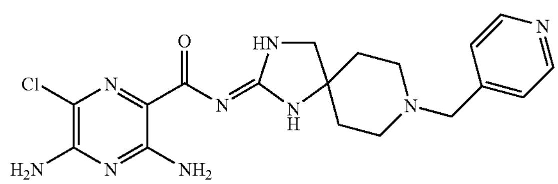 | 416 |
| 249 | 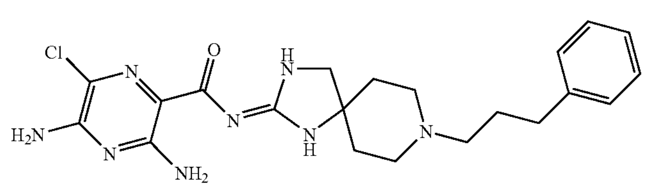 | 443 |
| 250 | 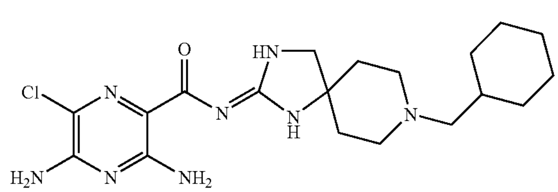 | 421 |

TABLE 1-continued

| Ex. | Structure | M/s [M + H]+ |
|---|---|---|
| 251 | 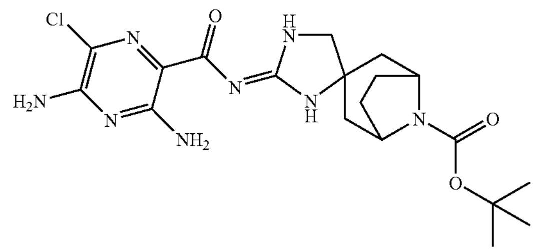 | 451 |
| 252 | 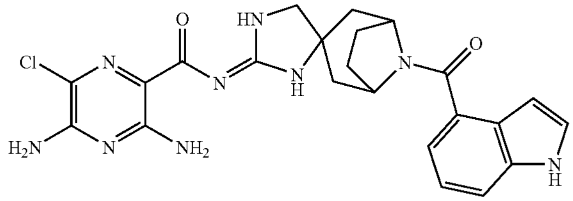 | 494.15 |
| 253 | 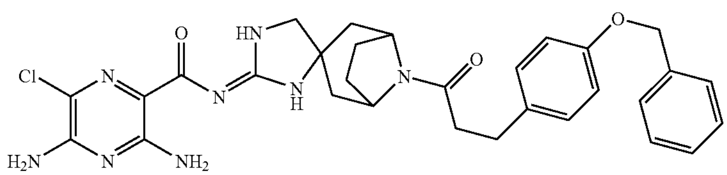 | 589.20 |

General Conditions

LCMS are recorded using a Phenomenex Gemini 50 mm×3.0 mm, 3 um column. Low pH methods use a gradient of 5-95% acetonitrile in water −0.1% TFA, high pH methods use 5-95% acetonitrile in water −0.1% NH$_3$. [M+H]$^+$ refer to monoisotopic molecular weights.

| | |
|---|---|
| 9-BBN | 9-Borabicyclo[3.3.1]nonane |
| DBU | Diazabicyclo [5.4.0] undec-7-ene |
| DMF | dimethylformamide |
| DMSO | dimethyl sulfoxide |
| DCM | dichloromethane |
| DEAD | diethyl azodicarboxylate |
| DIAD | diisopropyl azodicarboxylate |
| DIPEA | diisopropylethylamine |
| EDCI | 1-ethyl-3-(3'-dimethylaminopropyl) carbodiimide |
| EtOAc | ethyl acetate |
| HATU | 2-(7-Aza-1H-benzotriazole-1-yl)-1,1,3,3-tetramethyluronium hexafluorophosphate |
| HPLC | high performance liquid chromatography |
| IPA | Isopropyl alcohol (iso-propanol) |
| MeOH | methanol |
| MEMCl | 2- methoxyethoxymethyl chloride |
| NMR | nuclear magnetic resonance |
| PS | polymer supported |
| PPTS | Pyridinium para-toluenesulfonate |
| PEAX | PE-anion exchange (e.g. Isolute ® PE-AX columns from Biotage) |
| SCX-2 | strong cation exchange (e.g. Isolute ® SCX-2 columns from Biotage) |
| TEA | triethylamine |
| THF | tetrahydrofuran |
| TFA | trifluoroacetic acid |

PREPARATION OF EXAMPLES

For clarity in describing the Examples described below. Examples 2, 9, and 10 are racemic mixtures. Examples 4, 13 and 29 are mixtures of diastereomers. Examples 24 and 25 are single enantiomers wherein the stereochemistry of the unassigned stereocentre is not determined. All other examples are single enantiomers of defined stereochemistry.

Where not stated, the compounds are recovered from reaction mixtures and purified using conventional techniques such as flash chromatography, filtration, recrystallisation and trituration.

Example 1

3,5-Diamino-6-chloro-pyrazine-2-carboxylic acid [4,4-dimethyl-imidazolidin-(2Z)-ylidene]-amide A suspension of 1-(3,5-diamino-6-chloro-pyrazine-2-carbonyl)-2-methyl-isothiourea (Intermediate A) (0.2 g, 0.517 mmol) in EtOH (2 ml) is treated with triethylamine (0.029 ml, 0.258 mmol) followed by 1,2-diamino-2-methylpropane (0.07 ml, 0.672 mmol) and stirred at reflux overnight. The resulting suspension is filtered under vacuum to afford the title compound as a pale yellow solid; [M+H]$^+$ 284

Example 2

3,5-Diamino-6-chloro-pyrazine-2-carboxylic acid [4-methyl-imidazolidin-(2Z)-ylidene]-amide This compound is prepared analogously to Example 1 by replacing 1,2-diamino-2-methylpropane with 1,2,diaminopropane; [M+H]$^+$ 270

Example 3

3,5-Diamino-6-chloro-pyrazine-2-carboxylic acid [1-methyl-imidazolidin-(2Z)-ylidene]-amide This compound is prepared analogously to Example 1 by replacing 1,2-diamino-2-methylpropane with N-methylene-diamine; $[M+H]^+$ 270

Example 4

3,5-Diamino-6-chloro-pyrazine-2-carboxylic acid (4,5-diphenyl-imidazolidin-2-ylidene)-amide This compound is prepared analogously to Example 1 by replacing 1,2-diamino-2-methylpropane with 1,2 diphenyl-ethylene diamine; $[M+H]^+$ 408

Example 5

(4-{2-[(Z)-3,5-Diamino-6-chloro-pyrazine-2-carbonylimino]-imidazolidin-4-yl}-butyl)-carbamic acid benzyl ester This compound is prepared analogously to Example 1 by replacing 1,2-diamino-2-methylpropane with ((S)-5,6-Di-amino-hexyl)-carbamic acid benzyl ester (Intermediate B); $[M+H]^+$ 461

Example 6

3,5-Diamino-6-chloro-pyrazine-2-carboxylic acid [1-[4-(4-methoxy-phenyl)-butyl]-imidazolidin-(2Z)-ylidene]-amide This compound is prepared analogously to Example 1 by replacing 1,2-diamino-2-methylpropane with N*1*-[4-(4-methoxy-phenyl)-butyl]-ethane-1,2-diamine (Intermediate C); $[M+H]^+$ 418

Example 7

3,5-Diamino-6-chloro-pyrazine-2-carboxylic acid [1-[4-(4-hydroxy-phenyl)-butyl]-imidazolidin-(2Z)-ylidene]-amide This compound is prepared analogously to Example 1 by replacing 1,2-diamino-2-methylpropane with 4-[4-(2-amino-ethylamino)-butyl]-phenol (Intermediate C); $[M+H]^+$ 404

Example 8

3,5-Diamino-6-chloro-pyrazine-2-carboxylic acid [(S)-4-(4-methoxy-benzyl)-imidazolidin-(2Z)-ylidene]-amide This compound is prepared analogously to Example 1 by replacing 1,2-diamino-2-methylpropane with (S)-3-(4-methoxy-phenyl)-propane-1,2 diamine (Intermediate D); $[M+H]^+$ 376

Example 9

3,5-Diamino-6-chloro-pyrazine-2-carboxylic acid [4-(3,4-dichloro-phenyl)-imidazolidin-(2Z)-ylidene]-amide This compound is prepared analogously to Example 1 by replacing 1,2-diamino-2-methylpropane with 1-(3,4-Dichloro-phenyl)-ethane-1,2-diamine (Intermediate E); $[M+H]^+$ 400

Example 10

3-{2-[(Z)-3,5-Diamino-6-chloro-pyrazine-2-carbonylimino]-imidazolidin-4-yl}-propionic acid This compound is prepared analogously to Example 1 by replacing 1,2-diamino-2-methylpropane with 4,5-Diamino-pentanoic acid dihydrochloride (Intermediate F); $[M+H]^+$ 328

Examples 2-10

These compounds are recovered from reaction mixtures and purified using conventional techniques such as flash chromatography, filtration, capture release resin or preparative HPLC.

Example 11

3,5-Diamino-6-chloro-pyrazine-2-carboxylic acid (octahydro-benzoimidazol-2-ylidene)-amide This compound is prepared analogously to Example 1 by replacing 1,2-diamino-2-methylpropane with cyclohexane-1,2-diamine. The reaction is carried out in propan-2-ol; $[M+H]^+$ 310

Example 12

3,5-Diamino-6-chloro-pyrazine-2-carboxylic acid [8-benzyl-1,3,8-triazaspiro[4.5]dec-(2Z)-ylidene]-amide 4-Amino-1-benzyl-piperidine-4-carbonitrile (Intermediate G) (200 mg, 0.91 mmol) in dry propan-2-ol (10 ml) is treated with triethylamine (0.25 ml) followed by 1-(3,5-di-amino-6-chloro-pyrazine-2-carbonyl)-2-methyl-isothiourea (Intermediate A) (355 mg, 0.91 mmol). The mixture is heated at 70° C. for 5 hours and then allowed to cool to room temperature. The precipitate is collected and washed with methanol to afford the title compound as a light yellow solid, 190 mg; $[M+H]^+$ 415

Example 13

3,5-Diamino-6-chloro-pyrazine-2-carboxylic acid [4-[3-(4-methoxy-phenyl)-propyl]-imidazolidin-(2Z)-ylidene]-amide This compound is prepared analogously to Example 12 by replacing 4-Amino-1-benzyl-piperidine-4-carbonitrile (Intermediate G) with 5-(4-methoxy-phenyl)-pentane-1,2-diamine (Intermediate I); [M+H]+ 404

Example 14

3,5-Diamino-6-chloro-pyrazine-2-carboxylic acid (tetrahydro-pyrimidin-2-ylidene)-amide 1-(3,5-Diamino-6-chloro-pyrazine-2-carbonyl)-2-methyl-isothiourea (Intermediate A) (1.0 g, 2.58 mmol) is suspended in propan-2-ol (10 ml) and 1,3-diaminopropane (0.32 ml, 3.9 mmol) is added. The mixture is heated at 60° C. for 18 hours and then allowed to cool to room temperature and the solids present are collected by filtration. The solids are washed with THF and MeOH to yield the title compound as a yellow solid; [M+H]+ 270

Example 15

3,5-diamino-6-chloro-N-(1H-pyrrolo[1,2-c]imidazol-3(2H,5H,6H,7H,7aH)-ylidene)pyrazine-2-carboxamide 1-(3,5-Diamino-6-chloro-pyrazine-2-carbonyl)-2-methyl-isothiourea (Intermediate A) (195 mg, 0.5 mmol) is suspended in propan-2-ol (10 ml) and (S)-2-(aminomethyl)pyrrolidine (100 mg, 1 mmol) is added. The mixture is heated at 60° C. for 18 hours, allowed to cool to room temperature and the precipitate is removed by filtration. The filtrate is concentrated in vacuo and the residue purified by chromatography (SiO$_2$, DCM/MeOH) to afford the title compound as a light, yellow gum; [M+H]+ 296

Example 16

3,5-Diamino-6-chloro-pyrazine-2-carboxylic acid [1,3-diaza-spiro[4.4]non-(2Z)-ylidene]-amide A solution of crude 1-aminomethyl-cyclopentylamine (Intermediate J) (80 mg, 0.70 mmol) in propan-2-ol (1.0 ml) is added to a suspension of 1-(3,5-diamino-6-chloro-pyrazine-2-carbonyl)-2-methyl-isothiourea (Intermediate A) (208 mg, 0.54 mmol) in propan-2-ol (1.08 ml) and heated at 70° C. for 2 days. After cooling to room temperature, the reaction mixture is filtered under vacuum, and the solid is rinsed with MeOH. The filtrate is concentrated in vacuo to afford a bright yellow residue which is loaded onto a SCX-2 cartridge and eluted with 33% NH$_3$ (4 drops) in MeOH (5 ml×2). The methanolic ammonia fractions are combined and concentrated in vacuo. Purification using mass directed preparative LCMS eluting with 95% Water+0.1% NH$_3$: 5% Acetonitrile to affords the title compound; [M+H]+ 310.

Example 17

3,5-Diamino-6-chloro-pyrazine-2-carboxylic acid [(R)-4-[3-(4-hydroxy-phenyl)-propyl]-imidazolidin-(2E)-ylidene]-amide To a stirred solution of (4-((R)-4,5-Diamino-pentyl)-phenol (intermediate K) (1.5 g, 7.72 mmol) in propan-2-ol (100 ml) at 30° C. is added in one portion 1-(3,5-Diamino-6-chloro-pyrazine-2-carbonyl)-2-methyl-isothiourea (Intermediate A) and the reaction is heated at 30° C. for 18 hours followed by 50° C. for a further 18 hours. The reaction mixture is filtered hot and the filtrate solvent is removed in vacuo to afford a yellow foam. The foam is purified by chromatography (SiO$_2$, DCM/MeOH/5% NH$_3$) to afford the title compound; [M+H]+ 390

Example 18

3,5-Diamino-6-chloro-pyrazine-2-carboxylic acid [(S)-4-[3-(4-hydroxy-phenyl)-propyl]-imidazolidin-(2E)-ylidene]-amide This compound is prepared analogously to Example 17 replacing (4-((R)-4,5-Diamino-pentyl)-phenol (Intermediate K) with 4-((S)-4,5-Diamino-pentyl)-phenol (intermediate L; [M+H]+ 390

Example 19

3,5-Diamino-6-chloro-pyrazine-2-carboxylic acid [(R)-4-{3-[4-((S)-2,3-dihydroxy-propoxy)-phenyl]-propyl}-imidazolidin-(2Z)-ylidene]-amide To a stirred solution of 3,5-Diamino-6-chloro-pyrazine-2-carboxylic acid [(R)-4-[3-(4-hydroxy-phenyl)-propyl]-imidazolidin-(2E)-ylidene]-amide (Ex. 17) (1.0 g, 2.57 mmol) in 1,4 dioxane (38 ml) at 50° C. is added in one portion 0.5 M KOH (5.3 ml, 2.7 mmol) followed by (S)-(−)-Glycidiol (0.170 ml, 2.57 mmol). The resulting mixture is heated at 50° C. for 18 hours and then further (S)-(−)-Glycidiol (0.07 ml, 1.05 mmol) is added in one portion. The resulting mixture is heated at 50° C. for 60 hours and then allowed to cool to room temperature. The solvent is removed in vacuo to afford an orange oil which is dissolved in EtOAc/MeOH 9:1 (100 ml) and washed with 1 M NaOH (50 ml). The organic layer is dried over Na$_2$SO$_4$ and the solvent is removed in vacuo to afford a brown/orange foam. Purification by chromatography (SiO$_2$, DCM/MeOH/NH$_3$) affords the title compound as a yellow foam; [M+H]+ 464; $^1$H NMR (400 MHz, DMSO-d6): 1.65-1.40 (m, 4H), 2.52 (m, 2H), 3.13 (dd, J=9.6, 7.1 Hz, 1H), 3.42 (br d, J=4.7 Hz, 2H), 3.62 (dd, J=9.6, 9.6 Hz, 1H), 3.76 (m, 1H), 3.78 (m, 1H), 3.80 (m, 1H), 3.94 (dd, J=9.5, 4.0 Hz, 1H), 4.62 (br s, 1H), 4.89 (br s, 1H), 6.68 (br s, 2H), 6.82 (d, J=8.5 Hz, 2H), 7.09 (d, J=8.5 Hz, 2H), 7.2-6.0 (br s, 1H), 8.18 (br s, 1H), 9.3-7.5 (br s, 1H),

Example 20

3,5-Diamino-6-chloro-pyrazine-2-carboxylic acid [(S)-4-{3-[4-(S)-2,3-dihydroxy-propoxy)-phenyl]-propyl}-imidazolidin-(2Z)-ylidene]-amide To a solution of 3,5-Diamino-6-chloro-pyrazine-2-carboxylic acid [(S)-4-[3-(4-hydroxy-phenyl)-propyl]-imidazolidin-(2E)-ylidene]-amide (Example 18) (37.5 mg, 0.09 mmol) in Ethanol (2 ml) is added triethylamine (63 µl, 0.45 mmol) and (S)-glycidol (6.07 µl, 0.09 mmol). The resulting mixture is heated at reflux for 18 hours and then allowed to cool to room temperature. The reaction mixture is diluted with MeOH (1 ml) and purified on a Waters 3000 prep HPLC system, (Microsorb C18, Water (0.1% TFA): MeCN) to afford the title compound; [M+H]+ 464.

Example 21

(3,5-Diamino-6-chloro-pyrazine-2-carboxylic acid [(R)-4-{3-[4-((R)-2,3-dihydroxy-propoxy)-phenyl]-propyl}-imidazolidin-(2Z)-ylidene]-amide To a stirred solution of (R)-3-[4-((R)-4,5-Diamino-pentyl)-phenoxy]-propane-1,2-diol (Intermediate O) (32.8 mg, 0.122 mmol) in propan-2-ol (3 ml) is added 1-(3,5-Diamino-6-chloro-pyrazine-2-carbonyl)-2-methyl-isothiourea (Intermediate A) (45.8 mg, 0.122 mmol) and the resultant reaction mixture is heated at 90° C. for 18 hours. The reaction is allowed to cool to room temperature and diluted with DMSO (1.5 ml) and purified on a Waters 3000 preparative HPLC system (Microsorb™ C18, Water (0.1% TFA): MeCN). The fractions containing product are passed through a 1 g SCX-2 cartridge which is eluted with 1:1 Water:MeCN (20 ml), MeCN (20 ml) and 7M $NH_3$ in MeOH (20 ml). The ammonia elutions are concentrated in vacuo to afford the title compound; $[M+H]^+$ 464

Example 22

3,5-Diamino-6-chloro-pyrazine-2-carboxylic acid [(S)-4-{3-[4-((R)-2,3-dihydroxy-propoxy)-phenyl]-propyl}-imidazolidin-(2Z)-ylidene]-amide trifluoroacetate This compound is prepared analogously to Example 21 replacing (R)-3-[4-((R)-4,5-Diamino-pentyl)-phenoxy]-propane-1,2-diol (Intermediate O) with (R)-3-[4-((S)-4,5-Diamino-pentyl)-phenoxy]-propane-1,2-diol (Intermediate P); $[M+H]^+$ 464.

Example 23

3,5-Diamino-6-chloro-pyrazine-2-carboxylic acid [(R)-4-{3-[4-(2-morpholin-4-yl-2-oxo-ethoxy)-phenyl}-propyl]-imidazolidin-(2Z)-ylidene]-amide This compound is prepared analogously to Example 21 replacing (R)-3-[4-((R)-4,5-Diamino-pentyl)-phenoxy]-propane-1,2-diol (Intermediate O) with 2-[4-((R)-4,5-Diamino-pentyl)-phenoxy]-1-morpholin-4-yl-ethanone (Intermediate Q); $[M+H]^+$ 517

Examples 24 and 25

Both Enantiomers of 3,5-Diamino-6-chloro-pyrazine-2-carboxylic acid [4-[3-(4-methoxy-phenyl)-butyl]-imidazolidin-(2Z)-ylidene]-amide The racemate of these compounds is prepared analogously to Example 12 replacing 4-Amino-1-benzyl-piperidine-4-carbonitrile (Intermediate G) with 5-(4-methoxy-phenyl)-hexane-1,2-diamine (Intermediate K). The enantiomers are separated by chiral HPLC:
Mobile phase: 100% EtOH (0.2% IPAm)
Column: Chirapak-AD 25 cm×4.6 mm i.d
Flow rate: 1 ml/min
UV 280 nM
Concentration 1 mg/mL
Inj Vol 10 μL Example 26

3,5-Diamino-6-chloro-pyrazine-2-carboxylic acid [(S)-4-(4-benzyloxy-2,2-dimethyl-butyl-imidazolidin-(2Z)-ylidene]-amide Step 1
DEAD (4.49 ml, 28 mmol) is added to a stirred suspension of ((S)-5-benzyloxy-1-hydroxymethyl-3,-3-dimethyl-pentyl)-carbamic acid tert-butyl ester (prepared as described in EP 0702004 A2, Rueger et al., 10 g, 0.028 mmol), phthalimide (4.19 g, 0.028 mmol) and PS-triphenylphosphine (29.8 g, 56 mmol) in THF (500 ml), and the resulting reaction is stirred at room temperature for 3 days. The reaction is filtered to remove the PS-triphenylphosphine resin and the resin is washed with EtOAc (2×50 ml). The solvent is removed in vacuo and the residue is purified by flash chromatography ($SiO_2$, EtOAc/iso-hexane) to afford [(S)-5-benzyloxy-1-(1,3-dioxo-1,3-dihydro-isoindol-2-ylmethyl)-3,3-dimethyl-pentyl]-carbamic acid tert-butyl ester as a white solid; $[M+H]^+$ 481.
Step 2
Hydrazine (66.6 ml of a 1M solution in THF, 66.6 mmol) is added to a suspension of [(S)-5-benzyloxy-1-(1,3-dioxo-1,3-dihydro-isoindol-2-ylmethyl)-3,3-dimethyl-pentyl]-carbamic acid tert-butyl ester (4 g, 8.32 mmol) in ethanol (100 ml), and the resulting solution is heated at 40° C. overnight. A fluffy white precipitate forms. The reaction is allowed to cool to room temperature and diethyl ether (100 ml) is added and the resulting white suspension cooled at 0° C. for 30 minutes. The white precipitate is removed by filtration and the solvent removed in vacuo. The residue is then stirred with diethyl ether (100 ml) for 1 hour, filtered and the solvent is removed in vacuo to afford ((S)-1-Aminomethyl-5-benzyloxy-3,3-dimethyl-pentyl)-carbamic acid tert-butyl ester as a pale yellow oil; $[M+H]^+$ 351.
Step 3
Iodotrimethylsilane (1.63 ml, 11.94 mmol) is added dropwise to a solution of ((S)-1-Aminomethyl-5-benzyloxy-3,3-dimethyl-pentyl)-carbamic acid tert-butyl ester (2.79 g, 7.96 mmol) in DCM (30 ml) and the resulting yellow solution is stirred for 1 hour at room temperature. The reaction is filtered and the filtrate diluted with DCM (50 ml) and washed with 2 M NaOH (100 ml). The aqueous layer is allowed to stand overnight and any product which has oiled out of solution is extracted into EtOAc (100 ml). The organic layers are combined, dried over $MgSO_4$, and the solvent is removed in vacuo to yield (S)-Benzyloxy-4,4-dimethyl-hexane-1,2-diamine as a pale yellow oil; $[M+H]_+$251.
Step 4
A suspension of 1-(3,5-diamino-6-chloro-pyrazine-2-carbonyl)-2-methyl-isothiourea (Intermediate A) (2.56 g, 6.87 mmol) and (S)-Benzyloxy-4,4-dimethyl-hexane-1,2-diamine (1.72 g, 6.87 mmol) in propan-2-ol (50 ml) is heated at 90° C. for 3 hours. The reaction is allowed to cool to room temperature, filtered to remove any insoluble material and the filter paper is washed with MeOH (50 ml). The filtrate is loaded on to a SCX-2 cartridge which has been pre-eluted with MeOH. The cartridge is eluted with MeOH and then 7M $NH_3$ in MeOH. Upon standing, a pale yellow solid crystallises out of the $NH_3$ in MeOH solution. The solid is collected by filtration, washed with MeOH (20 ml) and dried in vacuo at 40° C. to afford the title compound. $[M+H]^+$ 446.

Example 27

3,5-Diamino-6-chloro-pyrazine-2-carboxylic acid [(S)-4-(hydroxyl-2,2-dimethyl-butyl)-imidazolidin-(2Z)-ylidene]-amide To a suspension of 3,5-Diamino-6-chloro-pyrazine-2-carboxylic acid [(S)-4-(4-benzyloxy-2,2-dimethyl-butyl-imidazolidin-(2Z)-ylidene]-amide (Ex. 26) (100 mg, 0.22 mmol) in DCM (5 ml) is added dropwise iodotrimethylsilane (0.061 ml, 0.448 mmol). The resulting yellow solution is heated at reflux for 2 days. The reaction is allowed to cool to room temperature and the yellow solid that has formed is collected by filtration, dissolved in MeOH (3 ml) and loaded onto a 10 g SCX-2 cartridge which has been pre-eluted with MeOH. The cartridge is eluted with MeOH (30 ml) and 7M NH₃ in MeOH (30 ml). The pale yellow 7M NH₃ in MeOH wash is concentrated in vacuo to afford the title compound as a yellow solid. [M+H]⁺ 356.

Example 28

3,5-Diamino-6-chloro-pyrazine-2-carboxylic acid [(S)-4-{4-[4-(S)-2,3-dihydroxy-propoxy)-phenyl]-2,2-dimethyl-butyl}-imidazolidin-(2Z)-ylidene]-amide Step 1

(S)-Glycidol (0.36 ml, 5.5 mmol) is added to a solution of 4-iodophenol (1 g, 4.5 mmol) and triethylamine (31 ml, 0.2 mmol) in ethanol (5 ml) and the resulting light brown solution is heated at reflux for 15 hours. The reaction is allowed to cool to room temperature and the solvent removed in vacuo. The residue is purified by chromatography (SiO₂, EtOAc/iso-hexane) to afford (S)-3-(4-Iodo-phenoxy)-propane-1,2-diol as a colourless oil.

Step 2

2,2-Dimethoxypropane (1.94 ml, 15.8 mmol) and PPTS (0.079 mg, 0.32 mmol) are added to a solution of (S)-3-(4-Iodo-phenoxy)-propane-1,2-diol (0.93 g, 3.16 mmol) in DMF (20 ml), and the resulting solution is left to stir at room temperature overnight. The solvent is removed in vacuo and the residue is purified by chromatography (SiO₂, EtOAc:Isohexane) to afford (R)-4-(4-Iodo-phenoxymethyl)-2,2-dimethyl-[1,3]dioxolane as a colourless oil.

Step 3

DEAD (0.63 ml, 4 mmol) is added to a suspension of ((S)-1-Hydroxymethyl-3,3-dimethyl-pent-4-enyl)-carbamic acid tert-butyl ester (1 g, 4 mmol), phthalimide (588 mg, 4 mmol) and PS-triphenylphosphine (3.72 g, 8 mmol) in THF (50 ml) and the resulting solution is stirred at room temperature overnight. The resin is removed by filtration, and the filtrate concentrated in vacuo. Purification by flash chromatography (SiO₂, EtOAc/iso-hexane) yields [(S)-1-(1,3-Dioxo-1,3-dihydro-isoindol-2-ylmethyl)-3,3-dimethyl-pent-4-enyl]-carbamic acid tert-butyl ester as a white solid; [M+H−BOC]⁺ 273.

Step 4

9-BBN (4.63 ml of a 0.5 M solution in THF, 0.23 mmol) is added to a solution of [(S)-1-(1,3-Dioxo-1,3-dihydro-isoindol-2-ylmethyl)-3,3-dimethyl-pent-4-enyl]-carbamic acid tert-butyl ester (0.43 g, 0.116 mmol) in THF (15 ml) and the resulting colourless solution is stirred at room temperature overnight. Anhydrous DMF (15 ml) is added to the solution, followed by 3 M aqueous K₃PO₄ solution (0.77 ml, 2.3 mmol), (R)-4-(4-Iodo-phenoxymethyl)-2,2-dimethyl-[1,3]dioxolane (267 mg, 0.28 mmol) and Pd(dppf)Cl₂.DCM (47 mg, 0.058 mmol). The reaction is stirred at room temperature for 3 hours, 50° C. for 2 hours and then is allowed to cool to room temperature and filtered through a pad of Celite™ (filter material) which is washed with EtOAc (3×50 ml). The combined filtrates are washed with sat. aq. NaHCO₃ solution (30 ml), dried (MgSO₄) and the solvent removed in vacuo to afford a black oil. Multiple chromatography (SiO₂, EtOAc/iso-hexane) yields [(S)-5-[4-((R)-2,2-Dimethyl-[1,3]dioxolan-4-ylmethoxy)-phenyl]-1-(1,3-dioxo-1,3-dihydro-isoindol-2-ylmethyl)-3,3-dimethyl-pentyl]-carbamic acid tert-butyl ester as a cream solid; [M+H−BOC]⁺ 481.

Step 5

Hydrazine (2.2 ml of a 1M solution in THF, 2.2 mmol) is added to a solution of [(S)-5-[4-((R)-2,2-Dimethyl-[1,3]dioxolan-4-ylmethoxy)-phenyl]-1-(1,3-dioxo-1,3-dihydro-isoindol-2-ylmethyl)-3,3-dimethyl-pentyl]-carbamic acid tert-butyl ester (0.16 g, 0.28 mmol) in ethanol (5 ml), and the resulting colourless solution is heated at 45° C. overnight. The reaction is allowed to cool to room temperature, and diethyl ether (30 ml) is added and the resulting white suspension cooled at 0° C. for 30 minutes. The white solid is removed by filtration, and the solvent removed in vacuo to yield {(S)-1-Aminomethyl-5-[4-((R)-2,2-dimethyl-[1,3]dioxolan-4-ylmethoxy)-phenyl]-3,3-dimethyl-pentyl}-carbamic acid tert-butyl ester as a colourless oil; [M+H]⁺ 451.

Step 6

A solution of {(S)-1-Aminomethyl-5-[4-((R)-2,2-dimethyl-[1,3]dioxolan-4-ylmethoxy)-phenyl]-3,3-dimethyl-pentyl}-carbamic acid tert-butyl ester (0.13 g, 0.28 mmol) and TFA (1 ml) in DCM (5 ml) is stirred at room temperature for 1 hour, then loaded onto an SCX-2 cartridge which has been pre-eluted with MeOH. The cartridge is eluted with MeOH (2×5 ml), followed by 7M NH₃ in MeOH (2×5 ml) to yield (S)-3-[4-((S)-5,6-Diamino-3,3-dimethyl-hexyl)-phenoxy]-propane-1,2-diol in 80% purity as a colourless oil; [M+H]⁺ 311

Step 7

A suspension of (S)-3-[4-((S)-5,6-Diamino-3,3-dimethyl-hexyl)-phenoxy]-propane-1,2-diol (60 mg, 0.19 mmol) and 1-(3,5-diamino-6-chloro-pyrazine-2-carbonyl)-2-methyl-isothiourea (Intermediate A) (72 mg, 0.19 mmol) in propan-2-ol (3 ml) is heated at 80° C. for 35 minutes. The reaction mixture is allowed to cool to room temperature and diluted with MeOH until any solid dissolves. The solution is passed through a SCX-2 cartridge which is then eluted with further MeOH. The combined methanol elutions are concentrated in vacuo. Reverse phase chromatography (Isolute™ C18, Water/CH₃CN/0.1% TFA) yields the title compound as a yellow solid; [M+H]+ 506

Example 29

(E)-3,5-diamino-6-chloro-N-(4-(3-(4-((S)-2,3-dihydroxypropoxy)phenyl)propyl)-5-propylimidazolidin-2-ylidene)pyrazine-2-carboxamide hydrochloride Step 1

4-(4-Methoxyphenyl)butyric acid (25 g, 129 mmol) is dissolved in 48% HBr (125 ml) and AcOH (125 ml). The resultant solution is heated at 150° C. overnight. The resultant mixture is concentrated in vacuo and the residue taken up in EtOAc (500 ml). This solution is washed with water (500 ml), dried (MgSO₄) and concentrated to give 4-(4-Hydroxy-phenyl)-butyric acid as a tan solid; ¹H NMR (d6-DMSO): 1.72 (2H, tt, J=7.4 and 7.8 Hz), 2.18 (2H, t, J=7.4 Hz), 2.45 (2H, t, J=7.8 Hz), 6.66 (2H, dd, J=1.98 and 9.3 Hz), 6.96 (2H, dd, J=2.8 and 9.3 Hz), 9.12 (1H, s), 12.0 (1H, s).

Step 2

4-(4-Hydroxy-phenyl)-butyric acid (22.1 g, 123 mmol) is dissolved in THF (750 ml) and borane-dimethyl sulfide (23.3 ml, 245 mmol) is slowly added. The yellow suspension formed is heated at reflux for 3 hours until most of the solid slowly dissolves. The flask is removed from the heating mantle, and MeOH is slowly added until bubbling ceases and the residual solid has dissolved. The flask is cooled to room temperature and water (1 L) is added. The pH is corrected to 3 with AcOH, then the mixture is extracted with EtOAc (2×500 ml). The organics are washed with brine, dried (MgSO₄) and concentrated. The crude product is slurried with silica (500 g) in 25% EtOAc/iso-hexanes (1 L). This is filtered, then flushed with 50% EtOAc/iso-hexanes (2 L) to elute the product. The organics are concentrated to give 4-(4-

Hydroxy-butyl)-phenol as a brown oil which crystallizes on standing; $^1$H NMR (CDCl$_3$): 1.55-1.72 (4H, m), 2.58 (2H, t, J=7.0 Hz), 3.1 (2H, br signal), 3.70 (2H, t, J=6.4 Hz), 6.77 (2H, d, J=8.4 Hz), 7.05 (2H, d, J=8.4 Hz).

Step 3

To 4-(Hydroxy-butyl)-phenol (32.7 g, 197 mmol) in acetone (600 ml) is added potassium carbonate (40.8 g, 295 mmol) followed by (S)-glycidol (13.7 ml, 207 mmol). The mixture is heated at reflux overnight. Further potassium carbonate (20 g) is added, followed by (S)-glycidol (5 g) and the mixture is heated at reflux for 72 hours. The suspension is cooled, filtered and the filtrate concentrated in vacuo. The residue is partitioned between EtOAc (500 ml) and 5% citric acid solution (500 ml). The organics are separated, dried (MgSO$_4$) and concentrated in vacuo to give (S)-3-[4-(4-Hydroxy-butyl)-phenoxy]-propane-1,2-diol as a brown oil; $^1$H NMR (CDCl$_3$): 1.56-1.74 (4H, m), 2.20 (1H, t, J=2.46 Hz), 2.61 (2H, t, J=7.6 Hz), 3.68 (2H, t, J=6.2 Hz), 3.78 (1H, dd, J=5.4 and 11.5 Hz), 3.86 (1H, dd, J=3.9 and 11.5 Hz), 4.0-4.16 (3H, m), 6.85 (2H, d, J=8.6 Hz), 7.12 (2H, d, J=8.6 Hz).

Step 4

To (S)-3-[4-(4-Hydroxy-butyl)-phenoxy]-propane-1,2-diol (43 g, 179 mmol) in THF (700 ml) is added 2,2-dimethoxypropane (94 ml, 760 mmol) followed by PPTS (4.5 g, 17.9 mmol). The resultant mixture is stirred at room temperature overnight. The solution is concentrated in vacuo and the residue taken up in DCM (500 ml). This is washed with water, dried (MgSO$_4$) and concentrated in vacuo. The residue is purified through a silica plug (300 g) eluting with 10% followed by 25% EtOAc/iso-hexanes. The desired fractions are concentrated to give 4-[4-((R)-2,2-Dimethyl-[1,3]dioxolan-4-ylmethoxy)-phenyl]-butan-1-ol as a clear oil; $^1$H NMR (CDCl$_3$): 1.42, (3H, s), 1.48 (3H, s), 1.53-1.73 (4H, m), 2.20 (1H, t, J=2.5 Hz), 2.60 (2H, t, J=7.2 Hz), 3.68 (2H, t, J=6.4 Hz), 3.92 (2H, dt, J=5.8 and 8.5 Hz), 4.07 (1H, dd, J=5.4 and 9.5 Hz), 4.19 (1H, dd, J=6.4 and 8.5 Hz), 4.49 (1H, p, J=5.7 Hz), 6.85 (2H, d, J=8.7 Hz), 7.11 (2H, d, J=8.7 Hz).

Step 5

To 4-[4-((R)-2,2-Dimethyl-[1,3]dioxolan-4-ylmethoxy)-phenyl]-butan-1-ol (5.0 g, 17.8 mmol) in DCM (180 ml) is added Dess-Martin periodinane (7.56 g, 17.8 mmol). The yellowish solution is stirred at room temperature for 1 hour. The resultant yellow suspension is treated with 1 N NaOH solution (200 ml) and stirred at room temperature for 30 minutes. The organic phase is separated, dried (MgSO$_4$) and concentrated to give 4-[4-((R)-2,2-Dimethyl-[1,3]dioxolan-4-ylmethoxy)-phenyl]-butyraldehyde as a clear oil; $^1$H NMR (CDCl$_3$): 1.42, (3H, s), 1.48 (3H, s), 1.95 (2H, dt, J=7.6 and 14.2 Hz), 2.46 (2H, dt, J=1.5 and 7.3 Hz), 2.62 (2H, t, J=7.6 Hz), 3.90-3.96 (2H, m), 4.07 (1H, dd, J=5.2 and 9.3 Hz), 4.19 (1H, dd, J=6.4 and 8.1 Hz), 4.49 (1H, p, J=5.8 Hz), 6.86 (2H, d, J=9.4 Hz), 7.10 (2H, d, J=9.4 Hz), 9.77 (1H, t, J=1.6 Hz).

Step 6

To 4-[4-((R)-2,2-Dimethyl-[1,3]dioxolan-4-ylmethoxy)-phenyl]-butyraldehyde (4.28 g, 15.4 mmol) in THF (150 ml) is added tert-butyl sulfinamide (2.05 g, 16.9 mmol) followed by titanium ethoxide (6.5 ml, 30.8 mmol). The yellow solution formed is stirred at room temperature overnight. The solution is quenched with 1 N NaOH (200 ml) and EtOAc (100 ml) and stirred for 30 minutes at room temperature. The resultant mixture is filtered through Celite™ (filter material) and the organic phase is separated and dried (MgSO$_4$). Concentration in vacuo gives 2-Methyl-propane-2-sulfinic acid [4-[4-((R)-2,2-dimethyl-[1,3]dioxolan-4-ylmethoxy)-phenyl]-but-(E)-ylidene]-amide as a yellow oil; [M+H]$^+$ 382.23

Step 7

To a solution of 2-Methyl-propane-2-sulfinic acid [4-[4-((R)-2,2-dimethyl-[1,3]dioxolan-4-ylmethoxy)-phenyl]-but-(E)-ylidene]-amide (4.51 g, 11.8 mmol) in THF (120 ml) at 0° C. is added vinylmagnesium bromide (11.8 ml of a 1 M solution in THF, 11.8 mmol) dropwise. After addition is complete, the mixture is stirred at 0° C. for 30 minutes then quenched with sat. aq. NH$_4$Cl solution (20 ml). This mixture is allowed to warm to room temperature and diluted with water (50 ml) and EtOAc (50 ml). The organic phase is separated, dried (MgSO$_4$) and concentrated in vacuo. Purification by chromatography (SiO$_2$, EtOAc/iso-hexane) affords 2-Methyl-propane-2-sulfinic acid {4-[4-((R)-2,2-dimethyl-[1,3]dioxolan-4-ylmethoxy)-phenyl]-1-vinyl-butyl}-amide as a mixture of diastereomers as a gum; [M+H]$^+$ 410.39

Step 8

A solution of 2-methyl-propane-2-sulfinic acid {4-[4-((R)-2,2-dimethyl-[1,3]dioxolan-4-ylmethoxy)-phenyl]-1-vinyl-butyl}-amide (1.0 g, 2.4 mmol) in DCM (25 ml) at −78° C. is saturated with oxygen, then ozone (generated using Fischer Technology Ozon Generator 500 m) until a blue solution is obtained. Dimethyl sulfide (1.8 ml, 24 mmol) is then added and the mixture stirred to room temperature over 30 minutes. The resultant solution is washed with water (25 ml) and the organic phase is concentrated under high vacuum at low temperature to give 2-Methyl-propane-2-sulfinic acid {4-[4-((R)-2,2-dimethyl-[1,3]dioxolan-4-ylmethoxy)-phenyl]-1-formyl-butyl}-amide as an oil; [M+H]$^+$ 412.36

Step 9

To a solution of 2-methyl-propane-2-sulfinic acid {4-[4-((R)-2,2-dimethyl-[1,3]dioxolan-4-ylmethoxy)-phenyl]-1-formyl-butyl}-amide in THF (20 ml) is added tert-butyl sulfinamide (323 mg, 2.7 mmol) followed by titanium ethoxide (1.0 ml, 4.8 mmol). The yellow solution formed is stirred at room temperature overnight. The solution is quenched with 1N NaOH (50 ml) and EtOAc (50 ml) and stirred for 30 minutes at room temperature. The resultant mixture is filtered through Celite™ (filter material) and the organic phase separated and dried (MgSO$_4$). Concentration gives 2-Methyl-propane-2-sulfinic acid (4-[4-((R)-2,2-dimethyl-[1,3]dioxolan-4-ylmethoxy)-phenyl]-1-{[(E)-2-methyl-propane-2-sulfinylimino]-methyl}-butyl)-amide as a mixture of diastereomers as a yellow oil; [M+H]$^+$ 515.38

Step 10

To a solution of 2-methyl-propane-2-sulfinic acid (4-[4-((R)-2,2-dimethyl-[1,3]dioxolan-4-ylmethoxy)-phenyl]-1-{[(E)-2-methyl-propane-2-sulfinylimino]-methyl}-butyl)-amide (907 mg, 1.7 mmol) in THF (20 ml) at 0° C. n-propylmagnesium chloride (1.76 ml of a 2M solution in diethyl ether, 3.52 mmol). The solution is stirred at 0° C. for 30 minutes then at room temperature for 3 hours. A further portion of n-propylmagnesium (1.76 ml of a 2M solution in diethyl ether, 3.52 mmol) is added and the mixture is stirred at room temperature overnight. The resulting mixture is quenched with sat. aq. NH$_4$Cl solution (50 ml) and extracted with EtOAc (2×50 ml). The organic phase is dried (MgSO$_4$) and concentrated in vacuo. The residue is dissolved in EtOAc (10 ml) and treated with 4M HCl/dioxan (10 ml). After 10 minutes, the solution is concentrated in vacuo and the residue diluted with DCM (100 ml). This is treated with sat. aq. NaHCO$_3$ solution (100 ml) and the organic phase is removed and dried (MgSO$_4$). The DCM solution is applied to a SCX-2 cartridge (10 g) and this is eluted with DCM and MeOH. The product is released with 2M NH$_3$ in MeOH, and the methanolic ammonia fraction concentrated to give (S)-3-[4-(4,5-Diamino-octyl)-phenoxy]-propane-1,2-diol as a mixture of diastereomers as a gum; [M+H]$^+$ 515.38

Step 11

To a solution of (S)-3-[4-(4,5-Diamino-octyl)-phenoxy]-propane-1,2-diol (100 mg, 0.32 mmol) in propan-2-ol (5 ml) is added 1-(3,5-diamino-6-chloro-pyrazine-2-carbonyl)-2-methyl-isothiourea (Intermediate A) (121 mg, 0.32 mmol). The resulting suspension is heated at 90° C. for 2 hours then cooled and concentrated in vacuo. The residue is dissolved in MeOH (20 ml) and applied to a 10 g SCX-2 cartridge. This is washed well with MeOH, water and MeCN, and then 2M $NH_3$ in MeOH. The methanolic ammonia fraction is concentrated then purified by chromatography ($SiO_2$, 5-10% 2M $NH_3$ in MeOH/DCM). Concentration of the relevant fractions gives the free base as a gum. This is dissolved in MeOH (10 ml) and treated with 1M HCl in diethyl ether (2 ml). Concentration yields the dihydrochloride salt of (E)-3,5-diamino-6-chloro-N-(4-(3-(4-((S)-2,3-dihydroxypropoxy)phenyl)propyl)-5-propylimidazolidin-2-ylidene)pyrazine-2-carboxamide as a yellow solid; $[M+H]^+$ 506.37, 508.36 for Cl isotopes Example 30

(3-{(S)-2-[(E)-3,5-Diamino-6-chloro-pyrazine-2-carbonylimino]-imidazolidin-4-yl}-propyl)-carbamic acid benzyl ester 1-(3,5-diamino-6-chloro-pyrazine-2-carbonyl)-2-methyl-isothiourea (Intermediate A) (0.97 g, 3.72 mmol) is stirred in a three necked round bottom flask fitted with a bleach trap and condenser and ((S)-4,5-Diamino-pentyl)-carbamic acid benzyl ester (Intermediate S) (0.85 g, 3.38 mmol) in propan-2-ol (20 ml) is added. The reaction mixture is stirred at 85° C. for 66 hours. Purification by catch and release resin (SCX-2) followed by elution through a silica pad flushed with EtOAc, ethanol and MeOH yields the title compound as an orange foam; $[M+H]^+$ 447.1

Example 31

3,5-Diamino-6-chloro-pyrazine-2-carboxylic acid [(S)-4-(3-amino-propyl)-imidazolidin-(2E)-ylidene]-amide To a solution of (3-{(S)-2-[(E)-3,5-Diamino-6-chloro-pyrazine-2-carbonylimino]-imidazolidin-4-yl}-propyl)-carbamic acid benzyl ester (Ex. 30) (0.44 g, 0.98 mmol) in DCM (20 ml) is added iodotrimethylsilane (0.27 ml, 1.96 mmol) in a dropwise manner. The orange suspension is stirred at room temperature for 65 minutes. Purification by catch and release resin (SCX-2) eluting with MeOH followed by 7M $NH_3$ in MeOH yields the title compound as a yellow foam; $[M+H]^+$ 313.1

Example 32

3,5-Diamino-6-chloro-pyrazine-2-carboxylic acid [(S)-4-[3-(3-benzyl-ureido)-propyl]-imidazolidin-(2E)-ylidene]-amide To a solution of 3,5-Diamino-6-chloro-pyrazine-2-carboxylic acid [(S)-4-(3-amino-propyl)-imidazolidin-(2E)-ylidene]-amide (Ex. 31) (0.040 g, 0.128 mmol) in DMF (2 ml) is added 1,1'-carbonyldiimidazole (0.023 g, 0.141 mmol) and the reaction mixture is stirred for 1 hour at room temperature. Benzylamine (0.014 ml, 0.128 mmol) is added and additional benzylamine (0.014 ml, 0.128 mmol) is added at hourly intervals for a total of 3 hours. Purification is by diluting the reaction with 2N NaOH (30 ml) and extracting the product into EtOAc (40 ml). The organic phase is washed with 2N NaOH (30 ml), dried over $MgSO_4$ and the solvent evaporated in vacuo to yield a yellow oil. The oil is dissolved in methanol (0.75 ml) and diethyl ether (5 ml) added to triturate a yellow solid. This solid is filtered off and the filtrate formed a further precipitate. This yellow solid is collected by filtration and rinsed with diethyl ether to give the title compound; $[M+H]^+$ 446.1

Example 33

3,5-Diamino-6-chloro-pyrazine-2-carboxylic acid [(S)-4-(3-phenyl methanesulfonylamino-propyl)-imidazolidin-(2E)-ylidene]-amide To a solution of 3,5-Diamino-6-chloro-pyrazine-2-carboxylic acid [(S)-4-(3-amino-propyl)-imidazolidin-(2E)-ylidene]-amide (Ex. 31) (0.030 g, 0.096 mmol) in DMF (5 ml) at 5° C. is added alpha-toluenesulfonyl chloride (0.018 g, 0.096 mmol) and triethylamine (0.013 ml, 0.096 mmol). The solution is stirred for 10 minutes. Purification by reverse phase chromatography (Isolute™ C18, 0-100% MeCN in water −0.1% TFA) to affords the title compound as a yellow solid; $[M+H]^+$ 467.0

Example 34

3,5-Diamino-6-chloro-pyrazine-2-carboxylic acid [(S)-4-(3-phenylacetylamino-propyl)-imidazolidin-(2E)-ylidene]-amide To a solution of 3,5-Diamino-6-chloro-pyrazine-2-carboxylic acid [(S)-4-(3-amino-propyl)-imidazolidin-(2E)-ylidene]-amide (Ex. 31) (0.030 g, 0.96 mmol) in DMF (2 ml), phenylacetyl chloride (0.013 ml, 0.096 mmol) is added. The yellow solution is stirred at room temperature for 10 minutes. Purification by catch and release resin (SCX-2) eluting with MeOH and 7M $NH_3$ in MeOH affords the title compound; $[M+H]^+$ 430.98

Example 35

3,5-Diamino-6-chloro-pyrazine-2-carboxylic acid [(S)-4-(4-phenylmethanesulfonylamino-butyl)-imidazolidin-(2E)-ylidene]-amide To a suspension of 3,5-Diamino-6-chloro-pyrazine-2-carboxylic acid [(S)-4-(4-amino-butyl)-imidazolidin-(2E)-ylidene]-amide (Intermediate T) (0.023 g, 0.071 mmol) in DMF (2 ml) is added triethylamine (0.010 ml, 0.071 mmol) followed by alpha-toluenesulfonyl chloride (0.014 g, 0.071 mmol). The suspension is stirred at room temperature for 30 minutes. Purification by reverse phase chromatography (Isolute™ C18, 0-100% MeCN in water −0.1% TFA) followed by catch and release resin (SCX-2) eluting with MeOH and 7M $NH_3$ in MeOH gives the title compound as a yellow solid; [M+H]+ 481.0

Example 36

3,5-Diamino-6-chloro-pyrazine-2-carboxylic acid [(S)-4-(4-phenylacetyl amino-butyl)-imidazolidin-(2E)-ylidene]-amide To a suspension of 3,5-Diamino-6-chloro-pyrazine-2-carboxylic acid [(S)-4-(4-amino-butyl)-imidazolidin-(2E)- ylidene]-amide (Intermediate T) (0.032 g, 0.098 mmol) in DMF (1 ml) is added triethylamine (0.014 ml, 0.098 mmol) followed by phenylacetyl chloride (0.013 ml, 0.098 mmol). The suspension is stirred at room temperature for 90 minutes before a further 0.5 equivalents of phenylacetyl chloride (0.006 ml, 0.049 mmol) is added. The reaction is left to stir at room temperature for a further 18 hours. Purification by reverse phase chromatography (Isolute™ C18, 0-100% MeCN in water −0.1% TFA) followed by catch and release resin (SCX-2) eluting with MeOH and 7M $NH_3$ in MeOH affords the title compound as an off-white solid; [M+H]+ 445.1

Example 37

2-[(E)-3,5-Diamino-6-chloro-pyrazine-2-carbonylimino]-1,3,8-triaza-spiro[4.5]decane-8-carboxylic acid tert-butyl ester trifluoroacetate A suspension of 4-amino-4-aminomethyl-piperidine-1-carboxylic acid tert-butyl ester (Intermediate U) (218 g, 0.95 mol) in tert-butanol (6 L) and 1-(3,5-diamino-6-chloro-pyrazine-2-carbonyl)-2-methyl-isothiourea (Intermediate A) (338 g, 0.82 mol) is stirred at 40° C. overnight. The temperature is then raised to 85° C. and the suspension stirred at this temperature for a further 4 days. The reaction mixture is concentrated in vacuo and the residue is taken up in water (1 L), sonicated and heated to 45-50° C. The solid is collected by vacuum filtration and washed with ice cold water, then dried under vacuum at 50° C. overnight to afford the title compound as a yellow solid; [M+H]+ 425.1.

Example 38

3,5-Diamino-6-chloro-pyrazine-2-carboxylic acid [1,3,8-triaza-spiro[4.5]dec-(2E)-ylidene]-amide dihydrochloride To a stirred solution of 4M HCl in dioxane (1 L) is added 2-[(E)-3,5-diamino-6-chloro-pyrazine-2-carbonylimino]-1,3,8-triaza-spiro[4.5]decane-8-carboxylic acid tert-butyl ester trifluoroacetate (Ex. 37) (104 g, 193 mmol). The resulting thick suspension is stirred at room temperature for 2 hours. The product is isolated by vacuum filtration, rinsing with dioxane. The solid is dried under vacuum at 50° C. to afford the title compound as a dihydrochloride salt as a dark yellow solid; [M+H]+=325.

Example 39

3,5-Diamino-6-chloro-pyrazine-2-carboxylic acid [8-[(S)-3-phenyl-2-(toluene-4-sulfonylamino)-propionyl]-1,3,8-triaza-spiro[4.5]dec-(2E)-ylidene]-amide To a solution of Tosyl-L-phenylalanine (1.0 g, 3.13 mmol) in DMF (25 ml) is added N-methyl morpholine (1.033 ml, 9.39 mmol) and 3,5-Diamino-6-chloro-pyrazine-2-carboxylic acid [1,3,8-triaza-spiro[4.5]dec-(2E)-ylidene]-amide dihydrochloride (Ex. 38) (1.37 g, 3.44 mmol), followed by HATU (1.31 g, 3.44 mmol) and the resulting solution is stirred at room temperature for 20 minutes. The crude product is diluted with water (300 ml) and the resultant solid is isolated. Purification by reverse phase chromatography (Isolute™ C18, 0-100% MeCN in water −0.1% TFA) followed by catch and release resin (SCX-2) eluted with MeOH and 7M $NH_3$ in MeOH yields a yellow solid which is triturated with MeOH and diethyl ether to give the title compound as a free base. The free base is stirred in 5M HCl at 100° C. for 30 minutes forming a gum. MeOH (5 ml) is added to the gum and then all solvent is removed in vacuo. The residue is triturated with MeOH and diethyl ether to give the title compound; [M+H]+ 626.4; $^1$H NMR (DMSO-d6): 1.12-1.71 (4H, m), 2.36-2.38 (3H, s), 2.59-2.83 (2H, m), 2.93-3.52 (4H, m), 3.41-3.60 (2H, m), 4.42 (1H, m), 7.12 (2H, d, J=6.9 Hz), 7.17-7.28 (3H, m), 7.35 (2H, d, J=7.7 Hz), 7.54-7.37 (2H, br), 7.57 (2H, d, J=7.7 Hz), 8.12 (1H, d, J=9.0 Hz), 7.70-8.26 (2H, br), 9.22 (1H, s), 9.95 (1H, s), 10.99 (1H, s).

Example 40

3,5-Diamino-6-chloro-pyrazine-2-carboxylic acid [8-(1-benzenesulfonyl-1H-indole-3-carbonyl)-1,3,8-triaza-spiro[4.5]dec-(2E)-ylidene]-amide To a solution of 1-(phenylsulfonyl)-1H-indole-3-carboxylic acid (1.0 g, 3.32 mmol) in DMF (15 ml) is added HATU (1.388 g, 3.65 mmol) and N-methyl morpholine (1.095 ml, 9.96 mmol) and the solution is stirred at room temperature for 5 minutes. 3,5-Diamino-6-chloro-pyrazine-2-carboxylic acid [1,3,8-triaza-spiro[4.5]dec-(2E)-ylidene]-amide dihydrochloride (Ex. 38) (1.452 g, 3.65 mmol) is added and the reaction stirred at room temperature for 45 minutes. The reaction mixture is diluted with water (100 ml) and the precipitate that forms is isolated by filtration. The crude product is suspended in 2N NaOH and extracted into EtOAc. The organic portion is dried over $MgSO_4$ and concentrated in vacuo to yield a brown solid. The solid is suspended in a 1:1 mixture of water (+0.1% TFA) and acetonitrile. A fine brown solid is removed by filtration and the yellow filtrate is concentrated in vacuo until 10 ml of solvent remains and a pale yellow solid has precipitated. This solid is washed with 2N NaOH (60 ml) and then suspended in 2N NaOH (100 ml) and extracted into EtOAc (2×100 ml). The organic phases are combined, dried over $MgSO_4$ and concentrated in vacuo to yield a pale cream solid. The cream solid is suspended in a 1:4 mixture of EtOAc:iso-hexane (100 ml) and the solid filtered off to give the free base of the title compound, which is suspended in 5 N HCl (20 ml) and stirred for 2 hours. MeOH (20 ml) is added to dissolve all solid and the solvent is concentrated in vacuo until a yellow solid precipitates. This solid is filtered off, rinsed with water and dried at 40° C. for 18 hours to give the title compound; [M+H]+ 607.42; $^1$H NMR (DMSO-d6): 1.86-1.92 (4H, m), 3.42-3.63 (4H, m), 3.68 (2H, s), 7.34 (1H, dd, J+7.5 Hz, J=7.5 Hz), 7.43 (1H, dd, J=7.5 Hz, J=7.5 Hz), 7.36-7.55 (2H, br), 7.62 (1H, d, J=7.5 Hz), 7.63 (2H, m), 7.73 (1H, m), 7.99 (1H, d, J=7.5 Hz), 8.06 (2H, obs), 8.07 (1H, s), 7.50-8.16 (2H, br), 9.18 (1H, s), 9.77 (1H, s), 11.09 (1H, s).

Example 41

3,5-Diamino-6-chloro-pyrazine-2-carboxylic acid [8-[3-(3-isopropoxy-propylsulfamoyl)-benzoyl]-1,3,8-triaza-spiro[4.5]dec-(2E)-ylidene]-amide To a solution of 3-(3-Isopropoxy-propylsulfamoyl)-benzoic acid (Intermediate V) (1.10 g, 3.65 mmol) in DMF (20 ml) is added HATU (1.53 g, 4.02 mmol) and N-methyl morpholine (1.204 ml, 10.95 mmol) and the solution is stirred at room temperature for 5 minutes. 3,5-Diamino-6-chloro-pyrazine-2-carboxylic acid [1,3,8-triaza-spiro[4.5]dec-(2E)-ylidene]-amide dihydrochloride (Ex. 38) (1.60 g, 4.02 mmol) is added and the reaction stirred at room temperature for 45 minutes. The reaction mixture is diluted with 2N NaOH (150 ml) and the crude product extracted into EtOAc (2×250 ml). The organic phase is dried over MgSO$_4$ and the solvent evaporated in vacuo to yield a yellow oil. Purification on a Waters preparative Delta 3000 HPLC using a gradient of water (+0.1% TFA) and acetonitrile yields a yellow oil. 2N NaOH is added to the oil and the product is extracted into EtOAc (2×400 ml). The organic phases are combined, dried over MgSO$_4$ and the solvent concentrated in vacuo to a volume of approximately 150 ml. To this solution is added iso-hexane (400 ml) and a pale yellow solid precipitates. This solid is collected by filtration and rinsed with iso-hexane to afford the title compound; [M+H]$^+$ 607.98; $^1$HNmr (DMSO): 1.00 (6H, d, J=6.0 Hz), 1.55 (2H, m), 1.69-1.79 (4H, m), 2.81 (2H, t, 5.9 Hz), 3.29 (2H, tr, J=6.0 Hz), 3.42 (1H, m), 3.44 (2H, br), 3.29-3.82 (4H, m), 6.15-7.30 (3H, br), 7.66 (1H, d, J=7.4 Hz), 7.70 (1H, dd, J=7.4 Hz, J=7.4 Hz), 7.76 (1H, s), 7.86 (1H, d, J=7.4 Hz), 7.44-8.00 (1H, br), 8.00-9.05 (3H, br).

Example 42

3,5-Diamino-6-chloro-pyrazine-2-carboxylic acid [8-[2-(5-phenyl-4H-[1,2,4]triazol-3-yl)-acetyl]-1,3,8-triaza-spiro[4.5]dec-(2E)-ylidene]-amide (5-Phenyl-4H[1,2,4]triazol-3-yl)acetic acid (0.48 g, 2.364 mmol), HATU (0.988 g, 2.6 mmol), 5-Diamino-6-chloro-pyrazine-2-carboxylic acid [1,3,8-triaza-spiro[4.5]dec-(2E)-ylidene]-amide dihydrochloride (Ex. 38) (1.033 g, 2.60 mmol), DMF (20 ml) and N-methyl morpholine (0.78 ml, 7.08 mmol) are added to a round bottomed flask and stirred at room temperature for 20 minutes. The crude product is precipitated from the reaction mixture by adding water (200 ml) and is isolated by filtration. Purification by reverse phase chromatography (Isolute™ C18, 0-100% MeCN in water –0.1% TFA) yields a yellow semi-solid. This is dissolved in MeOH (100 ml) and left to stand. An off white solid precipitates and this is collected by filtration to give the title compound; [M+H]$^+$ 510.0; NMR (DMSO-d6): 1.78-1.94 (4H, m), 3.67 (2H, s), 3.30-3.82 (4H, m), 4.05-4.08 (2H, m), 7.45-7.55 (3H m), 7.01-7.75 (3H, br), 8.05 (2H, d, J=7.1 Hz), 7.78-8.33 (2H, br), 9.24 (1H, s), 9.85 (1H, s), 11.04 (1H, s).

Example 43

3,5-Diamino-6-chloro-pyrazine-2-carboxylic acid [8-[3-(3-isopropyl-ureido)-benzoyl]-1,3,8-triaza-spiro[4.5]dec-(2E)-ylidene]-amide 3-(3-Isopropyl-ureido)-benzoic acid (Intermediate W) (1.08 g, 4.86 mmol) and HATU (2.03 g, 5.35 mmol) are stirred in DMF (25 ml) at room temperature and N-methyl morpholine (1.60 ml, 14.59 mmol) is added. The solution is stirred at room temperature for 5 minutes and 5-Diamino-6-chloro-pyrazine-2-carboxylic acid [1,3,8-triaza-spiro[4.5]dec-(2E)-ylidene]-amide dihydrochloride (Ex. 38) (2.13 g, 5.35 mmol) is added. The brown solution is stirred at room temperature for 45 minutes. The crude product is precipitated by the addition of 2N NaOH and collected by filtration. The solid is purified by reverse phase chromatography (Isolute™ C18, 0-100% MeCN in water –0.1% TFA). The clean fractions are concentrated in vacuo to approximately 30 ml and 2N NaOH added. The off white solid is collected by filtration and rinsed with water to give the title compound; [M+H]$^+$ 529.05; $^1$H NMR (DMSO-d6): 1.09 (6H, d, J=6.5 Hz), 1.67-1.73 (4H, m), 3.42 (2H, br), 3.75 (1H, septet, J=6.5 Hz), 3.31-3.79 (4H, br), 6.15 (1H, d, J=7.5 Hz), 6.70 (2H, br), 6.40-7.01 (1H, br), 6.86 (1H, d, J=7.2 Hz), 7.26 (1H, dd, J=8.3 Hz, J=7.2 Hz), 7.31 (1H, d, J=8.3 Hz), 7.53 (1H, s), 8.36 (1H, br), 8.48 (1H, br), 8.55 (1H, s), 8.00-9.00 (1H, br).

Example 44

3,5-Diamino-6-chloro-pyrazine-2-carboxylic acid [8-(2-Benzo[b]thiophen-3-yl-acetyl)-1,3,8-triaza-spiro[4.5]dec-(2E)-ylidene]-Amide This compound is prepared analogously to Example 43 by replacing 3-(3-Isopropyl-ureido)-benzoic acid (Intermediate W) with benzo[b]thiophene-3-acetic acid. [M+H]$^+$ 499.0; $^1$H NMR (DMSO-d6): 1.59-1.74 (4H, m), 3.42 (2H, s), 3.48-3.95 (4H, m), 3.97 (2H, s), 6.20-7.11 (3H, br), 7.38 (1H, m), 7.39 (1H, m), 7.50 (1H, s), 7.83 (1H, d, J=7.3 Hz), 7.97 (1H, d, J=7.6 Hz), 7.75-9.30 (3H, br).

Example 45

3,5-Diamino-6-chloro-pyrazine-2-carboxylic acid [8-[5-oxo-1-(3-pyrrol-1-yl-propyl)-pyrrolidine-3-carbonyl]-1,3,8-triaza-spiro[4.5]dec-(2E)-ylidene]-amide A solution of 5-Oxo-1-(3-pyrrol-1-yl-propyl)-pyrrolidine-3-carboxylic acid (Intermediate X) (1.15 g, 4.85 mmol), HATU (2.03 g, 5.33 mmol), DMF (20 ml) and N-methyl morpholine (1.60 ml, 14.54 mmol) is stirred at room temperature for 5 minutes before 5-Diamino-6-chloro-pyrazine-2-carboxylic acid [1,3,8-triaza-spiro[4.5]dec-(2E)-ylidene]-amide dihydrochloride (Ex. 38) (1.731 g, 5.33 mmol) is added. After stirring for 60 minutes at room temperature EtOAc (200 ml) is added and the organic phase is washed with 2N NaOH (2×100 ml) and brine (100 ml). The organic phase is dried over MgSO$_4$ and the solvent evaporated in vacuo. Purification by reverse phase chromatography (Isolute™ C18, 0-100% MeCN in water –0.1% TFA) followed by catch and release resin (SCX-2) eluting with MeOH and 7M NH$_3$ in MeOH yields a yellow oil. The oil is dissolved in DCM (10 ml) and product is precipitated out of solution by the addition of iso-hexane to yield a yellow solid which is filtered and rinsed with iso-hexane to yield the title product; [M+H] $^+$542.8; $^1$H NMR (DMSO-d6): 1.64-1.70 (4H, m), 1.84-1.89 (2H, m), 2.43-2.51 (2H, m), 3.39-3.43 (2H, m), 3.43-3.50 (2H, m), 3.55 (1H, m), 3.40-3.69 (4H, m), 3.84 (2H, m), 5.97 (2H, m), 6.65-6.74 (2H, br), 6.75 (2H, m), 6.2-7.6 (1H, br), 7.6-9.5 (1H, br).

Example 46

3,5-Diamino-6-chloro-pyrazine-2-carboxylic acid [8-(6,7,8,9-tetrahydro-5H-carbazole-3-carbonyl)-1,3,8-triaza-spiro[4.5]dec-(2E)-ylidene]-amide To a stirring solution of 6,7,8,9-Tetrahydro-5H-carbazole-3-carboxylic acid (0.05 g, 0.25 mmol) and HATU (0.11 g, 0.28 mmol) in dry DMF (5 ml) is added N-methyl morpholine (0.08 ml, 0.76 mmol). After 5 minutes stirring at room temperature, 5-Diamino-6-chloro-pyrazine-2-carboxylic acid [1,3,8-triaza-spiro[4.5]dec-(2E)-ylidene]-amide dihydrochloride (Ex. 38) (0.10 g, 0.28 mmol) is added and the reaction is left to stir at room temperature for 1 hour. Purification by reverse phase chromatography (Isolute™ C18, 0-100% MeCN in water) yields the title compound as a yellow powder; [M+H]$^+$ 524.2

Example 47

3,5-Diamino-6-chloro-pyrazine-2-carboxylic acid [8-(1H-indazole-3-carbonyl)-1,3,8-triaza-spiro[4.5]dec-(2E)-ylidene]-amide To a stirring solution of 1H-indazole-3-carboxylic acid (0.041 g, 0.25 mmol) and HATU (0.096 g, 0.25 mmol) in dry DMF (4 ml) is added N-methyl morpholine (0.08 ml, 0.76 mmol). After 5 minutes, 5-Diamino-6-chloro-pyrazine-2-carboxylic acid [1,3,8-triaza-spiro[4.5]dec-(2E)-ylidene]-amide dihydrochloride (Ex. 38) (0.10 g, 0.25 mmol) is added and the reaction left to stir at room temperature for 1 hour. Purification by reverse phase chromatography (Isolute™ C18, 0-100% MeCN in water −0.1% TFA) yields an oily residue that is ultrasonicated in acetonitrile to give a yellow suspension. The yellow solid is collected by filtration and rinsed with acetonitrile to afford the title compound; $[M+H]^+$ 469.17

Example 48

3,5-Diamino-6-chloro-pyrazine-2-carboxylic acid [8-[2-(2,3-dimethyl-1H-indol-5-yl)-acetyl]-1,3,8-triaza-spiro[4.5]dec-(2E)-ylidene]-amide This compound is prepared analogously to Example 47 by replacing 1H-indazole-3-carboxylic acid with 2-(2,3-dimethyl-1H-indol-5-yl)acetic acid with 2-(2,3-dimethyl-1H-indol-5-yl)acetic acid. $[M+H]^+$ 510.23

Example 49

3,5-Diamino-6-chloro-pyrazine-2-carboxylic acid [8-(1,2,3-trimethyl-1H-indole-5-carbonyl)-1,3,8-triaza-spiro[4.5]dec-(2E)-ylidene]-amide To a stirring solution of 1,2,3-trimethyl-1H-indole-5-carboxylic acid (0.051 g, 0.25 mmol) and HATU (0.11 g, 0.28 mmol) in dry DMF (5 ml) is added N-methyl morpholine (0.083 ml, 0.76 mmol). After 5 minutes 5-Diamino-6-chloro-pyrazine-2-carboxylic acid [1,3,8-triaza-spiro[4.5]dec-(2E)-ylidene]-amide dihydrochloride (Ex. 38) (0.10 g, 0.28 mmol) is added and the reaction left to stir at room temperature for 1 hour. Purification by chromatography ($SiO_2$, MeOH/DCM) yields the title compound; $[M+H]^+$ 510.1

Example 50

3,5-Diamino-6-chloro-pyrazine-2-carboxylic acid [8-(1-methyl-1H-indazole-3-carbonyl)-1,3,8-triaza-spiro[4.5]dec-(2E)-ylidene]-amide This compound is prepared analogously to Example 46 by replacing 6,7,8,9-Tetrahydro-5H-carbazole-3-carboxylic acid with 1-methyl-1H-indazole-3-carboxylic acid. $[M+H]^+$ 483.1

Example 51

3,5-Diamino-6-chloro-pyrazine-2-carboxylic acid [8-(4-benzyloxy-benzoyl)-1,3,8-triaza-spiro[4.5]dec-(2E)-ylidene]-amide 5-Diamino-6-chloro-pyrazine-2-carboxylic acid [1,3,8-triaza-spiro[4.5]dec-(2E)-ylidene]-amide dihydrochloride (Ex. 38) (0.05 g, 0.13 mmol), 4-(benzyloxy)benzoic acid (0.029 g, 0.13 mmol), HATU (0.05 g, 0.13 mmol), N-methyl morpholine (0.041 ml, 0.38 mmol) and DMF (2 ml) are stirred together at room temperature for 72 hours. The reaction mixture is diluted with EtOAc (25 ml) and washed with water (25 ml) and sat. $NaHCO_3$ (25 ml). The organic phase is dried over $MgSO_4$ and evaporated in vacuo to yield a yellow oil. The oil is dissolved in ethyl acetate and a drop of methanol and iso-hexane are added. The resulting pale yellow solid is collected by filtration to give the title compound; $[M+H]^+$ 535.1

Example 52

3,5-Diamino-6-chloro-pyrazine-2-carboxylic acid [8-(3-2,3-dihydro-benzofuran-5-yl-propionyl)-1,3,8-triaza-spiro[4.5]dec-(2E)-ylidene]-amide This compound is prepared analogously to Example 51 by replacing 4-(benzyloxy)benzoic acid with 3-(2,3-dihydrobenzofuran-5-yl)propanoic acid. $[M+H]^+$ 499.1

Example 53

3,5-Diamino-6-chloro-pyrazine-2-carboxylic acid [8-(1H-pyrrolo[2,3-b]pyridine-4-carbonyl)-1,3,8-triaza-spiro[4.5]dec-(2E)-ylidene]-amide This compound is prepared analogously to Example 47 by replacing 1H-indazole-3-carboxylic acid with 1H-pyrrolo[2,3-b]pyridine-4-carboxylic acid; $[M+H]^+$ 469.14

Example 54

3,5-Diamino-6-chloro-pyrazine-2-carboxylic acid [8-[3-(4-methoxy-phenyl)-propionyl]-1,3,8-triaza-spiro[4.5]dec-(2E)-ylidene]-amide 5-Diamino-6-chloro-pyrazine-2-carboxylic acid [1,3,8-triaza-spiro[4.5]dec-(2E)-ylidene]-amide dihydrochloride (Ex. 38) (0.05 g, 0.13 mmol), 3-(4-methoxyphenyl)-propionic acid (0.023 g, 0.13 mmol), HATU (0.048 g, 0.13 mmol), N-methyl morpholine (0.041 ml, 0.38 mmol) and DMF (2 ml) are stirred together at room temperature for 48 hours. The reaction mixture is diluted with EtOAc (50 ml) and product is extracted into 1 M HCl. The aqueous phase is basified to pH 12 with 2 N NaOH and product extracted into EtOAc (50 ml). The organic phase is dried over $MgSO_4$ and the solvent evaporated in vacuo to yield a brown glass. The product is triturated with MeOH and EtOAc to give a pale brown solid as the title compound; $[M+H]^+$ 487.0

Example 55

3,5-Diamino-6-chloro-pyrazine-2-carboxylic acid [8-[3-(4-hydroxy-phenyl)-propionyl]-1,3,8-triaza-spiro[4.5]dec-(2E)-ylidene]-amide This compound is prepared analogously to Example 49 by replacing 1,2,3-trimethyl-1H-indole-5-carboxylic acid with 13-(4-hydroxyphenyl)propionic acid; $[M+H]^+$ 472.98

Example 56

3,5-Diamino-6-chloro-pyrazine-2-carboxylic acid [8-(1H-indole-2-carbonyl)-1,3,8-triaza-spiro[4.5] dec-(2E)-ylidene]-amide This compound is prepared analogously to Example 46 by replacing 6,7,8,9-Tetrahydro-5H-carbazole-3-carboxylic acid with 1H-indole-2-carboxylic acid; [M+H]$^+$ 468.1

Example 57

3,5-Diamino-6-chloro-pyrazine-2-carboxylic acid [8-(quinoline-5-carbonyl)-1,3,8-triaza-spiro[4.5]dec-(2E)-ylidene]-amide This compound is prepared analogously to Example 46 by replacing 6,7,8,9-Tetrahydro-5H-carbazole-3-carboxylic acid with quinoline-5-carboxylic acid; [M+H]$^+$ 480.1

Example 58

3,5-Diamino-6-chloro-pyrazine-2-carboxylic acid [8-(4-methyl-2-phenyl-pyrimidine-5-carbonyl)-1,3,8-triaza-spiro[4.5]dec-(2E)-ylidene]-amide This compound is prepared analogously to Example 45 by replacing 5-Oxo-1-(3-pyrrol-1-yl-propyl)-pyrrolidine-3-carboxylic acid (Intermediate X) with 4-methyl-2-phenylpyrimidine-5-carboxylic acid; [M+H]$^+$ 521.1

Example 59

3,5-Diamino-6-chloro-pyrazine-2-carboxylic acid [8-(4-benzyl-morpholine-2-carbonyl)-1,3,8-triaza-spiro[4.5]dec-(2E)-ylidene]-amide This compound is prepared analogously to Example 51 by replacing 4-(benzyloxy)benzoic acid with 4-benzyl-2-morpholinecarboxylic acid hydrochloride; [M+H]$^+$ 528.2

Example 60

3,5-Diamino-6-chloro-pyrazine-2-carboxylic acid [8-(1H-pyrrolo[2,3-b]pyridine-5-carbonyl)-1,3,8-triaza-spiro[4.5]dec-(2E)-ylidene]-amide This compound is prepared analogously to Example 47 by replacing 1H-indazole-3-carboxylic acid with 1H-pyrrolo[2,3-b]pyridine-5-carboxylic acid; [M+H]$^+$ 469.1

Example 61

3,5-Diamino-6-chloro-pyrazine-2-carboxylic acid [8-[4-(4,6-dimethoxy-pyrimidin-2-ylmethoxy)-benzoyl]-1,3,8-triaza-spiro[4.5]dec-(2E)-ylidene]-amide This compound is prepared analogously to Example 51 by replacing 4-(benzyloxy)benzoic acid with 4-((4,6-dimethoxypyrimidin-2-yl)methoxy)benzoic acid; [M+H]$^+$ 597.07

Example 62

3,5-Diamino-6-chloro-pyrazine-2-carboxylic acid [8-[2-(3-isopropyl-ureido)-pyridine4-carbonyl]-1,3,8-triaza-spiro[4.5]dec-(2E)-ylidene]-amide This compound is prepared analogously to Example 51 by replacing 4-(benzyloxy)benzoic acid with 2-(3-Isopropyl-ureido)-isonicotinic acid (intermediate Y) [M+H]$^+$ 530.2; $^1$H NMR (DMSO-d6): 1.13 (6H, d, J=6.5), 1.77-1.94 (4H, m), 3.66 (2H, d, J=11), 3.25-3.99 (5H, m), 6.97 (1H, br m), 7.50 (1H, br s), 7.31-7.60 (2H, br s), 7.61 (1H, br s), 7.74-8.25 (2H, br s), 8.28 (1H, d, J=5.5), 9.08-9.21 (1H, br s), 9.60-9.80 (1H, br s), 9.70-10.25 (1H, br s), 11.07 (s, 1H)

Example 63

4-{2-[(E)-3,5-Diamino-6-chloro-pyrazine-2-carbonylimino]-1,3,8-triaza-spiro[4.5]decane-8-carbonyl}-indole-1-carboxylic acid isopropylamide This compound is prepared analogously to Example 51 by replacing 4-(benzyloxy)benzoic acid with 1-isopropylcarbamoyl-1H-indole-4-carboxylic acid (Intermediate Z): [M+H]$^+$ 553.5

Example 64

3,5-Diamino-6-chloro-pyrazine-2-carboxylic acid [8-[4-(3-isopropyl-ureido)-benzoyl]-1,3,8-triaza-spiro[4.5]dec-(2E)-ylidene]-amide This compound is prepared analogously to Example 51 by replacing 4-(benzyloxy)benzoic acid with 4-(3-isopropyl-ureido)-benzoic acid (Intermediate AA); [M+H]$^+$ 529.5

Example 65

3,5-Diamino-6-chloro-pyrazine-2-carboxylic acid [8-[6-(3-isopropyl-ureido)-pyridine-3-carbonyl]-1,3,8-triaza-spiro[4.5]dec-(2E)-ylidene]-amide This compound is prepared analogously to Example 51 by replacing 4-(benzyloxy)benzoic acid with 6-(3-isopropyl-ureido)-nicotinic acid (Intermediate AB); [M+H]$^+$ 530.5

Example 66

3,5-Diamino-6-chloro-pyrazine-2-carboxylic acid [8-[3-(4-allyloxy-phenyl)-propionyl]-1,3,8-triaza-spiro[4.5]dec-(2E)-ylidene]-amide This compound is prepared analogously to Example 51 by replacing 4-(benzyloxy)benzoic acid with 3-(4-allyloxy)phenyl)propanoic acid; [M+H]$^+$ 513.4

Example 67

3,5-Diamino-6-chloro-pyrazine-2-carboxylic acid [8-{2-[4-(2-methoxy-ethoxymethoxy)-phenyl]-acetyl}-1,3,8-triaza-spiro[4.5]dec-(2E)-ylidene]-amide This compound is prepared analogously to Example 51 by replacing 4-(benzyloxy)benzoic acid with [4-(2-methoxy-ethoxymethoxy)-phenyl]-acetic acid (Intermediate AC); 547.4

Example 68

3,5-Diamino-6-chloro-pyrazine-2-carboxylic acid [8-{3-[4-(2-methoxy-ethoxymethoxy)-phenyl]-propionyl}-1,3,8-triaza-spiro[4.5]dec-(2E)-ylidene]-amide This compound is prepared analogously to Example 2.13 by replacing 4-(benzyloxy)benzoic acid with 3-[4-(2-Methoxy-ethoxymethoxy)-phenyl]-propionic acid (Intermediate AD); $[M+H]^+$ 561.0

Example 69

3,5-Diamino-6-chloro-pyrazine-2-carboxylic acid [8-(3-{4-[2-(tetrahydro-pyran-2yloxy)-ethoxy]-phenyl}-propionyl)-1,3,8-triaza-spiro[4.5]dec-(2E)-ylidene]-amide This compound is prepared analogously to Example 51 by replacing 4-(benzyloxy)benzoic acid with 3-{4-[2-(tetrahydro-pyran-2-yloxy)-ethoxy]-phenyl}-propionic acid (Intermediate AE); $[M+H]^+$ 601.1

Example 70

3,5-Diamino-6-chloro-pyrazine-2-carboxylic acid [8-{3-[4-(pyridin-4-ylmethoxy)-phenyl]-propionyl}-1,3,8-triaza-spiro[4.5]dec-(2E)-ylidene]-amide This compound is prepared analogously to Example 51 by replacing 4-(benzyloxy)benzoic acid with 3-[4-(Pyridin-4-ylmethoxy)-phenyl]-propionic acid (Intermediate AF); $[M+H]^+$ 564.1

Example 71

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butyl This compound is prepared analogously to Example 51 by replacing 4-(benzyloxy)benzoic acid with 3-(4-tert-butoxycarbonylmethoxy-phenyl)-propionic acid (Intermediate AG); $[M+H]^+$ 587.5

Example 72

3,5-Diamino-6-chloro-pyrazine-2-carboxylic acid [8-[3-(4-carbamoylmethoxy-phenyl)-propionyl]-1,3,8-triaza-spiro[4.5]dec-(2E)-ylidene]-amide This compound is prepared analogously to Example 51 by replacing 4-(benzyloxy)benzoic acid with 3-(4-Carbamoylmethoxy-phenyl)-propionic acid (Intermediate AH); $[M+H]^+$ 530.1

Example 73

1-[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-cyclobutanecarboxylic acid ethyl ester This compound is prepared analogously to Example 51 by replacing 4-(benzyloxy)benzoic acid with 1-[4-(2-Carboxy-ethyl)-phenoxy]-cyclobutanecarboxylic acid ethyl ester (Intermediate AI); $[M+H]^+$ 599.1

Example 74

2-[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-2-methyl-propionic acid tert-butyl ester This compound is prepared analogously to Example 51 by replacing 4-(benzyloxy)benzoic acid with 2-[4-(2-Carboxyethyl)-phenoxy]-2-methyl-propionic acid tert-butyl ester (Intermediate AJ); $[M+H]^+$ 615.2

Example 75

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid methyl ester This compound is prepared analogously to Example 51 by replacing 4-(benzyloxy)benzoic acid with 3-(4-Methoxycarbonylmethoxy-phenyl)-propionic acid (Intermediate AK); $[M+H]^+$ 545.1

Example 76

4-{2-[(E)-3,5-Diamino-6-chloro-pyrazine-2-carbonylimino]-1,3,8-triaza-spiro[4.5]decane-8-carbonyl}-benzoic acid tert-butyl ester This compound is prepared analogously to Example 51 by replacing 4-(benzyloxy)benzoic acid with 4-(tert-Butoxycarbonyl)benzoic acid; $[M+H]^+$ 529.4

Example 77

3,5-Diamino-6-chloro-pyrazine-2-carboxylic acid [8-(3-isopropyl-2-methyl-1H-indole-5-carbonyl)-1,3,8-triaza-spiro[4.5]dec-(2E)-ylidene]-amide This compound is prepared analogously to Example 51 by replacing 4-(benzyloxy)benzoic acid with 3-isopropyl-2-methyl-1H-indole-5-carboxylic acid; $[M+H]^+$ 524

Example 78

3-[4-(3-{2-[(E)-3,5-Diamino-6-chloro-pyrazine-2-carbonylimino]-1,3,8-triaza-spiro[4.5]dec-8-yl}-3-oxo-propyl)-phenyl]-propionic acid propyl ester This compound is prepared analogously to Example 51 by replacing 4-(benzyloxy)benzoic acid with 3-[4-(2-Propoxycarbonyl-ethyl)-phenyl]-propionic acid (intermediate AL); $[M+H]^+$ 571

Example 79

3-[4-(3-{2-[(E)-3,5-Diamino-6-chloro-pyrazine-2-carbonylimino]-1,3,8-triaza-spiro[4.5]dec-8-yl}-3-oxo-propyl)-phenyl]-propionic acid ethyl ester This compound is prepared analogously to Example 51 by replacing 4-(benzyloxy)benzoic acid with 3-[4-(2-Ethoxycarbonyl-ethyl)-phenyl]-propionic acid (intermediate AM); $[M+H]^+$ 557

Example 80

3-[4-(3-{2-[(E)-3,5-Diamino-6-chloro-pyrazine-2-carbonylimino]-1,3,8-triaza-spiro[4.5]dec-8-yl}-3-oxo-propyl)-phenyl]-propionic acid methyl ester This compound is prepared analogously to Example 51 by replacing 4-(benzyloxy)benzoic acid with 3-[4-(2-Methoxy-carbonyl-ethyl)-phenyl]-propionic acid (intermediate AN); [M+H]⁺ 543

Example 81

3-[4-(3-{2-[(E)-3,5-Diamino-6-chloro-pyrazine-2-carbonylimino]-1,3,8-triaza-spiro[4.5]dec-8-yl}-3-oxo-propyl)-phenyl]-propionic acid This compound is prepared analogously to Example 51 by replacing 4-(benzyloxy)benzoic acid with 3,3'-(1,4-phenylene)dipropanoic acid; [M+H]⁺ 529

Example 82

3,5-Diamino-6-chloro-pyrazine-2-carboxylic acid [8-[1-(2-phenoxy-ethyl)-1H-indole-4-carbonyl]-1,3,8-triaza-spiro[4.5]dec-(2E)-ylidene]-amide This compound is prepared analogously to Example 51 by replacing 4-(benzyloxy)benzoic acid with 1-(2-Phenoxy-ethyl)-1H-indole-4-carboxylic acid (Intermediate AO); [M+H]⁺ 588

Example 83

3,5-Diamino-6-chloro-pyrazine-2-carboxylic acid [8-[1-(2-p-tolyl-ethyl)-1H-indole-4-carbonyl]-1,3,8-triaza-spiro[4.5]dec-(2E)-ylidene]-amide This compound is prepared analogously to Example 51 by replacing 4-(benzyloxy)benzoic acid with 1-(2-p-Tolyl-ethyl)-1H-indole-4-carboxylic acid (Intermediate AP); [M+H]⁺ 586

Example 84

3,5-Diamino-6-chloro-pyrazine-2-carboxylic acid [8-{1-[2-(tetrahydro-pyran-2-yloxy)-ethyl]-1H-indole-4-carbonyl}-1,3,8-triaza-spiro[4.5]dec-(2E)-ylidene]-amide This compound is prepared analogously to Example 51 by replacing 4-(benzyloxy)benzoic acid with 1-[4-(Tetrahydropyran-2-yloxy)-ethyl]-1H-indole-4-carboxylic acid (Intermediate AQ); [M+H]⁺ 597

Example 85

3,5-Diamino-6-chloro-pyrazine-2-carboxylic acid [8-{1-[2-(4-methoxy-phenoxy)-ethyl]-1H-indole-4-carbonyl}-1,3,8-triaza-spiro[4.5]dec-(2E)-ylidene]-amide This compound is prepared analogously to Example 51 by replacing 4-(benzyloxy)benzoic acid with 1-[2-(4-Methoxy-phenoxy)-ethyl]-1H-indole-4-carboxylic acid (Intermediate AR); [M+H]⁺ 618

Example 86

3,5-Diamino-6-chloro-pyrazine-2-carboxylic acid [8-{1-[2-(4-tert-butyl-phenoxy)-ethyl]-1H-indole-4-carbonyl}-1,3,8-triaza-spiro[4.5]dec-(2E)-ylidene]-amide This compound is prepared analogously to Example 51 by replacing 4-(benzyloxy)benzoic acid with 1-[2-(4-tert-Butyl-phenoxy)-ethyl]-1H-indole-4-carboxylic acid (Intermediate AS); [M+H]⁺ 644

Example 87

3,5-Diamino-6-chloro-pyrazine-2-carboxylic acid [8-[1-(2-[1,3]dioxan-2-yl-ethyl)-1H-indole-4-carbonyl]-1,3,8-triaza-spiro[4.5]dec-(2E)-ylidene]-amide This compound is prepared analogously to Example 51 by replacing 4-(benzyloxy)benzoic acid with 1-(2-[1,3]Dioxan-2-yl-ethyl)-1H-indole-4-carboxylic acid (Intermediate AT; [M+H]⁺ 582

Example 88

3,5-Diamino-6-chloro-pyrazine-2-carboxylic acid [8-[1-(2-hydroxy-ethyl)-2,3-dimethyl-1H-indole-5-carbonyl]-1,3,8-triaza-spiro[4.5]dec-(2E)-ylidene]-amide This compound is prepared analogously to Example 51 by replacing 4-(benzyloxy)benzoic acid with 2,3-Dimethyl-1-[2-(tetrahydro-pyran-2-yloxy)-ethyl]-1H-indole-5-carboxylic acid (Intermediate AU); [M+H]⁺ 540

Example 89

4-(4-{2-[(E)-3,5-Diamino-6-chloro-pyrazine-2-carbonylimino]-1,3,8-triaza-spiro[4.5]decane-8-carbonyl}-indol-1-yl)-butyric acid methyl ester This compound is prepared analogously to Example 51 by replacing 4-(benzyloxy)benzoic acid with 1-(4,4,4-Trimethoxy-butyl)-1H-indole-4-carboxylic acid (Intermediate AW); [M+H]⁺ 568

Example 90

3,5-Diamino-6-chloro-pyrazine-2-carboxylic acid [8-{1-[2-(2-methoxy-ethoxymethoxy)-ethyl]-1H-indole-4-carbonyl}-1,3,8-triaza-spiro[4.5]dec-(2E)-ylidene]-amide This compound is prepared analogously to Example 51 by replacing 4-(benzyloxy)benzoic acid with 1-[2-(2-Methoxy-ethoxymethoxy)-ethyl]-1H-indole-4-carboxylic acid (Intermediate AW); [M+H]⁺ 600

Example 91

3,5-Diamino-6-chloro-pyrazine-2-carboxylic acid [8-(1-diethylcarbamoylmethyl-1H-indole-4-carbonyl)-1,3,8-triaza-spiro[4.5]dec-(2E)-ylidene]-amide This compound is prepared analogously to Example 51 by replacing 4-(benzyloxy)benzoic acid with 1-Diethylcarbamoylmethyl-1H-indole-4-carboxylic acid (Intermediate AX); [M+H]⁺ 581

Example 92

3,5-Diamino-6-chloro-pyrazine-2-carboxylic acid [8-[1-(2-hydroxy-ethyl)-1H-indole-4-carbonyl]-1,3,8-triaza-spiro[4.5]dec-(2E)-ylidene]-amide p-Toluenesulfonic acid monohydrate (1.6 mg, 0.0084 mmol) is added to a stirred solution of 3,5-diamino-6-chloro-pyrazine-2-carboxylic acid [8-{1-[2-(tetrahydro-pyran-2-yloxy)-ethyl]-1H-indole-4-carbonyl}-1,3,8-triaza-spiro[4.5]dec-(2E)-ylidene]-amide (Ex. 84) (50 mg, 0.084 mmol) in MeOH (3 ml) and the resulting solution is stirred at room temperature for 3 hrs, then heated at 50° C. for 16 hours. The solvent is removed in vacuo and the residue is dissolved in MeOH (3 ml) and loaded onto a 1 g PEAX cartridge which is eluted with MeOH (20 ml). The filtrate is concentrated in vacuo to afford the title compound; [M+H]$^+$ 512/514

Example 93

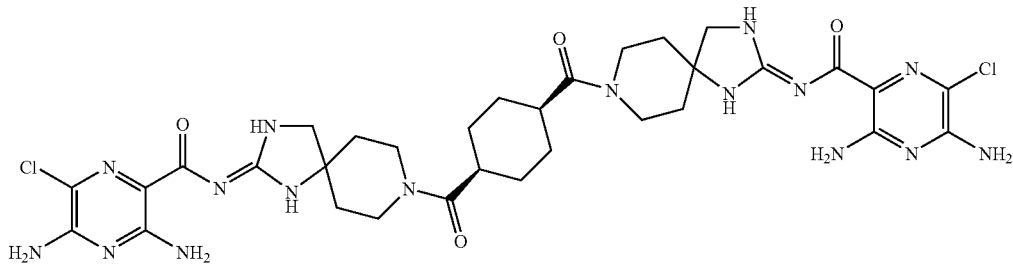

A mixture of 3,5-diamino-6-chloro-pyrazine-2-carboxylic acid [1,3,8-triaza-spiro[4.5]dec-(2E)-ylidene]-amide dihydrochloride (Ex. 38) (300 mg, 0.83 mmol), cis-1,4-cyclohexanedicarboxylic acid (72 mg, 0.42 mmol), N-methyl morpholine (0.30 ml, 2.73 mmol) and HATU (315 mg, 0.83 mmol) in anhydrous DMF is stirred at room temperature for 16 hours. The reaction mixture is concentrated in vacuo and is subjected to column chromatography (basic alumina, 0-3% MeOH in DCM) to obtain off-white solid. The product is dissolved in DCM and re-precipitated by addition of diethyl ether. The supernatant solvent mixture is decanted and the product is washed again with diethyl ether and dried under vacuum to afford the compound shown as off-white solid; [M+H]$^+$ 785.

Example 94

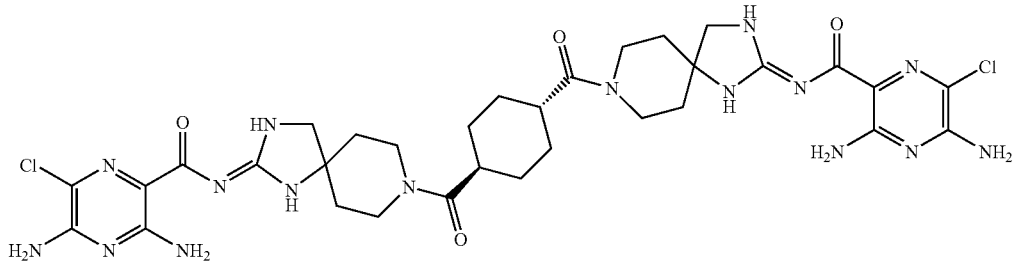

This compound is prepared analogously to Example 93 by replacing cis-1,4-cyclohexanedicarboxylic acid with trans-1,4-cyclohexanedicarboxylic acid; [M+2H]$^{2+}$ 393

Example 95

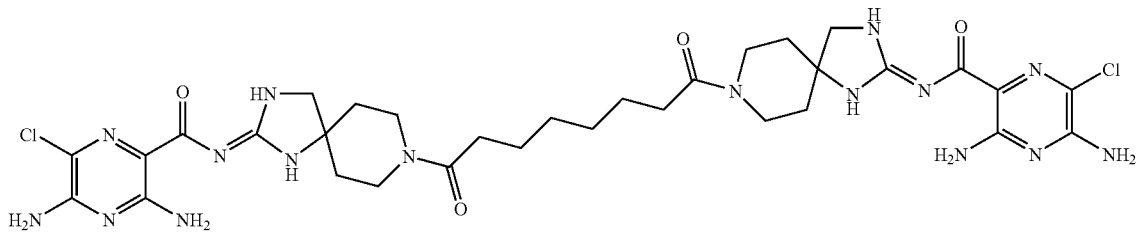

This compound is prepared analogously to Example 93 by replacing cis-1,4-cyclohexanedicarboxylic acid with suberic acid; [M+H]$^+$ 787

Example 96

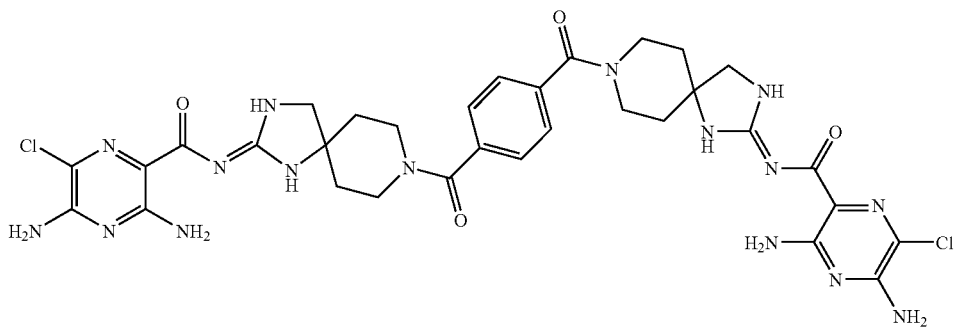

This compound is prepared analogously to Example 93 by replacing cis-1,4-cyclohexanedicarboxylic acid with terephthalic acid; [M+H]$^+$ 779

Example 97

3,5-Diamino-6-chloro-pyrazine-2-carboxylic acid [8-[2-(4-benzyloxy-phenyl)-acetyl]-1,3,8-triaza-spiro[4.5]dec-(2E)-ylidene]-amide A mixture of 3,5-diamino-6-chloro-pyrazine-2-carboxylic acid [1,3,8-triaza-spiro[4.5]dec-(2E)-ylidene]-amide dihydrochloride (Ex. 38) (300 mg, 0.83 mmol), 4-benzyloxyphenylacetic acid (200 mg, 0.83 mmol), N-methyl morpholine (0.40 ml, 3.64 mmol) and HATU (315 mg, 0.83 mmol) in anhydrous DMF (20 ml) is stirred at room temperature for 16 hours. The reaction mixture is concentrated in vacuo and subjected to column chromatography (basic alumina, 0-3% MeOH in DCM) to obtain pale yellow solid. The product is dissolved in DCM and MeOH and re-precipitated by adding diethyl ether. The supernatant solvent mixture is decanted and the product is washed again with diethyl ether and dried under vacuum to afford the title compound as a pale yellow solid; [M+H]$^+$ 549.

Example 98

3,5-Diamino-6-chloro-pyrazine-2-carboxylic acid [8-[3-(4-benzyloxy-phenyl)-propionyl]-1,3,8-triaza-spiro[4.5]dec-(2E)-ylidene]-amide This compound is prepared analogously to Example 97 by replacing 4-benzyloxyphenylacetic acid with 3-(4-benzyloxyphenyl)propionic acid; [M+H]$^+$ 563

Example 99

3,5-Diamino-6-chloro-pyrazine-2-carboxylic acid [8-(1H-indole-4-carbonyl)-1,3,8-triaza-spiro[4.5]dec-(2E)-ylidene]-amide This compound is prepared analogously to Example 97 by replacing 4-benzyloxyphenylacetic acid with indole-4-carboxylic acid; [M+H]$^+$ 468

Example 100

3,5-Diamino-6-chloro-pyrazine-2-carboxylic acid [8-(1H-indole-5-carbonyl)-1,3,8-triaza-spiro[4.5]dec-(2E)-ylidene]-amide This compound is prepared analogously to Example 97 by replacing 4-benzyloxyphenylacetic acid with indole-5-carboxylic acid; $[M+H]^+$ 468

Example 101

3,5-Diamino-6-chloro-pyrazine-2-carboxylic acid [8-phenylacetyl-1,3,8-triaza-spiro[4.5]dec-(2E)-ylidene]-amide This compound is prepared analogously to Example 97 by replacing 4-benzyloxyphenylacetic acid with phenylacetic acid; $[M+H]^+$ 443

Example 102

3,5-Diamino-6-chloro-pyrazine-2-carboxylic acid [8-{4-[6-((S)-2,3-dihydroxy-propoxy)-naphthalen-2-ylmethoxy]-benzoyl}-1,3,8-triaza-spiro[4.5]dec-(2E)-ylidene]-amide Step 1
3,5-Diamino-6-chloro-pyrazine-2-carboxylic acid [8-{4-[6-((R)-2,2-dimethyl-[1,3]dioxolan-4-ylmethoxy)-naphthalen-2-ylmethoxy]-benzoyl}-1,3,8-triaza-spiro[4.5]dec-(2E)-ylidene]-amide is prepared analogously to Example 97 by replacing 4-benzyloxyphenylacetic acid with 4-[6-((R)-2,2-dimethyl-[1,3]dioxolan-4-ylmethoxy)-naphthalen-2-ylmethoxy]-benzoic acid (Intermediate AY); $[M+H]^+$ 715

Step 2:
To a solution of 3,5-diamino-6-chloro-pyrazine-2-carboxylic acid [8-{4-[6-((R)-2,2-dimethyl-[1,3]-dioxolan-4-ylmethoxy)-naphthalen-2-ylmethoxy]-benzoyl}-1,3,8-triaza-spiro[4.5]dec-(2E)-ylidene]-amide (0.16 g, 0.22 mmol) in MeOH (10 ml) is added SCX-2 resin (~2 g), the resultant slurry is stirred for 0.5 hours and then the solvent is removed in vacuo. The slurry is loaded onto a column of SCX-2 resin (~3 g) and eluted with MeOH and then with 2 M $NH_3$ in MeOH. The methanolic ammonia fractions are concentrated in vacuo and the residue is triturated with diethyl ether to obtain 3,5-Diamino-6-chloro-pyrazine-2-carboxylic acid [8-{4-[6-((S)-2,3-dihydroxy-propoxy)-naphthalen-2-ylmethoxy]-benzoyl}-1,3,8-triaza-spiro[4.5]dec-(2E)-ylidene]-amide as yellow solid; $[M+H]^+$ 675

Example 103

3,5-Diamino-6-chloro-pyrazine-2-carboxylic acid [8-(4-chloro-benzoyl)-1,3,8-triaza-spiro[4.5]dec-(2E)-ylidene]-amide This compound is prepared analogously to Example 97 by replacing 4-benzyloxyphenylacetic acid with p-chlorobenzoic acid; $[M+H]^+$ 463

Example 104

3,5-Diamino-6-chloro-pyrazine-2-carboxylic acid [8-(4-{3-[4-((S)-2,3-dihydroxy-propoxy)-phenyl]-propoxy}-benzoyl)-1,3,8-triaza-spiro[4.5]dec-(2E)-ylidene]-amide This compound is prepared analogously to Example 102 by replacing 4-[6-((R)-2,2-dimethyl-[1,3]dioxolan-4-ylmethoxy)-naphthalen-2-ylmethoxy]-benzoic acid, (Intermediate AY) with 4-{3-[4-((R)-2,2-dimethyl-[1,3]dioxolan-4-ylmethoxy)-phenyl]-propoxy}-benzoic acid (Intermediate AZ); $[M+H]^+$ 653

Example 105

3,5-Diamino-6-chloro-pyrazine-2-carboxylic acid [8-[(E)-(3-phenyl-acryloyl)]-1,3,8-triaza-spiro[4.5]dec-(2E)-ylidene]-amide This compound is prepared analogously to Example 97 by replacing 4-benzyloxyphenylacetic acid with trans-cinnamic acid; $[M+H]^+$ 455

Example 106

3,5-Diamino-6-chloro-pyrazine-2-carboxylic acid [8-benzoyl-1,3,8-triaza-spiro[4.5]dec-(2E)-ylidene]-amide This compound is prepared analogously to Example 97 by replacing 4-benzyloxyphenylacetic acid with benzoic acid; $[M+H]^+$ 429

Example 107

3,5-Diamino-6-chloro-pyrazine-2-carboxylic acid [8-(benzofuran-5-carbonyl)-1,3,8-triaza-spiro[4.5]dec-(2E)-ylidene]-amide This compound is prepared analogously to Example 97 by replacing 4-benzyloxyphenylacetic acid with benzofuran-5-carboxylic acid; $[M+H]^+$ 469

Example 108

3,5-Diamino-6-chloro-pyrazine-2-carboxylic acid [8-hexanoyl-1,3,8-triaza-spiro[4.5]dec-(2E)-ylidene]-amide This compound is prepared analogously to Example 97 by replacing 4-benzyloxyphenylacetic acid with hexanoic acid; $[M+H]^+$ 423

Example 109

3,5-Diamino-6-chloro-pyrazine-2-carboxylic acid [8-(3-phenyl-propynoyl)-1,3,8-triaza-spiro[4.5]dec-(2E)-ylidene]-amide This compound is prepared analogously to Example 97 by replacing 4-benzyloxyphenylacetic acid with phenylpropiolic acid; $[M+H]^+$ 453

Example 110

3,5-Diamino-6-chloro-pyrazine-2-carboxylic acid [8-(1H-imidazole-2-carbonyl)-1,3,8-triaza-spiro[4.5]dec-(2E)-ylidene]-amide This compound is prepared analogously to Example 97 by replacing 4-benzyloxyphenylacetic acid with 2-imidazolecarboxylic acid; $[M+H]^+$ 419

Example 111

3,5-Diamino-6-chloro-pyrazine-2-carboxylic acid [8-isobutyryl-1,3,8-triaza-spiro[4.5]dec-(2E)-ylidene]-amide This compound is prepared analogously to Example 97 by replacing 4-benzyloxyphenylacetic acid with isobuteric acid; [M+H]$^+$ 395

Example 112

3,5-Diamino-6-chloro-pyrazine-2-carboxylic acid [8-(4-cyano-benzoyl)-1,3,8-triaza-spiro[4.5]dec-(2E)-ylidene]-amide This compound is prepared analogously to Example 97 by replacing 4-benzyloxyphenylacetic acid with p-cyanobenzoic acid; [M+H]$^+$ 454

Example 113

3,5-Diamino-6-chloro-pyrazine-2-carboxylic acid [8-(pyridine-3-carbonyl)-1,3,8-triaza-spiro[4.5]dec-(2E)-ylidene]-amide This compound is prepared analogously to Example 97 by replacing 4-benzyloxyphenylacetic acid with nicotinic acid; [M+H]$^+$ 430

Example 114

4-{2-[(E)-3,5-Diamino-6-chloro-pyrazine-2-carbonylimino]-1,3,8-triaza-spiro[4.5]decane-8-carbonyl}-benzoic acid methyl ester This compound is prepared analogously to Example 97 by replacing 4-benzyloxyphenylacetic acid with monomethyl terephthalate; [M+H]$^+$ 487

Example 115

3,5-Diamino-6-chloro-pyrazine-2-carboxylic acid [8-(pyrimidine-5-carbonyl)-1,3,8-triaza-spiro[4.5]dec-(2E)-ylidene]-amide This compound is prepared analogously to Example 97 by replacing 4-benzyloxyphenylacetic acid with pyrimidine-5-carboxylic acid; [M+H]$^+$ 431

Example 116

3,5-Diamino-6-chloro-pyrazine-2-carboxylic acid [8-(4-hydroxy-benzoyl)-1,3,8-triaza-spiro[4.5]dec-(2E)-ylidene]-amide This compound is prepared analogously to Example 97 by replacing 4-benzyloxyphenylacetic acid with 4-hydroxybenzoic acid; [M+H]$^+$ 445

Example 117

3,5-Diamino-6-chloro-pyrazine-2-carboxylic acid [8-cyclohexanecarbonyl-1,3,8-triaza-spiro[4.5]dec-(2E)-ylidene]-amide This compound is prepared analogously to Example 97 by replacing 4-benzyloxyphenylacetic acid with cyclohexanecarboxylic acid; [M+H]$^+$ 435

Example 118

3,5-Diamino-6-chloro-pyrazine-2-carboxylic acid [8-(oxazole-4-carbonyl)-1,3,8-triaza-spiro[4.5]dec-(2E)-ylidene]-amide This compound is prepared analogously to Example 97 by replacing 4-benzyloxyphenylacetic acid with oxazole-4-carboxylic acid; [M+H]$^+$ 420

Example 119

3,5-Diamino-6-chloro-pyrazine-2-carboxylic acid [8-(pyridine-2-carbonyl)-1,3,8-triaza-spiro[4.5]dec-(2E)-ylidene]-amide This compound is prepared analogously to Example 97 by replacing 4-benzyloxyphenylacetic acid with 2-picolinic acid; [M+H]$^+$ 430

Example 120

3,5-Diamino-6-chloro-pyrazine-2-carboxylic acid [8-(pyridine-4-carbonyl)-1,3,8-triaza-spiro[4.5]dec-(2E)-ylidene]-amide This compound is prepared analogously to Example 97 by replacing 4-benzyloxyphenylacetic acid with isonicotinic acid; [M+H]$^+$ 430

Example 121

3,5-Diamino-6-chloro-pyrazine-2-carboxylic acid [8-(piperidine-4-carbonyl)-1,3,8-triaza-spiro[4.5]dec-(2E)-ylidene]-amide hydrochloride 4 M HCl in dioxane (5 ml) is added to a solution of 4-{2-[(E)-3,5-diamino-6-chloro-pyrazine-2-carbonylimino]-1,3,8-triaza-spiro[4.5]decane-8-carbonyl}-piperidine-1-carboxylic acid tert-butyl ester (Intermediate BA) (0.14 g, 0.26 mmol) in dioxane (10 ml) and the reaction mixture is stirred at room temperature for 3 hours. The reaction mixture is concentrated in vacuo and the yellow solid obtained is triturated with DCM. The DCM layer is decanted and the compound is washed with MeOH and dried under vacuum to afford the title compound as yellow solid; [M+H]$^+$ 436

Example 122

3,5-Diamino-6-chloro-pyrazine-2-carboxylic acid [8-(1H-imidazole-4-carbonyl)-1,3,8-triaza-spiro[4.5]dec-(2E)-ylidene]-amide This compound is prepared analogously to Example 97 by replacing 4-benzyloxyphenylacetic acid with 4-imidazole-carboxylic acid; [M+H]$^+$ 419

Example 123

3,5-Diamino-6-chloro-pyrazine-2-carboxylic acid [8-(tetrahydro-pyran-4-carbonyl)-1,3,8-triaza-spiro[4.5]dec-(2E)-ylidene]-amide This compound is prepared analogously to Example 97 by replacing 4-benzyloxyphenylacetic acid with tetrahydropyran-4-carboxylic acid; [M+H]$^+$ 437

Example 124

3,5-Diamino-6-chloro-pyrazine-2-carboxylic acid [8-(pyrimidine-4-carbonyl)-1,3,8-triaza-spiro[4.5]dec-(2E)-ylidene]-amide This compound is prepared analogously to Example 97 by replacing 4-benzyloxyphenylacetic acid with pyrimidine-4-carboxylic acid; [M+H]$^+$ 431

Example 125

3,5-Diamino-6-chloro-pyrazine-2-carboxylic acid [8-(oxazole-5-carbonyl)-1,3,8-triaza-spiro[4.5]dec-(2E)-ylidene]-amide This compound is prepared analogously to Example 97 by replacing 4-benzyloxyphenylacetic acid with oxazole-5-carboxylic acid; [M+H]$^+$ 420

Example 126

3,5-Diamino-6-chloro-pyrazine-2-carboxylic acid [8-[3-(4-isobutoxy-piperidine-1-sulfonyl)-benzoyl]-1,3,8-triaza-spiro[4.5]dec-(2E)-ylidene]-amide Step 1
A solution of N,N-Diisopropylethylamine (0.0078 ml, 0.045 mmol) in THF (1 ml) is added to 4-Isobutoxy-piperidine (0.008 g, 0.05 mmol) followed by a solution of 3-(Chlorosulfonyl)benzoic acid (9.93 mg, 0.045 mmol) and shaken at room temperature for 48 hours. The solution is evaporated under vacuum to afford 3-(4-Isobutoxy-piperidine-1-sulfonyl)-benzoic acid which is used without purification; [M+H]$^+$ 342.00

Step 2
3-(4-Isobutoxy-piperidine-1-sulfonyl)-benzoic acid (0.03 mmol, 10.2 mg) is treated with a solution of HATU (11.4 mg, 0.03 mmol) in DMF (1 ml) followed by a solution of 3,5-Diamino-6-chloro-pyrazine-2-carboxylic acid [1,3,8-triaza-spiro[4.5]dec-(2E)-ylidene]-amide dihydrochloride (Ex. 38) (11.9 mg, 0.03 mmol) and N-methyl morpholine (0.010 ml, 0.03 mmol) in DMF (1 ml) and shaken at room temperature overnight. The solution is evaporated under vacuum, redissolved in DMSO (0.5 ml) and purified by mass-directed preparative HPLC. The purified fractions are evaporated under vacuum to afford the title compound; [M+H]$^+$ 648.4

Examples 127-145

These compounds, namely
3,5-Diamino-6-chloro-pyrazine-2-carboxylic acid [8-{3-[2-(1H-indol-3-yl)-ethylsulfamoyl]-benzoyl}-1,3,8-triaza-spiro[4.5]dec-(2E)-ylidene]-amide (Ex. 127);
1-(3-{2-[(E)-3,5-Diamino-6-chloro-pyrazine-2-carbonylimino]-1,3,8-triaza-spiro[4.5]decane-8-carbonyl}-benzenesulfonyl)-piperidine-3-carboxylic acid ethyl ester (Ex. 128);
3,5-Diamino-6-chloro-pyrazine-2-carboxylic acid [8-(3-cyclopentylsulfamoyl-benzoyl)-1,3,8-triaza-spiro[4.5]dec-(2E)-ylidene]-amide (Ex. 127);
3,5-Diamino-6-chloro-pyrazine-2-carboxylic acid [8-[3-(1-acetyl-piperidin-4-ylsulfamoyl)-benzoyl]-1,3,8-triaza-spiro[4.5]dec-(2E)-ylidene]-amide (Ex. 130);
3,5-Diamino-6-chloro-pyrazine-2-carboxylic acid [8-{3-[(tetrahydro-furan-2-ylmethyl)-sulfamoyl]-benzoyl}-1,3,8-triaza-spiro[4.5]dec-(2E)-ylidene]-amide (Ex. 131);
3,5-Diamino-6-chloro-pyrazine-2-carboxylic acid [8-{3-[(pyridin-3-ylmethyl)-sulfamoyl]-benzoyl}-1,3,8-triaza-spiro[4.5]dec-(2E)-ylidene]-amide (Ex. 132);
3,5-Diamino-6-chloro-pyrazine-2-carboxylic acid [8-{3-[(2,2-dimethoxy-ethyl)-methyl-sulfamoyl]-benzoyl}-1,3,8-triaza-spiro[4.5]dec-(2E)-ylidene]-amide (Ex. 133);
3,5-Diamino-6-chloro-pyrazine-2-carboxylic acid [8-[3-(2,4-difluoro-benzylsulfamoyl)-benzoyl]-1,3,8-triaza-spiro[4.5]dec-(2E)-ylidene]-amide (Ex. 134);
3,5-Diamino-6-chloro-pyrazine-2-carboxylic acid [8-[3-(1-pyridin-4-yl-ethylsulfamoyl)-benzoyl]-1,3,8-triaza-spiro[4.5]dec-(2E)-ylidene]-amide (Ex. 135);
3,5-Diamino-6-chloro-pyrazine-2-carboxylic acid [8-[3-(2-phenyl-morpholine-4-sulfonyl)-benzoyl]-1,3,8-triaza-spiro[4.5]dec-(2E)-ylidene]-amide (Ex. 136);
3,5-Diamino-6-chloro-pyrazine-2-carboxylic acid [8-[3-(3-difluoromethoxy-benzylsulfamoyl)-benzoyl]-1,3,8-triaza-spiro[4.5]dec-(2E)-ylidene]-amide (Ex. 137);
3,5-Diamino-6-chloro-pyrazine-2-carboxylic acid [8-[3-(4-pyrrolidin-1-yl-piperidine-1-sulfonyl)-benzoyl]-1,3,8-triaza-spiro[4.5]dec-(2E)-ylidene]-amide (Ex. 138);
3,5-Diamino-6-chloro-pyrazine-2-carboxylic acid [8-{3-[(5-methyl-pyrazin-2-ylmethyl)-sulfamoyl]-benzoyl}-1,3,8-triaza-spiro[4.5]dec-(2E)-ylidene]-amide (Ex. 139);
3,5-Diamino-6-chloro-pyrazine-2-carboxylic acid [8-[3-(dimethylcarbamoylmethyl-sulfamoyl)-benzoyl]-1,3,8-triaza-spiro[4.5]dec-(2E)-ylidene]-amide (Ex. 140);
3,5-Diamino-6-chloro-pyrazine-2-carboxylic acid [8-[3-(3-benzenesulfonyl-pyrrolidine-1-sulfonyl)-benzoyl]-1,3,8-triaza-spiro[4.5]dec-(2E)-ylidene]-amide (Ex. 141);
3,5-Diamino-6-chloro-pyrazine-2-carboxylic acid [8-{3-[([1,3]dioxolan-2-ylmethyl)-sulfamoyl]-benzoyl}-1,3,8-triaza-spiro[4.5]dec-(2E)-ylidene]-amide (Ex. 142);
3,5-Diamino-6-chloro-pyrazine-2-carboxylic acid [8-{3-[2-(pyridin-3-yloxy)-propylsulfamoyl]-benzoyl}-1,3,8-triaza-spiro[4.5]dec-(2E)-ylidene]-amide (Ex. 143);
3,5-Diamino-6-chloro-pyrazine-2-carboxylic acid [8-{3-[4-(5-trifluoromethyl-pyridin-2-yl)-[1,4]diazepane-1-sulfonyl]-benzoyl}-1,3,8-triaza-spiro[4.5]dec-(2E)-ylidene]-amide (Ex. 144);
3,5-Diamino-6-chloro-pyrazine-2-carboxylic acid [8-[3-(1,1-dioxo-tetrahydro-1lambda*6*-thiophen-3-ylsulfamoyl)-benzoyl]-1,3,8-triaza-spiro[4.5]dec-(2E)-ylidene]-amide (Ex. 145);
are made analogously to Examples 126 replacing 4-isobutoxy-piperidine in step 1 with the appropriate amines which are all commercially available. The compounds are recovered from the reaction mixture and purified using conventional techniques.

Example 146

3,5-Diamino-6-chloro-pyrazine-2-carboxylic acid [8-{3-[3-(4-chlorophenyl)-[1,2,4]oxadiazol-5-yl]-propionyl}-1,3,8-triaza-spiro[4.5]dec-(2E)-ylidene-amide trifluoroacetate N-methyl morpholine (33 □l, 0.3 mmol) is added to 3-(3-p-Tolyl-[1,2,4]oxadiazol-5-yl)-propionic acid (0.1 mmol), followed by HATU (41.8 mg, 0.11 mmol) dissolved in peptide grade DMF (250 □l) and 3,5-Diamino-6-chloro-pyrazine-2-carboxylic acid [1,3,8-triaza-spiro[4.5]dec-(2E)-ylidene]-amide dihydrochloride (Ex. 38) (40 mg, 0.1 mmol) dissolved in peptide grade DMF (250 □l). The reaction is

Example 147

3,5-Diamino-6-chloropyrazine-2-carboxylic acid [8-[1-(toluene-4-sulfonyl)-1H-pyrrole-3-carbonyl]-1,3,8-triaza-spiro[4.5]dec-(2E)-ylidene]-amide A solution of 1-(Toluene-4-sulfonyl)-1H-pyrrole-3-carboxylic acid (0.023 g, 0.085 mmol) in NMP (850 □l) is added to PS-carbodiimide (190 mg of 1.3 mmol/g loading, 0.24 mmol), followed by a solution of 3,5-Diamino-6-chloropyrazine-2-carboxylic acid [1,3,8-triaza-spiro[4.5]dec-(2E)-ylidene]-amide dihydrochloride (Ex. 38) (0.08 mmol) and N-methyl morpholine (8 □l, 0.08 mmol) in NMP (1 ml), and the resulting reaction mixture is shaken at room temperature. The reaction mixture is filtered and the resin is washed with NMP (1 ml). The collected filtrate is concentrated in vacuo and the residues are purified by mass-directed preparative HPLC. The purified fractions are evaporated under vacuum to afford the title compound; [M+H]$^+$ 572.08

Example 148

3,5-Diamino-6-chloro-pyrazine-2-carboxylic acid [8-[1-(3,4-difluoro-benzyl)-6-oxo-1,6-dihydro-pyridine-3-carbonyl]-1,3,8-triaza-spiro[4.5]dec-(2E)-ylidene]-amide A solution of 1-(3,4-Difluoro-benzyl)-6-oxo-1,6-dihydro-pyridine-3-carboxylic acid (0.15 mmol) in NMP (0.5 ml) is added to a solution of 3,5-Diamino-6-chloro-pyrazine-2-carboxylic acid [1,3,8-triaza-spiro[4.5]dec-(2E)-ylidene]-amide dihydrochloride (Ex. 38) (0.049 g, 0.15 mmol) and N-methyl morpholine (0.033 ml, 0.30 mmol) in NMP (1 ml), followed by a solution of HATU (0.11 g, 0.3 mmol) in NMP (0.5 ml). The reaction mixture is shaken at room temperature overnight. The reaction mixture is purified by mass-directed preparative HPLC. Fractions containing pure product are eluted through SCX-2 cartridges (Biotage 1 g/6 ml cartridge), and the cartridge is washed with MeOH (4 ml), followed by 3M NH$_3$ in MeOH solution (4 ml) to afford the title compound; [M+H]$^+$ 572.0

Examples 149-213

These compounds, namely
3,5-Diamino-6-chloro-pyrazine-2-carboxylic acid [8-[4-(3-phenyl-isoxazol-5-yl)-butyryl]-1,3,8-triaza-spiro[4.5]dec-(2E)-ylidene-amide (Ex. 149);
3,5-Diamino-6-chloro-pyrazine-2-carboxylic acid [8-[4-(5-fluoro-2,3-dihydro-indol-1-yl)-4-oxo-butyryl]-1,3,8-triaza-spiro[4.5]dec-(2E)-ylidene-amide (Ex. 150);
3,5-Diamino-6-chloro-pyrazine-2-carboxylic acid [8-{4-[3-(4-methoxy-phenyl)-[1,2,4]oxadiazol-5yl]-butyryl}-1,3,8-triaza-spiro[4.5]dec-(2E)-ylidene-amide (Ex. 151);
3,5-Diamino-6-chloro-pyrazine-2-carboxylic acid [8-(4-1H-indazol-3-yl-butyryl)-1,3,8-triaza-spiro[4.5]dec-(2E)-ylidene-amide (Ex. 152);
3,5-Diamino-6-chloro-pyrazine-2-carboxylic acid [8-[4-(5-methanesulfonyl-2,3-dihydro-indol-1yl)-4-oxo-butyryl]-1,3,8-triaza-spiro[4.5]dec-(2E)-ylidene-amide (Ex. 153);
3,5-Diamino-6-chloro-pyrazine-2-carboxylic acid [8-(4-benzothiazol-2-yl-butyryl)-1,3,8-triaza-spiro[4.5]dec-(2E)-ylidene-amide (Ex. 154);
3,5-Diamino-6-chloro-pyrazine-2-carboxylic acid [8-[4-(5-dimethylsulfamoyl-2,3-dihydro-indol-1yl)-4-oxo-butyryl]-1,3,8-triaza-spiro[4.5]dec-(2E)-ylidene-amide (Ex. 155);
3,5-Diamino-6-chloro-pyrazine-2-carboxylic acid [8-[4-(2-oxo-2,3-dihydro-1H-indol-3-yl)-butyryl]-1,3,8-triaza-spiro[4.5]dec-(2E)-ylidene-amide (Ex. 156);
3,5-Diamino-6-chloro-pyrazine-2-carboxylic acid [8-[4-(6-dimethylamino-9H-purin-8-yl)-butyryl]-1,3,8-triaza-spiro[4.5]dec-(2E)-ylidene-amide (Ex. 157);
3,5-Diamino-6-chloro-pyrazine-2-carboxylic acid [8-[4-(2-oxo-3-pyridin-3-yl-2,3-dihydro-benzoimidazol-1-yl)-butyryl]-1,3,8-triaza-spiro[4.5]dec-(2E)-ylidene-amide (Ex. 158);
3,5-Diamino-6-chloro-pyrazine-2-carboxylic acid [8-[4-(2-oxo-3-pyridine-3ylmethyl-2,3-dihydro-indol-1-yl)-butyryl]-1,3,8-triaza-spiro[4.5]dec-(2E)-ylidene-amide (Ex. 159);
3,5-Diamino-6-chloro-pyrazine-2-carboxylic acid [8-[4-(9-oxo-3,3a,4,9,10,10a-hexahydro-1H-2-aza-benzol[F]azulen-2yl)-butyryl]-1,3,8-triaza-spiro[4.5]dec-(2E)-ylidene-amide (Ex. 160);
3,5-Diamino-6-chloro-pyrazine-2-carboxylic acid [8-[4-(6-amino-9H-purine-8yl)-butyryl]-1,3,8-triaza-spiro[4.5]dec-(2E)-ylidene-amide (Ex. 161);
3,5-Diamino-6-chloro-pyrazine-2-carboxylic acid [8-(4-oxo-4-pyrrolidin-1-yl-butyryl)-1,3,8-triaza-spiro[4.5]dec-(2E)-ylidene-amide (Ex. 162);
3,5-Diamino-6-chloro-pyrazine-2-carboxylic acid [8-(4-[1,2,4]triazol-1-yl-butyryl)-1,3,8-triaza-spiro[4.5]dec-(2E)-ylidene-amide (Ex. 163);
3,5-Diamino-6-chloro-pyrazine-2-carboxylic acid [8-(5-dibenzylsulfamoyl-1-methyl-1H-pyrrole-2-carbonyl)-1,3,8-triaza-spiro[4.5]dec-(2E)-ylidene-amide (Ex. 164);
3,5-Diamino-6-chloro-pyrazine-2-carboxylic acid [8-{4-[3-(4-chloro-phenyl)-[1,2,4]oxadiazol-5-yl]-butyryl}-1,3,8-triaza-spiro[4.5]dec-(2E)-ylidene-amide (Ex. 165);
3,5-Diamino-6-chloro-pyrazine-2-carboxylic acid [8-{4-[(naphthalene-1-sulfonylamino)-methyl]-benzoyl}-1,3,8-triaza-spiro[4.5]dec-(2E)-ylidene-amide (Ex. 166);
3,5-Diamino-6-chloro-pyrazine-2-carboxylic acid [8-{2[3-(4-chlorophenyl)-[1,2,4]oxadiazol-5-yl]-acetyl}-1,3,8-triaza-spiro[4.5]dec-(2E)-ylidene-amide (Ex. 167);
3,5-Diamino-6-chloro-pyrazine-2-carboxylic acid [8-[3-(3-methoxy-propoxy)-benzoyl]-1,3,8-triaza-spiro[4.5]dec-(2E)-ylidene-amide (Ex. 168);
3,5-Diamino-6-chloro-pyrazine-2-carboxylic acid [8-(2-benzotriazol-2-yl-acetyl)-1,3,8-triaza-spiro[4.5]dec-(2E)-ylidene-amide (Ex. 169)
3,5-Diamino-6-chloro-pyrazine-2-carboxylic acid [8-(2-benzotriazol-2-yl-acetyl)-1,3,8-triaza-spiro[4.5]dec-(2E)-ylidene-amide (Ex. 170);
3,5-Diamino-6-chloro-pyrazine-2-carboxylic acid [8-[4-(2-isopropoxy-ethylamino)-benzoyl]-1,3,8-triaza-spiro[4.5]dec-(2E)-ylidene-amide (Ex. 171);
3,5-Diamino-6-chloro-pyrazine-2-carboxylic acid [8-[6-oxo-1-(3-trifluoromethyl-benzyl)-1,6-dihydro-pyridine-3-carbonyl]-1,3,8-triaza-spiro[4.5]dec-(2E)-ylidene]-amide (Ex. 172);
3,5-Diamino-6-chloro-pyrazine-2-carboxylic acid [8-[6-(4-methyl-piperazin-1-yl)-pyridine-3-carbonyl]-1,3,8-triaza-spiro[4.5]dec-(2E)-ylidene-amide (Ex. 173);
3,5-Diamino-6-chloro-pyrazine-2-carboxylic acid [8-[3-(4-fluoro-phenyl)-5-methyl-isoxazole-4-carbonyl]-1,3,8-triaza-spiro[4.5]dec-(2E)-ylidene-amide (Ex. 174);

3,5-Diamino-6-chloro-pyrazine-2-carboxylic acid [8-{3-[3-(4-methoxy-phenyl)-[1,2,4]oxadiazol-5-yl]-propionyl}-1,3,8-triaza-spiro[4.5]dec-(2E)-ylidene]-amide (Ex. 175);
3,5-Diamino-6-chloro-pyrazine-2-carboxylic acid [8-[2-(4-trifluoromethoxy-phenoxy)-acetyl]-1,3,8-triaza-spiro[4.5]dec-(2E)-ylidene]-amide (Ex. 176);
3,5-Diamino-6-chloro-pyrazine-2-carboxylic acid [8-{2-[4-(2-oxo-imidazolidin-1-yl)-phenyl]-acetyl}-1,3,8-triaza-spiro[4.5]dec-(2E)-ylidene]-amide (Ex. 177);
3,5-Diamino-6-chloro-pyrazine-2-carboxylic acid [8-[3-(3-phenyl-isoxazol-5-yl)-propionyl]-1,3,8-triaza-spiro[4.5]dec-(2E)-ylidene]-amide (Ex. 178);
3,5-Diamino-6-chloro-pyrazine-2-carboxylic acid [8-[2-(4-methanesulfonyl-phenyl)-acetyl]-1,3,8-triaza-spiro[4.5]dec-(2E)-ylidene]-amide (Ex. 179);
3,5-Diamino-6-chloro-pyrazine-2-carboxylic acid [8-[2-(4-chloro-phenyl)-thiazole-4-carbonyl]-1,3,8-triaza-spiro[4.5]dec-(2E)-ylidene]-amide (Ex. 180);
3,5-Diamino-6-chloro-pyrazine-2-carboxylic acid [8-[2-(5-methyl-3-trifluoromethyl-pyrazol-1-yl)-acetyl]-1,3,8-triaza-spiro[4.5]dec-(2E)-ylidene]-amide (Ex. 181);
3,5-Diamino-6-chloro-pyrazine-2-carboxylic acid [8-[5-(pyridin-3-yloxy)-furan-2-carbonyl]-1,3,8-triaza-spiro[4.5]dec-(2E)-ylidene]-amide (Ex. 182);
3,5-Diamino-6-chloro-pyrazine-2-carboxylic acid [8-[3-(4-methyl-thiazol-5-yl)-propionyl]-1,3,8-triaza-spiro[4.5]dec-(2E)-ylidene]-amide (Ex. 183);
3,5-Diamino-6-chloro-pyrazine-2-carboxylic acid [8-(2-methyl-5-propyl-2H-pyrazole-3-carbonyl)-1,3,8-triaza-spiro[4.5]dec-(2E)-ylidene]-amide (Ex. 184);
3,5-Diamino-6-chloro-pyrazine-2-carboxylic acid [8-[(S)-2-acetylamino-3-(4-isopropoxy-phenyl)-propionyl]-1,3,8-triaza-spiro[4.5]dec-(2E)-ylidene]-amide (Ex. 185);
3,5-Diamino-6-chloro-pyrazine-2-carboxylic acid [8-[3-(cyclohexyl-methyl-sulfamoyl)-4-methoxy-benzoyl]-1,3,8-triaza-spiro[4.5]dec-(2E)-ylidene]-amide (Ex. 186);
3,5-Diamino-6-chloro-pyrazine-2-carboxylic acid [8-{2-[4-(3,5-dimethyl-benzenesulfonyl)-piperazin-1-yl]-acetyl}-1,3,8-triaza-spiro[4.5]dec-(2E)-ylidene]-amide (Ex. 187);
3,5-Diamino-6-chloro-pyrazine-2-carboxylic acid [8-(3-1H-indol-3-yl-propionyl)-1,3,8-triaza-spiro[4.5]dec-(2E)-ylidene]-amide (Ex. 188);
3,5-Diamino-6-chloro-pyrazine-2-carboxylic acid [8-{3-[4-(4,6-dimethyl-pyrimidin-2-ylsulfamoyl)-phenylcarbamoyl]-propionyl}-1,3,8-triaza-spiro[4.5]dec-(2E)-ylidene]-amide (Ex. 189);
(Ex. 190);
3,5-Diamino-6-chloro-pyrazine-2-carboxylic acid [8-[3-(2-oxo-5-trifluoromethyl-2H-pyridin-1-yl)-propionyl]-1,3,8-triaza-spiro[4.5]dec-(2E)-ylidene]-amide (Ex. 191);
3,5-Diamino-6-chloro-pyrazine-2-carboxylic acid [8-[3-(4-sulfamoyl-phenylcarbamoyl)-propionyl]-1,3,8-triaza-spiro[4.5]dec-(2E)-ylidene]-amide (Ex. 192);
3,5-Diamino-6-chloro-pyrazine-2-carboxylic acid [8-(1-benzyl-5-oxo-pyrrolidine-3-carbonyl)-1,3,8-triaza-spiro[4.5]dec-(2E)-ylidene]-amide (Ex. 193);
3,5-Diamino-6-chloro-pyrazine-2-carboxylic acid [8-[(R)-2-acetylamino-3-(1H-indol-3-yl)-propionyl]-1,3,8-triaza-spiro[4.5]dec-(2E)-ylidene]-amide (Ex. 194);
3,5-Diamino-6-chloro-pyrazine-2-carboxylic acid [8-[4-(1-benzenesulfonyl-1H-pyrrol-3-yl)-4-oxo-butyryl]-1,3,8-triaza-spiro[4.5]dec-(2E)-ylidene-amide (Ex. 195);
3,5-Diamino-6-chloro-pyrazine-2-carboxylic acid [8-(1-furan-2-ylmethyl-5-oxo-pyrrolidine-3-carbonyl)-1,3,8-triaza-spiro[4.5]dec-(2E)-ylidene]-amide (Ex. 196);
3,5-Diamino-6-chloro-pyrazine-2-carboxylic acid [8-(6-pyrazol-1-yl-pyridine-3-carbonyl)-1,3,8-triaza-spiro[4.5]dec-(2E)-ylidene]-amide (Ex. 197);
3,5-Diamino-6-chloro-pyrazine-2-carboxylic acid [8-[3-((R)-1-phenyl-ethylcarbamoyl)-propionyl]-1,3,8-triaza-spiro[4.5]dec-(2E)-ylidene]-amide (Ex. 198);
3,5-Diamino-6-chloro-pyrazine-2-carboxylic acid [8-[1-(4-chloro-benzyl)-5-oxo-pyrrolidine-3-carbonyl]-1,3,8-triaza-spiro[4.5]dec-(2E)-ylidene]-amide (Ex. 199);
3,5-Diamino-6-chloro-pyrazine-2-carboxylic acid [8-[2-(3-tert-butyl-isoxazol-5-yl)-acetyl]-1,3,8-triaza-spiro[4.5]dec-(2E)-ylidene]-amide (Ex. 200);
3,5-Diamino-6-chloro-pyrazine-2-carboxylic acid [8-[6-(2,2,2-trifluoro-ethoxy)-pyridine-3-carbonyl]-1,3,8-triaza-spiro[4.5]dec-(2E)-ylidene]-amide (Ex. 201);
3,5-Diamino-6-chloro-pyrazine-2-carboxylic acid [8-(4-methyl-2-pyridin-3-yl-thiazole-5-carbonyl)-1,3,8-triaza-spiro[4.5]dec-(2E)-ylidene]-amide (Ex. 202);
3,5-Diamino-6-chloro-pyrazine-2-carboxylic acid [8-(3-pyridin-3-yl-propionyl)-1,3,8-triaza-spiro[4.5]dec-(2E)-ylidene]-amide (Ex. 203);
3,5-Diamino-6-chloro-pyrazine-2-carboxylic acid [8-(5-dimethylsulfamoyl-2-methyl-furan-3-carbonyl)-1,3,8-triaza-spiro[4.5]dec-(2E)-ylidene]-amide (Ex. 204);
3,5-Diamino-6-chloro-pyrazine-2-carboxylic acid [8-(1-ethyl-7-methyl-4-oxo-1,4-dihydro-[1,8]naphthyridine-3-carbonyl)-1,3,8-triaza-spiro[4.5]dec-(2E)-ylidene]-amide (Ex. 205);
3,5-Diamino-6-chloro-pyrazine-2-carboxylic acid [8-(2-pyrazol-1-yl-acetyl)-1,3,8-triaza-spiro[4.5]dec-(2E)-ylidene]-amide (Ex. 206);
3,5-Diamino-6-chloro-pyrazine-2-carboxylic acid [8-{3-chloro-5-methoxy-4-[2-(4-methyl-piperazin-1-yl)-ethoxy]-benzoyl}-1,3,8-triaza-spiro[4.5]dec-(2E)-ylidene]-amide (Ex. 207);
3,5-Diamino-6-chloro-pyrazine-2-carboxylic acid [8-(3-imidazol-1-yl-propionyl)-1,3,8-triaza-spiro[4.5]dec-(2E)-ylidene]-amide (Ex. 208);
3,5-Diamino-6-chloro-pyrazine-2-carboxylic acid [8-(1-benzyl-1H-imidazole-4-carbonyl)-1,3,8-triaza-spiro[4.5]dec-(2E)-ylidene]-amide (Ex. 209);
3,5-Diamino-6-chloro-pyrazine-2-carboxylic acid [8-[2-(1,1-dioxo-1lambda*6*-thiomorpholin-4-yl)-3-methyl-butyryl]-1,3,8-triaza-spiro[4.5]dec-(2E)-ylidene]-amide (Ex. 210);
3,5-Diamino-6-chloro-pyrazine-2-carboxylic acid [8-[4-(toluene-4-sulfonylamino)-butyryl]-1,3,8-triaza-spiro[4.5]dec-(2E)-ylidene]-amide (Ex. 211);
3,5-Diamino-6-chloro-pyrazine-2-carboxylic acid [8-(1,5-dimethyl-3-oxo-2-phenyl-2,3-dihydro-1H-pyrazole-4-carbonyl)-1,3,8-triaza-spiro[4.5]dec-(2E)-ylidene]-amide (Ex. 212);
3,5-Diamino-6-chloro-pyrazine-2-carboxylic acid [8-(3-hydroxy-pyridine-2-carbonyl)-1,3,8-triaza-spiro[4.5]dec-(2E)-ylidene]-amide (Ex. 213);
are made analogously to Examples 146, 147 or 148 replacing the carboxylic acid reagents with the appropriate carboxylic acids which are all commercially available or prepared as described in section 'Preparation of Intermediate Compounds'. The compounds are recovered from the reaction mixture and purified using conventional techniques.

Example 214

1-(3-{2-[(E)-3,5-Diamino-6-chloro-pyrazine-2-carbonylimino]-1,3,8-triayrazine-2-carbonylimino]-1,3,8-triazenesulfonyl)-piperidine-3-carboxylic acid 1-(3-{2-[(E)-3,5-Diamino-6-chloro-pyrazine-2-carbonylimino]-1,3,8-triaza-spiro[4.5]decane-8-carbonyl}-benzenesulfonyl)-piperidine-3-carboxylic acid ethyl ester (Ex. 128) (0.29 g, 0.45 mmol) is dissolved in THF (4 ml) and 2M LiOH (0.22 ml, 0.45 mmol) added. The yellow solution is stirred at room temperature for 5 hours. On concentration in vacuo the resulting sticky yellow solid is ultrasonicated in water (15 ml) until complete dissolution. The pH is adjusted to pH 2 by addition of 1 N HCl. The resultant yellow solid is collected by filtration and rinsed with water to yield the title compound; [M+H]$^+$ 620.1

Example 215

2-[(E)-3,5-Diamino-6-chloro-pyrazine-2-carbonylimino]-1,3,8-triaza-spiro[4.5]decane-8-carboxylic acid benzylamide To a solution of benzylamine (0.017 ml, 0.154 mmol) in DMF (1 ml) is added 1,1'-carbonyldiimidazole (0.03 g, 0.17 mmol) and the resulting solution is stirred at room temperature for 45 minutes. To this is added 5-Diamino-6-chloro-pyrazine-2-carboxylic acid [1,3,8-triaza-spiro[4.5]dec-(2E)-ylidene]-amide dihydrochloride (Ex. 38) (0.05 g, 0.15 mmol) and the yellow suspension is stirred for 24 hours. Purification by reverse phase chromatography (Isolute™ C18, 0-100% MeCN in water –0.1% TFA) followed by catch and release resin (SCX-2) eluting with MeOH and 7M NH$_3$ in MeOH affords the title compound as an off white solid; [M+H]$^+$ 458.1

Examples 216-231

These compounds, namely
2-[(E)-3,5-Diamino-6-chloro-pyrazine-2-carbonylimino]-1,3,8-triaza-spiro[4.5]decane-8-carboxylic acid phenylamide (Ex. 216),
2-[(E)-3,5-Diamino-6-chloro-pyrazine-2-carbonylimino]-1,3,8-triaza-spiro[4.5]decane-8-carboxylic acid [1-(toluene-4-sulfonyl)-1H-indol-5-yl]amide (Ex. 217);
2-[(E)-3,5-Diamino-6-chloro-pyrazine-2-carbonylimino]-1,3,8-triaza-spiro[4.5]decane-8-carboxylic acid 3-(4-chloro-phenoxymethyl)-benzylamide (Ex. 218);
2-[(E)-3,5-Diamino-6-chloro-pyrazine-2-carbonylimino]-1,3,8-triaza-spiro[4.5]decane-8-carboxylic acid [3-(2,4-dichloro-phenyl)-propyl]-amide (Ex. 219);
2-[(E)-3,5-Diamino-6-chloro-pyrazine-2-carbonylimino]-1,3,8-triaza-spiro[4.5]decane-8-carboxylic acid [2-(3-benzyloxy-phenyl)-ethyl]-amide (Ex. 220);
2-[(E)-3,5-Diamino-6-chloro-pyrazine-2-carbonylimino]-1,3,8-triaza-spiro[4.5]decane-8-carboxylic acid [2-(5,6-dimethyl-1H-indol-3-yl)-ethyl]amide (Ex. 221);
2-[(E)-3,5-Diamino-6-chloro-pyrazine-2-carbonylimino]-1,3,8-triaza-spiro[4.5]decane-8-carboxylic acid 4-morpholin-4-ylmethyl-benzylamide (Ex. 222);
2-[(E)-3,5-Diamino-6-chloro-pyrazine-2-carbonylimino]-1,3,8-triaza-spiro[4.5]decane-8-carboxylic acid 3-benzyloxy-benzylamide (Ex. 223);
2-[(E)-3,5-Diamino-6-chloro-pyrazine-2-carbonylimino]-1,3,8-triaza-spiro[4.5]decane-8-carboxylic acid (2-{4-[2-(4-fluoro-phenyl)-ethoxy]-phenyl}-ethyl)-amide (Ex. 224);
2-[(E)-3,5-Diamino-6-chloro-pyrazine-2-carbonylimino]-1,3,8-triaza-spiro[4.5]decane-8-carboxylic acid [2-(3,5-dimethoxy-phenyl)-ethyl]-amide (Ex. 225);
2-[(E)-3,5-Diamino-6-chloro-pyrazine-2-carbonylimino]-1,3,8-triaza-spiro[4.5]decane-8-carboxylic acid [3-(4-methoxy-naphthalen-1-yl)-propyl]-amide (Ex. 226);
2-[(E)-3,5-Diamino-6-chloro-pyrazine-2-carbonylimino]-1,3,8-triaza-spiro[4.5]decane-8-carboxylic acid [2-(4,6-dimethyl-1H-indol-3-yl)-ethyl]-amide (Ex. 227);
2-[(E)-3,5-Diamino-6-chloro-pyrazine-2-carbonylimino]-1,3,8-triaza-spiro[4.5]decane-8-carboxylic acid (3-pyridin-2-yl-propyl)-amide (Ex. 228);
2-[(E)-3,5-Diamino-6-chloro-pyrazine-2-carbonylimino]-1,3,8-triaza-spiro[4.5]decane-8-carboxylic acid {2-[4-(4-phenyl-butoxy)-phenyl]-ethyl}-amide (Ex. 229);
2-[(E)-3,5-Diamino-6-chloro-pyrazine-2-carbonylimino]-1,3,8-triaza-spiro[4.5]decane-8-carboxylic acid [2-(4-phenoxy-phenyl)-ethyl]-amide (Ex. 230);
2-[(E)-3,5-Diamino-6-chloro-pyrazine-2-carbonylimino]-1,3,8-triaza-spiro[4.5]decane-8-carboxylic acid [2-(4-benzyloxy-phenyl)-ethyl]-amide (Ex. 231);
are prepared by an analogous procedure to Example 215, replacing benzylamine with the appropriate amines which are either commercially available or synthesized as described in the section 'Preparation of Intermediate compounds'. The compounds are recovered from reaction mixtures and purified using conventional techniques such as flash chromatography, filtration, recrystallisation and trituration.

Example 232

3,5-Diamino-6-chloro-pyrazine-2-carboxylic acid [8-phenylmethanesulfonyl-1,3,8-triaza-spiro[4.5]dec-(2E)-ylidene]-amide To a solution of 5-Diamino-6-chloro-pyrazine-2-carboxylic acid [1,3,8-triaza-spiro[4.5]dec-(2E)-ylidene]-amide dihydrochloride (Ex. 38) (0.05 g, 0.15 mmol) in DMF (2 ml) is added alpha-toluenesulfonyl chloride (0.04 g, 0.20 mmol) and triethylamine (0.02 ml, 0.15 mmol) and the yellow solution is stirred at room temperature for 2 hours. Purification by reverse phase chromatography (Isolute™ C18, 0-100% MeCN in water –0.1% TFA) followed by catch and release resin (SCX-2) eluting with MeOH and 7M NH$_3$ in MeOH affords the title compound as a yellow solid; [M+H]$^+$ 478.98

Examples 233-245

The following compounds, namely
3,5-Diamino-6-chloro-pyrazine-2-carboxylic acid [8-benzenesulfonyl-1,3,8-triaza-spiro[4.5]dec-(2E)-ylidene]-amide (Ex. 233);
3,5-Diamino-6-chloro-pyrazine-2-carboxylic acid [8-(1-methyl-1H-indole-4-sulfonyl)-1,3,8-triaza-spiro[4.5]dec-(2E)-ylidene]-amide (Ex. 234);
3,5-Diamino-6-chloro-pyrazine-2-carboxylic acid [8-(1-methyl-1H-indole-5-sulfonyl)-1,3,8-triaza-spiro[4.5]dec-(2E)-ylidene]-amide (Ex. 235);
3,5-Diamino-6-chloro-pyrazine-2-carboxylic acid [8-(7-chloro-benzo[1,2,5]oxadiazole-4-sulfonyl)-1,3,8-triaza-spiro[4.5]dec-(2E)-ylidene]-amide (Ex. 236);
3,5-Diamino-6-chloro-pyrazine-2-carboxylic acid [8-(2-phenyl-ethanesulfonyl)-1,3,8-triaza-spiro[4.5]dec-(2E)-ylidene]-amide (Ex. 237);
3,5-Diamino-6-chloro-pyrazine-2-carboxylic acid [8-[4-(5-methyl-2-phenyl-oxazol-4-ylmethoxy)-benzenesulfonyl]-1,3,8-triaza-spiro[4.5]dec-(2E)-ylidene]-amide (Ex. 238);
3,5-Diamino-6-chloro-pyrazine-2-carboxylic acid [8-(4-phenyl-5-trifluoromethyl-thiophene-3-sulfonyl)-1,3,8-triaza-spiro[4.5]dec-(2E)-ylidene]-amide (Ex. 239);
3,5-Diamino-6-chloro-pyrazine-2-carboxylic acid [8-(5-cyano-2-methoxy-benzenesulfonyl)-1,3,8-triaza-spiro[4.5]dec-(2E)-ylidene]-amide (Ex. 240);

3,5-Diamino-6-chloro-pyrazine-2-carboxylic acid [8-[2-(4-chloro-phenyl)-ethanesulfonyl]-1,3,8-triaza-spiro[4.5]dec-(2E)-ylidene]-amide (Ex. 241);

3,5-Diamino-6-chloro-pyrazine-2-carboxylic acid [8-(2-phenyl-3H-benzoimidazole-5-sulfonyl)-1,3,8-triaza-spiro[4.5]dec-(2E)-ylidene]-amide (Ex. 242);

3,5-Diamino-6-chloro-pyrazine-2-carboxylic acid [8-[2-(2-chloro-phenyl)-ethanesulfonyl]-1,3,8-triaza-spiro[4.5]dec-(2E)-ylidene]-amide (Ex. 243);

3,5-Diamino-6-chloro-pyrazine-2-carboxylic acid [8-[2-(2,2,2-trifluoro-acetyl)-1,2,3,4-tetrahydro-isoquinoline-7-sulfonyl]-1,3,8-triaza-spiro[4.5]dec-(2E)-ylidene]-amide (Ex. 244);

3,5-Diamino-6-chloro-pyrazine-2-carboxylic acid [8-[2-(3-chloro-phenyl)-ethanesulfonyl]-1,3,8-triaza-spiro[4.5]dec-(2E)-ylidene]-amide (Ex. 245);

are prepared by an analogous procedure to Example 232, replacing alpha-toluenesulfonyl chloride with the appropriate sulfonyl chlorides which are either commercially available or synthesized as described in the section 'Preparation of Intermediate compounds'. The compounds are recovered from reaction mixtures and purified using conventional techniques such as flash chromatography, filtration, recrystallisation and trituration.

Example 246

3,5-Diamino-6-chloro-pyrazine-2-carboxylic acid [8-(1-phenyl-ethyl)-1,3,8-triaza-spiro[4.5]dec-(2E)-ylidene]-amide A mixture of 1-(3,5-diamino-6-chloro-pyrazine-2-carbonyl)-2-methyl-isothiourea (Intermediate A) (1.7 g, 4.54 mmol) and 4-aminomethyl-1-(1-phenyl-ethyl)-piperidin-4-ylamine (Intermediate BM) (1.6 g, 4.59 mmol) in propan-2-ol (50 ml) is stirred at 80° C. for 16 hours. The reaction mixture is concentrated in vacuo and purified by column chromatography (basic alumina, 0-2% MeOH in DCM) to obtain pale yellow solid. The compound obtained is further dissolved in MeOH and precipitated by adding diethyl ether. The supernatant solvent mixture is decanted and the product is washed again with diethyl ether and dried under vacuum to afford the title compound as off-white solid; $[M+H]^+$ 429

Example 247

3,5-Diamino-6-chloro-pyrazine-2-carboxylic acid [8-(4-methoxy-benzyl)-1,3,8-triaza-spiro[4.5]dec-(2E)-ylidene]-amide This compound is prepared analogously to Example 246 by replacing 4-aminomethyl-1-(1-phenyl-ethyl)-piperidin-4-ylamine (Intermediate BM) with 4-aminomethyl-1-(4-methoxy-benzyl)-piperidin-4-ylamine (Intermediate BN) $[M+H]^+$ 445.

Example 248

3,5-Diamino-6-chloro-pyrazine-2-carboxylic acid [8-pyridin-4-ylmethyl-1,3,8-triaza-spiro[4.5]dec-(2E)-ylidene]-amide This compound is prepared analogously to Example 246 by replacing 4-aminomethyl-1-(1-phenyl-ethyl)-piperidin-4-ylamine (Intermediate BM) with 4-aminomethyl-1-pyridin-4-ylmethyl-piperidin-4-ylamine (Intermediate BO); $[M+H]^+$=416

Example 249

3,5-Diamino-6-chloro-pyrazine-2-carboxylic acid [8-(3-phenyl-propyl)-1,3,8-triaza-spiro[4.5]dec-(2E)-ylidene]-amide This compound is prepared analogously to Example 246 by replacing 4-aminomethyl-1-(1-phenyl-ethyl)-piperidin-4-ylamine (Intermediate BM) with 4-aminomethyl-1-(3-phenyl-propyl)-piperidin-4-ylamine (Intermediate BP) $[M+H]^+$ 443

Example 250

3,5-Diamino-6-chloro-pyrazine-2-carboxylic acid [8-cyclohexylmethyl-1,3,8-triaza-spiro[4.5]dec-(2E)-ylidene]-amide This compound is prepared analogously to Example 246 by replacing 4-aminomethyl-1-(1-phenyl-ethyl)-piperidin-4-ylamine (Intermediate BM) with 4-aminomethyl-1-cyclohexylmethyl-piperidin-4-ylamine (Intermediate BQ) $[M+H]^+$ 421

Example 251

(E)-tert-Butyl 2'-(3,5-diamino-6-chloropyrazine-2-carbonylimino)-8-azaspiro[bicyclo[3.2.1]octane-3,4'-imidazolidine]-8-carboxylate This compound is prepared analogously to Example 246 by replacing 4-aminomethyl-1-(1-phenyl-ethyl)-piperidin-4-ylamine (Intermediate BM) with 3-amino-3-aminomethyl-8-aza-bicyclo[3.2.1]octane-8-carboxylic acid tert-butyl ester (Intermediate BR) $[M+H]^+$ 451

Example 252

(E)-N-(8-(1H-indole-4-carbonyl)-8-azaspiro[bicyclo[3.2.1]octane-3,4'-imidazolidine]-2'-ylidene)-3,5-diamino-6-chloropyrazine-2-carboxamide Step 1

Iodotrimethylsilane (0.23 ml, 1.66 mmol) is added to a suspension of (E)-tert-Butyl 2'-(3,5-diamino-6-chloropyrazine-2-carbonylimino)-8-azaspiro[bicyclo[3.2.1]octane-3,4'-imidazolidine]-8-carboxylate (Ex. 251) (500 mg, 1.11 mmol) in DCM (10 ml). DMF (5 ml) is then added and the reaction is stirred at room temperature overnight. Iodotrimethylsilane (0.5 ml) is added and the reaction mixture is concentrated in vacuo. The yellow solid is suspended in DCM and collected by filtration. The solid is dissolved in 1:1 MeOH/DCM and loaded onto an SCX-2 cartridge eluted with DCM followed by MeOH and NH$_3$/MeOH. The methanolic ammonia fractions are concentrated in vacuo to afford (E)-3,5-diamino-6-chloro-N-(8-azaspiro[bicyclo[3.2.1]octane-3,4'-imidazolidine]-2'-ylidene)pyrazine-2-carboxamide as a yellow gum; $[M+H]^+$ 351

Step 2

(E)-3,5-diamino-6-chloro-N-(8-azaspiro[bicyclo[3.2.1]octane-3,4'-imidazolidine]-2'-ylidene)pyrazine-2-carboxamide (170 mg, 0.49 mmol) is dissolved in DMF (10 ml) along with HATU (184 mg, 0.49 mmol) and 4-indole-carboxylic acid (78 mg, 0.49 mmol). N-Methyl morpholine (160 ml, 1.45 mmol) is added and the solution stirred at room temperature overnight. The mixture is then concentrated in vacuo. EtOAc (100 ml) is added and the solution washed with water (100 ml). The organic phase is dried (MgSO$_4$) and concentrated in vacuo. Purification by flash chromatography (SiO$_2$, DCM/

MeOH) gives the title compound as a yellow solid; [M+H]+ 494.15, 496.27 for Cl isotopes.

Example 253

(E)-3,5-diamino-N-(8-(3-(4-(benzyloxy)phenyl)propanoyl)-8-azaspiro[bicyclo[3.2.1]octane-3,4'-imidazolidine]-2'-ylidene)-6-chloropyrazine-2-carboxamide (E)-3,5-diamino-6-chloro-N-(8-azaspiro[bicyclo[3.2.1]octane-3,4'-imidazolidine]-2'-ylidene)pyrazine-2-carboxamide (prepared as described for Ex. 252) (280 mg, 0.798 mmol) is dissolved in DMF (8 ml) along with HATU (303 mg, 0.798 mmol) and 3-(4-benzyloxy-phenyl)-propionic acid (205 mg, 0.798 mmol). N-Methyl morpholine (0.263 ml, 2.394 mmol) is added and the solution stirred at room temperature for 6 hours. The mixture is then concentrated in vacuo. EtOAc (100 ml) is added and the solution washed with water (100 ml). The organic phase is dried (MgSO$_4$) and concentrated. The residue is dissolved in MeOH (20 ml) and dry loaded onto silica (5 g). Purification by flash chromatography (SiO$_2$, DCM/MeOH) gives the title compound as a tan solid; [M+H]+ 589.20, 591.19 for Cl isotopes.

Preparation of Intermediate Compounds

Intermediate A 1-(3,5-Diamino-6-chloro-pyrazine-2-carbonyl)-2-methyl-isothiourea hydroiodide Method 1
This compound is prepared according to Cragoe, Edward J., Jr.; Woltersdorf, Otto W., Jr.; De Solms, Susan Jane. Heterocyclic-substituted pyrazinoylguanidines, and a pharmaceutical composition containing them. EP 17152, Page 4
Method 2
Step 1
A stirred suspension of 3,5-diamino-6-chloro-pyrazine-2-carboxylic acid methyl ester (110 g, 542.9 mmol) in MeOH (500 ml) at 5-10° C. (ice-bath) is treated dropwise with a suspension of lithium hydroxide (46.6 g, 1111 mmol) in water (500 ml). The reaction mixture is heated to 50° C. for 5 hours then cooled to room temperature and stirred overnight. The resulting precipitate is collected by filtration and dried in a vacuum oven to afford Lithium 3,5-diamino-6-chloro-pyrazine-2-carboxylic acid as the lithium salt (di-hydrate); [M-Li]− 187
Step 2
A stirred suspension of S-methyl-iso-thiourea sulphate (10 g, 35.9 mmol) in toluene (75 ml) is treated with 4 M NaOH (15 ml) at room temperature. To the two-phase mixture is added di-tert butyl dicarbonate (3.27 g, 15 mmol) in one portion. The reaction mixture is stirred at room temperature for 1 hour, then heated to 60° C. overnight. The organic portion is separated, washed with brine solution, then dried over Na$_2$SO$_4$, filtered and concentrated in vacuo to a viscous oil, which crystallised under high vacuum to afford tert-Butyl amino(methylthio)methylenecarbamate as a colourless solid.
Step 3
A stirring suspension of lithium 3,5-diamino-6-chloro-pyrazine-2-carboxylic acid (22.6 g, 98.03 mmol) in DMF (400 ml) is treated portionwise with HATU (41 g, 107.83 mmol), under an inert atmosphere of nitrogen. The reaction mixture is stirred at room temperature for 2 hours and then tert-butyl amino(methylthio)methylenecarbamate (20.5 g, 107.83 mmol) is added portion wise over a period of 10 minutes. The reaction mixture is stirred at room temperature for a further 1.5 hours then heated to 50° C. and stirred overnight. The resulting precipitate is hot filtered, washing with water and dried in a vacuum oven (40° C.) overnight to afford tert-Butyl (3,5-diamino-6-chloropyrazine-2-carboxamido)(methylthio) methylene carbamate; [M+H]+ 361
Step 4
tert-Butyl (3,5-diamino-6-chloropyrazine-2-carboxamido)(methylthio) methylene carbamate (50 g, 139 mmol) is slurried in DCM (500 ml). TFA (53.4 ml, 693 mmol) is dissolved in DCM (100 ml) and added dropwise over 45 mins to form a brown solution. The solution is stirred at room temperature overnight, after which time a yellow precipitate has formed. The solid is collected by filtration, and dried in vacuo to yield the title compound; [M+H]+ 261.1

Intermediate B ((S)-5,6-Diamino-hexyl)-carbamic acid benzyl ester

Step 1
A solution of BOC-lysinol-(Z)-OH (0.5 g, 1.36 mmol) in dry THF (1 ml) under an inert atmosphere of argon is treated with PS-triphenylphosphine (0.91 g, 3.00 mmol/g loading). To this mixture is added phthalimide (0.2 g, 1.36 mmol) and DEAD (0.24 ml, 1.50 mmol) in dry THF (4 ml) and the reaction mixture is stirred at room temperature overnight. The resin is removed by filtration under vacuum and the filtrate is concentrated in vacuo. Purification of the crude white solid by chromatography on silica eluting with 20-50% EtOAc in iso-hexane (1% TEA) affords [(S)-5-Benzyloxycarbonylamino-1-(1,3-dioxo-1,3-dihydro-isoindol-2-ylmethyl)-pentyl]-carbamic acid tert-butyl ester as a white crystalline solid; [M+H]+ 496
Step 2
A solution of [(S)-5-benzyloxycarbonylamino-1-(1,3-dioxo-1,3-dihydro-isoindol-2-ylmethyl)-pentyl]-carbamic acid tert-butyl ester (0.63 g, 1.27 mmol) in DCM (5.1 ml) and EtOH (5.1 ml) is treated with hydrazine hydrate (0.318 g, 6.35 mmol) and the reaction mixture is stirred at room temperature overnight. A white precipitate forms which is removed by filtration and washed with DCM (3×10 ml). The filtrate is concentrated in vacuo and redissolved in DCM (15 ml) and MeOH (2 ml). Undissolved material is removed by filtration and the filtrate is concentrated in vacuo. The resulting oily yellow solid is purified by chromatography on silica eluting with 10-50% MeOH in DCM (1% TEA) to afford ((S)-1-Aminomethyl-5-benzyloxycarbonylamino-pentyl)-carbamic acid tert-butyl ester as a clear oil; [M+H]+ 366
Step 3
A solution of ((S)-1-aminomethyl-5-benzyloxycarbonylamino-pentyl)-carbamic acid tert-butyl ester (0.24 g, 0.657 mmol) in DCM (2.4 ml) is treated dropwise with TFA (0.6 ml) and stirred at room temperature for 3 days. The solvent is removed in vacuo to afford ((S)-5,6-Diamino-hexyl)-carbamic acid benzyl ester as a yellow oil; [M+H]+ 266

Intermediate C

A mixture of 4-[4-(2-amino-ethylamino)-butyl]-phenol and N*1*-[4-(4-methoxy-phenyl)-butyl]-ethane-1,2-diamine Step 1
A solution of 4-methoxyphenylbutryric acid (6.99 g, 36 mmol) in THF (70 ml) is treated with EDCI (7.6 g, 36.9 mmol) followed by N-ethylmorpholine (9.2 ml, 72 mmol). After stirring at room temperature for 1 hour, N—BOC-ethylene diamine (5.84 g, 36 mmol) is added and the resulting mixture is stirred at room temperature overnight. The reaction is quenched by addition of saturated sodium hydrogen carbonate solution and extracted with EtOAc. The organic portion is washed with citric acid solution, brine, dried (MgSO$_4$) and concentrated in vacuo until 25 ml of solvent remained. The suspension is filtered to afford {2-[4-(4-Methoxy-phenyl)-butyrylamino]-ethyl}-carbamic acid tert-butyl ester: as a white solid.
Step 2

A solution of {2-[4-(4-methoxy-phenyl)-butyrylamino]-ethyl}-carbamic acid tert-butyl ester (6 g, 17.88 mmol) in dry THF (60 ml) under an inert atmosphere of Argon is treated carefully with borane. THF complex (53.88 ml, 1M Borane in THF). The reaction mixture is heated at reflux for 2 hours and then allowed to cool to room temperature overnight. The mixture is quenched by addition of MeOH and then heated to 70° C. for a further 2 hours. After cooling to room temperature, the solvent is removed in vacuo to afford {2-[4-(4-Methoxy-phenyl)-butylamino]-ethyl}-carbamic acid tert-butyl ester as a viscous oil; [M+H]$^+$ 323
Step 3

A suspension of {2-[4-(4-methoxy-phenyl)-butylamino]-ethyl}-carbamic acid tert-butyl ester (5.85 g, 18.1 mmol) in HBr (30 ml of a 48% solution) is heated at reflux for 2 hours. After cooling to room temperature, the solvent is removed in vacuo. The crude residue is suspended in EtOAc and filtered to afford a solid which consisted of a mixture of 4-[4-(2-amino-ethylamino)-butyl]-phenol and N*1*-[4-(4-methoxy-phenyl)-butyl]-ethane-1,2-diamine in approximately 1:1 ratio; [M+H]$^+$ 209 and 223.

Intermediate D (S)-3-(4-methoxy-phenyl)-propane-1,2 diamine (S)-2-Amino-3-(4-methoxy-phenyl)-propionamide is prepared according to the procedure described on page 3880, Method 2.1.3 of Journal of Physical Chemistry B, 108(12), 3879-3889; 2004 and is reduced analogously to Intermediate C.

Intermediate E 1-(3,4-Dichloro-phenyl)-ethane-1,2-diamine

This compound is prepared according to the procedure described on page 907, Method 5 in the Journal of Medicinal Chemistry (1973), 16(8), 901-8.

Intermediate F 4,5-Diaminopentanoic acid dihydrochloride

This compound is prepared according to the procedure described in 'Radiolabeling chelating compounds comprising sulfur atoms, with metal radionuclides.' EP 300431 page 12, Intermediate 3.

Intermediate G

4-Amino-1-benzyl-piperidine-4-carbonitrile

Step 1

To a solution of ammonium chloride (1.73 g, 32.3 mmol) in water (20 ml) is added a 30% ammonia solution (2 ml) followed by 1-benzyl-4-piperidone. After 20 minutes sodium cyanide (1.47 g, 30 mmol) is added portionwise over 15 minutes. After stirring for one hour, water (50 ml) is added and the products are extracted with DCM (3×50 ml), dried (MgSO$_4$) filtered and concentrated in vacuo. Purification by chromatography on silica eluting with 50-100% EtOAc in iso-hexane affords 4-Aminomethyl-1-benzyl-piperidine-4-ylamine; [M+H]$^+$ 216
Step 2

To a solution of lithium aluminium hydride (1 M in THF, 10.4 ml) in dry diethyl ether (15 ml), cooled to 0° C., under an argon atmosphere is added dropwise 4-amino methyl-1-benzyl-piperidine-4-ylamine (900 mg, 4.18 mmol) in dry diethyl ether (15 ml). The reaction mixture is heated at reflux for 24 h and then cooled to 0° C. Water (0.25 ml) is added followed by a 15% aqueous NaOH (0.25 ml) and then water (0.7 ml). After warming to room temperature MgSO$_4$ (150 mg) is added and stirred for 15 minutes. The solids are removed by suction filtration and the filtrate evaporated to give an oil. The solids are extracted with refluxing diethyl ether (80 ml) using a Soxhlet extractor for 14 hours. The diethyl ether is removed in vacuo and the two oils combined and purified by chromatography on silica eluting with 10-25% 2M ammonia in methanol solution in dichloromethane to give 4-Amino-1-benzyl-piperidine-4-carbonitrile; [M+H]$^+$ 220

Intermediate H

5-[4-((R)-2,2-Dimethyl-[1,3]dioxolane-4-yl-methoxy)-phenyl]-pentane-1,2-diamine

Step 1

To 3-(4-hydroxyphenyl)-1-propanol (10 g, 66 mmol) and potassium carbonate (13.5 g, 100 mmol) in acetone (200 ml) is added (S)-glycidol (6.5 ml, 100 mmol). The mixture is heated at reflux for 18 hours. After cooling to room temperature the solvent is removed in vacuo and the residue partitioned between EtOAc and water. The aqueous layer is further extracted twice with EtOAc and the combined organic portions are washed with water, brine, dried (MgSO$_4$), filtered and concentrated in vacuo. The crude residue is purified by flash column chromatography on silica eluting with 1:1 EtOAc/iso-hexane to afford (S)-3-[4-(3-Hydroxy-propyl)-phenoxy]-propane-1,2-diol as a white solid; $^1$H NMR (CDCl$_3$): 1.20 (1H, br), 1.85 (2H, pent, J=6.8 Hz), 1.98 (1H, br), 2.58 (1H, br), 2.65 (2H, tr, J=6.9 Hz), 3.56 (2H, tr, J=6.8 Hz), 3.72 (1H, m), 3.83 (1H, m), 4.00 (2H, dd, J=2.1 Hz, J=6.5 Hz), 4.09 (1H, br), 6.82 (2H, d, J=7.4 Hz), 7.10 (2H, d, J=7.4 Hz).
Step 2

To (S)-3-[4-(3-hydroxy-propyl)-phenoxy]-propane-1,2-diol (11.5 g, 50.9 mmol) in dry DMF (150 ml) is added pyridinium p-toluenesulfonate (1.28 g, 5 mmol) and 2,2-dimethoxypropane (31 ml, 250 mmol). The mixture is stirred at room temperature for 18 hours and then the solvent is removed in vacuo. The residue is dissolved in EtOAc (150 ml) and washed with water, saturated aqueous sodium hydrogen carbonate solution, brine, dried (MgSO$_4$) and concentrated in vacuo. The residue is purified by chromatography on silica eluting with 1:4 EtOAc/iso-hexane to 1:1 EtOAc/iso-hexane to afford (3-[4-((R)-2,2-Dimethyl-[1,3]dioxolan-4-yl-methoxy)-phenyl]-propan-1-ol as a colourless oil; $^1$H NMR (CDCl$_3$): 1.25 (1H, br), 1.39 (3H, s), 1.43 (3H, s), 1.85 (2H, pent, J=6.9 Hz), 2.63 (2H, tr, J=6.9 Hz), 3.63 (2H, tr, J=6.9 Hz), 3.90 (2H, m), 4.02 (1H, m), 4.12 (1H, m), 4.50 (1H, pent, J=6.8 Hz), 6.82 (2H, d, J=7.4 Hz), 7.10 (2H, d, J=7.4 Hz).
Step 3

To (3-[4-((R)-2,2-dimethyl-[1,3]dioxolan-4-ylmethoxy)-phenyl]-propan-1-ol (12.2 g, 46 mmol) in dry ether (150 ml) is added TEA (12.8 ml, 92 mmol). The mixture is cooled to 0°

C. and treated dropwise with methanesulfonyl chloride (5.3 ml, 69 mmol). The reaction mixture is allowed to warm to room temperature and then stirring continued for 3 hours. The resulting mixture is washed with water (2×100 ml), saturated aqueous sodium hydrogencarbonate, brine, dried (MgSO$_4$) and concentrated in vacuo to give Methanesulfonic acid 3-[4-((R)-2,2-dimethyl[1,3]dioxolan-4-ylmethoxy)-phenyl]-propylester as a white solid; $^1$H NMR (CDCl$_3$): 1.39 (3H, s), 1.43 (3H, s), 2.02 (2H, pent, J=6.9 Hz), 2.63 (2H, tr, J=6.9 Hz), 3.00 (3H, s), 3.90 (2H, m), 4.05 (1H, m), 4.14 (3 h, m), 4.46 (1H, pent, J=6.8 Hz), 6.82 (2H, d, J=7.4 Hz), 7.10 (2H, d, J=7.4 Hz).

Step 4

Methanesulfonic acid 3-[4-((R)-2,2-dimethyl[1,3]dioxolan-4-ylmethoxy)-phenyl]-propylester (11.8 g, 34.2 mmol) in acetone (200 ml) is treated with lithium bromide (8.9 g, 100 mmol) and then heated at reflux for 5 h. After cooling to room temperature, the mixture is concentrated in vacuo. The resulting residue is dissolved in EtOAc (150 ml), washed with water (2×50 ml), brine, dried (MgSO$_4$), filtered and concentrated in vacuo to give an oil. Purification by chromatography on silica eluting with 4:1 iso-hexane/EtOAc gives (R)-4-[4-(3-Bromo-propyl)-phenoxymethyl]-2,2-dimethyl-[1,3]dioxolane as a colourless oil which solidifies; $^1$H NMR (CDCl$_3$): 1.39 (3H, s), 1.43 (3H, s), 2.02 (2H, pent, J=6.9 Hz), 2.63 (2H, tr, J=6.9 Hz), 3.38 (2H, tr, J=6.9 Hz), 3.90 (2H, m), 4.02 (1H, m), 4.15 (1H, m), 4.46 (1H, pent, J=6.9 Hz), 6.82 (2H, d, J=7.4 Hz), 7.10 (2H, d, J=7.4 Hz).

Step 5

A solution of N-(diphenylmethylene) aminoacetonitrile (5.14 g, 23.4 mmol) in DCM (12 ml) is treated with (R)-4-[4-(3-bromo-propyl)-phenoxymethyl]-2,2-dimethyl-[1,3]dioxolane (8.1 g, 24 mmol) in DCM (12 ml) and cooled to 0° C. 48% aqueous NaOH (20 ml) is added followed by benzyltriethylammonium chloride (530 mg, 2.4 mmol) and the resulting mixture is allowed to warm to room temperature. After stirring vigorously for 4 hours mixture is diluted with DCM (100 ml) and the aqueous portion is removed. The organic layer is washed with water (2×50 ml), brine, dried (MgSO$_4$), filtered and concentrated in vacuo. The crude product is purified by chromatography on silica eluting with 15:1 iso-hexane/diethyl ether to 4:1 iso-hexane/diethyl ether to yield 2-(Benzhydrylidene-amino)-5-[4-((R)-2,2-dimethyl-[1,3]dioxolan-4-ylmethoxy)-phenyl]pentanenitrile as a yellow oil; $^1$H NMR (CDCl$_3$): mix of diastereoisomers 1.39 (3H, s), 1.43 (3H, s), 1.71 (2H, m), 1.80-1.98 (2H, m), 2.52 (2H, tr, J=7.0 Hz) 3.90, (2H, m), 4.02 (1H, m), 4.10-4.22 (2H, m), 4.47 (1H, pent, J=6.9 Hz), 6.82 (2H, d, J=7.4 Hz), 7.05 (2H, d, J=7.4 Hz), 7.19 (2H, m), 7.35 (2H, tr, J=7.2 Hz), 7.40-7.50 (4H, m), 7.60 (2H, d, J=7.1 Hz).

Step 6

To a solution of 2-(benzhydrylidene-amino)-5-[4-((R)-2,2-dimethyl-[1,3]dioxolan-4-ylmethoxy)-phenyl]pentanenitrile (7.2 g, 15.5 mmol) in THF (50 ml) is added a 2M HCl (aq) (5 ml). The solution is heated at 40° C. for 4 hours and then allowed to cool to room temperature. The pH is adjusted to pH 9-10 using saturated aqueous sodium hydrogen carbonate solution and the organic solvent is removed in vacuo. The crude residue is dissolved in EtOAc (100 ml) and washed with water, brine, dried (MgSO$_4$), filtered and concentrated in vacuo. The resulting residue is purified by chromatography on silica eluting with 5:1 to 1:1 iso-hexane/ethyl aEtOAc and 1% triethylamine to yield 2-Amino-5-[4-((R)-2,2-dimethyl-[1,3]dioxolan-4-ylmethoxy)-phenyl]-pentanenitrile as a colourless oil which solidifies; $^1$H NMR (CDCl$_3$): mixture of diastereoisomers 1.39 (3H, s), 1.43 (3H, s), 1.70-1.87 (4H, m), 2.60 (2H, tr, J=7.1 Hz), 3.62 (1H, br), 3.90 (2H, m), 4.00-4.18 (2H, m), 4.48 (1H, pent, J=6.9 Hz), 6.82 (2H, d, J=7.4 Hz), 7.10 (2H, d, J=7.4 Hz). [M+H]$^+$ 305

Step 7

A solution of 2-amino-5-[4-((R)-2,2-dimethyl-[1,3]dioxolan-4-ylmethoxy)-phenyl]-pentanenitrile (1.7 g, 4.28 mmol) in a 2M ammonia in methanol solution (50 ml) is passed through a H-CUBE apparatus fitted with a Raney nickel CatCart at 50° C. and a hydrogen pressure of 50 bar and a flow rate of 1.5 ml/min. After 5 hours of continuous cycling of the solution the reaction mixture is concentrated in vacuo to give 5-[4-((R)-2,2-Dimethyl-[1,3]dioxolane-4-ylmethoxy)-phenyl]-pentane-1,2-diamine as a light-yellow oil; [M+H]$^+$ 309

Intermediate I 5-(4-Methoxy-phenyl)-pentane-1,2-diamine

This compound is prepared analogously to Intermediate H by replacing (3-[4-((R)-2,2-dimethyl-[1,3]dioxolan-4-ylmethoxy)-phenyl]-propan-1-ol with 4-(4-methoxyphenyl)-1-butanol.

Intermediate J

1-Aminomethyl-cyclopentylamine

Step 1

To a cooled 0° C. solution of (1-cyano-cyclopentyl)-carbamic acid tert-butyl ester (430 mg, 2.04 mmol) in dry THF (4.3 ml) under an atmosphere of argon is added dropwise 1.0 M LiAlH$_4$ (6.13 ml, 6.13 mmol). The reaction mixture is allowed to warm to room temperature and stirred for 3.5 hours. The mixture is then re-cooled to 0° C. and cautiously quenched with water (0.4 ml): 15% NaOH (0.8 ml): water (1.2 ml) (1:2:3 eq). The resultant mixture is filtered through Celite® (filter material) to remove the inorganic solids and rinsed with MeOH. The filtrate is concentrated in vacuo, to yield a white solid, which is purified by chromatography on silica eluting with 30% MeOH in DCM to afford (1-Aminomethyl-cyclopentyl)-carbamic acid tert-butyl ester; [M+H]$^+$ 215.

Step 2

Iodotrimethylsilane (0.091 ml, 0.67 mmol) is added dropwise to a solution of (1-aminomethyl-cyclopentyl)-carbamic acid tert-butyl ester (120 mg, 0.56 mmol) in DCM (2.4 ml) and left to stir overnight. The resulting suspension is quenched with MeOH (2.4 ml) and concentrated in vacuo to yield 1-Aminomethyl-cyclopentylamine as a dark oil, which is used without further purification.

Intermediate K (4-((R)-4,5-Diamino-pentyl)-phenol

Steps 1 and 2

(R)-2-tert-Butoxycarbonylamino-5-(4-tert-butoxy-phenyl)-pentanoic acid ethyl ester is prepared according to the procedure of Ding, Chuanyong.; Ma, Rujian.; Rong, Guobin. Preparation of w-Phenyl-(2S)—N-Boc-amino Acid Ethyl esters; Chinese Journal of Organic Chemistry Vol 26(12) 2006, 1694 &1695, replacing Ethyl Boc-L-pyroglutamate with Ethyl Boc-D-pyroglutamate & Bromomethyl-benzene with 1-Bromo-4-tert-butoxy-benzene in Example 2a, using preparation steps 2.2, 2.3, and 2.5; [M+H]$^+$ 394

Step 3

(R)-2-tert-Butoxycarbonylamino-5-(4-tert-butoxy-phenyl)-pentanoic acid ethyl ester (179 g, 460 mmol) is dissolved in 7M $NH_3$ in MeOH (400 ml, 2800 mmol) and stirred at room temperature for 4 days. The reaction is concentrated in vacuo keeping the temperature below 30° C. to afford [(R)-4-(4-tert-Butoxy-phenyl)-1-carbamoyl-butyl]-carbamic acid tert-butyl ester [M+H]$^+$ 364

Step 4

A solution of [(R)-4-(4-tert-Butoxy-phenyl)-1-carbamoyl-butyl]-carbamic acid tert-butyl ester (167 g, 458 mmol) in 1 M HCl in $Et_2O$ (4000 ml) is stirred at room temperature for 3 days. After this time, a white solid forms which is collected by filtration and washed with $Et_2O$ to yield (R)-2-Amino-5-(4-hydroxy-phenyl)-pentanoic acid amide; [M+H]$^+$ 209

Step 5

To a stirred solution of (R)-2-Amino-5-(4-hydroxy-phenyl)-pentanoic acid amide (5 g, 24.01 mmol) in THF (250 ml) is added imidazole (4.90 g, 72 mmol), followed by tert-butyldimethylchlorosilane (3.98 g, 26.4 mmol). The resulting solution is heated at 70° C. for 4 hours and then allowed to cool to room temperature. Dilution with $Et_2O$ (200 ml) washing with water (2×100 ml) and brine (100 ml), drying $MgSO_4$, and concentration in vacuo yields (R)-2-Amino-5-[4-(tert-butyl-dimethyl-silanyloxy)-phenyl]-pentanoic acid amide; [M+H]$^+$ 323

Step 6

A solution of (R)-2-Amino-5-[4-(tert-butyl-dimethyl-silanyloxy)-phenyl]-pentanoic acid amide (7.74 g, 24 mmol) in THF is stirred at 5° C. and borane (96 ml of a 1 M solution in THF, 96 mmol) is added. The mixture is stirred at 5° C. until a homogeneous mixture is obtained and then stirred at room temperature for 30 minutes and 35° C. for 3 hours. After this time, further borane (24 ml of a 1 M solution in THF, 24 mmol) is added and the reaction is heated at 35° C. for 18 hours. After this time, a further portion of borane (24 ml of a 1 M solution in THF, 24 mmol) is added and the reaction heated at 35° C. for a further 24 hours. After this time, the reaction is cooled to 10° C., and quenched by adding dropwise to MeOH (50 ml) at −5° C. After allowing to warm to room temperature the solvent is removed in vacuo to afford a yellow oil. The oil is dissolved in MeOH (250 ml) and SCX-2 silica (180 g, 0.63 mmol/g, 120 mmol) is added. The silica suspension is shaken for 18 hours, the silica is removed by filtration, washed with MeOH (3×100 ml), then suspended in 7M $NH_3$ in MeOH and shaken for 18 hours. The silica is removed by filtration and the 7M $NH_3$ in MeOH is removed in vacuo to afford the title compound as a yellow oil; [M+H]$^+$ 195

Intermediate L 4-((S)-4,5-Diamino-pentyl)-phenol

This compound is prepared analogously to Intermediate K (NVP-QBM333), replacing Ethyl Boc-D-pyroglutamate in step 1 with Ethyl Boc-L-pyroglutamate; [M+H]$^+$ 195

Intermediate M (R)-tert-butyl 5-(4-hydroxyphenyl)pentane-1,2-diyldicarbamate

To a solution of (4-((R)-4,5-Diamino-pentyl)-phenol (Intermediate K) (775 mg, 1.99 mmol) in DCM (10 ml) is added triethylamine (1.14 ml, 8.08 mmol) and a solution of di-tert-butyl dicarbonate (1.33 g, 6.08 mmol) in DCM (10 ml) and the resulting solution is stirred at room temperature for 18 hours. The solvent is removed in vacuo and the residue purified by chromatography ($SiO_2$, EtOAc/iso-hexane) to afford the title compound; [M+H]$^+$ 395

Intermediate N (S)-tert-butyl 5-(4-hydroxyphenyl)pentane-1,2-diyldicarbamate

This compound is prepared analogously to Intermediate M, (R)-tert-butyl 5-(4-hydroxyphenyl)pentane-1,2-diyldicarbamate replacing Intermediate K, (4-((R)-4,5-Diamino-pentyl)-phenol with Intermediate L, 4-((S)-4,5-Diamino-pentyl)-phenol; [M+H]$^+$ 395

Intermediate O (R)-3-[4-((R)-4,5-Diamino-pentyl)-phenoxy]-propane-1,2-diol

Step 1

Triethylamine (8.37 □l, 0.06 mmol) and (R)-(+)-glycidol (96 □l, 1.442 mmol) are added to a solution of (R)-tert-butyl 5-(4-hydroxyphenyl)pentane-1,2-diyldicarbamate (Intermediate M) (474 mg, 1.20 mmol) in EtOH (5 ml) and the resulting solution is heated at 90° C. for 18 hours. The reaction is allowed to cool to room temperature and concentrated in vacuo. Purification by chromatography ($SiO_2$, EtOAc/iso-hexane) affords {(R)-2-tert-Butoxycarbonylamino-5-[4-((R)-2,3-dihydroxy-propoxy)-phenyl]-pentyl}-carbamic acid tert-butyl ester; [M+H]$^+$ 469

Step 2

{(R)-2-tert-Butoxycarbonylamino-5-[4-((R)-2,3-dihydroxy-propoxy)-phenyl]-pentyl}-carbamic acid tert-butyl ester (94 mg, 0.201 mmol) is stirred with a solution of 1 M HCl in $Et_2O$ (3 ml) for 18 hours and then loaded onto a 1 g SCX-2 cartridge washed with MeOH (30 ml), followed by 7M $NH_3$ in MeOH (30 ml). The $NH_3$ fraction is concentrated in vacuo to give the title compound, (R)-3-[4-((R)-4,5-Diamino-pentyl)-phenoxy]-propane-1,2-diol Intermediate H(R)-3-[4-((R)-4,5-Diamino-pentyl)-phenoxy]-propane-1,2-diol; [M+H]$^+$ 269

Intermediate P (R)-3-[4-((S)-4,5-Diamino-pentyl)-phenoxy]-propane-1,2-diol

This compound is prepared analogously to Intermediate O replacing (R)-tert-butyl 5-(4-hydroxyphenyl)pentane-1,2-diyldicarbamate (Intermediate M with (S)-tert-butyl 5-(4-hydroxyphenyl)pentane-1,2-diyldicarbamate (Intermediate N); [M+H]$^+$ 269

Intermediate Q

2-[4-((R)-4,5-Diamino-pentyl)-phenoxy]-1-morpholin-4-yl-ethanone (R)-tert-butyl 5-(4-hydroxyphenyl)pentane-1,2-diyldicarbamate (Intermediate M) (446 mg, 0.565 mmol) is dissolved in DMF (10 ml) and $Cs_2CO_3$ (368 mg, 1.131 mmol) and 2-bromo-1-morpholinethanone (118 mg, 0.565 mmol) are added. The reaction is stirred at room temperature for 40 minutes, then diluted with water (20 ml) and extracted with EtOAc (2×50 ml). The organic layers are dried over $MgSO_4$ and the solvent concentrated in vacuo to give a clear oil. Purification by chromatography on a Waters 3000 prep HPLC system (Microsorb™ C18 Water/MeCN +0.1% TFA) yields a clear oil, which is dissolved in dioxane (4 ml) and treated with 4 M HCl in dioxane (4 ml) and stirred at room temperature for 4 days. Concentration in vacuo affords a white foam which is dissolved in MeOH (3 ml) and loaded onto a 10 g SCX-2 cartridge which is washed with MeOH (60 ml) and 7M $NH_3$ in MeOH (60 ml). The $NH_3$ fractions are combined and concentrated in vacuo to give the title compound as a colourless oil; [M+H]$^+$ 322

Intermediate R 5-(4-Methoxy-phenyl)-hexane-1,2-diamine

This compound is prepared analogously to Intermediate I by replacing 4-(4-methoxyphenyl)-1-butanol with 4-(4-methoxyphenyl)-1-pentanol.

Intermediate S ((S)-4,5-Diamino-pentyl)-carbamic acid benzyl ester

Step 1
Concentrated HCl (15 ml) is added to a suspension of N☐-BOC-N☐-Z-L-ornithine (5.00 g, 13.65 mmol) in 2,2-dimethoxypropane (150 ml). An endotherm occurs and the resulting solution is left to stir at room temperature for 6 hours. The solvent is then reduced in vacuo to approximately 50 ml and diethyl ether (100 ml) is added to turn the solution turbid. On stirring a thick white suspension forms. The white solid is collected by filtration and rinsed with diethyl ether (100 ml). The white solid is dissolved in MeOH (30 ml) and diethyl ether (200 ml) is added to precipitate a white solid that is collected by filtration and rinsed with diethyl ether. The solid is dissolved in DCM and washed with 2 N NaOH (75 ml). The organic phase is dried over $MgSO_4$ and the solvent evaporated in vacuo to yield (S)-2-Amino-5-benzyloxycarbonylamino-pentanoic acid methyl ester as a colourless oil; [M+H]$^+$ 280.78
Step 2
(S)-2-Amino-5-benzyloxycarbonylamino-pentanoic acid methyl ester (2.80 g, 9.99 mmol) and 7M $NH_3$ in MeOH (20 ml) is stirred at room temperature for 72 hours. The reaction mixture is evaporated to dryness in vacuo to yield a white solid. The white solid is suspended in diethyl ether before filtration and drying to yield ((S)-4-Amino-4-carbamoyl-butyl)-carbamic acid benzyl ester.
Step 3
((S)-4-Amino-4-carbamoyl-butyl)-carbamic acid benzyl ester (1.87 g, 7.071 mmol) is suspended in dry THF (40 ml) and cooled to 10° C. in an ice bath under nitrogen. Borane (28.3 ml of a 1 M solution in THF, 28.3 mmol) is added. The ice bath is removed and the suspension heated to 70° C. and then left to stir at this temperature for 3 hours. Further borane (28.3 ml of a 1 M solution in THF, 28.3 mmol) is added and then after an hour the same amount of 1M borane in THF is added again. After a final hour at 70° C. the reaction mixture is quenched with MeOH (40 ml). The solvent is reduced in vacuo to approximately 50 ml. This is diluted with 5 M HCl (100 ml) and washed with diethyl ether (3×100 ml). The aqueous phase is basified to pH12 with 2N NaOH and product extracted into EtOAc (3×100 ml). The organic phases are combined, dried over $MgSO_4$ and the solvent evaporated in vacuo to yield the title compound as a colourless oil.

Intermediate T 3,5-Diamino-6-chloro-pyrazine-2-carboxylic acid [(S)-4-(4-amino-butyl)-imidazolidin-(2E)-ylidene]-amide To a suspension of (4-{(S)-2-[(E)-3,5-Diamino-6-chloro-pyrazine-2-carbonylimino]-imidazolidin-4-yl}-butyl)-carbamic acid benzyl ester (Ex. 5) (0.110 g, 0.239 mmol) in dry DCM (20 ml) is added iodotrimethylsilane (0.130 ml, 0.956 mmol). The reaction mixture is stirred at room temperature for 3.5 hours. MeOH is added to the suspension yielding a solution. Purification by catch and release resin (SCX-2) eluting with MeOH and 7 M $NH_3$ in MeOH yields the title compound as a brown oil; [M+H]$^+$ 327.1

Intermediate U

4-Amino-4-aminomethyl-piperidine-1-carboxylic acid tert-butyl ester

Step 1
To a solution of 4-amino-4-cyano-piperidine-1-carboxylic acid tert-butyl ester (11.5 g, 51.0 mmol) in pyridine (20 ml) at 0° C. is added trifluoroacetic anhydride (11.0 ml) slowly and the reaction mixture is stirred at 0° C. for 4 h. The reaction mixture is diluted with DCM, washed with brine, dried over $Na_2SO_4$ and concentrated in vacuo. The residue obtained is dissolved in DCM and re-precipitated by adding petroleum ether. The supernatant solvent mixture is decanted and the product is washed again with petroleum ether and dried under vacuum to afford 4-Cyano-4-(2,2,2-trifluoro-acetylamino)-piperidine-1-carboxylic acid tert-butyl ester as an oil; $^1$H NMR ($d_6$-DMSO): 1.40 (9H, s), 1.81-1.88 (2H, m), 2.26-2.32 (2H, m), 2.99-3.15 (2H, m), 3.79-3.82 (2H, m), 10.1 (1H, s).
Step 2
To a solution of cyano-4-(2,2,2-trifluoro-acetylamino)-piperidine-1-carboxylic acid tert-butyl ester (10.0 g, 31.0 mmol) in EtOH (150 ml) is added Raney nickel (~1.5 g) and the reaction mixture is stirred under an atmosphere of hydrogen for 3 days. A further quantity of Raney nickel (~1.5 g) is added and the reaction mixture is further stirred for 2 days. The reaction mixture is filtered through a plug of Celite™ (filter material) and the filtrate is concentrated in vacuo to obtain 4-Aminomethyl-4-(2,2,2-trifluoro-acetylamino)-piperidine-1-carboxylic acid tert-butyl ester as a viscous oil that is used crude without further purification.
Step 3
4-Amino-4-aminomethyl-piperidine-1-carboxylic acid tert-butyl ester
To a solution of 4-aminomethyl-4-(2,2,2-trifluoro-acetylamino)-piperidine-1-carboxylic acid tert-butyl ester in MeOH (70 ml) is added a 30% aqueous solution of ammonia (70 ml) and the reaction mixture is stirred at 80° C. overnight. The reaction mixture is concentrated in vacuo to 4-Amino-4-aminomethyl-piperidine-1-carboxylic acid tert-butyl ester as a brown oil that is used crude without further purification; [M+H]$^+$ 230.

Intermediate V 3-(3-Isopropoxy-propylsulfamoyl)-benzoic acid

3-Isopropoxypropylamine (1.1 eq.) is dissolved in THF with stirring at room temperature. N,N-diisopropylethylamine (1 eq.) is added followed by methyl 3-(chlorosulfonyl) benzoic acid (1 eq.). The reaction mixture is stirred at room temperature for 2 hours before the solvent is evaporated in vacuo to yield the crude titled product.

Intermediate W 3-(3-Isopropyl-ureido)-benzoic acid

A suspension of 3-Aminobenzoic acid (20 g, 145.8 mmol) in THF (300 ml) is heated to 60° C. to form a clear solution. I-propylisocyanate (14.9 g, 175 mmol) is added over 30 minutes. During the addition the product starts to precipitate. After complete addition toluene (300 ml) is added. The reaction mixture is stirred at 60° C. for 4.5 hours. The heating bath is removed and the mixture is stirred overnight at room temperature. Finally the suspension is filtered and washed with a mixture of 1:1 THF:toluene (200 ml). The product is dried at 60° C. for 18 hours to yield 3-(3-Isopropyl-ureido)-benzoic acid

Intermediate X

5-Oxo-1-(3-pyrrol-1-yl-propyl)-pyrrolidine-3-carboxylic acid

Step 1
To a solution of 5-Oxo-pyrrolidine-3-carboxylic acid methyl ester (1 eq.) in dry DMF is added NaH (1.1 eq.) followed by 1-(3-bromo-propyl)-1H-pyrrole (1 eq.). The reaction mixture is stirred at room temperature overnight. Purification is by normal phase chromatography to yield 5-Oxo-1-(3-pyrrol-1-yl-propyl)-pyrrolidine-3-carboxylic acid methyl ester.
Step 2
To a cooled solution (0° C.) of 5-Oxo-1-(3-pyrrol-1-yl-propyl)-pyrrolidine-3-carboxylic acid methyl ester in THF, 0.2M LiOH is added and RM is stirred for 3 hours gradually warming to room temperature. Reaction mixture is acidified with 1N HCl and product extracted into ethyl acetate. The organic phase is washed with brine, dried over magnesium sulphate and the solvent evaporated in vacuo to yield 5-Oxo-1-(3-pyrrol-1-yl-propyl)-pyrrolidine-3-carboxylic acid.

Intermediate Y 2-(3-Isopropyl-ureido)-isonicotinic acid

Step 1
To a solution of ethyl 2-aminoisonicotinate (500 mg, 3.01 mmol) in DMF (10 ml) is added triethylamine (1.26 ml, 9.03 mmol) and then isopropyl isocyanate (512 mg, 6.02 mmol). The reaction mixture is heated in a microwave at 140° C. for 2 hours. The reaction mixture is diluted with EtOAc, washed with water (×5), brine, dried (MgSO$_4$) and concentrated in vacuo. Chromatography (SiO$_2$, MeOH/DCM) affords 2-(3-Isopropyl-ureido)-isonicotinic acid ethyl ester; [M+H]$^+$ 252
Step 2
To a solution of 2-(3-Isopropyl-ureido)-isonicotinic acid ethyl ester (130 mg, 0.52 mmol) in MeOH (5 ml) is added 2 M NaOH (2.5 ml) and the resulting solution is stirred for 1.5 hours at room temperature. The solvent is removed in vacuo and sat. aq. NH$_4$Cl solution is added. The pH of the aqueous phase is adjusted to 1 using 1 M HCl and the product extracted into EtOAc, dried (MgSO$_4$) the solvent removed in vacuo to afford 2-(3-Isopropyl-ureido)-isonicotinic acid as a white solid; [M+H]$^+$ 224

Intermediate Z

1-Isopropylcarbamoyl-1H-indole-4-carboxylic acid

This compound is prepared analogously to Intermediate Y by replacing ethyl 2-aminoisonicotinate in step 1 with methyl indol-4-carboxylate; [M+H]$^+$ 247

Intermediate AA 4-(3-Isopropyl-ureido)-benzoic acid

This compound is prepared analogously to Intermediate Y by replacing ethyl 2-aminoisonicotinate in step 1 with methyl 4-aminobenzoate; [M+H]$^+$ 237.

Intermediate AB 6-(3-Isopropyl-ureido)-nicotinic acid

This compound is prepared analogously to Intermediate Y by replacing ethyl 2-aminoisonicotinate in step 1 with methyl 6-aminonicotinate; [M+H]$^+$ 224.

Intermediate AC

[4-(2-Methoxy-ethoxymethoxy)-phenyl]-acetic acid

Step 1
To a solution of methyl 4-hydroxyphenylacetate (200 mg, 1.20 mmol) in DCM (5 ml) is added DIPEA (0.315 ml, 1.81 mmol), and then MEMCl (0.204 ml, 1.81 mmol), and the resulting reaction mixture is stirred for 2 hours at room temperature. An additional portion of MEMCl (0.102 ml, 1 mmol) and of DIPEA (0.158 ml, 1 mmol) are added, and the reaction mixture is stirred for a further 16 hours. An additional portion of MEMCl (0.102 ml, 1 mmol) and of DIPEA (0.158 ml, 1 mmol) are added and the reaction mixture is stirred for 3 hours. The reaction mixture is diluted with DCM and washed with 0.5 M HCl, 1 M NaOH and then 0.5 M HCl, dried (MgSO$_4$) and concentrated in vacuo to afford [4-(2-Methoxy-ethoxymethoxy)-phenyl]-acetic acid methyl ester
Step 2
To a solution of [4-(2-Methoxy-ethoxymethoxy)-phenyl]-acetic acid methyl ester (192 mg, 0.76 mmol) in MeOH (3 ml) is added 2 M NaOH (3 ml). The reaction mixture is stirred for 16 hours at room temperature. The solvent is removed in vacuo and the residue dissolved in EtOAc and washed with sat. aq. NH$_4$Cl solution, dried (MgSO$_4$) and concentrated in vacuo to yield [4-(2-Methoxy-ethoxymethoxy)-phenyl]-acetic acid

Intermediate AD

3-[4-(2-Methoxy-ethoxymethoxy)-phenyl]-propionic acid

This compound is prepared analogously to Intermediate AC by replacing methyl 4-hydroxyphenylacetate in step 1 with methyl-3-(4-hydroxyphenyl)propionate.

Intermediate AE

3-{4-[2-(Tetrahydro-pyran-2-yloxy)-ethoxy]-phenyl}-propionic acid

Step 1
Methyl 3-(4-hydroxyphenyl)propionate (0.1 g, 0.55 mmol) is dissolved in DMF (5 ml) and NaH (0.033 g of a 60% dispersion in mineral oil, 0.83 mmol) is added. The reaction mixture is stirred at room temperature for 15 minutes then 2-(2-bromethoxy)tetrahydro-2-H-pyran (0.109 ml, 0.72 mmol) is added and the reaction mixture is left to stir for 18 hours. Dilution with EtOAc (50 ml), washing with water (25 ml), saturated NaHCO$_3$ (25 ml) and brine (25 ml), drying over MgSO$_4$, and concentration in vacuo yields 3-{4-[2-(Tetrahydro-pyran-2-yloxy)-ethoxy]-phenyl}-propionic acid methyl ester as a colourless oil; [M+H]$^+$ 309

Step 2

3-{4-[2-(Tetrahydro-pyran-2-yloxy)-ethoxy]-phenyl}-propionic acid methyl ester (0.12 g, 0.39 mmol) is dissolved in MeOH (3 ml) and 2M NaOH solution (3 ml) is added and the resulting solution is stirred at room temperature for 18 hours. The reaction mixture is diluted with saturated ammonium chloride solution (20 ml) and extracted with EtOAc (100 ml×2). The organic phased are combined, dried over MgSO$_4$, the solvent removed in vacuo to yield the title compound as a colourless oil; [M+H]$^+$=295

Intermediate AF

3-[4-(Pyridin-4-ylmethoxy)-phenyl]-propionic acid

Step 1

To a solution of Methyl 3-(4-hydroxyphenyl)propanoate (0.5 g, 2.77 mmol) in dry DMF (10 ml) is added potassium carbonate (0.76 g, 5.55 mmol) followed by 4-(bromomethyl)pyridine hydrobromide (0.7 g, 2.77 mmol). The reaction mixture is stirred at room temperature overnight then poured into water (80 ml) and extracted with EtOAc (40 ml). The organic phase is washed with brine, dried (MgSO$_4$) and the solvent removed in vacuo to yield a dark brown oil. Chromatography (SiO$_2$, EtOAc) yields 3-[4-(Pyridin-4-ylmethoxy)-phenyl]-propionic acid methyl ester as a colourless oil; [M+H]+ 272.0

Step 2

To a solution of 3-[4-(Pyridin-4-ylmethoxy)-phenyl]-propionic acid methyl ester (0.28 g, 1.03 mmol) in THF (5 ml) and MeOH (5 ml) at room temperature is added 2 N LiOH (0.52 ml, 1.032 mmol) and the resulting solution is stirred overnight. Further 2 N LiOH (0.103 ml) is added and the reaction mixture stirred for a further 1 hour. The reaction mixture is concentrated in vacuo and the residue is diluted with water (50 ml) followed by EtOAc. The aqueous phase is acidified to pH2 with 1 N HCl, and extracted with DCM. The organic phase is concentrated to a third of its volume in vacuo until a white powder precipitates which is collected by filtration to yield the title compound; [M+H]$^+$ 258.0

Intermediate AG 3-(4-tert-Butoxycarbonylmethoxy-phenyl)-propionic acid

Step 1

To a stirring solution of methyl 3-(4-hydroxyphenyl)propanoate (2 g, 11.10 mmol) in dry DMF (30 ml) at room temperature is added potassium carbonate (1.53 g, 11.10 mmol) followed by tert-butyl 2-bromoacetate (2.17 g, 11.10 mmol). The reaction mixture is purged with nitrogen, then stoppered and left stirring at room temperature for 7 days. The reaction mixture is poured into water (200 ml) and extracted with EtOAc (100 ml), washed with brine, dried (MgSO$_4$), filtered and evaporated in vacuo to yield a pale yellow oil. Flash chromatography (SiO$_2$, EtOAc/iso-hexane) yields 3-(4-tert-Butoxycarbonylmethoxy-phenyl)-propionic acid methyl ester as a clear oil.

Step 2

To a solution of 3-(4-tert-Butoxycarbonylmethoxy-phenyl)-propionic acid methyl ester (2.70 g, 9.17 mmol) in THF (80 ml) is added 0.2N lithium hydroxide (45.9 ml, 9.17 mmol) at 0° C. and the reaction mixture is stirred at 0° C. for 4.5 hours. 1M HCl (15 ml) is added and the product is extracted using EtOAc (×3). The organic phase is dried (Na$_2$SO$_4$) and concentrated in vacuo to yield a white solid. Flash chromatography (SiO$_2$, 10% EtOAc in CH$_2$Cl$_2$, then 20% EtOAc in CH$_2$Cl$_2$) yields 3-(4-tert-Butoxycarbonylmethoxy-phenyl)-propionic acid as a white solid.

Intermediate AH 3-(4-Carbamoylmethoxy-phenyl)-propionic acid

This compound is prepared analogously to Intermediate AG by replacing tert-butyl 2-bromoacetate in step 1 with 2-bromoacetamide; [M+H]$^+$ 530.1

Intermediate AI

1-[4-(2-Carboxy-ethyl)-phenoxy]-cyclobutanecarboxylic acid ethyl ester

This compound is prepared analogously to Intermediate AG by replacing tert-butyl 2-bromoacetate in step 1 with ethyl 1-bromocyclobutane-carboxylate; [M+H]$^+$ 293.0

Intermediate AJ

2-[4-(2-Carboxy-ethyl)-phenoxy]-2-methyl-propionic acid tert-butyl ester

This compound is prepared analogously to Intermediate AG by replacing tert-butyl 2-bromoacetate in step 1 with tert-butyl 2-bromoisobutyrate. $^1$H NMR (DMSO-d6): 1.40 (9H, s), 1.48 (6H, s), 2.49 (2H, t, J=7.5), 2.75 (2H, t, J=7.5), 6.71 (2H, d, J=8.5), 7.11 (2H, d, J=8.50), 12.10 (1H, s).

Intermediate AK 3-(4-Methoxycarbonylmethoxy-phenyl)-propionic acid

Step 1

To a solution of 3-(4-hydroxyphenyl)propanoic acid (3.32 g, 20 mmol) in dry DMF (20 ml) is carefully added 1,1'-carbonyldiimidazole (3.24 g, 20 mmol) portionwise. The reaction mixture is stirred at 40° C. for 2 hours after which time DBU (6.02 ml, 40 mmol) and tert-butanol (4.78 ml, 50 mmol) are added and the reaction mixture is now stirred at 65° C. for 2 days. The reaction mixture is allowed to cool to room temperature and poured into water (50 ml) and the product is extracted with diethyl ether (3×30 ml). The organics are combined, dried (MgSO$_4$) and the solvent removed in vacuo to give a yellow oil. Purification by flash chromatography (SiO$_2$, EtOAc/iso-hexane) yields 3-(4-Hydroxy-phenyl)-propionic acid tert-butyl ester as a colourless oil. $^1$H NMR (DMSO-d6) 9.1 (1H, s), 7.0 (2H, d, J=8.45), 6.65 (2H, d, J=8.45), 2.7 (2H, t, J=7.28), 2.4 (2H, t, J=7.28), 1.4 (9H, s).

Step 2

To a solution of -(4-Hydroxy-phenyl)-propionic acid tert-butyl ester (1 g, 4.50 mmol) in dry DMF (20 ml) at room temperature under argon is added potassium carbonate (0.62 g, 4.50 mmol) followed by methyl bromoacetate (0.43 ml, 4.50 mmol) and the reaction mixture is stirred at room temperature. The reaction mixture is diluted with EtOAc and washed with water, dried (MgSO$_4$) and evaporated in vacuo to yield a clear colourless liquid. Purification on a Waters 3000 prep HPLC system (C18, MeCN/water) yields 3-(4-Methoxycarbonylmethoxy-phenyl)-propionic acid tert-butyl ester as a pale yellow oil.

Step 3

To 3-(4-Methoxycarbonylmethoxy-phenyl)-propionic acid tert-butyl ester (0.097 g, 0.33 mmol) is added a 90% solution of TFA in DCM (2 ml) and the resulting solution is stirred at room temperature for 1 hour. The solvents are removed in vacuo to yield 3-(4-Methoxycarbonylmethoxy-phenyl)-propionic acid as an off-white powder; [M+H-18]$^+$ 256.0

Intermediate AL

3-[4-(2-Propoxycarbonyl-ethyl)-phenyl]-propionic acid

To a solution of 3,3'-(1,4-phenylene)dipropanoic acid (250 mg, 1.125 mmol) DCM (15 ml) is added 4-dimethylaminopyridine (137 mg, 1.125 mmol) and propanol (3 ml, 40.1 mmol). The solution is cooled to 0° C. and dicyclohexylcarbodiimide (232 mg, 1.125 mmol) is added and the resulting solution is stirred at 0° C. for 30 minutes and 2 hours, at room temperature. Concentration in vacuo affords a white solid which is suspended in Et$_2$O (50 ml) and filtered to remove any insoluble material. The filtrate is concentrated in vacuo and purification by chromatography (SiO$_2$, EtOAc/iso-hexane) affords the title compound.

Intermediate AM

3-[4-(2-Ethoxycarbonyl-ethyl)-phenyl]-propionic acid

This compound is prepared analogously to Intermediate AL replacing propanol with ethanol.

Intermediate AN

3-[4-(2-Methoxycarbonyl-ethyl)-phenyl]-propionic acid

This compound is prepared analogously to Intermediate AL replacing propanol with methanol.

Intermediate AO 1-(2-Phenoxy-ethyl)-1H-indole-4-carboxylic acid

Step 1

NaH (60% dispersion in mineral oil, 68.5 mg, 1.71 mmol) is added to solution of methyl indole-4-carboxylate (200 mg, 1.142 mmol) in DMF (5 ml) and the resulting suspension is stirred at room temperature for 20 minutes. After this time (2-bromoethoxy)benzene (298 mg, 1.484 mmol) is added and the reaction is stirred at room temperature for 18 hours. Dilution with EtOAc (50 ml) and washing with water (25 ml×2), saturated NaHCO$_3$ (25 ml) and brine (25 ml), drying over MgSO$_4$, concentration in vacuo and purification by chromatography (SiO$_2$, EtOAc/iso-hexane) affords 1-(2-Phenoxy-ethyl)-1H-indole-4-carboxylic acid methyl ester; [M+H]$^+$ 296

Step 2

1-(2-Phenoxy-ethyl)-1H-indole-4-carboxylic acid methyl ester (185 mg, 0.626 mmol) is suspended in a mixture of MeOH (3 ml) and 2 M NaOH (2 ml). The suspension is stirred at room temperature for 2 hours, THF (1 ml) is added and the reaction is heated at 60° C. for 1 hour. The reaction is allowed to cool to room temperature and diluted with sat. NH$_4$Cl solution (10 ml), extracted with EtOAc (10 ml×3), dried over MgSO$_4$, and concentrated in vacuo to give the title compound; [M+H]$^+$ 282

Intermediate AP 1-(2-p-Tolyl-ethyl)-1H-indole-4-carboxylic acid

This compound is prepared analogously to Intermediate AO replacing (2-bromoethoxy)benzene with 4-methylphenethyl bromide; [M+H]$^+$ 280

Intermediate AQ

1-[2-(Tetrahydro-pyran-2-yloxy)-ethyl]-1H-indole-4-carboxylic acid

This compound is prepared analogously to Intermediate AO replacing (2-bromoethoxy)benzene with 2-(2-bromoethoxy)tetrahydro-2H-pyran; [M+H]$^+$ 290

Intermediate AR

1-[2-(4-Methoxy-phenoxy)-ethyl]-1H-indole-4-carboxylic acid

This compound is prepared analogously to Intermediate AO replacing (2-bromoethoxy)benzene with 1-(2-bromoethoxy)-4-methoxybenzene; [M+H]$^+$ 312

Intermediate AS

1-[2-(4-tert-Butyl-phenoxy)-ethyl]-1H-indole-4-carboxylic acid

This compound is prepared analogously to Intermediate AO replacing (2-bromoethoxy)benzene with 1-(2-bromoethoxy)-4-tert-butylbenzene; [M+H]$^+$ 338

Intermediate AT 1-(2-[1,3]Dioxan-2-yl-ethyl)-1H-indole-4-carboxylic acid

This compound is prepared analogously to Intermediate AO replacing (2-bromoethoxy)benzene with (2-bromethyl)1,3-dioxane; [M+H]$^+$ 276

Intermediate AU 2,3-Dimethyl-1-[2-(tetrahydro-pyran-2-yloxy)-ethyl]-1H-indole-5-carboxylic acid This compound is prepared analogously to Intermediate AO replacing (2-bromoethoxy)benzene with (2-(2-bromoethoxy)tetrahydro-2H-pyran and replacing Methyl indole-4-carboxylate with 2,3-dimethyl-1H-indole-5-carboxylate; [M+H]+ 318

Intermediate AV 1-(4,4,4-Trimethoxy-butyl)-1H-indole-4-carboxylic acid

This compound is prepared analogously to Intermediate AO 1-(2-Phenoxy-ethyl)-1H-indole-4-carboxylic acid replacing (2-bromoethoxy)benzene with trimethyl 4-bromoorthobutyrate.

Intermediate AW

1-[2-(2-Methoxy-ethoxymethoxy)-ethyl]-1H-indole-4-carboxylic acid

Step 1
NaH (60% dispersion in mineral oil, 86 mg, 2.14 mmol) is added to a solution of methyl indole-4-carboxylate (250 mg, 1.427 mmol) in DMF (20 ml) and the resulting suspension is stirred at room temperature for 30 minutes. After this time (2-(2-bromoethoxy)tetrahydro-2H-pyran (388 mg, 1.86 mmol) is added and the reaction is stirred at room temperature for 22 hours. Dilution with EtOAc (50 ml), washing with water (25 ml×3), saturated NaHCO$_3$ (25 ml×2) and brine (25 ml), drying over MgSO$_4$, concentration in vacuo and purification by chromatography (SiO$_2$, DCM/MeOH) affords 1-[2-(Tetrahydro-pyran-2-yloxy)-ethyl]-1H-indole-4-carboxylic acid methyl ester; [M+H]+ 304
Step 2
To a solution of 1-[2-(Tetrahydro-pyran-2-yloxy)-ethyl]-1H-indole-4-carboxylic acid methyl ester (120 mg, 0.396 mmol) in MeOH (10 ml) is added p-toluenesulfonic acid monohydrate (7.25 mg, 0.04 mmol). The reaction is stirred at room temperature for 16 hours and the solvent is removed in vacuo. The residue is dissolved in MeOH (3 ml) and loaded onto a 1 g PEAX cartridge washed with MeOH (20 ml). The filtrate is concentrated in vacuo to give 1-(2-Hydroxy-ethyl)-1H-indole-4-carboxylic acid methyl ester; [M+H]+ 220
Step 3
To a solution of -(2-Hydroxy-ethyl)-1H-indole-4-carboxylic acid methyl ester in DCM (3 ml) is added DIPEA (0.129 ml, 0.739 mmol) and 1-Chloromethoxy-2-methoxy-ethane (0.084 ml, 0.739 mmol). The solution is stirred at room temperature for 72 hours. The reaction is diluted with DCM (50 ml) and washed with 0.5 M HCl (20 ml), 1 M NaOH (20 ml) and 0.5 M HCl (20 ml). The organic layer is dried over MgSO$_4$ and the solvent is removed in vacuo. Purification by chromatography (SiO$_2$, DCM/MeOH) affords 1-[2-(2-Methoxy-ethoxymethoxy)-ethyl]-1H-indole-4-carboxylic acid methyl ester; [M+H]+ 308
Step 4
To a solution of 1-[2-(2-Methoxy-ethoxymethoxy)-ethyl]-1H-indole-4-carboxylic acid methyl ester (69 mg, 0.225 mmol) in MeOH (2 ml) is added 2 M NaOH (1 ml) and the reaction is stirred at room temperature for 19.5 hours, then for 2 hours at 50° C. The reaction is allowed to cool to room temperature and the solvent removed in vacuo. To the residue is added sat. NH$_4$Cl (10 ml), and the product is extracted with EtOAc (5×25 ml), washed with brine (10 ml), dried over Na$_2$SO$_4$, and the solvent is removed in vacuo, to give the title compound 1-[2-(2-Methoxy-ethoxymethoxy)-ethyl]-1H-indole-4-carboxylic acid; [M+H]+ 294

Intermediate AX

1-Diethylcarbamoylmethyl-1H-indole-4-carboxylic acid

Step 1
Methyl indole-4-carboxylate (50 mg, 2.85 mmol) and 2-chloro-N,N-diethylacetamide (854 mg, 5.71 mmol) are dissolved in DMF (10 ml) and to the solution is added potassium carbonate (986 mg, 7.14 mmol). The reaction is heated using microwave radiation at 100° C. for 2 hours, then diluted with DCM (60 ml) and washed with water (5×10 ml). Drying over MgSO$_4$, concentration in vacuo, and trituration with Et$_2$O affords 1-Diethylcarbamoylmethyl-1H-indole-4-carboxylic acid methyl ester; [M+H]+ 289.
Step 2
To a solution of Diethylcarbamoylmethyl-1H-indole-4-carboxylic acid methyl ester (480 mg, 1.665 mmol) in MeOH (5 ml) is added 2 M NaOH (5 ml). The reaction is heated at 50° C. for 20 hours and then allowed to cool to room temperature. The solvent is removed in vacuo and the residue dissolved in water (10 ml). The pH of the solution is adjusted to 5 using 1 M HCl and the resulting solid is collected by filtration to give the title compound I-Diethylcarbamoylmethyl-1H-indole-4-carboxylic acid; [M+H]+ 275

Intermediate AY

4-[6-((R)-2,2-Dimethyl-[1,3]dioxolan-4-ylmethoxy)-naphthalen-2-ylmethoxy]-benzoic acid Step 1
To a solution of methyl 6-hydroxy-2-naphthoate (4.55 g, 22.5 mmol) in anhydrous acetone (60 ml) are added S-(−)-glycidol (2.0 g, 27.0 mmol) and K$_2$CO$_3$ (9.3 g, 67.3 mmol). The reaction mixture is heated to reflux for 3 days. The reaction mixture is filtered through Celite™ (filter material) and the filtrate is concentrated in vacuo to afford 6-((S)-2,3-Dihydroxy-propoxy)-naphthalene-2-carboxylic acid methyl ester as a white solid; $^1$H NMR (DMSO-d$_6$): 3.49 (2H, t, J=6.0 Hz), 3.85-3.88 (1H, m), 3.89 (3H, s), 4.02 (1H, dd, J=9.9, 6.0 Hz), 4.16 (1H, dd, J=9.9, 4.0 Hz), 4.73 (1H, t, J=6.0 Hz), 5.04 (1H, d, J=5.2 Hz), 7.26 (1H, dd, J=9.0, 2.0 Hz), 7.41 (1H, d, J=2.0 Hz), 7.88-7.94 (2H, m), 8.04 (1H, d, J=9.0 Hz), 8.55 (1H, s).
Step 2
To 6-((S)-2,3-dihydroxy-propoxy)-naphthalene-2-carboxylic acid methyl ester (0.9 g, 3.26 mmol) in anhydrous DMF (10 ml) is added 2,2-dimethoxypropane (2.0 ml, 16.3 mmol) and pyridinium p-toluenesulfonate (0.08 g, 0.32 mmol) and the reaction mixture is stirred at room temperature for 16 hours. The reaction mixture is concentrated in vacuo and the residue is dissolved in EtOAc. The EtOAc layer is washed with 10% NaHCO$_3$, water, and brine, dried over anhydrous Na$_2$SO$_4$ and the solvent is evaporated in vacuo to obtain 6-((R)-2,2-Dimethyl-[1,3]dioxolan-4-ylmethoxy)-naphthalene-2-carboxylic acid methyl ester as solid; $^1$H NMR (DMSO-d6): 1.32 (3H, s), 1.37 (3H, s), 3.78-3.82 (1H, m), 3.88 (3H, s), 4.11-4.20 (3H, m), 4.45-4.50 (1H, m), 7.26 (1H, dd, J=9.0, 2.0 Hz), 7.45 (1H, d, J=2.0 Hz), 7.88 (1H, d, J=9.0 Hz), 7.93 (1H, d, J=9.0 Hz), 8.04 (1H, d, J=9.0 Hz), 8.55 (1H, s).
Step 3
To a solution of 6-((R)-2,2-dimethyl-[1,3]-dioxolan-4-yl-methoxy)-naphthalene-2-carboxylic acid methyl ester (1.0 g, 3.16 mmol) in anhydrous THF (20 ml) at 0° C. is added LiAlH$_4$ (1.9 ml of a 2M solution in THF, 3.8 mmol). The reaction mixture is stirred at room temperature overnight. The reaction mixture is concentrated in vacuo and the residue is purified by column chromatography (SiO$_2$, DCM) to afford [6-((R)-2,2-Dimethyl-[1,3]dioxolan-4-ylmethoxy)-naphthalen-2-yl]-MeOH as a colourless viscous oil which solidified on standing; $^1$H NMR (d$_6$-DMSO): 1.32 (3H, s), 1.37 (3H, s), 3.78 (1H, dd, J=8.3, 6.0 Hz), 4.01-4.15 (3H, m), 4.45-4.48 (1H, m), 4.60 (2H, d, J=6.0 Hz), 5.24 (1H, t, J=6.0 Hz), 7.14 (1H, dd, J=8.5, 2.5 Hz), 7.32 (1H, d, J=2.5 Hz), 7.41 (1H, dd, J=8.5, 1.5 Hz), 7.33-7.80 (3H, m).
Step 4
A mixture of methyl 4-hydroxybenzoate (0.5 g, 3.28 mmol), [6-((R)-2,2-dimethyl-[1,3]dioxolan-4-ylmethoxy)-naphthalen-2-yl]-methanol (0.9 g, 3.12 mmol) and triphenylphosphine (0.83 g, 3.16 mmol) in DCM (20 ml) is cooled to 0° C. Diethyl azodicarboxylate (0.5 ml, 3.17 mmol) is added dropwise. The reaction mixture is stirred at room temperature overnight. The reaction mixture is concentrated in vacuo and purified by column chromatography (SiO$_2$, EtOAc/iso-hexane) to obtain white solid. The product obtained is once again purified by column chromatography (neutral alumina, EtOAc/petroleum ether) to obtain 4-[6-((R)-2,2-Dimethyl-[1,3]dioxolan-4-ylmethoxy)-naphthalen-2-ylmethoxy]-benzoic acid methyl ester as white solid; $^1$H NMR (d$_6$-DMSO): 1.32 (3H, s), 1.38 (3H, s), 3.77-3.82 (4H, m), 4.08-4.16 (3H, m), 4.46-4.49 (1H, m), 5.30 (2H, s), 7.15-7.21 (3H, m), 7.37 (1H, d, J=2.0 Hz), 7.53 (1H, dd, J=8.50, 1.5 Hz), 7.83 (2H, dd, J=9.0, 6.0 Hz), 7.92 (3H, m).
Step 5
To a solution of 4-[6-((R)-2,2-dimethyl-[1,3]dioxolan-4-ylmethoxy)-naphthalen-2-ylmethoxy]-benzoic acid methyl ester (0.46, 1.09 mmol) in THF/water (10 ml of a 1:1 mixture) is added lithium hydroxide (0.15 g, 3.57 mmol). The reaction mixture is stirred at room temperature overnight, then at 70° C. for 24 h. The reaction mixture is cooled to room temperature, neutralized with 1.5 M HCl and the white solid obtained is collected by vacuum filtration, washed with water and dried under vacuum to afford 4-[6-((R)-2,2-Dimethyl-[1,3]dioxolan-4-ylmethoxy)-naphthalen-2-ylmethoxy]-benzoic acid. [M]$^-$ 407.

Intermediate AZ

4-{3-[4-((R)-2,2-Dimethyl-[1,3]dioxolan-4-ylmethoxy)-phenyl]-propoxy}-benzoic acid This compound is prepared analogously to Intermediate AY by replacing [6-((R)-2,2-dimethyl-[1,3]dioxolan-4-ylmethoxy)-naphthalen-2-yl]-methanol in Step 4 with 3-[4-((R)-2,2-dimethyl-[1,3]dioxolan-4-ylmethoxy)-phenyl]-propan-1-ol; $^1$H NMR (DMSO-d6): 1.30 (3H, s), 1.35 (3H, s), 1.97-2.01 (2H, m), 2.68 (2H, t, J=7.5 Hz), 3.72-3.75 (1H, m), 3.93-4.00 (4H, m), 4.06-4.10 (1H, m), 4.38 (1H, dd, J=6.0, 5.0), 6.87 (2H, d, J=9.0 Hz), 6.92 (2H, d, J=9.0 Hz), 7.14 (2H, d, J=, 9.0 Hz), 7.84 (2H, d, J=9.0 Hz).

Intermediate BA

4-{2-[(E)-3,5-Diamino-6-chloro-pyrazine-2-carbonylimino]-1,3,8-triaza-spiro[4.5]decane-8-carbonyl}-piperidine-1-carboxylic acid tert-butyl ester This compound is prepared analogously to Example 97 by replacing 4-benzyloxyphenylacetic acid with 1-Boc-piperidine-4-carboxylic acid; [M+H]$^+$ 536.

Intermediate BB

4-[(Naphthalene-1-sulfonylamino)-methyl]-benzoic acid

4 N NaOH solution (30 ml) is added to a suspension of 4-(aminomethyl)benzoic acid (5.01 g, 31.82 mmol) in acetone (100 ml). Toluene (100 ml) is added and the reaction is heated at 40° C. to obtain dissolution. The solution is cooled to 0° C. and treated with 1-naphthalene sulfonyl chloride (12 g, 51.35 mmol) in acetone (100 ml) and the resulting reaction mixture is stirred for 3 hours. The reaction is acidified using citric acid and concentrated in vacuo. The residue is taken up in EtOAc and washed with water. The aqueous layer is back extracted with EtOAc and the combined organic layers are washed with water, brine, dried (Na$_2$SO$_4$) and the solvent removed in vacuo to yield a light brown solid. Trituration with Et$_2$O yields the title compound.

Intermediate BC 3-(Cyclohexyl-methyl-sulfamoyl)-4-methoxy-benzoic acid

Step 1
A solution of methyl 3-(chlorosulfonyl)-4-methoxybenzoate (2.0 g, 7.56 mmol) and diisopropylethylamine (1.94 ml, 11.34 mmol) in DCM (50 ml) is treated with N-methyl cyclohexylamine (0.70 ml, 9.07 mmol) at 0° C. The solution is stirred at room temperature for 3 hours and N-methyl cyclohexylamine (0.70 ml, 9.07 mmol) is added. The solution is partitioned between DCM (250 ml) and 0.5 N HCl (100 ml). The organic layer is washed with 0.5 N HCl (2×100 ml), sat. aq. NaHCO$_3$ (2×100 ml) and water (100 ml), dried over MgSO$_4$, and the solvent removed in vacuo to yield a yellow oil. Crystallisation (iPr$_2$O/EtOAc) yields 3-(Cyclohexyl-methyl-sulfamoyl)-4-m ethoxy-benzoic acid methyl ester as yellow crystals; [M+H] 342.
Step 2
A solution of 3-(Cyclohexyl-methyl-sulfamoyl)-4-methoxy-benzoic acid methyl ester (1.50 g, 4.39 mmol) in 1,4 dioxane (40 ml) is treated with 2 N NaOH (10 ml) and the resulting solution is stirred at room temperature for 21 hours. The solvent is removed in vacuo and ice cold 2 N HCl (25 ml) is added and the white solid which forms is extracted into DCM (150 ml). The organic layer is washed with water, dried (MgSO$_4$) and the solvent removed in vacuo to yield the title compound as a white solid; [M–1]$^-$ 326.

Intermediate BD

3-Chloro-5-methoxy-4-[2-(4-methyl-piperazin-1-yl)-ethoxy]-benzoic acid

Step 1
A mixture of 5-chlorovanillic acid (5.0 g, 24.6 mmol) and conc. HCl (5 ml) in MeOH (100 ml) is heated at reflux for 48 hours. The solvent is removed in vacuo and water is added to the residue to yield a white precipitate, which is collected by filtration, washed with water, and then dissolved in Et$_2$O. The solution is dried (Na$_2$SO$_4$) and the solvent removed in vacuo to yield 3-Chloro-4-hydroxy-5-methoxy-benzoic acid methyl ester as a white solid.
Step 2
Triphenylphosphine (6.4 g, 24.4 mmol) and DIAD (4.8 ml, 202.2 mmol) are added to a solution of 3-Chloro-4-hydroxy-5-methoxy-benzoic acid methyl ester (2.5 g, 11.5 mmol) in THF (40 ml) at 0° C. and the resulting solution is stirred for 2 hours at 0° C. and 16 hours at room temperature. The solvent is removed in vacuo, and water is added to the residue. The product is extracted in EtOAc, dried (Na$_2$SO$_4$) and the solvent removed in vacuo to afford a yellow oil. Flash chromatography (SiO$_2$, EtOAc/MeOH) yields 3-Chloro-5-methoxy-4-[2-(4-methyl-piperazin-1-yl)-ethoxy]-benzoic acid methyl ester as an orange solid.

Step 3

A solution of 3-Chloro-5-methoxy-4-[2-(4-methyl-piperazin-1-yl)-ethoxy]-benzoic acid methyl ester (3.7 g, 10.7 mmol) in 2 N NaOH (20 ml) and THF (40 ml) is heated at reflux for 1 hour. The reaction mixture is washed with Et$_2$O. The aqueous phase is concentrated in vacuo, and water (50 ml) is added. The pH is adjusted to 3-4 using 2 N HCl. To this solution is added DOWEX 50WX4 (previously washed with MeOH, 2 N HCl and water), and the resulting mixture is stirred at room temperature for 1 hour. The resin is filtered, washed with water, and the product is released from the resin by washing with MeOH/NH$_4$OH. The solution is concentrated in vacuo, diluted with DCM and MeOH, dried (Na$_2$SO$_4$) and the solvent removed in vacuo to yield the title compound as a light cream solid.

Intermediate BE

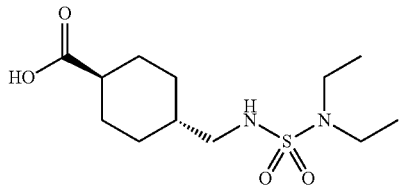

Step 1

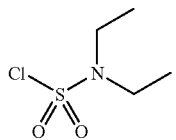

To a stirred solution of diethyl amine (500 ml, 4.8 mol) in Et$_2$O (1200 ml) is added sulfuryl chloride (177.3 ml, 2.19 mol) over 80 minutes at −15° C. The reaction is stirred at room temperature for 2.5 hours. Et$_2$O (1000 ml) is added and the white solid present is removed by filtration, and washed with Et$_2$O (2000 ml). The combined filtrates are concentrated under reduced pressure to yield as a colourless oil.

Step 2

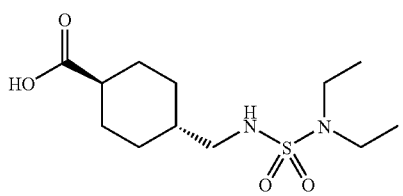

To a stirred solution of trans-4-(aminomethyl)-cyclohexane carboxylic acid (10 g, 63.6 mmol) in 1 N NaOH (153 ml) is added (10.91 g, 63.6 mmol) and the resulting mixture is stirred at room temperature for 15 hours. The reaction is cooled to 10° C. and conc. HCl solution (15 ml) is added and the mixture stirred for 10 minutes at this temperature. White crystals form which are isolated by filtration and washed with Et$_2$O (40 ml) to yield the title compound.

Intermediate BF 3-(3-Phenyl-isoxazol-5-yl)-propionic acid

This compound is prepared as described by G. S. d'Alcontres; C Caristi; A Ferlazzo; M Gattuso, *J. Chem. Soc. Perkin* 1, (1976) 16, 1694.

Intermediate BG 3-(4-Chloro-phenoxymethyl)-benzylamine

This compound is prepared as described in US 2008200523.

Intermediate BH

2-{4-[2-(4-Fluoro-phenyl)-ethoxy]-phenyl}-ethylamine

Step 1

A suspension of 4-Hydroxybenzyl cyanide (7.9 g, 59.57 mmol), 1-(2-Bromo-ethyl)-4-fluoro-benzene (17.4 g, 71.48 mmol), potassium carbonate (19.8 g, 143 mmol) and sodium iodide (2.68 g, 17.87 mmol) in acetonitrile (120 ml) is heated at reflux for 44 hours. The reaction mixture is cooled and filtered and the solvent removed in vacuo to yield a dark brown oil. Flash chromatography (SiO$_2$, EtOAc/iso-hexane) yields {4-[2-(4-Fluoro-phenyl)-ethoxy]-phenyl}-acetonitrile as a yellow oil.

Step 2

2 N NaOH solution (45.2 ml, 90.3 mmol) is added to a solution of {4-[2-(4-Fluoro-phenyl)-ethoxy]-phenyl}-acetonitrile (3.29 g, 12.9 mmol) in EtOH (45.2 mol) followed by Al—Ni Alloy (2.5 g) and the resulting reaction mixture is stirred for 1 hour at room temperature. The reaction mixture is filtered and the EtOH removed in vacuo. The product is extracted into DCM (2×80 ml), dried (MgSO$_4$) and the solvent removed in vacuo to yield the title compound as a yellow oil.

Intermediate BI 2-(4,6-Dimethyl-1H-indol-3-yl)-ethylamine

This compound is prepared as described in EP 620222

Intermediate BJ

2-[4-(4-Phenyl-butoxy)-phenyl]-ethylamine

This compound is prepared as described in WOP 2004016601

Intermediate BK

4-(5-Methyl-2-phenyl-oxazol-4-ylmethoxy)-benzenesulfonyl chloride

This compound is prepared as described in WO 2005026134

Intermediate BL

2-Phenyl-3H-benzoimidazole-5-sulfonyl chloride

This compound is prepared as described in EP 1205475

Intermediate BM

4-Aminomethyl-1-(1-phenyl-ethyl)-piperidin-4-ylamine

Step 1

1-(1-Phenyl-ethyl)-piperidin-4-one is prepared according to the procedure described on page 525 of *J. Org. Chem.* 1991, 56(2), 513-528.

To a mixture of 1-(1-phenyl-ethyl)-piperidin-4-one (10.9 g, 53.6 mmol), ammonium chloride (4.3 g, 80.4 mmol) and 30% aqueous ammonia solution (30 ml) in water (30 ml) at room temperature is added sodium cyanide (4.0 g, 81.6 mmol) portion wise. The reaction mixture is stirred at room temperature for 18 hours, then diluted with water and extracted with DCM. The organic phase is washed with brine, dried over $Na_2SO_4$, filtered and concentrated in vacuo to obtain 4-Amino-1-(1-phenyl-ethyl)-piperidine-4-carbonitrile as a brown oil; $[M+H]^+$ 230.

Step 2

4-Aminomethyl-1-(1-phenyl-ethyl)-piperidin-4-ylamine is prepared analogously to Intermediate U by replacing 4-amino-4-cyano-piperidine-1-carboxylic acid tert-butyl ester in Step 1 with 4-amino-1-(1-phenyl-ethyl)-piperidine-4-carbonitrile; $[M+H]^+$ 234.

Intermediate BN

4-Aminomethyl-1-(4-methoxy-benzyl)-piperidin-4-ylamine

This compound is prepared analogously to Intermediate BM by replacing 1-(1-phenyl-ethyl)-piperidin-4-one with 1-(4-methoxybenzyl)piperidin-4-one in step 2; $^1H$ NMR (DMSO-d6): 1.46-1.64 (4H, m), 2.38-2.55 (4H, m), 2.67 (2H, s), 3.26 (2H, s), 4.08 (3H, s), 6.87 (2H, d, J=8.2 Hz), 7.18 (2H, d, J=8.2 Hz).

Intermediate BO

4-Aminomethyl-1-pyridin-4-ylmethyl-piperidin-4-ylamine

Step 1

To a solution of 4-aminomethyl-4-(2,2,2-trifluoro-acetylamino)-piperidine-1-carboxylic acid tert-butyl ester (Intermediate U, Step 2) (5.0 g, 15.4 mmol) in DCM (50 ml) at 0° C. is added pyridine (10 ml) followed by trifluoroacetic anhydride (3.5 ml, 25.3 mmol) and the reaction mixture is stirred at room temperature for 16 hours. The reaction mixture is diluted with DCM, washed with brine, dried over $Na_2SO_4$ and concentrated in vacuo. The residue obtained is dissolved in diethyl ether and re-precipitated by adding petroleum ether. The solvent mixture is decanted and the solid dried under vacuum to afford 4-(2,2,2-Trifluoro-acetylamino)-4-[(2,2,2-trifluoro-acetylamino)-methyl]-piperidine-1-carboxylic acid tert-butyl ester; $[M+H]^+$ 420.

Step 2

To a solution of 4-(2,2,2-trifluoro-acetylamino)-4-[(2,2,2-trifluoro-acetylamino)-methyl]-piperidine-1-carboxylic acid tert-butyl ester (5.25 g, 12.5 mmol) in dioxane (50 ml) is added 4 M HCl in dioxane (15 ml) and the reaction mixture is stirred at room temperature for 3 hours. The reaction mixture is concentrated in vacuo and the off-white solid obtained dissolved in the minimum amount of MeOH and re-precipitated by adding diethyl ether. The supernatant solvent mixture is decanted and the product is washed again with diethyl ether and dried under vacuum to afford 2,2,2-Trifluoro-N-{4-[(2,2,2-trifluoro-acetylamino)-methyl]-piperidin-4-yl}-acetamide hydrochloride; $[M+H]^+$ 322.

Step 3

To a suspension of NaH (170 mg of a 60% dispersion in mineral oil, 4.25 mmol) in anhydrous DMF (20 ml) is added 2,2,2-trifluoro-N-{4-[(2,2,2-trifluoro-acetylamino)-methyl]-piperidin-4-yl}-acetamide hydrochloride) (500 mg, 1.4 mmol) followed by 4-bromomethylpyridine hydrobromide (350 mg, 1.4 mmol). The reaction mixture is stirred at room temperature for 3 hours. The reaction mixture is quenched with sat. $NH_4Cl$ solution and is concentrated in vacuo. The residue is purified by column chromatography (basic alumina, MeOH/DCM) to obtain 2,2,2-Trifluoro-N-[1-pyridin-4-ylmethyl-4-(2,2,2-trifluoro-acetylamino)-piperidin-4-ylmethyl]-acetamide as off-white solid; $[M+H]^+$ 413

Step 4

To a solution of 2,2,2-trifluoro-N-[1-pyridin-4-ylmethyl-4-(2,2,2-trifluoro-acetylamino)-piperidin-4-ylmethyl]-acetamide (200 mg, 0.49 mmol) in MeOH (10 ml) is added 30% aqueous ammonia solution (10 ml) and the reaction mixture is stirred at 60° C. for 3 h. The reaction mixture is concentrated in vacuo to obtain 4-Aminomethyl-1-pyridin-4-ylmethyl-piperidin-4-ylamine as a colourless gummy oil that is used without further purification; $^1H$ NMR (DMSO-d6): 1.63-1.77 (4H, m), 2.45-2.54 (4H, m), 2.49 (2H, s), 3.57 (3H, s), 7.30 (2H, d, J=5.5 Hz), 8.68 (2H, d, J=5.5 Hz).

Intermediate BP

4-Aminomethyl-1-(3-phenyl-propyl)-piperidin-4-ylamine

This compound is prepared analogously to Intermediate BO by replacing -bromomethylpyridine hydrobromide (Step 3) with 1-bromo-3-phenylpropane; $[M+H]^+$ 248

Intermediate BQ

4-Aminomethyl-1-cyclohexylmethyl-piperidin-4-ylamine

This compound is prepared analogously to Intermediate BO by replacing -bromomethylpyridine hydrobromide (Step 3) with cyclohexylmethylbromide. This intermediate is used crude in the preparation of Example 250.

Intermediate BR

3-Amino-3-aminomethyl-8-aza-bicyclo[3.2.1]octane-8-carboxylic acid tent-butyl ester This compound is prepared analogously to Intermediate BM by replacing 1-(1-phenyl-ethyl)-piperidin-4-one (Step 1)

with N-Boc-nortropinone; $^1$H NMR (DMSO-d6): 1.40 (9H, s), 1.63-1.85 (8H, m), 2.79 (2H, s), 4.06 (2H, s).
The invention claimed is:
1. A compound selected from the group consisting of
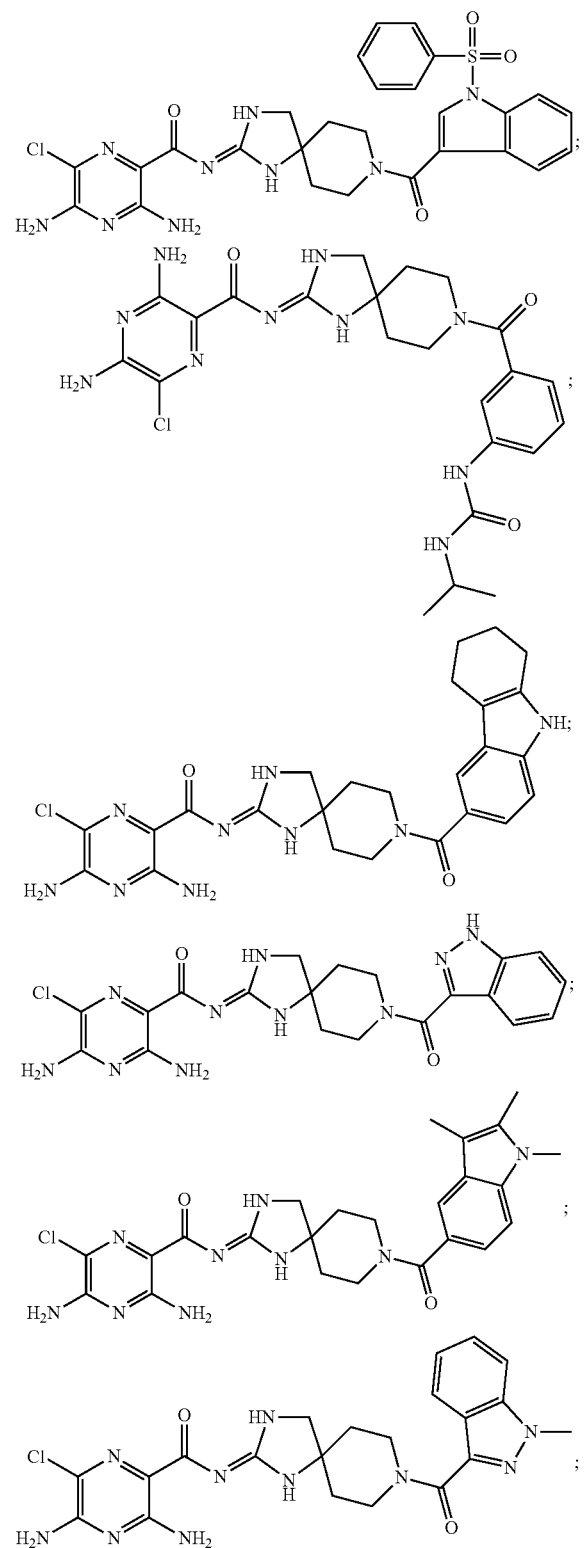
-continued
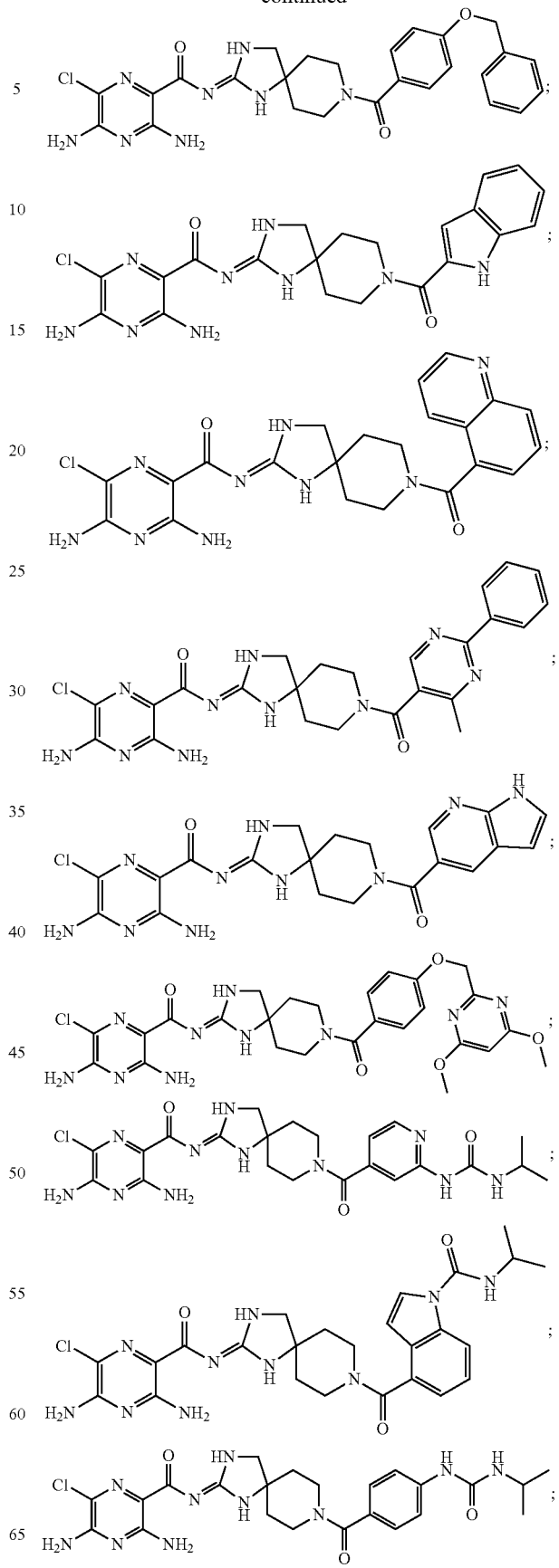

233
-continued
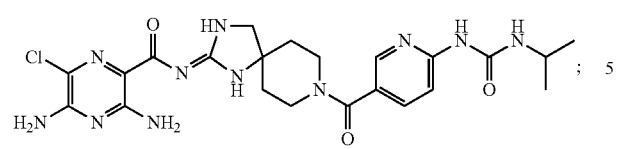
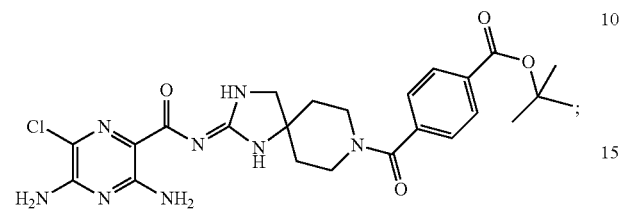
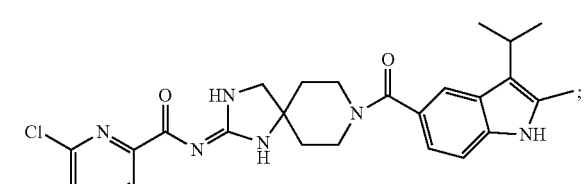
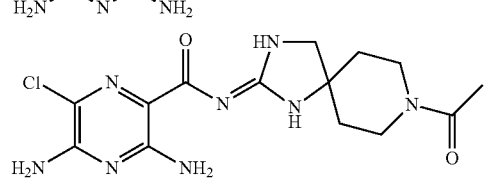
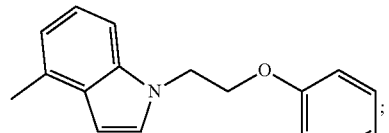
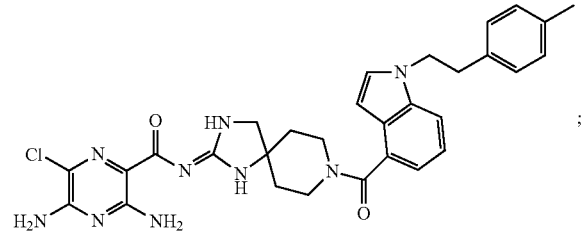
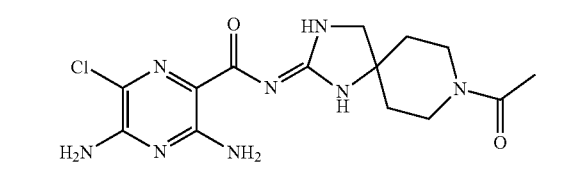
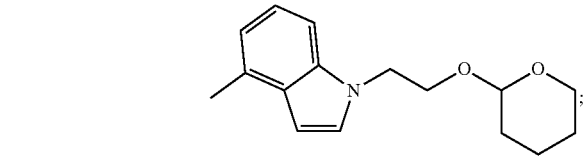
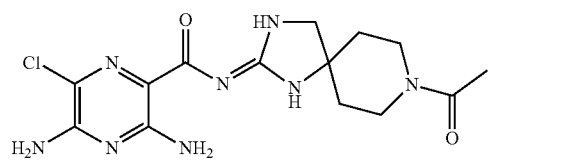
234
-continued
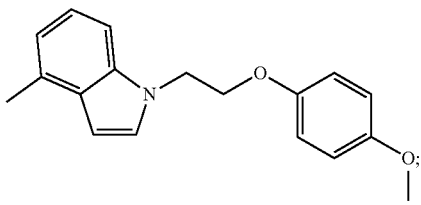
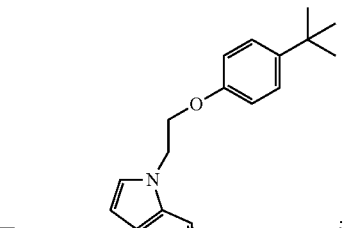
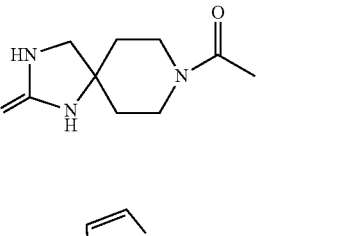
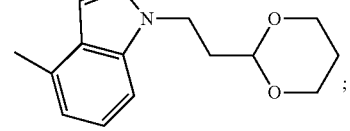
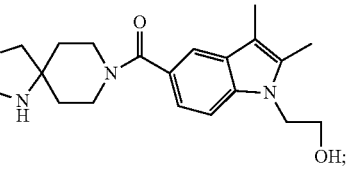
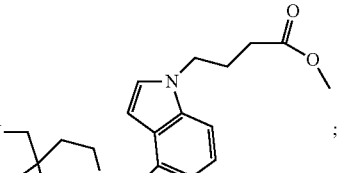
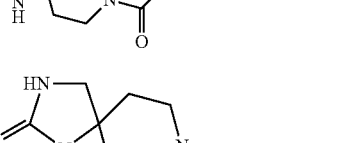
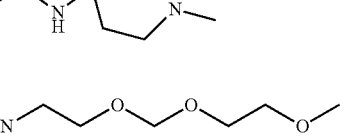

235
-continued
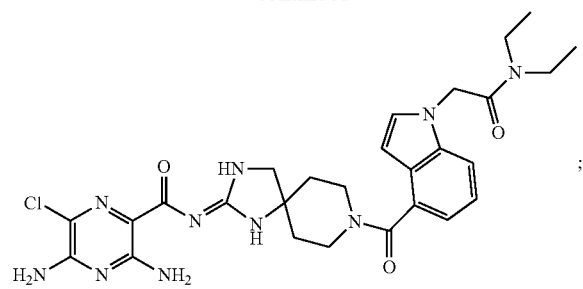
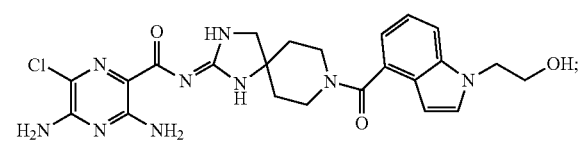
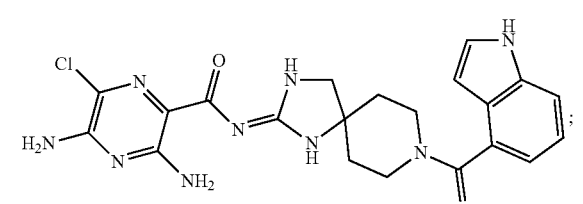
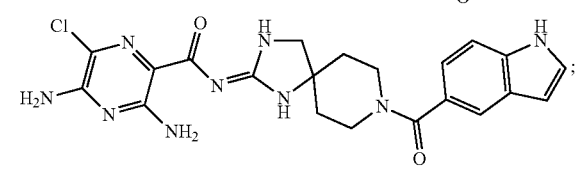
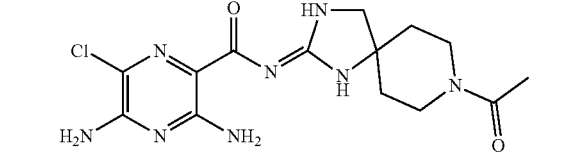
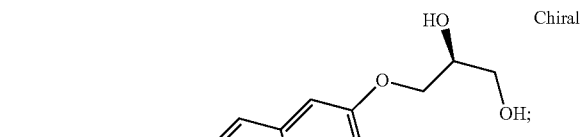
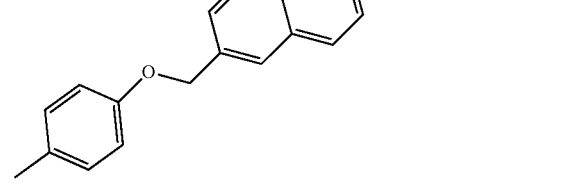
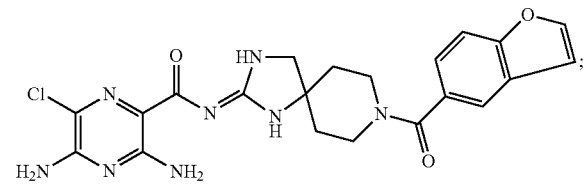
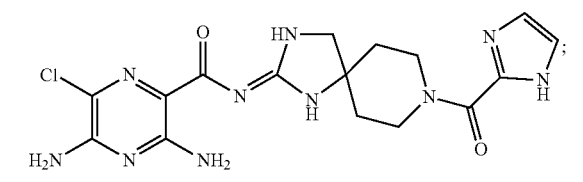
236
-continued
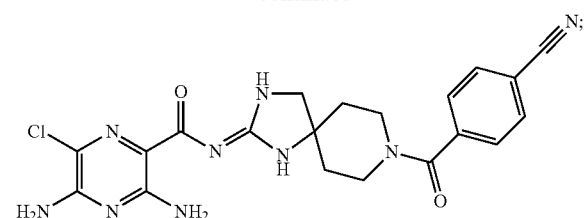
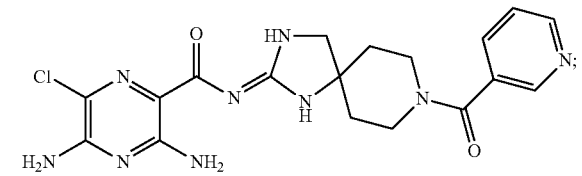
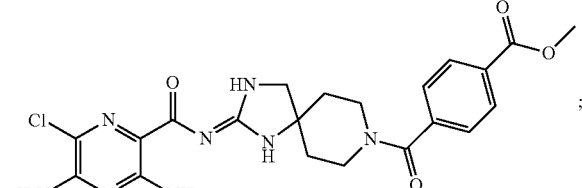
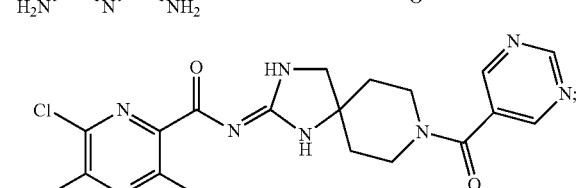
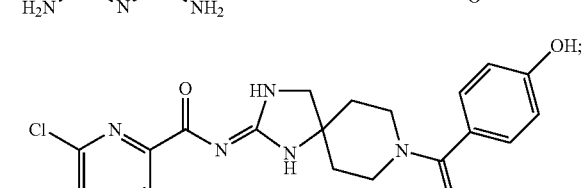
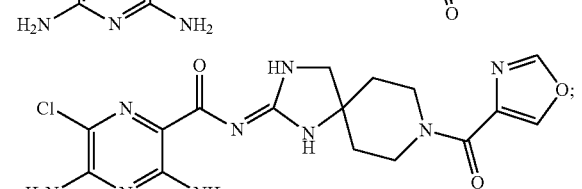
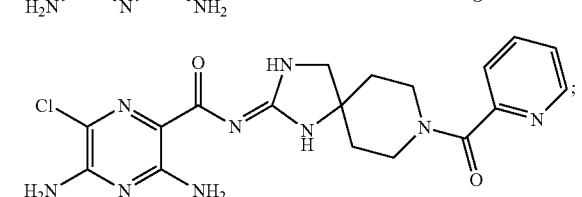
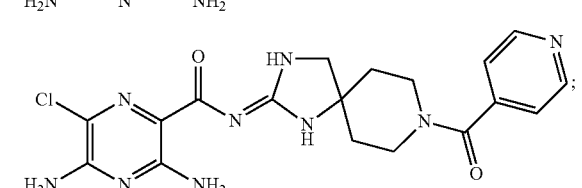
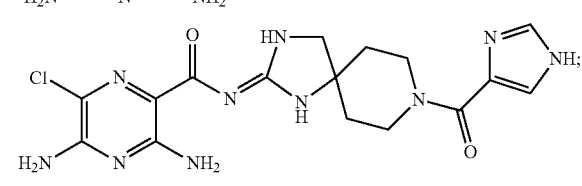

237
-continued
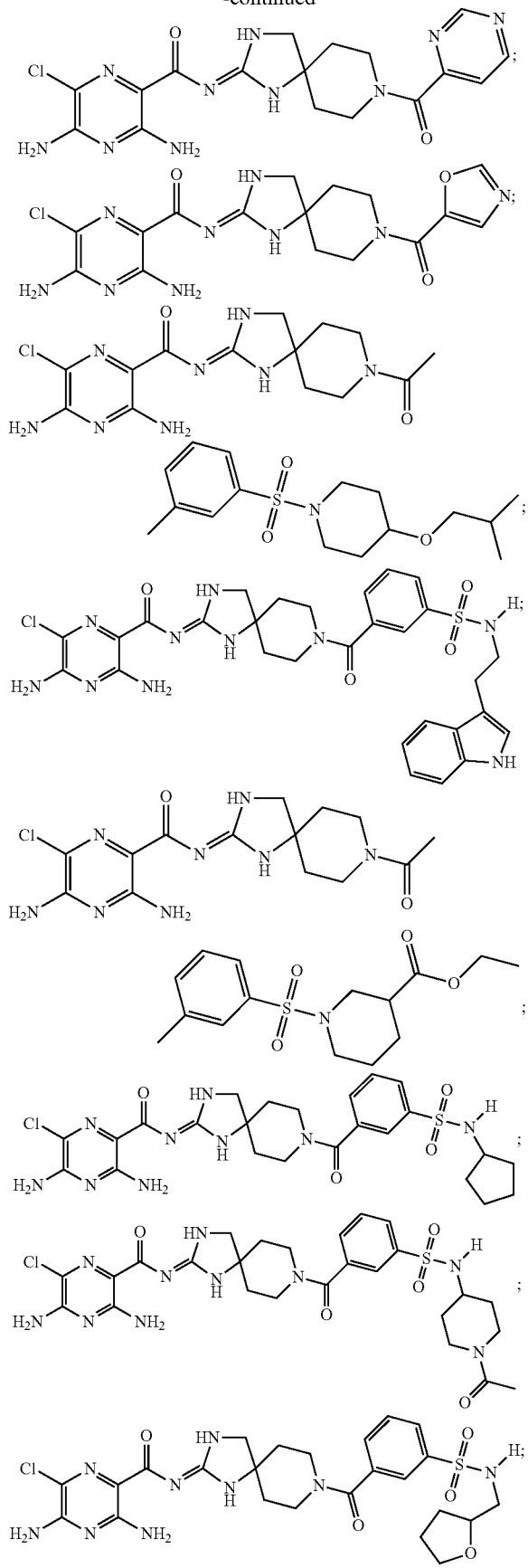
238
-continued
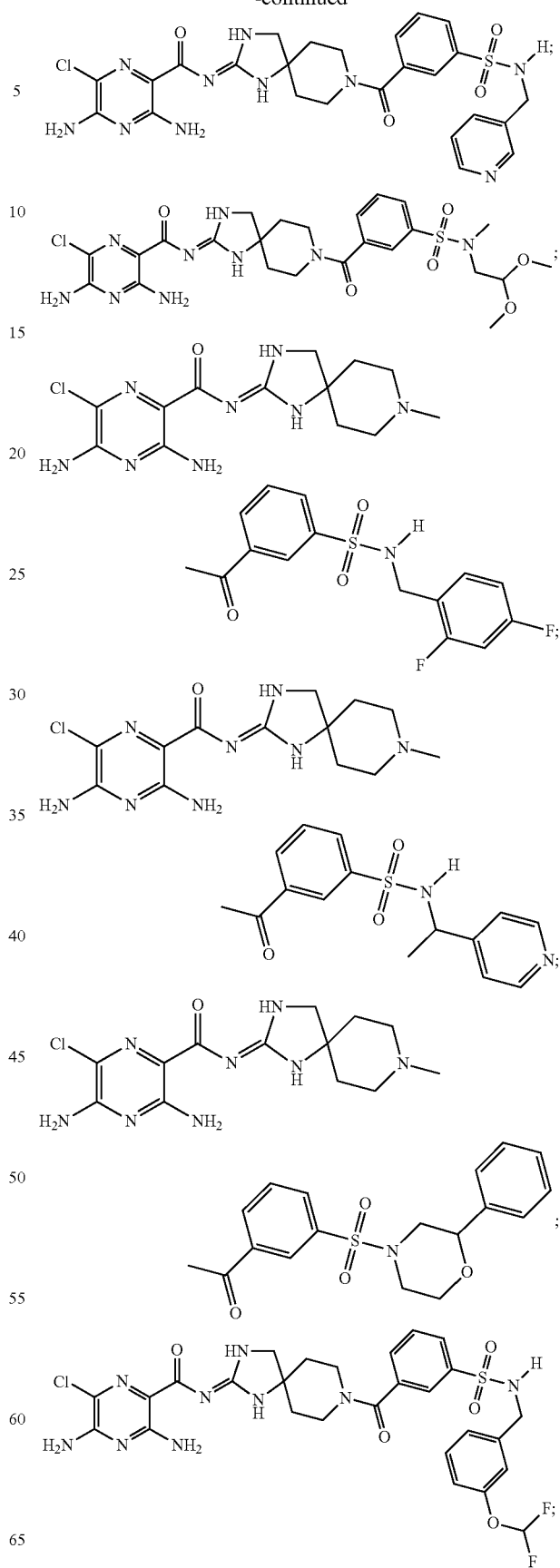

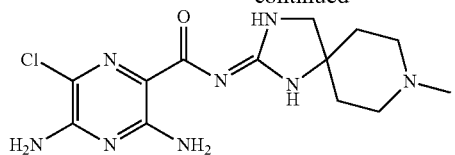
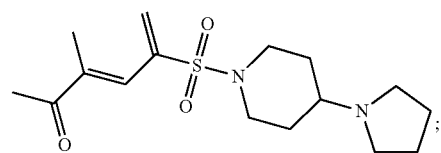
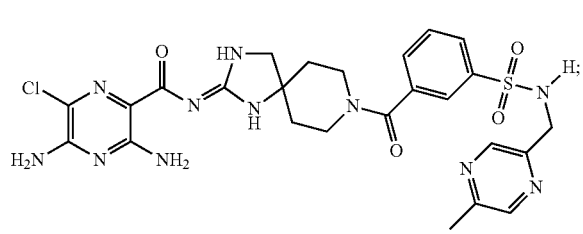
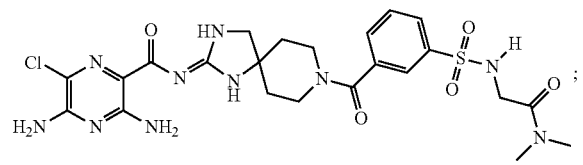
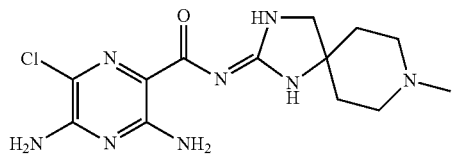
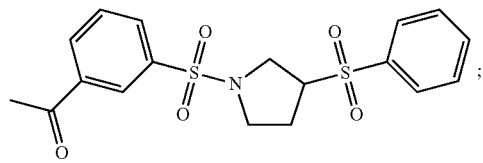
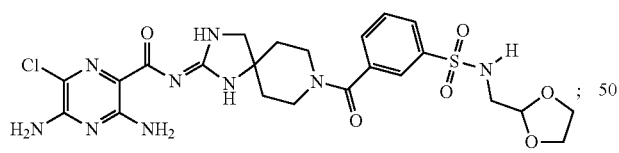
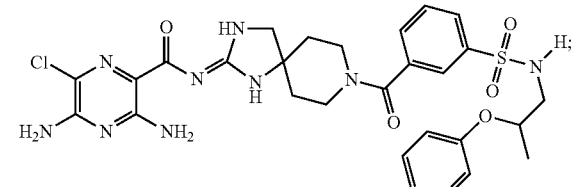
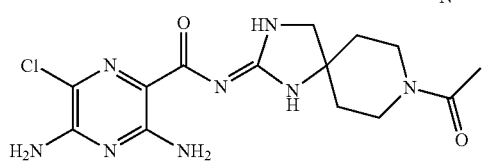
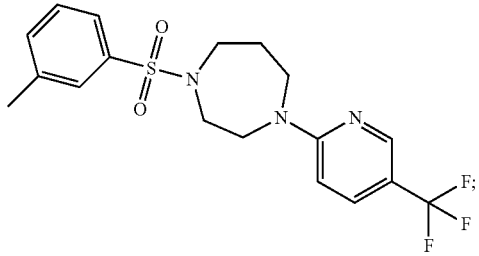
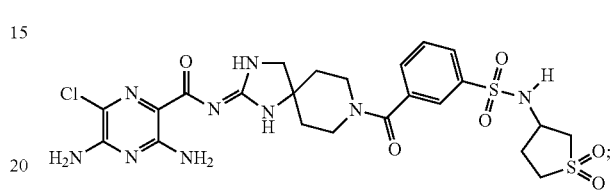
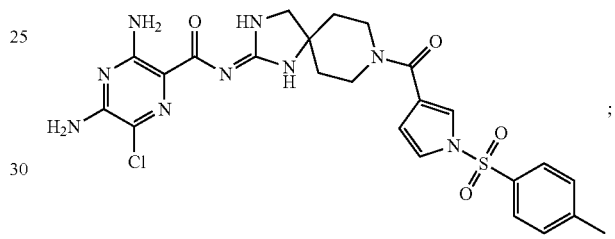
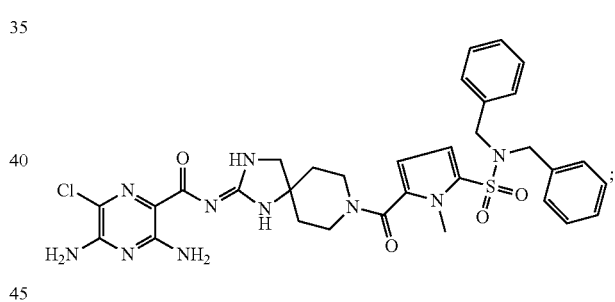
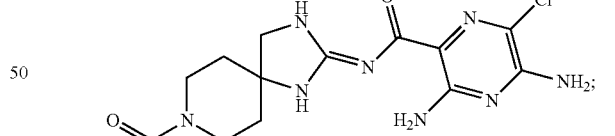
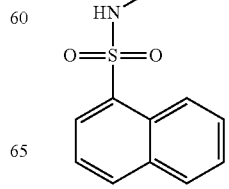

241
-continued
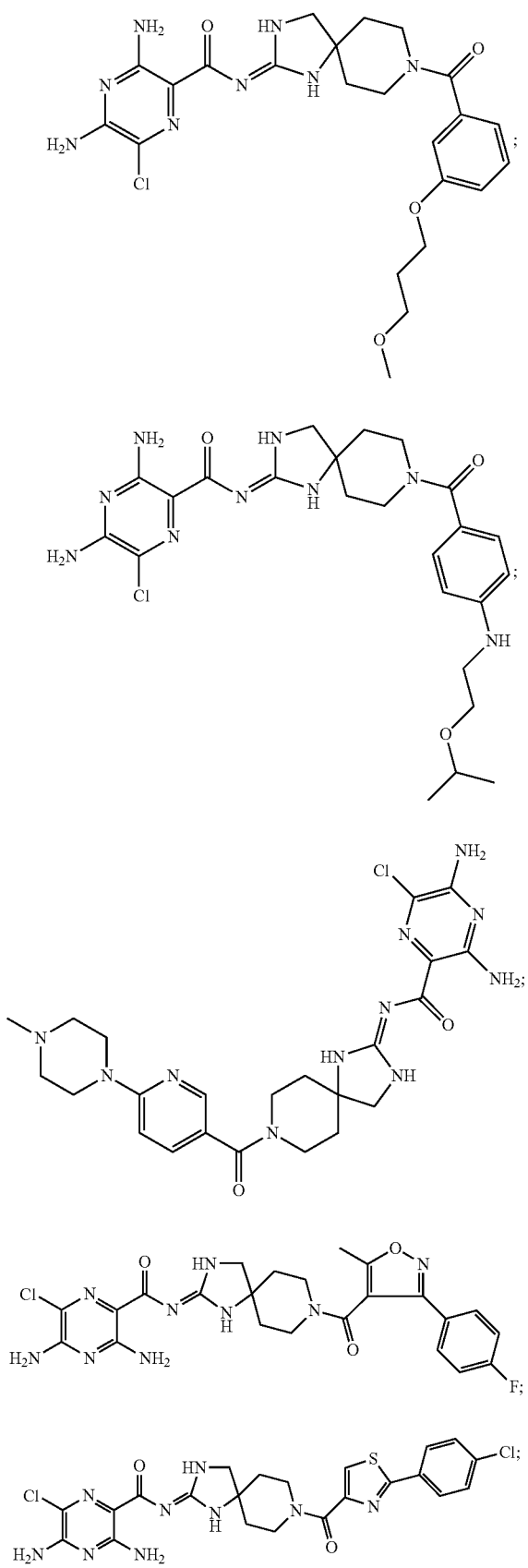
242
-continued
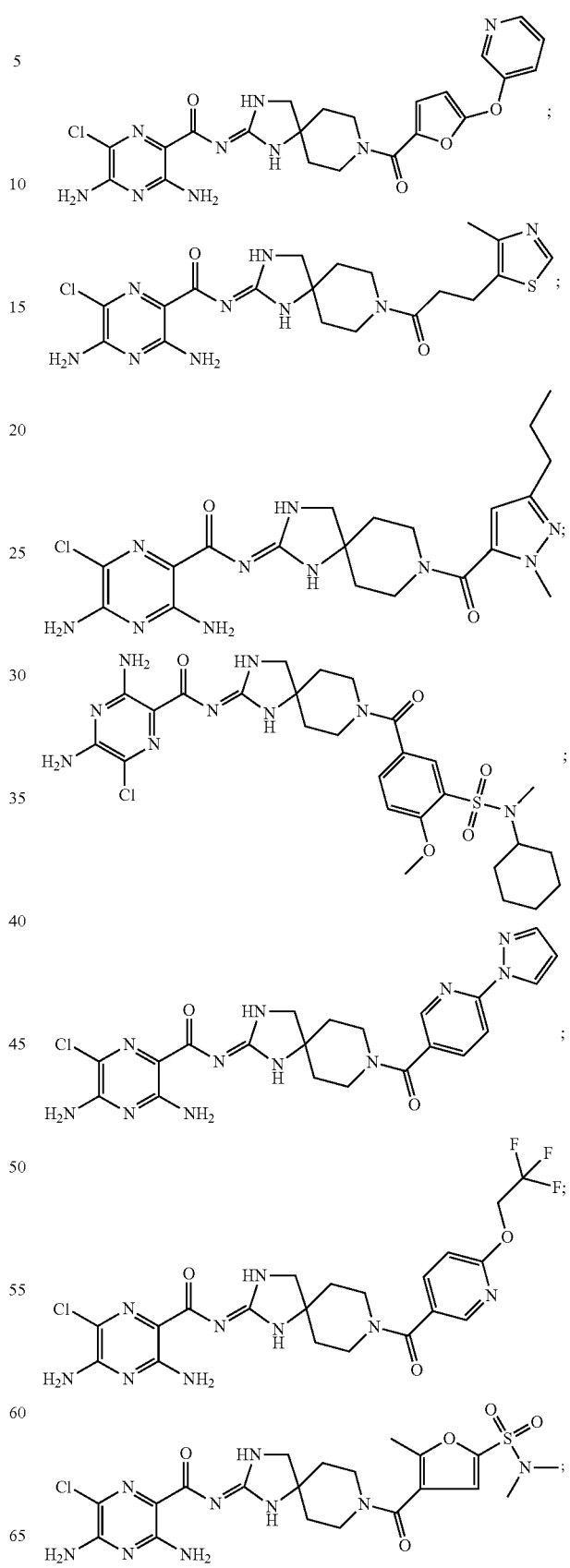

-continued
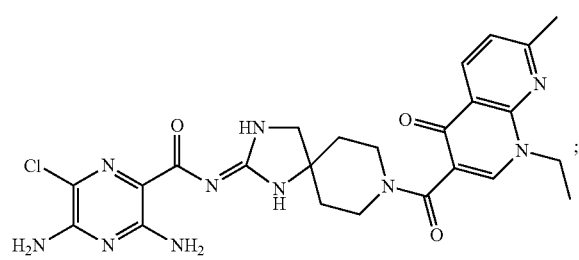
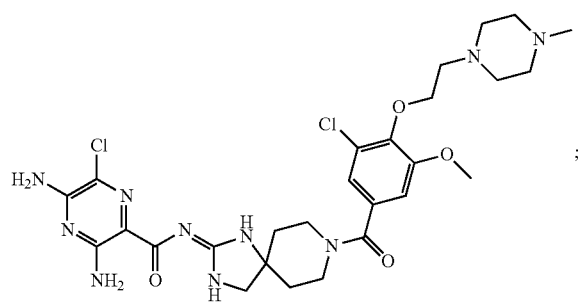
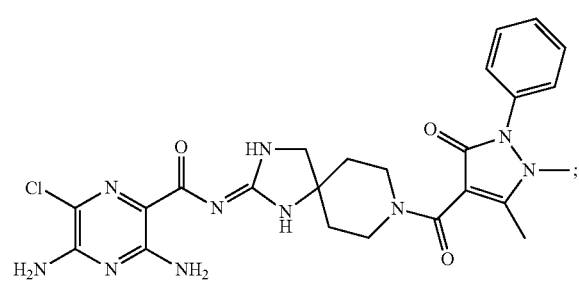
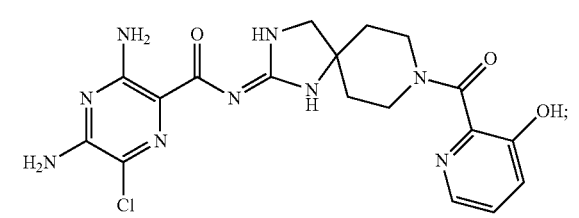
and
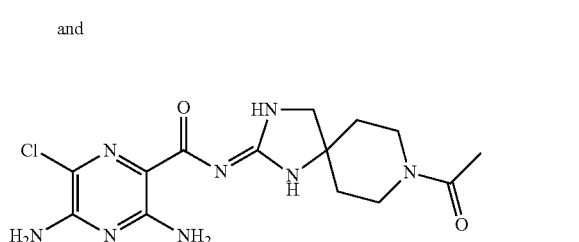
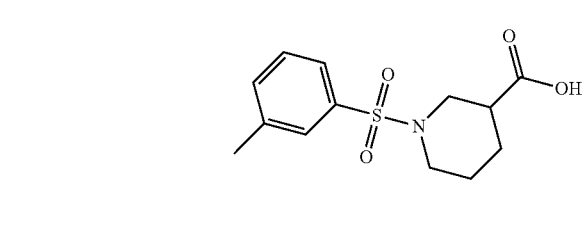
and the pharmaceutically acceptable salts thereof.
2. A compound selected from the group consisting of
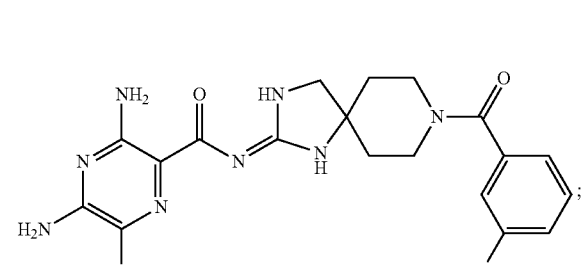
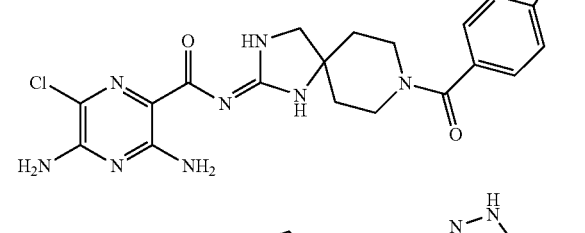
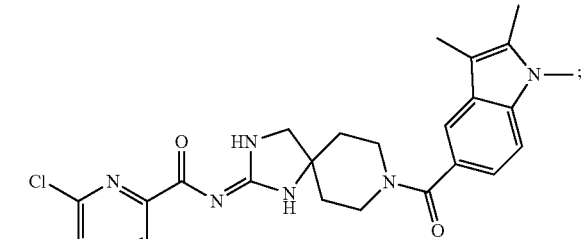
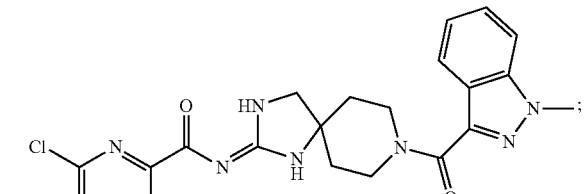
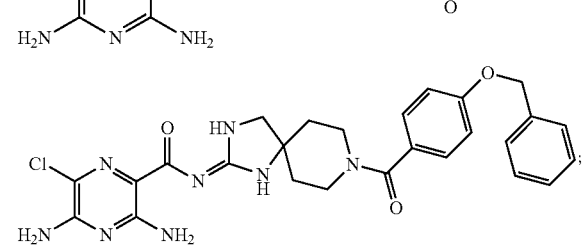

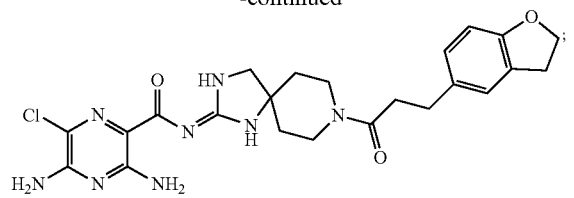
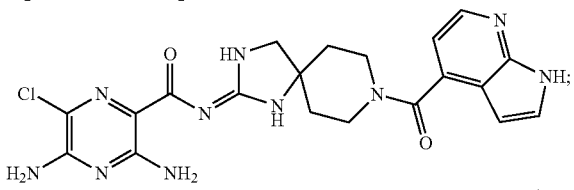
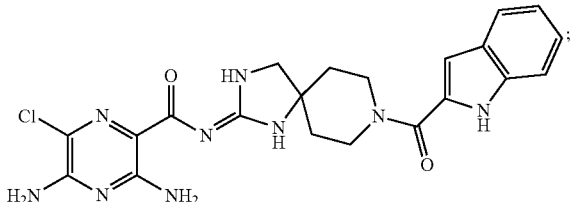
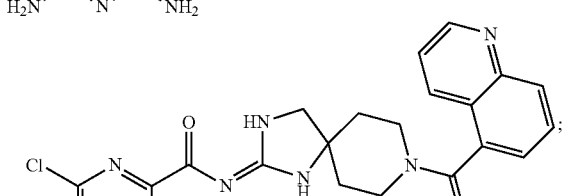
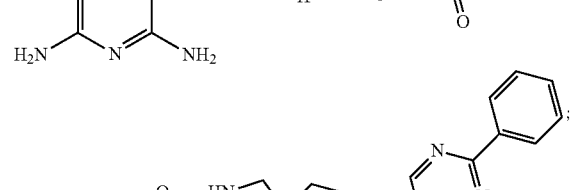
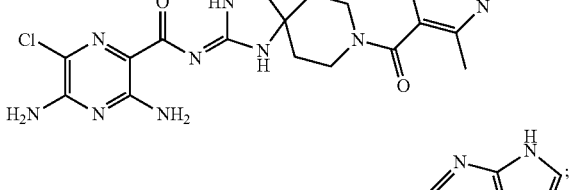
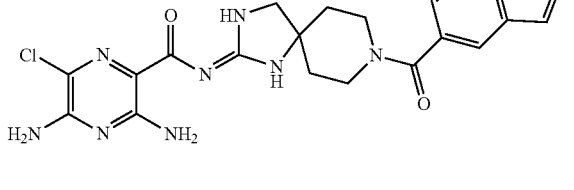
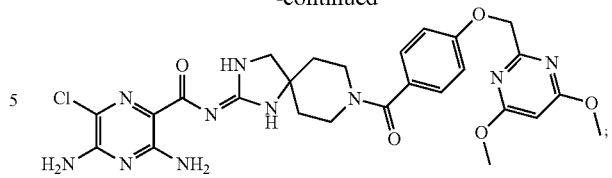
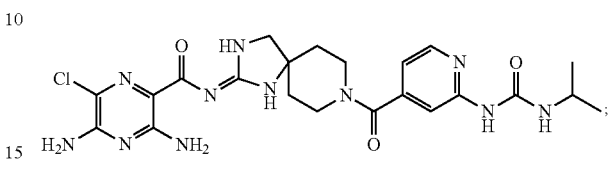
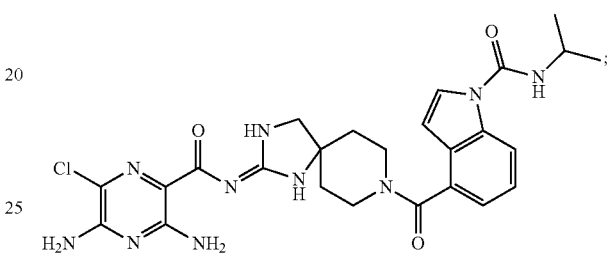
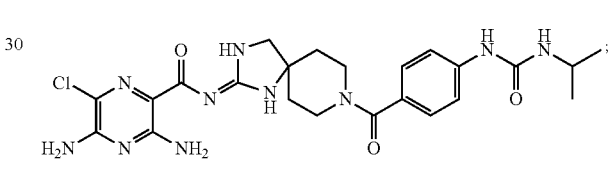
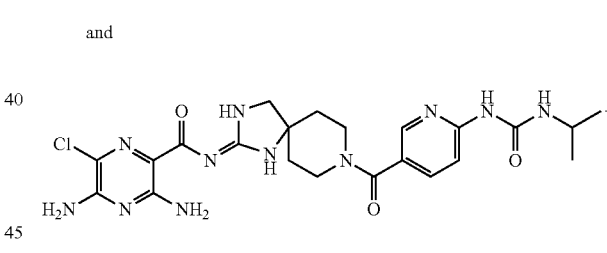
and the pharmaceutically acceptable salts thereof.
3. The compound according to claim 1, wherein the compound is selected from the group consisting of
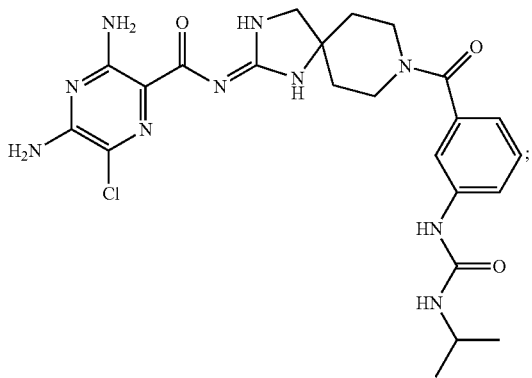

-continued
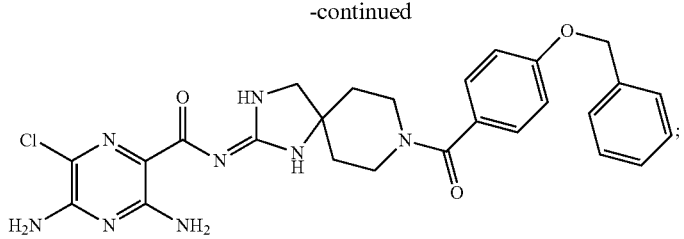
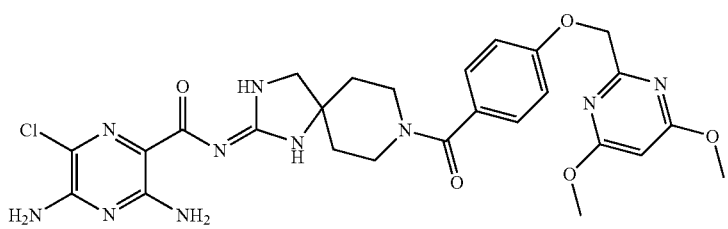
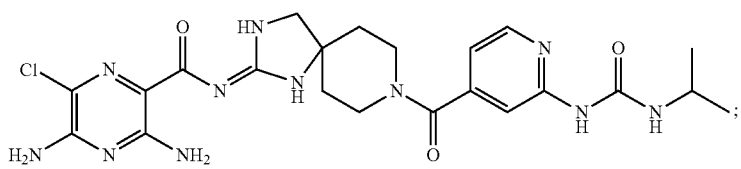
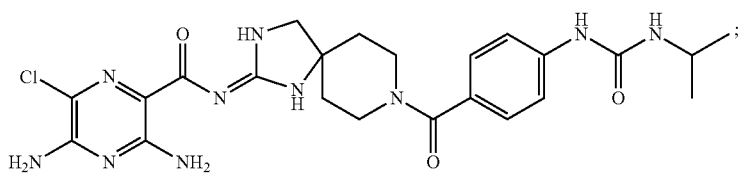
and
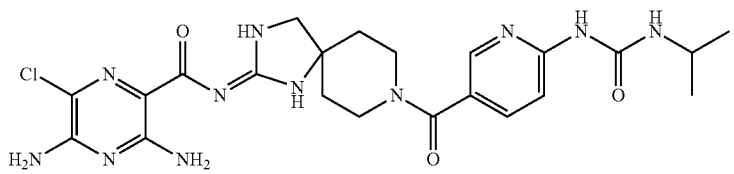
and the pharmaceutically acceptable salts thereof.
4. The compound according to claim 1, wherein the compound is
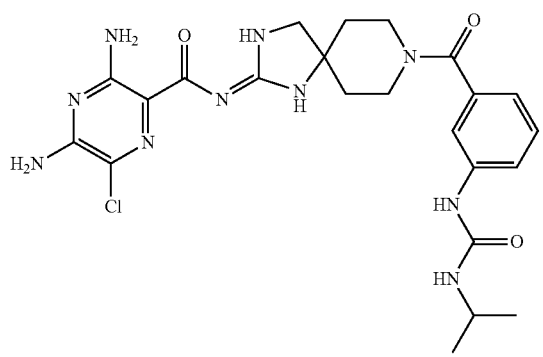
or a pharmaceutically acceptable salt thereof.
5. The compound according to claim 1, wherein the compound is
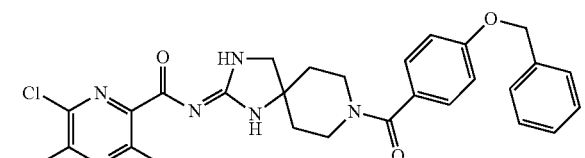
or a pharmaceutically acceptable salt thereof.

6. The compound according to claim 1, wherein the compound is

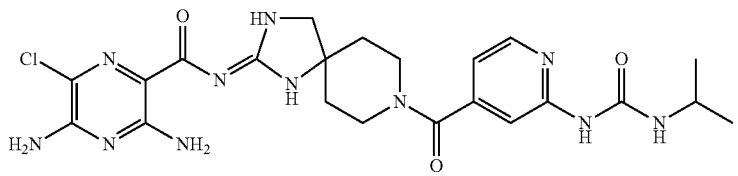

or a pharmaceutically acceptable salt thereof.

7. The compound according to claim 1, wherein the compound is

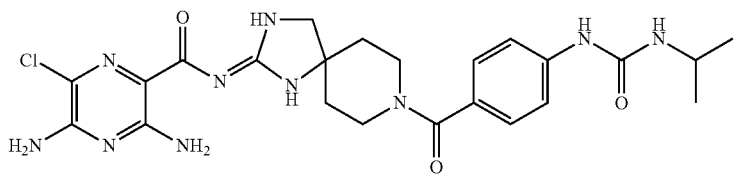

or pharmaceutically acceptable salt thereof.

8. The compound according to claim 1, wherein the compound is

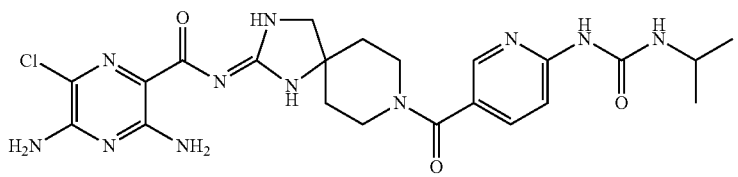

or a pharmaceutically acceptable salt thereof.

9. The compound according to claim 1, wherein the compound is

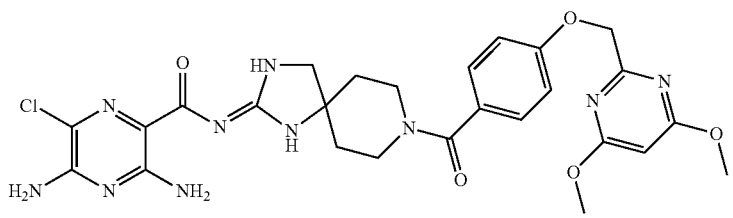

or a pharmaceutically acceptable salt thereof.

10. A pharmaceutical composition, comprising:
the compound according to claim 3, and
one or more pharmaceutically acceptable excipients.

11. A pharmaceutical composition, comprising:
the compound according to claim 1, and
one or more pharmaceutical excipients.

12. A pharmaceutical composition, comprising:
the compound according to claim 2, and
one or more pharmaceutical excipients.

13. A pharmaceutical combination, comprising:
the compound according to claim 1, and
an anti-inflammatory, bronchodilatory, antihistamine or anti-tussive drug substance.

14. The compound according to claim 4, wherein the compound is the hydrochloric acid salt.

15. The compound according to claim 5, wherein the compound is the hydrochloric acid salt.

16. The compound according to claim 6, wherein the compound is the hydrochloric acid salt.

17. The compound according to claim 7, wherein the compound is the hydrochloric acid salt.

18. The compound according to claim 8, wherein the compound is the hydrochloric acid salt.

19. The compound according to claim 9, wherein the compound is the hydrochloric acid salt.

* * * * *